US012202911B2

(12) United States Patent
Urech et al.

(10) Patent No.: US 12,202,911 B2
(45) **Date of Patent: *Jan. 21, 2025**

(54) MULTISPECIFIC ANTIBODY COMPRISING CD137 BINDING DOMAIN AND PDL1 BINDING DOMAIN

(71) Applicant: Numab Therapeutics AG, Wädenswil (CH)

(72) Inventors: David Urech, Jona (CH); Tea Gunde, Zurich (CH); Sebastian Meyer, Eggenwil (CH); Matthias Brock, Aesch (CH); Christian Hess, Zurich (CH); Alexandre Simonin, Rosenau (FR); Stefan Warmuth, Au (CH)

(73) Assignee: Numab Therapeutics AG, Horgen (CH)

( * ) Notice: Subject to any disclaimer, the term of this patent is extended or adjusted under 35 U.S.C. 154(b) by 1292 days.

This patent is subject to a terminal disclaimer.

(21) Appl. No.: 16/754,604

(22) PCT Filed: Oct. 9, 2018

(86) PCT No.: PCT/EP2018/077509

§ 371 (c)(1),
(2) Date: Apr. 8, 2020

(87) PCT Pub. No.: WO2019/072868

PCT Pub. Date: Apr. 18, 2019

(65) Prior Publication Data

US 2023/0192897 A1 Jun. 22, 2023

(30) Foreign Application Priority Data

Oct. 10, 2017 (EP) .................................... 17195779
Jan. 5, 2018 (EP) .................................... 18150465
Apr. 12, 2018 (EP) .................................... 18167093
Jun. 29, 2018 (EP) .................................... 18180814

(51) Int. Cl.
*C07K 16/30* (2006.01)
*A61P 35/00* (2006.01)
*C07K 16/28* (2006.01)
*C07K 16/46* (2006.01)

(52) U.S. Cl.
CPC ............ *C07K 16/468* (2013.01); *A61P 35/00* (2018.01); *C07K 16/30* (2013.01); *C07K 2317/31* (2013.01); *C07K 2317/35* (2013.01); *C07K 2317/565* (2013.01); *C07K 2317/567* (2013.01); *C07K 2317/92* (2013.01)

(58) Field of Classification Search
CPC .................................................... C07K 16/468
See application file for complete search history.

(56) References Cited

U.S. PATENT DOCUMENTS

2003/0157561 A1* 8/2003 Kolkman ............... A61K 47/62 435/7.1
2016/0244528 A1* 8/2016 Gray ....................... A61P 13/12

FOREIGN PATENT DOCUMENTS

WO WO-2016086189 A2 * 6/2016 .............. A61P 35/00
WO 2016/149201 A2 9/2016
WO 2017/123650 A2 7/2017

OTHER PUBLICATIONS

Herbst (Nature, vol. 515, p. 563-567, 2014) (Year: 2014).*
Rudikoff et al. (Proceedings of the National Academy of Sciences USA, vol. 79, p. 1979-1983, 1982) (Year: 1982).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Shindo et al., International J of Cancer Research and Treatment 35(1):129-136 (Jan. 1, 2015).

* cited by examiner

*Primary Examiner* — Michael Allen
(74) *Attorney, Agent, or Firm* — Prismatic Law Group, PLLC; Ronald J. Kamis

(57) ABSTRACT

The present invention relates to a multispecific antibody comprising at least one CD137 binding domain and at least one PDL1 binding domain, and pharmaceutical compositions and methods of use thereof. The present invention further relates to a nucleic acid encoding said multispecific antibody, a vector comprising said nucleic acid, a host cell comprising said nucleic acid or said vector, and a method of producing said multispecific antibody.

3 Claims, 45 Drawing Sheets

Specification includes a Sequence Listing.

Figure 1:
(A)
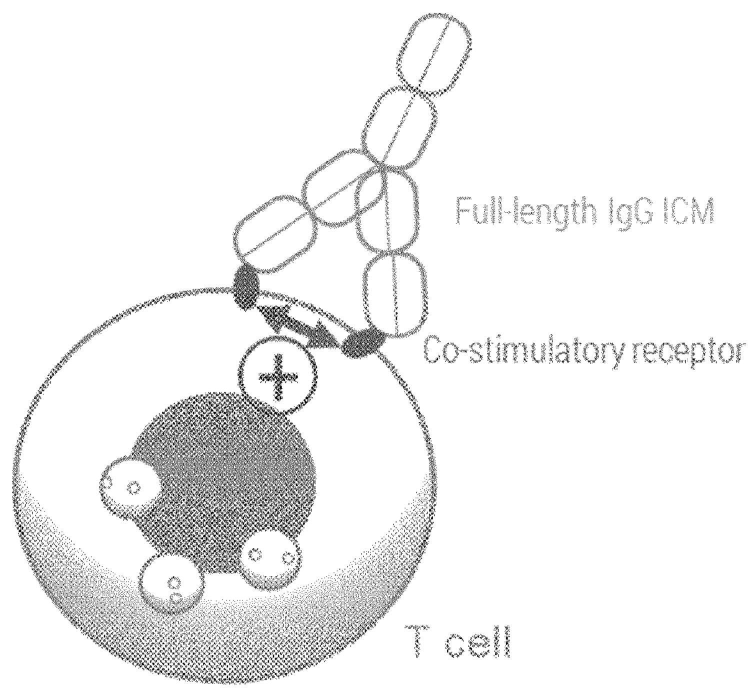
(B)
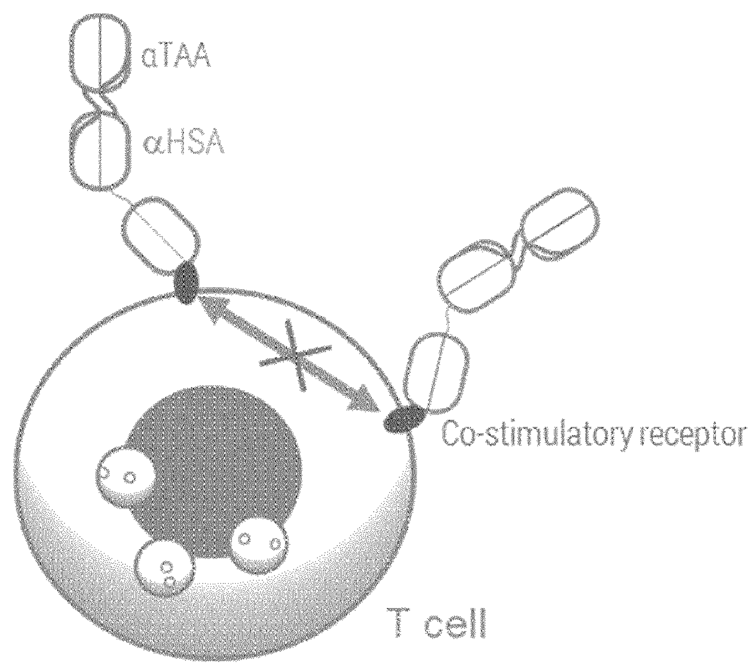

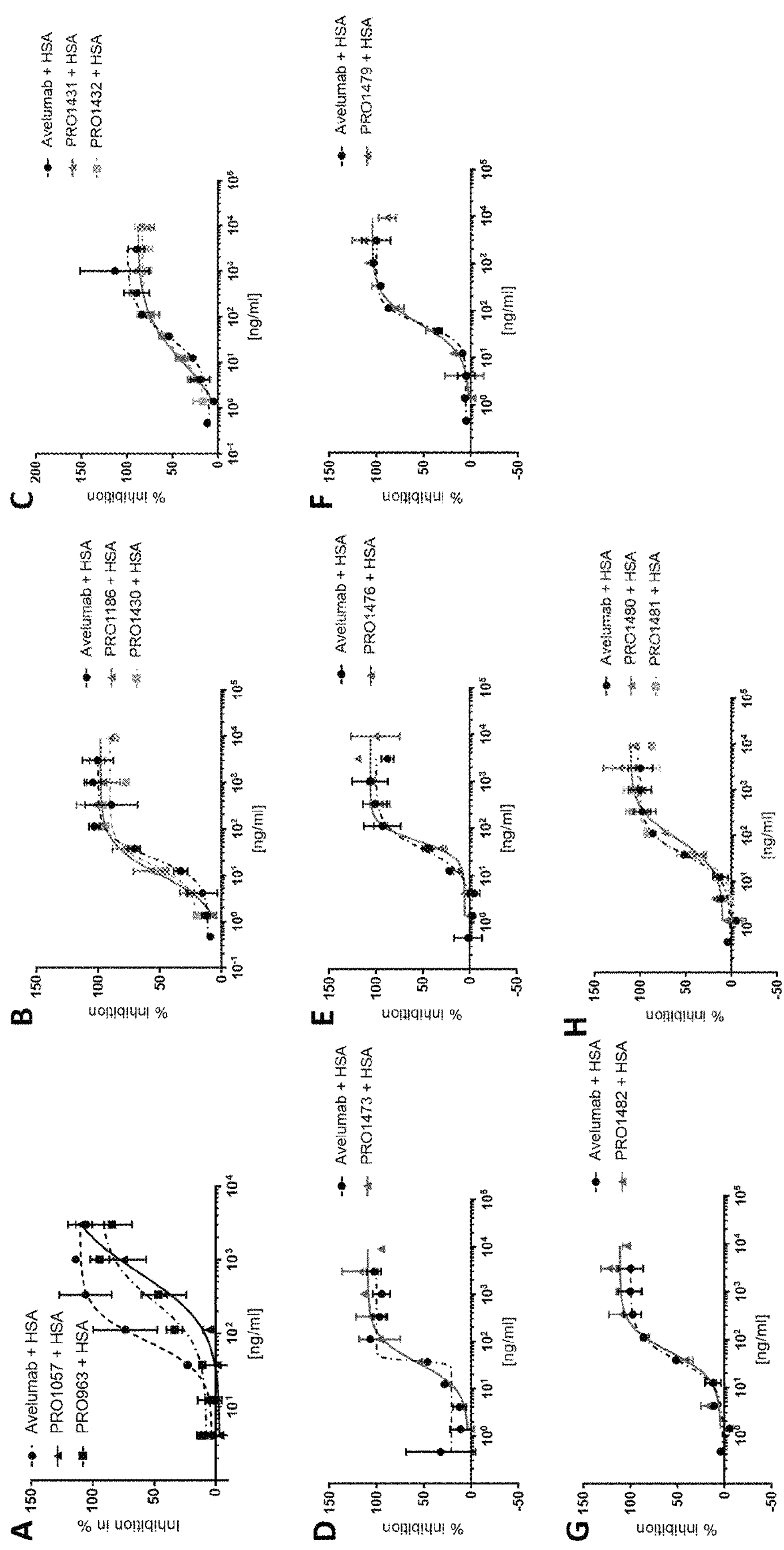
Figure 5:
A
Inhibition in %
[ng/ml]
Avelumab + HSA
PRO1057 + HSA
PRO963 + HSA
B
% inhibition
[ng/ml]
Avelumab + HSA
PRO1186 + HSA
PRO1430 + HSA
C
% inhibition
[ng/ml]
Avelumab + HSA
PRO1431 + HSA
PRO1432 + HSA
D
% inhibition
[ng/ml]
Avelumab + HSA
PRO1473 + HSA
E
% inhibition
[ng/ml]
Avelumab + HSA
PRO1476 + HSA
F
% inhibition
[ng/ml]
Avelumab + HSA
PRO1479 + HSA
G
% inhibition
[ng/ml]
Avelumab + HSA
PRO1482 + HSA
H
% inhibition
[ng/ml]
Avelumab + HSA
PRO1480 + HSA
PRO1481 + HSA A
OD (450-690 nm)
molecule conc. [ug/ml]
goat anti-huCD137
PRO885
B
OD (450-690 nm)
molecule conc. [ug/ml]
goat anti-huCD137
PRO951
C
OD (450-690 nm)
protein concentration [µg/ml]
goat anti-human CD137
PRO1359
PRO1360

| Heatmap | Urelumab | Utomilumab | PRO885 | PRO951 |
|---|---|---|---|---|
| PRO885 | 29% | 35% | 0% | 48% |
| PRO951 | 34% | 0% | 22% | 0% |

| Heatmap | 38-27-A11 | Urelumab | Utomilumab |
|---|---|---|---|
| 38-27-A11 | 0% | 0% | 52% |
| Urelumab | 0% | 0% | 41% |
| Utomilumab | 17% | 21% | 0% |

Binding level normalized to theroretical $R_{max}$ [%]

Figure 23(A)-(E):
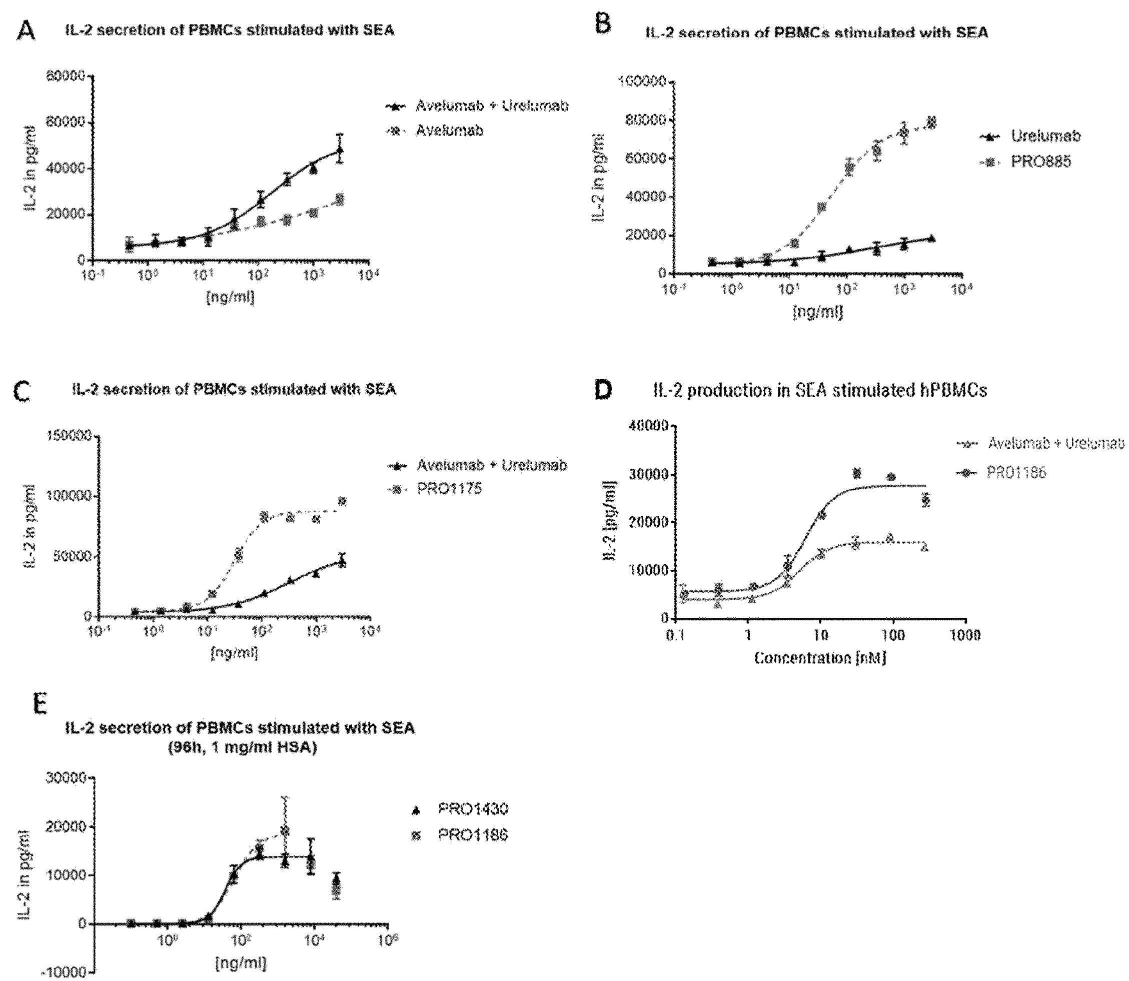

Figure 23(F)-(K):
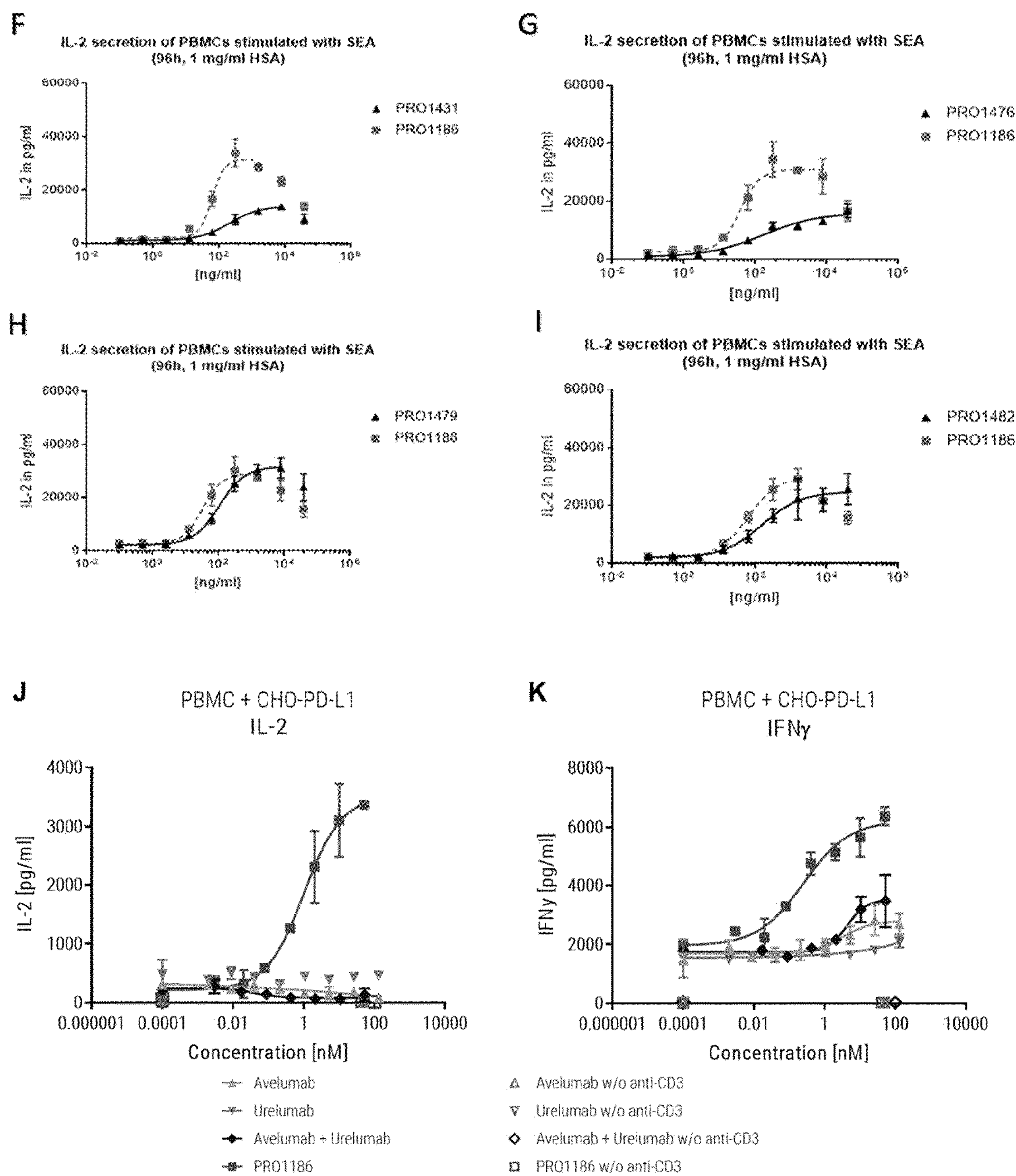

Figure 23(L)-(M):
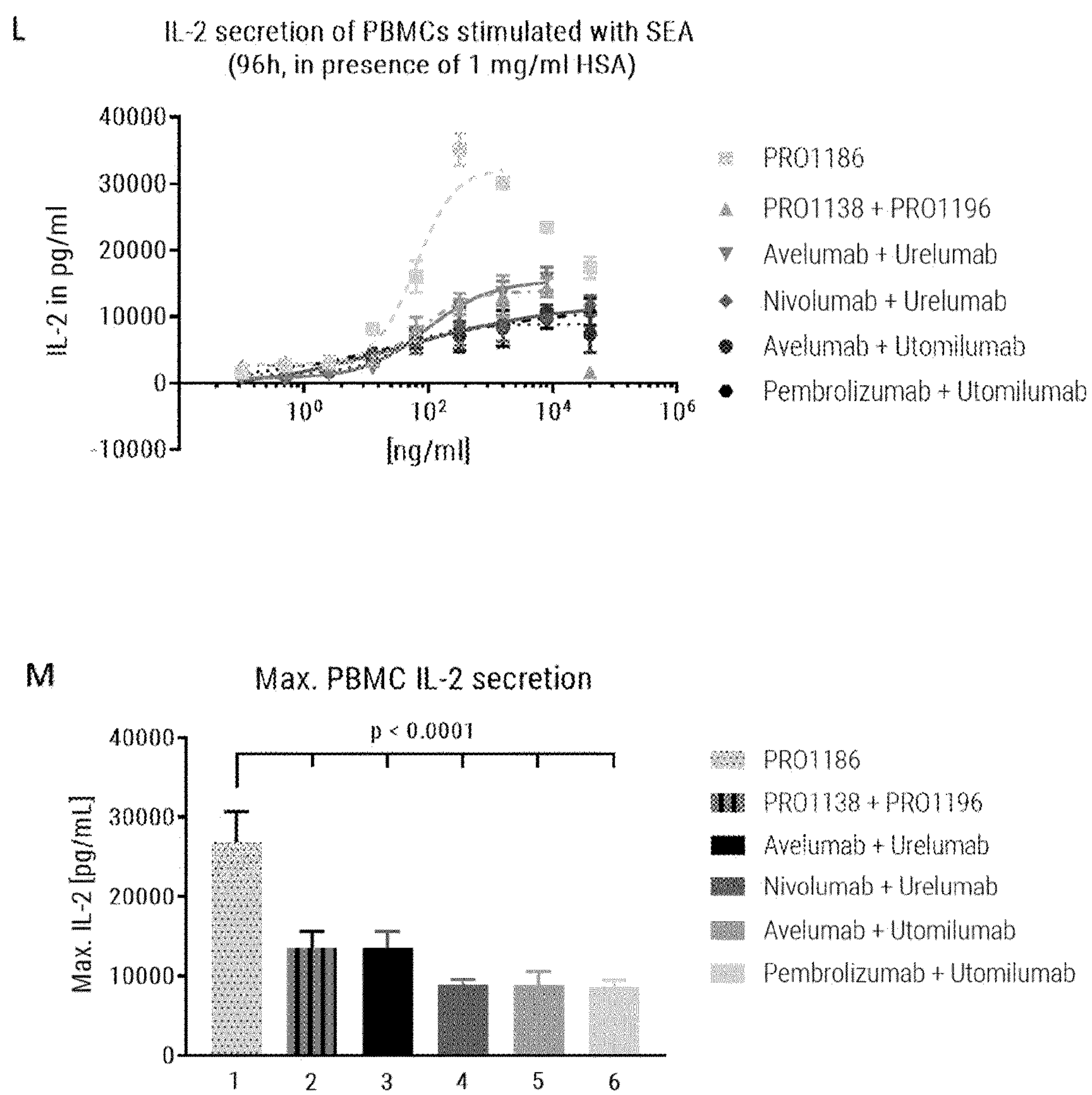

A
relative tumor volume
Mean relative tumor volume [%]
Day
dose (i.p.)
Vehicle
PDL1 PRO1137 (1 r.U/0.2mg)
CD137 PRO1138 (0.2mg)
CD137 Urelumab (0.2mg)
PDL1xCD137 PRO1057 (0.04 r.U)
PDL1xCD137 PRO1057 (0.2 r.U)
PDL1xCD137 PRO1057 (1 r.U)
PDL1xCD137 PRO1060 (1 r.U)
B
relative tumor volume - Donor B
C
RTV at d17 - tumor volume distribution
RTV [%]
D
RTV d17 - tumor volume distribution - Donor B Figure 26:
A
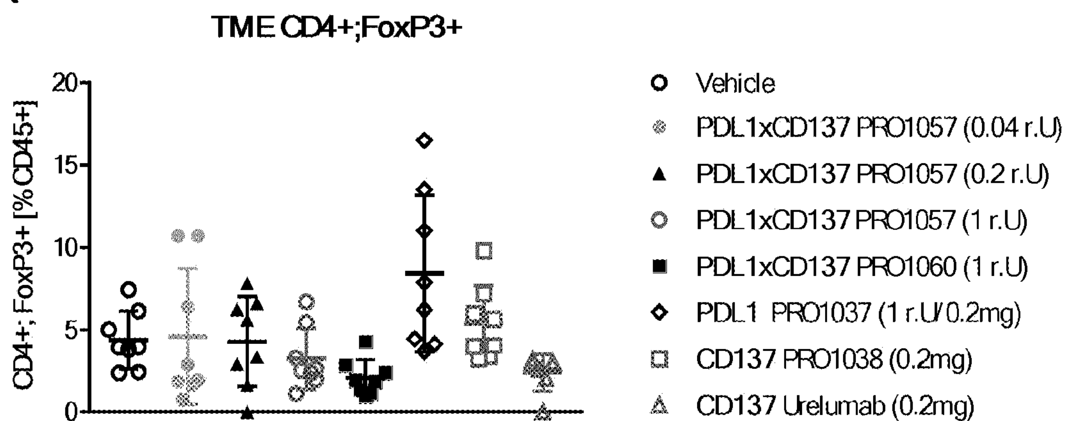
B
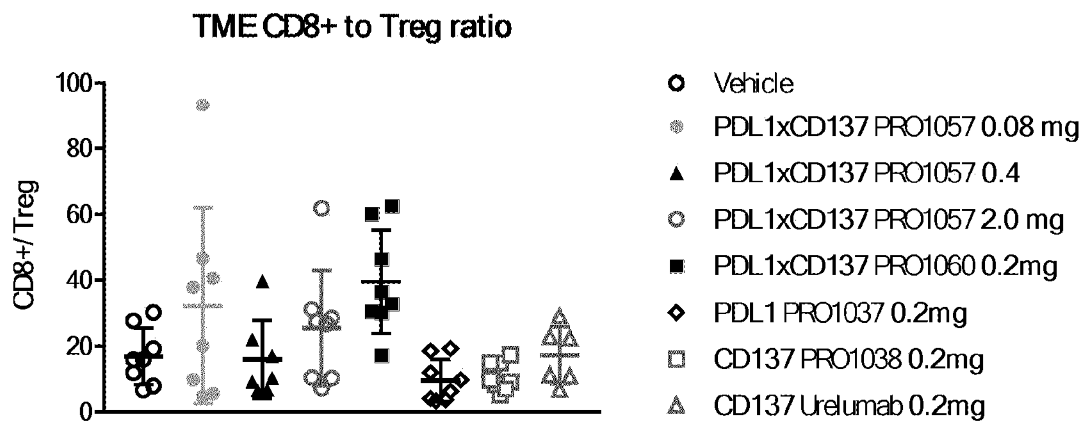

○ Irrelevant IgG (Palivizumab)
● PD-L1xCD137 PRO1186 (combined groups)
■ PDL1 PRO1196 + CD137 PRO1138
■ PDL1 (combined groups Avelumab & PRO1196)
▲ CD137 Urelumab

Figure 34:

| PRO ID | Clone ID PD-L1 | Clone ID CD137 | Clone ID SA | Format | Affinity to human PD-L1 | | | Affinity to cynomolgus PD-L1 | | |
|---|---|---|---|---|---|---|---|---|---|---|
| | | | | | $k_a$ ($M^{-1}s^{-1}$) | $k_d$ ($s^{-1}$) | KD (M) | $k_a$ ($M^{-1}s^{-1}$) | $k_d$ ($s^{-1}$) | KD (M) |
| PRO885 | 33-03-G02 CDR | 38-02-A04 CDR | NA | scDb | 2.1E+06 | 1.4E-04 | 6.5E-11 | ND | ND | ND |
| PRO951 | 33-03-G02 CDR | 38-27-C05 CDR | NA | scDb | 2.2E+06 | 1.5E-04 | 7.0E-11 | ND | ND | ND |
| PRO1123 | 33-03-G02 CDR | 38-02-A04 IF | NA | scDb | 2.3E+06 | 1.7E-04 | 7.5E-11 | ND | ND | ND |
| PRO1124 | 33-03-G02 CDR | 38-02-A04 STR | NA | scDb | 3.1E+06 | 2.0E-04 | 6.7E-11 | ND | ND | ND |
| PRO1125 | 33-03-G02 IF | 38-02-A04 CDR | NA | scDb | 1.7E+06 | 1.1E-04 | 6.7E-11 | ND | ND | ND |
| PRO1126 | 33-03-G02 STR | 38-02-A04 CDR | NA | scDb | 2.8E+06 | <1.0E-05 | 3.5E-12 | ND | ND | ND |
| PRO1134 | 33-03-G02 STR2, VH3 | 38-02-A04 CDR | NA | scDb | 2.8E+06 | 7.6E-05 | 2.8E-11 | ND | ND | ND |
| PRO963 | 33-03-G02 CDR | 38-02-A04 CDR | 19-01-H04 STR | scDb-scFv | 2.0E+06 | 1.3E-04 | 6.6E-11 | ND | ND | ND |
| PRO966 | 33-03-G02 CDR | 38-27-C05 CDR | 19-01-H04 STR | scDb-scFv | 1.6E+06 | 1.4E-04 | 8.3E-11 | ND | ND | ND |
| PRO1057 | 33-03-G02 CDR | 38-02-A04 CDR | 23-13-A01 STR | scDb-scFv | 1.6E+06 | 1.7E-04 | 1.1E-10 | ND | ND | ND |
| PRO1058 | 33-03-G02 CDR | 38-27-C05 CDR | 23-13-A01 STR | scDb-scFv | 1.2E+06 | 1.9E-04 | 1.6E-10 | ND | ND | ND |
| PRO1059 | 33-03-G02 CDR | 38-02-A04 CDR | NA | Morrison-L | 1.2E+06 | 6.5E-05 | 5.6E-11 | ND | ND | ND |
| PRO1060 | 33-03-G02 CDR | 38-02-A04 CDR | NA | Morrison-H | 1.3E+06 | 4.6E-05 | 3.6E-11 | ND | ND | ND |
| PRO1061 | 33-03-G02 CDR | 38-27-C05 CDR | NA | Morrison-L | ND | ND | ND | ND | ND | ND |
| PRO1062 | 33-03-G02 CDR | 38-27-C05 CDR | NA | Morrison-H | 1.3E+06 | 5.0E-05 | 3.8E-11 | ND | ND | ND |
| PRO997 | 37-20-B03 CDR | NA | NA | scFv | 5.9E+06 | <1.0E-05 | 1.7E-12 | 6.0E+06 | <1.0E-05 | <1.67E-12 |
| PRO1013 | 37-20-B03 CDR, VH1 | NA | NA | scFv | 6.0E+06 | 2.7E-04 | 4.5E-11 | 5.9E+06 | 3.2E-04 | 5.3E-11 |
| PRO830 | 33-03-G02 CDR | NA | NA | scFv | 2.1E+06 | 1.6E-04 | 7.6E-11 | 2.2E+06 | 2.0E-04 | 9.4E-11 |
| PRO1186 | 37-20-B03 sc01 | 38-02-A04 sc01 | 23-13-A01 sc03 | scDb-scFv | 6.2E+06 | 2.3E-05 | 3.7E-12 | TBD | TBD | TBD |
| PRO1430 | 37-20-B03 sc01 | 38-02-A04 sc013 | 19-01-H04 sc03 | scDb-scFv | 5.3E+06 | 2.4E-05 | 4.5E-12 | TBD | TBD | TBD |
| PRO1479 | 37-20-B03 sc09.1 | 38-02-A04 sc013 | 19-01-H04 sc03 | scDb-scFv | 4.2E+06 | 3.9E-05 | 9.2E-12 | TBD | TBD | TBD |
| PRO1482 | 37-20-B03 sc09.1 | 38-02-A04 sc013 | 19-01-H04 sc03 | scDb-scFv | 3.4E+06 | 3.3E-05 | 9.8E-12 | TBD | TBD | TBD |
| PRO1431 | 33-03-G02 sc18 | 38-02-A04 sc013 | 19-01-H04 sc03 | scDb-scFv | 3.3E+06 | 4.5E-05 | 1.4E-11 | ND | ND | ND |
| PRO1473 | 33-03-G02 sc03 | 38-02-A04 sc013 | 19-01-H04 sc03 | scDb-scFv | 3.6E+06 | 2.9E-05 | 8.2E-12 | ND | ND | ND |
| PRO1476 | 33-03-G02 sc03 | 38-02-A04 sc013 | 19-01-H04 sc03 | scDb-scFv | 3.4E+06 | 3.1E-05 | 9.0E-12 | ND | ND | ND |
| PRO1432 | 33-03-G02 sc18 | 38-02-A04 sc013 | 19-01-H04 sc03 | scDb-scFv | 4.2E+06 | 4.4E-05 | 1.1E-11 | ND | ND | ND |
| PRO1480 | 37-20-B03 sc09.1 | 38-27-A11 sc02 | 19-01-H04-sc03 | scDb-scFv | 3.5E+06 | 5.1E-05 | 1.5E-11 | 4.0E+06 | 3.4E-05 | 8.5E-12 |
| PRO1481 | 37-20-B03 sc09.1 | 38-27-A11 sc03 | 19-01-H04-sc03 | scDb-scFv | 4.7E+06 | 4.3E-05 | 9.2E-12 | ND | ND | ND |

NA: not applicable
TBD: to be determined
NB: no significant binding
ND: not determined

Figure 34 (continued):

| PRO ID | Affinity to human CD137 | | | Affinity to cynomolgus CD137 | | | Affinity to mouse CD137 | | | Affinity to human SA | | | Affinity to mouse SA | | |
|---|---|---|---|---|---|---|---|---|---|---|---|---|---|---|---|
| | $k_a (M^{-1}s^{-1})$ | $k_d (s^{-1})$ | KD (M) | $k_a (M^{-1}s^{-1})$ | $k_d (s^{-1})$ | KD (M) | $k_a (M^{-1}s^{-1})$ | $k_d (s^{-1})$ | KD (M) | $k_a (M^{-1}s^{-1})$ | $k_d (s^{-1})$ | KD (M) | $k_a (M^{-1}s^{-1})$ | $k_d (s^{-1})$ | KD (M) |
| PRO885 | 2.4E+05 | 7.6E-04 | 3.2E-09 | 3.4E+05 | 7.0E-04 | 2.1E-09 | 2.9E+05 | 1.8E-01 | 6.0E-07 | NA | NA | NA | NA | NA | NA |
| PRO951 | 1.5E+06 | 6.3E-03 | 4.2E-09 | 1.5E+06 | 1.0E-02 | 6.9E-09 | NB | NB | NB | NA | NA | NA | NA | NA | NA |
| PRO1123 | 3.1E+05 | 2.7E-04 | 8.8E-10 | 2.6E+05 | 3.3E-04 | 1.3E-09 | 6.5E+04 | 2.7E-02 | 4.1E-07 | NA | NA | NA | NA | NA | NA |
| PRO1124 | 6.8E+05 | < 1.0E-05 | 1.5E-11 | 5.6E+05 | 3.3E-04 | 5.9E-10 | 2.0E+05 | 2.2E-03 | 1.1E-08 | NA | NA | NA | NA | NA | NA |
| PRO1125 | 2.0E+05 | 7.5E-04 | 3.7E-09 | ND | ND | ND | 5.4E+05 | 2.7E-01 | 5.1E-07 | NA | NA | NA | NA | NA | NA |
| PRO1126 | 2.1E+05 | 7.5E-04 | 3.5E-09 | ND | ND | ND | NB | NB | NB | NA | NA | NA | NA | NA | NA |
| PRO1134 | 2.5E+05 | 8.4E-04 | 3.4E-09 | ND | ND | ND | 4.5E+05 | 1.9E-01 | 4.2E-07 | NA | NA | NA | NA | NA | NA |
| PRO963 | 2.0E+05 | 6.2E-04 | 3.0E-09 | ND | ND | ND | NB | NB | NB | 1.1E+05 | 3.0E-04 | 2.8E-09 | NB | NB | NB |
| PRO966 | 1.0E+06 | 2.2E-03 | 2.2E-09 | ND | ND | ND | 5.1E+03 | 1.0E-03 | 2.0E-07 | ND | ND | ND | NA | NA | NA |
| PRO1057 | 1.4E+05 | 7.0E-04 | 5.1E-09 | 1.6E+05 | 7.9E-04 | 4.8E-09 | 6.9E+04 | 8.5E-02 | 1.2E-06 | 2.4E+05 | 6.7E-04 | 2.8E-09 | 1.3E+05 | 8.5E-03 | 6.6E-08 |
| PRO1058 | 1.7E+06 | 2.1E-03 | 1.2E-09 | ND | ND | ND | 1.1E+06 | 7.5E-04 | 7.0E-10 | ND | ND | ND | ND | ND | ND |
| | | | | | | | | | | NA | NA | NA | NA | NA | NA |
| PRO1059 | 1.8E+05 | 4.2E-04 | 2.3E-09 | ND | ND | ND | ND | ND | ND | NA | NA | NA | NA | NA | NA |
| PRO1060 | 3.0E+05 | 3.9E-04 | 1.3E-09 | ND | ND | ND | ND | ND | ND | NA | NA | NA | NA | NA | NA |
| PRO1061 | ND | ND | ND | ND | ND | ND | ND | ND | ND | NA | NA | NA | NA | NA | NA |
| PRO1062 | 2.8E+05 | 3.7E-04 | 1.3E-09 | ND | ND | ND | ND | ND | ND | NA | NA | NA | NA | NA | NA |
| PRO897 | NA | NA | NA | NA | NA | NA | NA | NA | NA | NA | NA | NA | NA | NA | NA |
| PRO1013 | NA | NA | NA | NA | NA | NA | NA | NA | NA | NA | NA | NA | NA | NA | NA |
| PRO830 | NA | NA | NA | NA | NA | NA | NA | NA | NA | NA | NA | NA | NA | NA | NA |
| PRO1186 | 1.9E+05 | 5.0E-04 | 2.6E-09 | TBD | TBD | TBD | ND | ND | ND | 2.5E+05 | 7.2E-04 | 2.9E-09 | 2.2E+05 | 9.5E-03 | 4.3E-08 |
| PRO1430 | 4.6E+05 | 7.1E-04 | 1.5E-09 | TBD | TBD | TBD | ND | ND | ND | 2.9E+05 | 3.0E-04 | 1.0E-09 | NA | NA | NA |
| PRO1479 | 3.3E+05 | 5.4E-04 | 1.7E-09 | TBD | TBD | TBD | ND | ND | ND | 3.39E+05 | 3.31E-04 | 9.76E-10 | NA | NA | NA |
| PRO1482 | 3.2E+05 | 3.6E-04 | 1.1E-09 | TBD | TBD | TBD | ND | ND | ND | TBD | TBD | TBD | NA | NA | NA |
| PRO1431 | 4.5E+05 | 7.5E-04 | 1.7E-09 | TBD | TBD | TBD | ND | ND | ND | ND | ND | ND | NA | NA | NA |
| PRO1473 | 3.1E+05 | 6.0E-04 | 2.0E-09 | TBD | TBD | TBD | ND | ND | ND | ND | ND | ND | NA | NA | NA |
| PRO1476 | 3.5E+05 | 3.7E-04 | 1.1E-09 | TBD | TBD | TBD | ND | ND | ND | ND | ND | ND | NA | NA | NA |
| PRO1432 | 6.0E+05 | 4.5E-04 | 7.5E-10 | TBD | TBD | TBD | ND | ND | ND | ND | ND | ND | NA | NA | NA |
| PRO1480 | 5.8E+05 | 2.2E-04 | 3.7E-10 | 6.4E+05 | 3.0E-04 | 4.7E-10 | ND | ND | ND | 3.27E+05 | 3.37E-04 | 1.03E-09 | ND | ND | ND |
| PRO1481 | 6.3E+05 | 2.0E-04 | 3.3E-10 | ND | ND | ND | ND | ND | ND | ND | ND | ND | ND | ND | ND |

NA: not applicable
TBD: to be determin
NB: no significant bi
ND: not determined

Figure 35:

| PRO ID | Clone ID PD-L1 | Clone ID CD137 | Clone ID SA | Format | Neutralization of PD-L1 in NF-AT Potency assay | | |
|---|---|---|---|---|---|---|---|
| | | | | | $IC_{50}$ (ng/ml) | rel. $IC_{50}^{*}$ | HSA |
| PRO885 | 33-03-G02 CDR | 38-02-A04 CDR | NA | scDb | 137.20 | 0.28 | no |
| PRO951 | 33-03-G02 CDR | 38-27-C05 CDR | NA | scDb | 88.50 | 0.47 | no |
| PRO963 | 33-03-G02 CDR | 38-02-A04 CDR | 19-01-H04 STR | scDb-scFv | 274.80 | 0.25 | yes |
| PRO1057 | 33-03-G02 CDR | 38-02-A04 CDR | 23-13-A01 STR | scDb-scFv | 665.10 | 0.10 | yes |
| PRO1059 | 33-03-G02 CDR | 38-02-A04 CDR | NA | Morrison-L | 93.76 | 0.52 | no |
| PRO1060 | 33-03-G02 CDR | 38-02-A04 CDR | NA | Morrison-H | 132.70 | 0.44 | no |
| PRO1062 | 33-03-G02 CDR | 38-27-C05 CDR | NA | Morrison-H | 96.55 | 0.68 | no |
| PRO997 | 37-20-B03 CDR | NA | NA | scFv | 11.12 | 3.07 | no |
| PRO1013 | 37-20-B03 CDR, VH1 | NA | NA | scFv | 21.29 | 1.60 | no |
| PRO830 | 33-03-G02 CDR | NA | NA | scFv | 42.88 | 0.73 | no |
| PRO1186 | 37-20-B03 sc01 | 38-02-A04 sc01 | 23-13-A01 sc03 | scDb-scFv | 10.17 | 2.31 | yes |
| PRO1430 | 37-20-B03 sc01 | 38-02-A04 sc013 | 19-01-H04 sc03 | scDb-scFv | 16.19 | 1.45 | yes |
| PRO1479 | 37-20-B03 sc09.1 | 38-02-A04 sc013 | 19-01-H04 sc03 | scDb-scFv | 50.36 | 1.04 | yes |
| PRO1482 | 37-20-B03 sc09.1 | 38-02-A04 sc013 | 19-01-H04 sc03 | scDb-scFv | 54.79 | 0.68 | yes |
| PRO1431 | 33-03-G02 sc18 | 38-02-A04 sc013 | 19-01-H04 sc03 | scDb-scFv | 9.83 | 3.73 | yes |
| PRO1473 | 33-03-G02 sc03 | 38-02-A04 sc013 | 19-01-H04 sc03 | scDb-scFv | 35.17 | 1.11 | yes |
| PRO1476 | 33-03-G02 sc03 | 38-02-A04 sc013 | 19-01-H04 sc03 | scDb-scFv | 53.53 | 0.66 | yes |
| PRO1432 | 33-03-G02 sc18 | 38-02-A04 sc013 | 19-01-H04 sc03 | scDb-scFv | 18.51 | 1.98 | yes |
| PRO1480 | 37-20-B03 sc09.1 | 38-27-A11 sc02 | 19-01-H04-sc03 | scDb-scFv | 84.84 | 0.61 | yes |
| PRO1481 | 37-20-B03 sc09.1 | 38-27-A11 sc03 | 19-01-H04-sc03 | scDb-scFv | 40.58 | 0.92 | yes |

NA: not applicable

*: $IC_{50,\ Avelumab}$ (ng/ml)/$IC_{50,\ test\ molecule}$ (ng/ml)

Figure 36:

| PRO ID | Clone ID PD-L1 | Clone ID CD137 | Clone ID SA | Format | Blocking of PD-L1/ PD-1 interaction | | Blocking of PD-L1/ B7.1 interaction | |
|---|---|---|---|---|---|---|---|---|
| | | | | | $IC_{50}$ (ng/ml) | rel. $IC_{50}$* | $IC_{50}$ (ng/ml) | rel. $IC_{50}$* |
| PRO885 | 33-03-G02 CDR | 38-02-A04 CDR | NA | scDb | 8.35 | 0.17 | 12.2 | 0.59 |
| PRO951 | 33-03-G02 CDR | 38-27-C05 CDR | NA | scDb | 9.50 | 0.15 | 9.30 | 0.78 |
| PRO1126 | 33-03-G02 STR | 38-02-A04 CDR | NA | scDb | 1.28 | 1.59 | TBD | TBD |
| PRO1057 | 33-03-G02 CDR | 38-02-A04 CDR | 23-13-A01 STR | scDb-scFv | 8.61 | 0.20 | 16.29 | 0.53 |
| PRO1059 | 33-03-G02 CDR | 38-02-A04 CDR | NA | Morrison-L | 4.54 | 0.37 | 28.98 | 0.30 |
| PRO1060 | 33-03-G02 CDR | 38-02-A04 CDR | NA | Morrison-H | 5.67 | 0.30 | 17.42 | 0.49 |
| PRO1062 | 33-03-G02 CDR | 38-27-C05 CDR | NA | Morrison-H | 11.33 | 0.32 | 19.53 | 0.51 |
| PRO997 | 37-20-B03 CDR | NA | NA | scFv | 0.50 | 4.16 | 6.359 | 2.34 |
| PRO1013 | 37-20-B03 CDR, VH1 | NA | NA | scFv | 0.57 | 3.67 | 4.05 | 3.68 |
| PRO830 | 33-03-G02 CDR | NA | NA | scFv | 3.40 | 0.61 | 12.87 | 1.16 |
| PRO1186 | 37-20-B03 sc01 | 38-02-A04 sc01 | 23-13-A01 sc03 | scDb-scFv | 1.74 | 1.26 | 7.81 | 1.58 |
| PRO1430 | 37-20-B03 sc01 | 38-02-A04 sc013 | 19-01-H04 sc03 | scDb-scFv | 1.92 | 0.73 | 2.42 | 1.15 |
| PRO1479 | 37-20-B03 sc09.1 | 38-02-A04 sc013 | 19-01-H04 sc03 | scDb-scFv | 2.65 | 0.86 | 10.71 | 1.38 |
| PRO1482 | 37-20-B03 sc09.1 | 38-02-A04 sc013 | 19-01-H04 sc03 | scDb-scFv | 1.78 | 1.24 | 8.18 | 1.51 |
| PRO1431 | 33-03-G02 sc18 | 38-02-A04 sc013 | 19-01-H04 sc03 | scDb-scFv | 2.75 | 0.51 | 3.31 | 0.84 |
| PRO1473 | 33-03-G02 sc03 | 38-02-A04 sc013 | 19-01-H04 sc03 | scDb-scFv | 4.14 | 0.56 | 8.89 | 1.49 |
| PRO1476 | 33-03-G02 sc03 | 38-02-A04 sc013 | 19-01-H04 sc03 | scDb-scFv | 2.84 | 0.80 | 9.49 | 1.10 |
| PRO1432 | 33-03-G02 sc18 | 38-02-A04 sc013 | 19-01-H04 sc03 | scDb-scFv | 3.26 | 0.43 | 2.83 | 0.99 |
| PRO1480 | 37-20-B03 sc09.1 | 38-27-A11 sc02 | 19-01-H04-sc03 | scDb-scFv | 2.27 | 1 | 11.19 | 1.32 |
| PRO1481 | 37-20-B03 sc09.1 | 38-27-A11 sc03 | 19-01-H04-sc03 | scDb-scFv | 2.69 | 0.84 | 10.15 | 1.45 |

NA: not applicable

*: $IC_{50,\ Avelumab}$ (ng/ml)/$IC_{50,\ test\ molecule}$ (ng/ml)

Figure 37:

| | | Affinity to human CD137: SPR data | | | | Affinity to mouse CD137: SPR data | | | | Affinity to human PD-L1: SPR data | | | |
|---|---|---|---|---|---|---|---|---|---|---|---|---|---|
| PRO Number | Protein description | $k_a$ [$M^{-1} s^{-1}$] | $k_d$ [$s^{-1}$] | $K_D$ [M] | Binding level normalized to theoretical Rmax (%) | $k_a$ [$M^{-1} s^{-1}$] | $k_d$ [$s^{-1}$] | $K_D$ [M] | Binding level normalized to theoretical Rmax (%) | $k_a$ [$M^{-1} s^{-1}$] | $k_d$ [$s^{-1}$] | $K_D$ [M] | Binding level normalized to theoretical Rmax (%) |
| PRO1118 | 38-02-A04 sc01 scDb-i/33_02_G02 sc01 scDb-o | 2.75E+05 | 7.23E-04 | 2.63E-09 | 79.8 | 8.29E+04 | 2.27E-04 | 2.73E-09 | 11.5 | 1.34E+06 | < 1.00E-05 | < 7.46E-12 | 79.2 |
| PRO1119 | 38-02-A04 sc05 IF scDb-i/33_02_G02 sc01 scDb-o | 3.81E+05 | 2.76E-04 | 7.24E-10 | 79.1 | 1.40E+05 | 2.48E-02 | 1.77E-07 | 81.0 | 1.50E+06 | < 1.00E-05 | < 6.67E-12 | 77.5 |
| PRO1120 | 38-02-A04 sc06 Full scDb-i/33_02_G02 sc01 scDb-o | 5.78E+05 | < 1.00E-05 | < 1.73E-11 | 74.7 | 2.12E+05 | 3.25E-03 | 1.54E-08 | 87.5 | 1.27E+06 | < 1.00E-05 | < 7.87E-12 | 76.8 |

Figure 38 (A):

| | | | | | Activation of NF-kB reporter gene CHO-PD-L1 | | | | Activation of NF-kB reporter gene HCC827 -IFNg | | | Activation of NF-kB reporter gene HCC827 +IFNg | | | |
|---|---|---|---|---|---|---|---|---|---|---|---|---|---|---|---|
| PRO ID | Clone ID PD-L1 | Clone ID CD137 | Clone ID SA | Format | $IC_{50}$ (ng/ml) | rel. $IC_{50}$[b] | max. activation (%) | HSA | $IC_{50}$ (ng/ml) | rel. $IC_{50}$[b] | max. activation (%) | $IC_{50}$ (ng/ml) | rel. $IC_{50}$[b] | max. activation (%) | HSA |
| PRO885 | 33-03-G02 CDR | 38-02-A04 CDR | NA | scDb | 11.72 | 6.75 | 499.42 | no | 13.06 | 8.42 | 111.10 | 8.88 | 16.30 | 134.20 | no |
| PRO951 | 33-03-G02 CDR | 38-27-C05 CDR | NA | scDb | 33.68 | 2.35 | 431.70 | no | ND | ND | ND | ND | ND | ND | ND |
| PRO1123 | 33-03-G02 CDR | 38-02-A04 IF | NA | scDb | 5.75 | 18.31 | 219.20 | no | 16.12 | 6.82 | 123.20 | 11.87 | 12.20 | 154.40 | no |
| PRO1124 | 33-03-G02 CDR | 38-02-A04 STR | NA | scDb | 3.68 | 23.50 | 228.60 | no | 5.62 | 19.89 | 113.20 | 4.83 | 22.39 | 188.50 | no |
| PRO1126 | 33-03-G02 STR | 38-02-A04 CDR | NA | scDb | 6.00 | 14.43 | 242.10 | no | 6.97 | 16.04 | 135.10 | 5.48 | 19.74 | 207.70 | no |
| PRO963 | 33-03-G02 CDR | 38-02-A04 CDR | 19-01-H04 STR | scDb-scFv | ND | ND | 368.67 | yes, 24h | ND | ND | ND | ND | ND | ND | ND |
| PRO1057 | 33-03-G02 CDR | 38-02-A04 CDR | 23-13-A01 STR | scDb-scFv | 792.40 | 0.10 | 662.79 | yes, 24h | 76.61 | 0.62 | 68.99 | 135.00 | 0.46 | 135.34 | yes, 24h |
| PRO1058 | 33-03-G02 CDR | 38-27-C05 CDR | 23-13-A01 STR | scDb-scFv | 121.40 | 0.64 | 36.23 | yes, 24h | ND | ND | ND | ND | ND | ND | ND |
| PRO1059 | 33-03-G02 CDR | 38-02-A04 CDR | NA | Morrison-L | 289.10 | 0.09 | 189.09 | no, 24h | ND | ND | ND | ND | ND | ND | ND |
| PRO1060 | 33-03-G02 CDR | 38-02-A04 CDR | NA | Morrison-H | 80.85 | 0.58 | 144.13 | no, 24h | 13.57 | 3.50 | 54.94 | 17.51 | 3.01 | 97.04 | no, 24h |
| PRO1061 | 33-03-G02 CDR | 38-27-C05 CDR | NA | Morrison-L | ND | ND | ND | ND | ND | ND | ND | ND | ND | ND | ND |
| PRO1062 | 33-03-G02 CDR | 38-27-C05 CDR | NA | Morrison-H | 86.87 | 0.54 | 133.52 | no, 24h | ND | ND | ND | ND | ND | ND | ND |
| PRO1186 | 37-20-B03 sc01 | 38-02-A04 sc01 | 23-13-A01 sc03 | scDb-scFv | 50.96 | 0.97 | 152.06 | yes, 24h | ND | ND | ND | 16.68 | 1.88 | 128.88 | yes, 24h |

NA: not applicable

ND: not determined

[b]: $IC_{50,\ urelumab}$ (ng/ml)/$IC_{50,\ test\ molecule}$ (ng/ml)

Figure 38 (B):

| PRO ID | Clone ID PD-L1 | Clone ID CD137 | Clone ID SA | Format | Activation of NF-kB reporter gene HCC827 +IFNg | | | | |
|---|---|---|---|---|---|---|---|---|---|
| | | | | | Timepoint (h) | $IC_{50}$ (ng/ml) | rel. $IC_{50}$ [&] | max. activation (%) | HSA |
| PRO1430 | 37-20-B03 sc01 | 38-02-A04 sc013 | 19-01-H04 sc03 | scDb-scFv | 6 | 9.80 | 1.31 | 110.1 | yes |
| | | | | | 24 | 4.42 | 1.51 | 98.6 | yes |
| PRO1479 | 37-20-B03 sc09.1 | 38-02-A04 sc013 | 19-01-H04 sc03 | scDb-scFv | 6 | 7.38 | 1.74 | 108.2 | yes |
| | | | | | 24 | 7.61 | 0.87 | 118.6 | yes |
| PRO1482 | 37-20-B03 sc09.1 | 38-02-A04 sc013 | 19-01-H04 sc03 | scDb-scFv | 6 | 20.05 | 0.55 | 108.6 | yes |
| | | | | | 24 | 7.24 | 1.23 | 92.7 | yes |
| PRO1431 | 33-03-G02 sc18 | 38-02-A04 sc013 | 19-01-H04 sc03 | scDb-scFv | 6 | 21.02 | 0.68 | 55.3 | yes |
| | | | | | 24 | 18.39 | 1.02 | 68.6 | yes |
| PRO1473 | 33-03-G02 sc03 | 38-02-A04 sc013 | 19-01-H04 sc03 | scDb-scFv | 6 | 2.40 | 2.30 | 36.2 | yes |
| | | | | | 24 | 0.91 | 3.55 | 67.4 | yes |
| PRO1476 | 33-03-G02 sc03 | 38-02-A04 sc013 | 19-01-H04 sc03 | scDb-scFv | 6 | 5.97 | 2.02 | 36.4 | yes |
| | | | | | 24 | 3.90 | 1.83 | 76.1 | yes |
| PRO1432 | 33-03-G02 sc18 | 38-02-A04 sc013 | 19-01-H04 sc03 | scDb-scFv | 6 | 19.36 | 0.67 | 63.4 | yes |
| | | | | | 24 | 21.89 | 0.75 | 83.8 | yes |
| PRO1480 | 37-20-B03 sc09.1 | 38-27-A11 sc02 | 19-01-H04 sc03 | scDb-scFv | 6 | 6.44 | 1.93 | 114.3 | yes |
| | | | | | 24 | 4.67 | 1.00 | 120.9 | yes |
| PRO1481 | 37-20-B03 sc09.1 | 38-27-A11 sc03 | 19-01-H04 sc03 | scDb-scFv | 6 | 7.22 | 1.04 | 147.3 | yes |
| | | | | | 24 | 5.51 | 0.58 | 116.8 | yes |

NA: not applicable

ND: not determined

[&]: $IC_{50,\ PRO1186}$ (ng/ml)/$IC_{50,\ test\ molecule}$ (ng/ml)

Figure 39:

| | Plate 1 | | Plate 2 | | Plate 3 | |
|---|---|---|---|---|---|---|
| | Avelumab + Urelumab | Avelumab | Urelumab | PRO885 | Avelumab + Urelumab | PRO1175 |
| Bottom | 5974 | -747.6 | 5005 | 4453 | 3912 | 5300 |
| Top | 53127 | N.A. | 21739 | 77855 | 53626 | 87743 |
| EC50 | 174.1 | N.A. | 278.3 | 55.21 | 318.6 | 31.11 |
| R square | 0.9594 | 0.9315 | 0.8602 | 0.9875 | 0.976 | 0.9832 |

Figure 40:

| | Monomeric content by SE-HPLC [%] time [day] | | | | | | | | | | | | | | |
|---|---|---|---|---|---|---|---|---|---|---|---|---|---|---|---|
| 4°C | 0 | 1 | 3 | 7 | 14 | 21 | 28 | 35 | 42 | 49 | 56 | 63 | 70 | 77 | 84 |
| PRO1430 | 98.96 | 98.8 | 98.6 | 98.56 | 98.4 | 98.47 | 98.35 | 98.17 | 98.11 | 98.11 | 98.25 | 97.942 | 0 | 98.28 | 0 |
| PRO1431 | 98.88 | 97.94 | 98.13 | 97.95 | 98.23 | 98.29 | 98.25 | 98.59 | 97.69 | 98.08 | 97.87 | 98.08 | 97.73 | 0 | 0 |
| PRO1432 | 98.62 | 97.87 | 97.96 | 97.7 | 97.82 | 97.86 | 97.9 | 96.95 | 97.37 | 97.66 | 97.58 | 97.81 | 97.35 | 0 | 0 |
| PRO1473 | 99.55 | 99.51 | 99.47 | 99.17 | 99.2 | 99.14 | 98.9 | 98.99 | 99.22 | 99.18 | 99.09 | 98.86 | 98.28 | 0 | 98.82 |
| PRO1476 | 99.33 | 99.28 | 99.31 | 99.07 | 98.99 | 98.99 | 98.82 | 98.98 | 98.98 | 98.74 | 98.9 | 98.71 | 0 | 0 | 97.78 |
| PRO1479 | 99.28 | 99.25 | 99.2 | 98.83 | 98.77 | 98.87 | 98.82 | 98.84 | 98.8 | 98.77 | 98.84 | 98.65 | 98.07 | 98.511 | 97.75 |
| PRO1480 | 99.56 | 99.12 | 99.09 | 99.13 | 98.86 | 98.69 | 98.63 | 98.74 | 98.75 | 98.57 | 98.21 | 98.28 | 98.232 | 97.75 | 97.93 |
| PRO1481 | 99.42 | 98.86 | 98.83 | 98.82 | 98.47 | 98.23 | 98.47 | 98.43 | 98.55 | 98.26 | 97.87 | 97.92 | 97.906 | 97.61 | 97.57 |
| PRO1482 | 98.76 | 98.7 | 98.55 | 98.19 | 98.14 | 98.23 | 98.02 | 98.16 | 98.01 | 98.02 | 97.86 | 97.88 | 0 | 97.799 | 97 |

| | Monomeric content by SE-HPLC [%] time [day] | | | | | | | | | | | | | | |
|---|---|---|---|---|---|---|---|---|---|---|---|---|---|---|---|
| 20°C | 0 | 1 | 3 | 7 | 14 | 21 | 28 | 35 | 42 | 49 | 56 | 63 | 70 | 77 | 84 |
| PRO1430 | 98.96 | 98.74 | 98.53 | 98.48 | 97.53 | 98.01 | 97.35 | 97.53 | 97.18 | 97.04 | 96.992 | 96.197 | 0 | 96.64 | 0 |
| PRO1431 | 98.88 | 97.96 | 98.03 | 98.07 | 97.59 | 97.25 | 97.21 | 96.26 | 96.01 | 96.24 | 95.61 | 95.77 | 95.49 | 95.66 | 0 |
| PRO1432 | 98.62 | 97.81 | 97.76 | 97.46 | 97.28 | 96.98 | 96.86 | 96.18 | 95.98 | 96.09 | 95.74 | 95.79 | 95.42 | 95.35 | 0 |
| PRO1473 | 99.55 | 99.48 | 99.38 | 98.99 | 98.88 | 98.75 | 97.84 | 97.56 | 97.58 | 97.41 | 96.96 | 96.6 | 0 | 0 | 95.66 |
| PRO1476 | 99.33 | 99.23 | 98.99 | 98.73 | 98.56 | 98.52 | 98.19 | 97.72 | 97.66 | 97.59 | 97.3 | 96.93 | 0 | 0 | 95.7 |
| PRO1479 | 99.28 | 99.21 | 99.12 | 98.63 | 98.33 | 98.26 | 97.95 | 97.59 | 97.1 | 97.3 | 97.03 | 96.56 | 0 | 96.162 | 95.67 |
| PRO1480 | 99.56 | 99.03 | 98.9 | 98.59 | 97.88 | 97.15 | 96.84 | 95.93 | 96.26 | 95.7 | 95.17 | 95.27 | 94.179 | 93.86 | 94.15 |
| PRO1481 | 99.42 | 98.71 | 98.6 | 98.16 | 97.23 | 96.57 | 96.42 | 96.47 | 95.67 | 95.07 | 94.47 | 94.37 | 93.562 | 93.05 | 93.4 |
| PRO1482 | 98.76 | 98.63 | 98.31 | 97.9 | 97.63 | 97.42 | 97.14 | 96.71 | 96.26 | 96.31 | 96.07 | 95.67 | 0 | 95.063 | 94.46 |

| | Monomeric content by SE-HPLC [%] time [day] | | | | | | | | | | | | | | |
|---|---|---|---|---|---|---|---|---|---|---|---|---|---|---|---|
| 40°C | 0 | 1 | 3 | 7 | 14 | 21 | 28 | 35 | 42 | 49 | 56 | 63 | 70 | 77 | 84 |
| PRO1430 | 98.96 | 98.11 | 96.72 | 94.32 | 93.19 | 93.23 | 92.47 | 92.33 | 91.77 | 91.43 | 89.837 | 89.533 | 0 | 88.3 | 0 |
| PRO1431 | 98.88 | 97.04 | 95.43 | 94.05 | 93.36 | 92.66 | 92.35 | 91.16 | 90.38 | 89.86 | 88.02 | 87.54 | 87.35 | 87.15 | 0 |
| PRO1432 | 98.62 | 96.79 | 95.24 | 93.81 | 93.28 | 92.6 | 92.41 | 91.15 | 90.81 | 90.63 | 89.27 | 88.82 | 87.98 | 0 | 0 |
| PRO1473 | 99.55 | 98.4 | 96.92 | 95.61 | 94.71 | 94.29 | 93.069 | 92.52 | 91.88 | 91.4 | 90.69 | 89.92 | 0 | 82.415 | 87.16 |
| PRO1476 | 99.33 | 98.26 | 96.99 | 95.49 | 94.4 | 93.94 | 93.29 | 92.93 | 92.36 | 91.99 | 91.45 | 90.9 | 0 | 89.808 | 88.78 |
| PRO1479 | 99.28 | 98.41 | 96.98 | 95.28 | 94.46 | 93.94 | 93.35 | 93.02 | 92.23 | 92.07 | 91.44 | 90.87 | 0 | 89.586 | 89.08 |
| PRO1480 | 99.56 | 97.46 | 96.12 | 94.48 | 93.49 | 92.87 | 92.34 | 91.46 | 91.06 | 89.89 | 89.12 | 88.49 | 87.102 | 86.12 | 85.71 |
| PRO1481 | 99.42 | 96.75 | 95.29 | 94.01 | 93 | 92.53 | 92.02 | 91.35 | 90.71 | 89.5 | 88.78 | 88.02 | 86.489 | 85.67 | 85.08 |
| PRO1482 | 98.76 | 97.45 | 96.02 | 94.41 | 93.41 | 93.03 | 92.61 | 92.29 | 91.56 | 91.59 | 91.06 | 90.56 | 0 | 89.586 | 88.85 |

| | Monomeric content by SE-HPLC [%] time [day] | | | |
|---|---|---|---|---|
| -20°C | 0 | 28 | 56 | 84 |
| PRO1430 | 98.96 | 98.42 | 98.385 | 0 |
| PRO1431 | 98.88 | 98.37 | 98.2 | 98.935 |
| PRO1432 | 98.62 | 98.2 | 97.95 | 98.579 |
| PRO1473 | 99.55 | 98.67 | 99.32 | 98.99 |
| PRO1476 | 99.33 | 98.96 | 99.16 | 98.97 |
| PRO1479 | 99.28 | 98.88 | 99.15 | 98.18 |
| PRO1480 | 99.56 | 99.18 | 99 | 99.38 |
| PRO1481 | 99.42 | 98.98 | 98.86 | 99.16 |
| PRO1482 | 98.76 | 98.15 | 98.34 | 97.44 |

SEQUENCE LISTING

<160> NUMBER OF SEQ ID NOS: 250

<210> SEQ ID NO 1
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 1

Gly Phe Ser Phe Ser Asn Ser Tyr Trp Ile Cys
1 5 10

<210> SEQ ID NO 2
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 2

Cys Thr Phe Val Gly Ser Ser Asp Ser Thr Tyr Tyr Ala Asn Trp Ala
1 5 10 15

Lys Gly

<210> SEQ ID NO 3
<211> LENGTH: 14
<212> TYPE: PRT

<213> ORGANISM: Artificial Sequence
<220> FEATURE:
<223> OTHER INFORMATION: sequence of recombinant antibody or functional
      part thereof

<400> SEQUENCE: 3

Arg His Pro Ser Asp Ala Val Tyr Gly Tyr Ala Asn Asn Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 4

Val Ser Gly Phe Ser Phe Ser Asn Ser Tyr Trp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 5

Ala Ser Gly Phe Ser Phe Ser Asn Ser Tyr Trp
1               5                   10

<210> SEQ ID NO 6
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 6

Thr Phe Val Gly Ser Ser Asp Ser Thr Tyr Tyr Ala Asn Trp Ala Lys
1               5                   10                  15

Gly Arg

<210> SEQ ID NO 7
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 7

His Pro Ser Asp Ala Val Tyr Gly Tyr Ala Asn Asn
1               5                   10

<210> SEQ ID NO 8
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 8

Asn Ser Tyr Trp Ile Cys
1               5

<210> SEQ ID NO 9
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 9

Cys Thr Phe Val Gly Ser Ser Asp Ser Thr Tyr Tyr Ala Asn Trp Ala
1               5                   10                  15

Lys Gly

<210> SEQ ID NO 10
<211> LENGTH: 13
<212> TYPE: PRT
<213> ORGANISM: Artificial Sequence
<220> FEATURE:
<223> OTHER INFORMATION: sequence of recombinant antibody or functional part thereof

<400> SEQUENCE: 10

His Pro Ser Asp Ala Val Tyr Gly Tyr Ala Asn Asn Leu
1               5                   10

<210> SEQ ID NO 11
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 11

Gly Phe Ser Phe Ser Asn Ser Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: sequence of recombinant antibody or functional part thereof

<400> SEQUENCE: 12

Val Gly Ser Ser Asp
1               5

<210> SEQ ID NO 13
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 13

Pro Ser Asp Ala Val Tyr Gly Tyr Ala Asn Asn
1               5                   10

<210> SEQ ID NO 14
<211> LENGTH: 124
<212> TYPE: PRT

```
<213> ORGANISM: Artificial Sequence
<220> FEATURE:
<223> OTHER INFORMATION: sequence of recombinant antibody or functional
      part thereof

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Ile Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120


<210> SEQ ID NO 15
<211> LENGTH: 124
<212> TYPE: PRT
<213> ORGANISM: Artificial Sequence
<220> FEATURE:
<223> OTHER INFORMATION: sequence of recombinant antibody or functional
      part thereof

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Val Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Val Ser Leu Lys Leu Ser Ser Val Thr Ala Ala Asp Thr Ala Val Tyr
                85                  90                  95

Phe Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120


<210> SEQ ID NO 16
<211> LENGTH: 124
<212> TYPE: PRT
<213> ORGANISM: Artificial Sequence
<220> FEATURE:
<223> OTHER INFORMATION: sequence of recombinant antibody or functional
      part thereof

<400> SEQUENCE: 16

Gln Val Gln Leu Gln Glu Ser Gly Pro Gly Leu Val Lys Pro Ser Glu
1               5                   10                  15
```

```
Thr Leu Ser Leu Thr Cys Lys Ala Ser Gly Phe Ser Phe Ser Asn Ser
            20                  25                  30

Tyr Trp Ile Cys Trp Val Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Lys Asp Ser Ser Lys Asn Gln
65                  70                  75                  80

Val Ser Leu Lys Leu Ser Ser Val Thr Ala Ala Asp Thr Ala Val Tyr
                85                  90                  95

Phe Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120
```

<210> SEQ ID NO 17
<211> LENGTH: 124
<212> TYPE: PRT
<213> ORGANISM: Artificial Sequence
<220> FEATURE:
<223> OTHER INFORMATION: sequence of recombinant antibody or functional part thereof

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Ser
            20                  25                  30

Tyr Trp Ile Cys Trp Val Arg Gln Ala Pro Gly Lys Cys Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120
```

<210> SEQ ID NO 18
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 18

```
Gln Ala Ser Gln Ser Ile Asn Asn Val Leu Ala
1               5                   10
```

<210> SEQ ID NO 19
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 19

Arg Ala Ser Thr Leu Ala Ser
1 5

<210> SEQ ID NO 20
<211> LENGTH: 9
<212> TYPE: PRT
<213> ORGANISM: Artificial Sequence
<220> FEATURE:
<223> OTHER INFORMATION: sequence of recombinant antibody or functional part thereof

<400> SEQUENCE: 20

Gln Ser Ser Tyr Gly Asn Tyr Gly Asp
1 5

<210> SEQ ID NO 21
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 21

Ala Ser Gln Ser Ile Asn Asn Val
1 5

<210> SEQ ID NO 22
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 22

Arg Ala Ser Thr Leu Ala Ser Gly Val Pro Ser Arg
1 5 10

<210> SEQ ID NO 23
<211> LENGTH: 6
<212> TYPE: PRT
<213> ORGANISM: Artificial Sequence
<220> FEATURE:
<223> OTHER INFORMATION: sequence of recombinant antibody or functional part thereof

<400> SEQUENCE: 23

Ser Tyr Gly Asn Tyr Gly
1 5

<210> SEQ ID NO 24
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 24

Ser Gln Ser Ile Asn Asn Val
1 5

<210> SEQ ID NO 25
<211> LENGTH: 3

```
<212> TYPE: PRT
<213> ORGANISM: Artificial Sequence
<220> FEATURE:
<223> OTHER INFORMATION: sequence of recombinant antibody or functional
      part thereof

<400> SEQUENCE: 25

Arg Ala Ser
1


<210> SEQ ID NO 26
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 26

Ser Tyr Gly Asn Tyr Gly
1               5


<210> SEQ ID NO 27
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105


<210> SEQ ID NO 28
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Pro Pro Lys Leu Leu Ile
        35                  40                  45

Tyr Arg Ala Ser Thr Leu Ala Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105


<210> SEQ ID NO 29
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 29

Asp Leu Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105


<210> SEQ ID NO 30
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly
            100                 105


<210> SEQ ID NO 31
<211> LENGTH: 252
<212> TYPE: PRT
<213> ORGANISM: Artificial Sequence
```

```
<220> FEATURE:
<223> OTHER INFORMATION: sequence of recombinant antibody or functional
      part thereof

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Lys Val Ser Gly Phe Ser Phe Ser Asn Ser
145                 150                 155                 160

Tyr Trp Ile Cys Trp Ile Arg Gln Pro Pro Gly Lys Gly Leu Glu Trp
                165                 170                 175

Ile Gly Cys Thr Phe Val Gly Ser Ser Asp Ser Thr Tyr Tyr Ala Asn
            180                 185                 190

Trp Ala Lys Gly Arg Val Thr Ile Ser Val Asp Ser Ser Lys Asn Gln
        195                 200                 205

Phe Ser Leu Lys Leu Ser Ser Val Thr Ala Ala Asp Thr Ala Val Tyr
    210                 215                 220

Tyr Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250


<210> SEQ ID NO 32
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Lys Val Ser Gly Phe Ser Phe Ser Asn Ser
145                 150                 155                 160

Tyr Trp Ile Cys Trp Val Arg Gln Pro Pro Gly Lys Gly Leu Glu Trp
                165                 170                 175

Ile Gly Cys Thr Phe Val Gly Ser Ser Asp Ser Thr Tyr Tyr Ala Asn
            180                 185                 190

Trp Ala Lys Gly Arg Val Thr Ile Ser Val Asp Ser Ser Lys Asn Gln
        195                 200                 205

Val Ser Leu Lys Leu Ser Ser Val Thr Ala Ala Asp Thr Ala Val Tyr
    210                 215                 220

Phe Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250


<210> SEQ ID NO 33
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 33

Asp Leu Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Lys Ala Ser Gly Phe Ser Phe Ser Asn Ser
145                 150                 155                 160

Tyr Trp Ile Cys Trp Val Arg Gln Pro Pro Gly Lys Gly Leu Glu Trp
                165                 170                 175

Ile Gly Cys Thr Phe Val Gly Ser Ser Asp Ser Thr Tyr Tyr Ala Asn
```

```
            180                 185                 190

Trp Ala Lys Gly Arg Val Thr Ile Ser Lys Asp Ser Ser Lys Asn Gln
        195                 200                 205

Val Ser Leu Lys Leu Ser Ser Val Thr Ala Ala Asp Thr Ala Val Tyr
    210                 215                 220

Phe Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250


<210> SEQ ID NO 34
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Ser Phe Ser Asn Ser
145                 150                 155                 160

Tyr Trp Ile Cys Trp Val Arg Gln Ala Pro Gly Lys Cys Leu Glu Trp
                165                 170                 175

Ile Gly Cys Thr Phe Val Gly Ser Ser Asp Ser Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250


<210> SEQ ID NO 35
<211> LENGTH: 11
<212> TYPE: PRT
<213> ORGANISM: Artificial Sequence
<220> FEATURE:
```

<223> OTHER INFORMATION: sequence of recombinant antibody or functional part thereof

<400> SEQUENCE: 35

Gly Phe Ser Phe Asn Asn Asp Tyr Asp Met Cys
1 5 10

<210> SEQ ID NO 36
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 36

Cys Ile Asp Thr Gly Asp Gly Ser Thr Tyr Tyr Ala Ser Trp Ala Lys
1 5 10 15

Gly

<210> SEQ ID NO 37
<211> LENGTH: 16
<212> TYPE: PRT
<213> ORGANISM: Artificial Sequence
<220> FEATURE:
<223> OTHER INFORMATION: sequence of recombinant antibody or functional part thereof

<400> SEQUENCE: 37

Arg Glu Ala Ala Ser Ser Ser Gly Tyr Gly Met Gly Tyr Phe Asp Leu
1 5 10 15

<210> SEQ ID NO 38
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 38

Val Ser Gly Phe Ser Phe Asn Asn Asp Tyr Asp
1 5 10

<210> SEQ ID NO 39
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 39

Ile Asp Thr Gly Asp Gly Ser Thr Tyr Tyr Ala Ser Trp Ala Lys Gly
1 5 10 15

Arg

<210> SEQ ID NO 40
<211> LENGTH: 14
<212> TYPE: PRT
<213> ORGANISM: Artificial Sequence
<220> FEATURE:
<223> OTHER INFORMATION: sequence of recombinant antibody or functional part thereof

<400> SEQUENCE: 40

Glu Ala Ala Ser Ser Ser Gly Tyr Gly Met Gly Tyr Phe Asp
1 5 10

<210> SEQ ID NO 41
<211> LENGTH: 6
<212> TYPE: PRT
<213> ORGANISM: Artificial Sequence
<220> FEATURE:
<223> OTHER INFORMATION: sequence of recombinant antibody or functional part thereof

<400> SEQUENCE: 41

Asn Asp Tyr Asp Met Cys
1 5

<210> SEQ ID NO 42
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 42

Cys Ile Asp Thr Gly Asp Gly Ser Thr Tyr Tyr Ala Ser Trp Ala Lys
1 5 10 15

Gly

<210> SEQ ID NO 43
<211> LENGTH: 15
<212> TYPE: PRT
<213> ORGANISM: Artificial Sequence
<220> FEATURE:
<223> OTHER INFORMATION: sequence of recombinant antibody or functional part thereof

<400> SEQUENCE: 43

Glu Ala Ala Ser Ser Ser Gly Tyr Gly Met Gly Tyr Phe Asp Leu
1 5 10 15

<210> SEQ ID NO 44
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 44

Gly Phe Ser Phe Asn Asn Asp Tyr
1 5

<210> SEQ ID NO 45
<211> LENGTH: 4
<212> TYPE: PRT
<213> ORGANISM: Artificial Sequence
<220> FEATURE:
<223> OTHER INFORMATION: sequence of recombinant antibody or functional part thereof

<400> SEQUENCE: 45

Thr Gly Asp Gly
1

<210> SEQ ID NO 46
<211> LENGTH: 13
<212> TYPE: PRT

<213> ORGANISM: Artificial Sequence
<220> FEATURE:
<223> OTHER INFORMATION: sequence of recombinant antibody or functional part thereof

<400> SEQUENCE: 46

Ala Ala Ser Ser Ser Gly Tyr Gly Met Gly Tyr Phe Asp
1 5 10

<210> SEQ ID NO 47
<211> LENGTH: 125
<212> TYPE: PRT
<213> ORGANISM: Artificial Sequence
<220> FEATURE:
<223> OTHER INFORMATION: sequence of recombinant antibody or functional part thereof

<400> SEQUENCE: 47

Gln Val Gln Leu Gln Glu Ser Gly Pro Gly Leu Val Lys Pro Ser Glu
1 5 10 15

Thr Leu Ser Leu Thr Cys Lys Val Ser Gly Phe Ser Phe Asn Asn Asp
20 25 30

Tyr Asp Met Cys Trp Ile Arg Gln Pro Pro Gly Lys Gly Leu Glu Trp
35 40 45

Ile Gly Cys Ile Asp Thr Gly Asp Gly Ser Thr Tyr Tyr Ala Ser Trp
50 55 60

Ala Lys Gly Arg Val Thr Ile Ser Val Asp Ser Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Ala Ala Ser Ser Ser Gly Tyr Gly Met Gly Tyr Phe
100 105 110

Asp Leu Trp Gly Gln Gly Thr Leu Val Thr Val Ser Ser
115 120 125

<210> SEQ ID NO 48
<211> LENGTH: 13
<212> TYPE: PRT
<213> ORGANISM: Artificial Sequence
<220> FEATURE:
<223> OTHER INFORMATION: sequence of recombinant antibody or functional part thereof

<400> SEQUENCE: 48

Gln Ser Ser Gln Ser Val Tyr Asp Asn Asn Trp Leu Ala
1 5 10

<210> SEQ ID NO 49
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 49

Arg Ala Ser Asn Leu Ala Ser
1 5

<210> SEQ ID NO 50
<211> LENGTH: 12
<212> TYPE: PRT
<213> ORGANISM: Artificial Sequence
<220> FEATURE:

```
<223> OTHER INFORMATION: sequence of recombinant antibody or functional
      part thereof

<400> SEQUENCE: 50

Gln Gly Thr Tyr Leu Ser Ser Asn Trp Tyr Trp Ala
1               5                   10


<210> SEQ ID NO 51
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 51

Ser Ser Gln Ser Val Tyr Asp Asn Asn Trp
1               5                   10


<210> SEQ ID NO 52
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 52

Arg Ala Ser Asn Leu Ala Ser Gly Val Pro Ser Arg
1               5                   10


<210> SEQ ID NO 53
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 53

Thr Tyr Leu Ser Ser Asn Trp Tyr Trp
1               5


<210> SEQ ID NO 54
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 54

Ser Gln Ser Val Tyr Asp Asn Asn Trp
1               5


<210> SEQ ID NO 55
<211> LENGTH: 3
<212> TYPE: PRT
<213> ORGANISM: Artificial Sequence
<220> FEATURE:
<223> OTHER INFORMATION: sequence of recombinant antibody or functional
      part thereof

<400> SEQUENCE: 55

Arg Ala Ser
1
```

<210> SEQ ID NO 56
<211> LENGTH: 9
<212> TYPE: PRT
<213> ORGANISM: Artificial Sequence
<220> FEATURE:
<223> OTHER INFORMATION: sequence of recombinant antibody or functional part thereof

<400> SEQUENCE: 56

```
Thr Tyr Leu Ser Ser Asn Trp Tyr Trp
1               5
```

<210> SEQ ID NO 57
<211> LENGTH: 113
<212> TYPE: PRT
<213> ORGANISM: Artificial Sequence
<220> FEATURE:
<223> OTHER INFORMATION: sequence of recombinant antibody or functional part thereof

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asp Asn
            20                  25                  30

Asn Trp Leu Ala Trp Tyr Gln Gln Lys Pro Gly Lys Ala Pro Lys Leu
        35                  40                  45

Leu Ile Tyr Arg Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Thr Tyr Leu Ser
                85                  90                  95

Ser Asn Trp Tyr Trp Ala Phe Gly Thr Gly Thr Lys Val Thr Val Leu
            100                 105                 110

Gly
```

<210> SEQ ID NO 58
<211> LENGTH: 258
<212> TYPE: PRT
<213> ORGANISM: Artificial Sequence
<220> FEATURE:
<223> OTHER INFORMATION: sequence of recombinant antibody or functional part thereof

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asp Asn
            20                  25                  30

Asn Trp Leu Ala Trp Tyr Gln Gln Lys Pro Gly Lys Ala Pro Lys Leu
        35                  40                  45

Leu Ile Tyr Arg Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Thr Tyr Leu Ser
                85                  90                  95

Ser Asn Trp Tyr Trp Ala Phe Gly Thr Gly Thr Lys Val Thr Val Leu
            100                 105                 110
```

```
Gly Gly Gly Gly Gly Ser Gly Gly Gly Gly Ser Gly Gly Gly Gly Ser
        115                 120                 125

Gly Gly Gly Gly Ser Gln Val Gln Leu Gln Glu Ser Gly Pro Gly Leu
    130                 135                 140

Val Lys Pro Ser Glu Thr Leu Ser Leu Thr Cys Lys Val Ser Gly Phe
145                 150                 155                 160

Ser Phe Asn Asn Asp Tyr Asp Met Cys Trp Ile Arg Gln Pro Pro Gly
                165                 170                 175

Lys Gly Leu Glu Trp Ile Gly Cys Ile Asp Thr Gly Asp Gly Ser Thr
            180                 185                 190

Tyr Tyr Ala Ser Trp Ala Lys Gly Arg Val Thr Ile Ser Val Asp Ser
        195                 200                 205

Ser Lys Asn Gln Phe Ser Leu Lys Leu Ser Ser Val Thr Ala Ala Asp
    210                 215                 220

Thr Ala Val Tyr Tyr Cys Ala Arg Glu Ala Ala Ser Ser Ser Gly Tyr
225                 230                 235                 240

Gly Met Gly Tyr Phe Asp Leu Trp Gly Gln Gly Thr Leu Val Thr Val
                245                 250                 255

Ser Ser


<210> SEQ ID NO 59
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 59

Gly Phe Ser Phe Ser Ala Asn Tyr Tyr Pro Cys
1               5                   10


<210> SEQ ID NO 60
<211> LENGTH: 17
<212> TYPE: PRT
<213> ORGANISM: Artificial Sequence
<220> FEATURE:
<223> OTHER INFORMATION: sequence of recombinant antibody or functional
      part thereof

<400> SEQUENCE: 60

Cys Ile Tyr Gly Gly Ser Ser Asp Ile Thr Tyr Asp Ala Asn Trp Thr
1               5                   10                  15

Lys


<210> SEQ ID NO 61
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 61

Arg Ser Ala Trp Tyr Ser Gly Trp Gly Gly Asp Leu
1               5                   10


<210> SEQ ID NO 62
<211> LENGTH: 11
<212> TYPE: PRT
<213> ORGANISM: Artificial Sequence
<220> FEATURE:
```

<223> OTHER INFORMATION: sequence of recombinant antibody or functional part thereof

<400> SEQUENCE: 62

Ala Ser Gly Phe Ser Phe Ser Ala Asn Tyr Tyr
1 5 10

<210> SEQ ID NO 63
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 63

Ile Tyr Gly Gly Ser Ser Asp Ile Thr Tyr Asp Ala Asn Trp Thr Lys
1 5 10 15

Gly

<210> SEQ ID NO 64
<211> LENGTH: 10
<212> TYPE: PRT
<213> ORGANISM: Artificial Sequence
<220> FEATURE:
<223> OTHER INFORMATION: sequence of recombinant antibody or functional part thereof

<400> SEQUENCE: 64

Ser Ala Trp Tyr Ser Gly Trp Gly Gly Asp
1 5 10

<210> SEQ ID NO 65
<211> LENGTH: 6
<212> TYPE: PRT
<213> ORGANISM: Artificial Sequence
<220> FEATURE:
<223> OTHER INFORMATION: sequence of recombinant antibody or functional part thereof

<400> SEQUENCE: 65

Ala Asn Tyr Tyr Pro Cys
1 5

<210> SEQ ID NO 66
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 66

Cys Ile Tyr Gly Gly Ser Ser Asp Ile Thr Tyr Asp Ala Asn Trp Thr
1 5 10 15

Lys

<210> SEQ ID NO 67
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 67

```
Ser Ala Trp Tyr Ser Gly Trp Gly Gly Asp Leu
1               5                   10


<210> SEQ ID NO 68
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 68

Gly Phe Ser Phe Ser Ala Asn Tyr
1               5


<210> SEQ ID NO 69
<211> LENGTH: 4
<212> TYPE: PRT
<213> ORGANISM: Artificial Sequence
<220> FEATURE:
<223> OTHER INFORMATION: sequence of recombinant antibody or functional
      part thereof

<400> SEQUENCE: 69

Gly Gly Ser Ser
1


<210> SEQ ID NO 70
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 70

Ala Trp Tyr Ser Gly Trp Gly Gly Asp
1               5


<210> SEQ ID NO 71
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Tyr Pro Cys Trp Val Arg Gln Ala Pro Gly Lys Gly Leu Glu Trp
        35                  40                  45

Ile Gly Cys Ile Tyr Gly Gly Ser Ser Asp Ile Thr Tyr Asp Ala Asn
    50                  55                  60

Trp Thr Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Ala Trp Tyr Ser Gly Trp Gly Gly Asp Leu Trp
            100                 105                 110

Gly Gln Gly Thr Leu Val Thr Val Ser Ser
        115                 120
```

<210> SEQ ID NO 72
<211> LENGTH: 122
<212> TYPE: PRT
<213> ORGANISM: Artificial Sequence
<220> FEATURE:
<223> OTHER INFORMATION: sequence of recombinant antibody or functional part thereof

<400> SEQUENCE: 72

```
Glu Ser Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Tyr Pro Cys Trp Val Arg Gln Ala Pro Gly Lys Gly Leu Glu Trp
        35                  40                  45

Ile Gly Cys Ile Tyr Gly Gly Ser Ser Asp Ile Thr Tyr Asp Ala Asn
    50                  55                  60

Trp Thr Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Ser Ala Trp Tyr Ser Gly Trp Gly Gly Asp Leu Trp
            100                 105                 110

Gly Pro Gly Thr Leu Val Thr Val Ser Ser
        115                 120
```

<210> SEQ ID NO 73
<211> LENGTH: 122
<212> TYPE: PRT
<213> ORGANISM: Artificial Sequence
<220> FEATURE:
<223> OTHER INFORMATION: sequence of recombinant antibody or functional part thereof

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Tyr Pro Cys Trp Val Arg Gln Ala Pro Gly Lys Cys Leu Glu Trp
        35                  40                  45

Ile Gly Cys Ile Tyr Gly Gly Ser Ser Asp Ile Thr Tyr Asp Ala Asn
    50                  55                  60

Trp Thr Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Ala Trp Tyr Ser Gly Trp Gly Gly Asp Leu Trp
            100                 105                 110

Gly Gln Gly Thr Leu Val Thr Val Ser Ser
        115                 120
```

<210> SEQ ID NO 74
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 74

Gln Ala Ser Gln Ser Ile Ser Asn Arg Leu Ala
1 5 10

<210> SEQ ID NO 75
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 75

Ser Ala Ser Thr Leu Ala Ser
1 5

<210> SEQ ID NO 76
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 76

Gln Ser Thr Tyr Tyr Gly Asn Asp Gly Asn Ala
1 5 10

<210> SEQ ID NO 77
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 77

Ala Ser Gln Ser Ile Ser Asn Arg
1 5

<210> SEQ ID NO 78
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 78

Ser Ala Ser Thr Leu Ala Ser Gly Val Pro Ser Arg
1 5 10

<210> SEQ ID NO 79
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 79

Thr Tyr Tyr Gly Asn Asp Gly Asn
1 5

<210> SEQ ID NO 80
<211> LENGTH: 7

<212> TYPE: PRT
<213> ORGANISM: Artificial Sequence
<220> FEATURE:
<223> OTHER INFORMATION: sequence of recombinant antibody or functional part thereof

<400> SEQUENCE: 80

```
Ser Gln Ser Ile Ser Asn Arg
1               5
```

<210> SEQ ID NO 81
<211> LENGTH: 3
<212> TYPE: PRT
<213> ORGANISM: Artificial Sequence
<220> FEATURE:
<223> OTHER INFORMATION: sequence of recombinant antibody or functional part thereof

<400> SEQUENCE: 81

```
Ser Ala Ser
1
```

<210> SEQ ID NO 82
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 82

```
Thr Tyr Tyr Gly Asn Asp Gly Asn
1               5
```

<210> SEQ ID NO 83
<211> LENGTH: 110
<212> TYPE: PRT
<213> ORGANISM: Artificial Sequence
<220> FEATURE:
<223> OTHER INFORMATION: sequence of recombinant antibody or functional part thereof

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Thr Gly Thr Lys Val Thr Val Leu Gly
            100                 105                 110
```

<210> SEQ ID NO 84
<211> LENGTH: 110
<212> TYPE: PRT
<213> ORGANISM: Artificial Sequence
<220> FEATURE:
<223> OTHER INFORMATION: sequence of recombinant antibody or functional part thereof

<400> SEQUENCE: 84

```
Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Thr Gly Thr Lys Val Thr Val Leu Gly
            100                 105                 110
```

<210> SEQ ID NO 85
<211> LENGTH: 110
<212> TYPE: PRT
<213> ORGANISM: Artificial Sequence
<220> FEATURE:
<223> OTHER INFORMATION: sequence of recombinant antibody or functional part thereof

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Cys Gly Thr Lys Val Thr Val Leu Gly
            100                 105                 110
```

<210> SEQ ID NO 86
<211> LENGTH: 252
<212> TYPE: PRT
<213> ORGANISM: Artificial Sequence
<220> FEATURE:
<223> OTHER INFORMATION: sequence of recombinant antibody or functional part thereof

<400> SEQUENCE: 86

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Thr Gly Thr Lys Val Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ala Asn Tyr Tyr Pro Cys Trp Val Arg Gln Ala Pro Gly Lys Gly Leu
                165                 170                 175

Glu Trp Ile Gly Cys Ile Tyr Gly Gly Ser Ser Asp Ile Thr Tyr Asp
            180                 185                 190

Ala Asn Trp Thr Lys Gly Arg Phe Thr Ile Ser Arg Asp Asn Ser Lys
        195                 200                 205

Asn Thr Val Tyr Leu Gln Met Asn Ser Leu Arg Ala Glu Asp Thr Ala
    210                 215                 220

Val Tyr Tyr Cys Ala Arg Ser Ala Trp Tyr Ser Gly Trp Gly Gly Asp
225                 230                 235                 240

Leu Trp Gly Gln Gly Thr Leu Val Thr Val Ser Ser
                245                 250
```

```
<210> SEQ ID NO 87
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 87

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Thr Gly Thr Lys Val Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Ser Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ala Asn Tyr Tyr Pro Cys Trp Val Arg Gln Ala Pro Gly Lys Gly Leu
                165                 170                 175
```

Glu Trp Ile Gly Cys Ile Tyr Gly Gly Ser Ser Asp Ile Thr Tyr Asp
180 185 190

Ala Asn Trp Thr Lys Gly Arg Phe Thr Ile Ser Arg Asp Asn Ser Lys
195 200 205

Asn Thr Val Tyr Leu Gln Met Asn Ser Leu Arg Ala Glu Asp Thr Ala
210 215 220

Val Tyr Phe Cys Ala Arg Ser Ala Trp Tyr Ser Gly Trp Gly Gly Asp
225 230 235 240

Leu Trp Gly Pro Gly Thr Leu Val Thr Val Ser Ser
245 250

<210> SEQ ID NO 88
<211> LENGTH: 252
<212> TYPE: PRT
<213> ORGANISM: Artificial Sequence
<220> FEATURE:
<223> OTHER INFORMATION: sequence of recombinant antibody or functional part thereof

<400> SEQUENCE: 88

Asp Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Ser Asn Arg
20 25 30

Leu Ala Trp Tyr Gln Gln Lys Pro Gly Lys Ala Pro Lys Leu Leu Ile
35 40 45

Tyr Ser Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Ser Thr Tyr Tyr Gly Asn Asp
85 90 95

Gly Asn Ala Phe Gly Cys Gly Thr Lys Val Thr Val Leu Gly Gly Gly
100 105 110

Gly Gly Ser Gly Gly Gly Gly Ser Gly Gly Gly Gly Ser Gly Gly Gly
115 120 125

Gly Ser Glu Val Gln Leu Val Glu Ser Gly Gly Gly Leu Val Gln Pro
130 135 140

Gly Gly Ser Leu Arg Leu Ser Cys Ala Ala Ser Gly Phe Ser Phe Ser
145 150 155 160

Ala Asn Tyr Tyr Pro Cys Trp Val Arg Gln Ala Pro Gly Lys Cys Leu
165 170 175

Glu Trp Ile Gly Cys Ile Tyr Gly Gly Ser Ser Asp Ile Thr Tyr Asp
180 185 190

Ala Asn Trp Thr Lys Gly Arg Phe Thr Ile Ser Arg Asp Asn Ser Lys
195 200 205

Asn Thr Val Tyr Leu Gln Met Asn Ser Leu Arg Ala Glu Asp Thr Ala
210 215 220

Val Tyr Tyr Cys Ala Arg Ser Ala Trp Tyr Ser Gly Trp Gly Gly Asp
225 230 235 240

Leu Trp Gly Gln Gly Thr Leu Val Thr Val Ser Ser
245 250

<210> SEQ ID NO 89
<211> LENGTH: 11
<212> TYPE: PRT

<213> ORGANISM: Artificial Sequence
<220> FEATURE:
<223> OTHER INFORMATION: sequence of recombinant antibody or functional part thereof

<400> SEQUENCE: 89

Gly Phe Ser Phe Asn Ser Asp Tyr Trp Ile Tyr
1 5 10

<210> SEQ ID NO 90
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 90

Ser Ile Tyr Gly Gly Ser Ser Gly Asn Thr Gln Tyr Ala Ser Trp Ala
1 5 10 15

Gln Gly

<210> SEQ ID NO 91
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 91

Arg Gly Tyr Val Asp Tyr Gly Gly Ala Thr Asp Leu
1 5 10

<210> SEQ ID NO 92
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 92

Val Ser Gly Phe Ser Phe Asn Ser Asp Tyr Trp
1 5 10

<210> SEQ ID NO 93
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 93

Ala Ser Gly Phe Ser Phe Asn Ser Asp Tyr Trp
1 5 10

<210> SEQ ID NO 94
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 94

Ile Tyr Gly Gly Ser Ser Gly Asn Thr Gln Tyr Ala Ser Trp Ala Gln
1 5 10 15

Gly Arg

<210> SEQ ID NO 95
<211> LENGTH: 10
<212> TYPE: PRT
<213> ORGANISM: Artificial Sequence
<220> FEATURE:
<223> OTHER INFORMATION: sequence of recombinant antibody or functional part thereof

<400> SEQUENCE: 95

Gly Tyr Val Asp Tyr Gly Gly Ala Thr Asp
1 5 10

<210> SEQ ID NO 96
<211> LENGTH: 6
<212> TYPE: PRT
<213> ORGANISM: Artificial Sequence
<220> FEATURE:
<223> OTHER INFORMATION: sequence of recombinant antibody or functional part thereof

<400> SEQUENCE: 96

Ser Asp Tyr Trp Ile Tyr
1 5

<210> SEQ ID NO 97
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 97

Ser Ile Tyr Gly Gly Ser Ser Gly Asn Thr Gln Tyr Ala Ser Trp Ala
1 5 10 15

Gln Gly

<210> SEQ ID NO 98
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 98

Gly Tyr Val Asp Tyr Gly Gly Ala Thr Asp Leu
1 5 10

<210> SEQ ID NO 99
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 99

Gly Phe Ser Phe Asn Ser Asp Tyr
1 5

<210> SEQ ID NO 100

<211> LENGTH: 5
<212> TYPE: PRT
<213> ORGANISM: Artificial Sequence
<220> FEATURE:
<223> OTHER INFORMATION: sequence of recombinant antibody or functional part thereof

<400> SEQUENCE: 100

```
Gly Gly Ser Ser Gly
1               5
```

<210> SEQ ID NO 101
<211> LENGTH: 9
<212> TYPE: PRT
<213> ORGANISM: Artificial Sequence
<220> FEATURE:
<223> OTHER INFORMATION: sequence of recombinant antibody or functional part thereof

<400> SEQUENCE: 101

```
Tyr Val Asp Tyr Gly Gly Ala Thr Asp
1               5
```

<210> SEQ ID NO 102
<211> LENGTH: 122
<212> TYPE: PRT
<213> ORGANISM: Artificial Sequence
<220> FEATURE:
<223> OTHER INFORMATION: sequence of recombinant antibody or functional part thereof

<400> SEQUENCE: 102

```
Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Ser Asp
            20                  25                  30

Tyr Trp Ile Tyr Trp Ile Arg Gln Pro Pro Gly Lys Gly Leu Glu Trp
        35                  40                  45

Ile Gly Ser Ile Tyr Gly Gly Ser Ser Gly Asn Thr Gln Tyr Ala Ser
    50                  55                  60

Trp Ala Gln Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Tyr Val Asp Tyr Gly Gly Ala Thr Asp Leu Trp
            100                 105                 110

Gly Gln Gly Thr Leu Val Thr Val Ser Ser
        115                 120
```

<210> SEQ ID NO 103
<211> LENGTH: 122
<212> TYPE: PRT
<213> ORGANISM: Artificial Sequence
<220> FEATURE:
<223> OTHER INFORMATION: sequence of recombinant antibody or functional part thereof

<400> SEQUENCE: 103

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Asn Ser Asp
            20                  25                  30

Tyr Trp Ile Tyr Trp Val Arg Gln Ala Pro Gly Gln Gly Leu Glu Trp
```

```
        35                  40                  45

Met Gly Ser Ile Tyr Gly Gly Ser Ser Gly Asn Thr Gln Tyr Ala Ser
    50                  55                  60

Trp Ala Gln Gly Arg Val Thr Met Thr Arg Asp Thr Ser Ile Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Tyr Val Asp Tyr Gly Gly Ala Thr Asp Leu Trp
            100                 105                 110

Gly Gln Gly Thr Leu Val Thr Val Ser Ser
        115                 120


<210> SEQ ID NO 104
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asn Ser Asp
            20                  25                  30

Tyr Trp Ile Tyr Trp Val Arg Gln Ala Pro Gly Lys Gly Leu Glu Trp
        35                  40                  45

Ile Ala Ser Ile Tyr Gly Gly Ser Ser Gly Asn Thr Gln Tyr Ala Ser
    50                  55                  60

Trp Ala Gln Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Gly Tyr Val Asp Tyr Gly Gly Ala Thr Asp Leu Trp
            100                 105                 110

Gly Gln Gly Thr Leu Val Thr Val Ser Ser
        115                 120


<210> SEQ ID NO 105
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 105

Gln Ala Ser Gln Ser Ile Gly Thr Tyr Leu Ala
1               5                   10


<210> SEQ ID NO 106
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 106

Arg Ala Phe Ile Leu Ala Ser
1               5
```

<210> SEQ ID NO 107
<211> LENGTH: 15
<212> TYPE: PRT
<213> ORGANISM: Artificial Sequence
<220> FEATURE:
<223> OTHER INFORMATION: sequence of recombinant antibody or functional part thereof

<400> SEQUENCE: 107

Gln Ser Asn Phe Tyr Ser Asp Ser Thr Thr Ile Gly Pro Asn Ala
1               5                   10                  15

<210> SEQ ID NO 108
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 108

Ala Ser Gln Ser Ile Gly Thr Tyr
1               5

<210> SEQ ID NO 109
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 109

Arg Ala Phe Ile Leu Ala Ser Gly Val Pro Ser Arg
1               5                   10

<210> SEQ ID NO 110
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 110

Asn Phe Tyr Ser Asp Ser Thr Thr Ile Gly Pro Asn
1               5                   10

<210> SEQ ID NO 111
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 111

Ser Gln Ser Ile Gly Thr Tyr
1               5

<210> SEQ ID NO 112
<211> LENGTH: 3
<212> TYPE: PRT
<213> ORGANISM: Artificial Sequence
<220> FEATURE:
<223> OTHER INFORMATION: sequence of recombinant antibody or functional part thereof

<400> SEQUENCE: 112

Arg Ala Phe
1

<210> SEQ ID NO 113
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 113

Asn Phe Tyr Ser Asp Ser Thr Thr Ile Gly Pro Asn
1               5                   10

<210> SEQ ID NO 114
<211> LENGTH: 114
<212> TYPE: PRT
<213> ORGANISM: Artificial Sequence
<220> FEATURE:
<223> OTHER INFORMATION: sequence of recombinant antibody or functional part thereof

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly

<210> SEQ ID NO 115
<211> LENGTH: 114
<212> TYPE: PRT
<213> ORGANISM: Artificial Sequence
<220> FEATURE:
<223> OTHER INFORMATION: sequence of recombinant antibody or functional part thereof

<400> SEQUENCE: 115

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly


<210> SEQ ID NO 116
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Gly Gly Gly Gly Ser Gly Gly Gly Gly
        115                 120                 125

Ser Gly Gly Gly Gly Ser Gln Val Gln Leu Gln Glu Ser Gly Pro Gly
    130                 135                 140

Leu Val Lys Pro Ser Glu Thr Leu Ser Leu Thr Cys Lys Val Ser Gly
145                 150                 155                 160

Phe Ser Phe Asn Ser Asp Tyr Trp Ile Tyr Trp Ile Arg Gln Pro Pro
                165                 170                 175

Gly Lys Gly Leu Glu Trp Ile Gly Ser Ile Tyr Gly Gly Ser Ser Gly
            180                 185                 190

Asn Thr Gln Tyr Ala Ser Trp Ala Gln Gly Arg Val Thr Ile Ser Val
        195                 200                 205

Asp Ser Ser Lys Asn Gln Phe Ser Leu Lys Leu Ser Ser Val Thr Ala
    210                 215                 220

Ala Asp Thr Ala Val Tyr Tyr Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255


<210> SEQ ID NO 117
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 117
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Gly Gly Gly Gly Ser Gly Gly Gly Gly
        115                 120                 125

Ser Gly Gly Gly Gly Ser Gln Val Gln Leu Val Gln Ser Gly Ala Glu
    130                 135                 140

Val Lys Lys Pro Gly Ala Ser Val Lys Val Ser Cys Lys Ala Ser Gly
145                 150                 155                 160

Phe Ser Phe Asn Ser Asp Tyr Trp Ile Tyr Trp Val Arg Gln Ala Pro
                165                 170                 175

Gly Gln Gly Leu Glu Trp Met Gly Ser Ile Tyr Gly Gly Ser Ser Gly
            180                 185                 190

Asn Thr Gln Tyr Ala Ser Trp Ala Gln Gly Arg Val Thr Met Thr Arg
        195                 200                 205

Asp Thr Ser Ile Ser Thr Ala Tyr Met Glu Leu Ser Ser Leu Arg Ser
    210                 215                 220

Glu Asp Thr Ala Val Tyr Tyr Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255
```

<210> SEQ ID NO 118
<211> LENGTH: 256
<212> TYPE: PRT
<213> ORGANISM: Artificial Sequence
<220> FEATURE:
<223> OTHER INFORMATION: sequence of recombinant antibody or functional part thereof

<400> SEQUENCE: 118

```
Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110
```

Leu Gly Gly Gly Gly Gly Ser Gly Gly Gly Gly Ser Gly Gly Gly Gly
115 120 125

Ser Gly Gly Gly Gly Ser Glu Val Gln Leu Val Glu Ser Gly Gly Gly
130 135 140

Leu Val Gln Pro Gly Gly Ser Leu Arg Leu Ser Cys Ala Ala Ser Gly
145 150 155 160

Phe Ser Phe Asn Ser Asp Tyr Trp Ile Tyr Trp Val Arg Gln Ala Pro
165 170 175

Gly Lys Gly Leu Glu Trp Ile Ala Ser Ile Tyr Gly Gly Ser Ser Gly
180 185 190

Asn Thr Gln Tyr Ala Ser Trp Ala Gln Gly Arg Phe Thr Ile Ser Arg
195 200 205

Asp Asn Ser Lys Asn Thr Val Tyr Leu Gln Met Asn Ser Leu Arg Ala
210 215 220

Glu Asp Thr Ala Val Tyr Phe Cys Ala Arg Gly Tyr Val Asp Tyr Gly
225 230 235 240

Gly Ala Thr Asp Leu Trp Gly Gln Gly Thr Leu Val Thr Val Ser Ser
245 250 255

<210> SEQ ID NO 119
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 119

Gly Phe Ser Phe Ser Ser Gly Tyr Asp Met Cys
1 5 10

<210> SEQ ID NO 120
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 120

Cys Val Val Ala Gly Ser Val Asp Ile Thr Tyr Tyr Ala Ser Trp Ala
1 5 10 15

Lys Gly

<210> SEQ ID NO 121
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 121

Arg Lys Asp Ala Tyr Ser Asp Ala Phe Asn Leu
1 5 10

<210> SEQ ID NO 122
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 122

Val Ser Gly Phe Ser Phe Ser Ser Gly Tyr Asp
1               5                   10

<210> SEQ ID NO 123
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 123

Ala Ser Gly Phe Ser Phe Ser Ser Gly Tyr Asp
1               5                   10

<210> SEQ ID NO 124
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 124

Val Val Ala Gly Ser Val Asp Ile Thr Tyr Tyr Ala Ser Trp Ala Lys
1               5                   10                  15

Gly Arg

<210> SEQ ID NO 125
<211> LENGTH: 9
<212> TYPE: PRT
<213> ORGANISM: Artificial Sequence
<220> FEATURE:
<223> OTHER INFORMATION: sequence of recombinant antibody or functional part thereof

<400> SEQUENCE: 125

Lys Asp Ala Tyr Ser Asp Ala Phe Asn
1               5

<210> SEQ ID NO 126
<211> LENGTH: 6
<212> TYPE: PRT
<213> ORGANISM: Artificial Sequence
<220> FEATURE:
<223> OTHER INFORMATION: sequence of recombinant antibody or functional part thereof

<400> SEQUENCE: 126

Ser Gly Tyr Asp Met Cys
1               5

<210> SEQ ID NO 127
<211> LENGTH: 18
<212> TYPE: PRT
<213> ORGANISM: Artificial Sequence
<220> FEATURE:
<223> OTHER INFORMATION: sequence of recombinant antibody or functional part thereof

<400> SEQUENCE: 127

Cys Val Val Ala Gly Ser Val Asp Ile Thr Tyr Tyr Ala Ser Trp Ala
1               5                   10                  15

Lys Gly

<210> SEQ ID NO 128
<211> LENGTH: 10
<212> TYPE: PRT
<213> ORGANISM: Artificial Sequence
<220> FEATURE:
<223> OTHER INFORMATION: sequence of recombinant antibody or functional part thereof

<400> SEQUENCE: 128

Lys Asp Ala Tyr Ser Asp Ala Phe Asn Leu
1               5                   10

<210> SEQ ID NO 129
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 129

Gly Phe Ser Phe Ser Ser Gly Tyr
1               5

<210> SEQ ID NO 130
<211> LENGTH: 5
<212> TYPE: PRT
<213> ORGANISM: Artificial Sequence
<220> FEATURE:
<223> OTHER INFORMATION: sequence of recombinant antibody or functional part thereof

<400> SEQUENCE: 130

Ala Gly Ser Val Asp
1               5

<210> SEQ ID NO 131
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 131

Asp Ala Tyr Ser Asp Ala Phe Asn
1               5

<210> SEQ ID NO 132
<211> LENGTH: 121
<212> TYPE: PRT
<213> ORGANISM: Artificial Sequence
<220> FEATURE:
<223> OTHER INFORMATION: sequence of recombinant antibody or functional part thereof

<400> SEQUENCE: 132

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser

```
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser
        115                 120


<210> SEQ ID NO 133
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 133

Gln Ser Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Ser Gly
            20                  25                  30

Tyr Asp Met Cys Trp Val Arg Gln Pro Pro Gly Lys Gly Leu Glu Trp
        35                  40                  45

Ile Ala Cys Val Val Ala Gly Ser Val Asp Ile Thr Tyr Tyr Ala Ser
    50                  55                  60

Trp Ala Lys Gly Arg Val Thr Ile Ser Lys Asp Ser Ser Lys Asn Gln
65                  70                  75                  80

Val Ser Leu Lys Leu Ser Ser Val Thr Ala Ala Asp Thr Ala Val Tyr
                85                  90                  95

Phe Cys Ala Arg Lys Asp Ala Tyr Ser Asp Ala Phe Asn Leu Trp Gly
            100                 105                 110

Gln Gly Thr Leu Val Thr Val Ser Ser
        115                 120


<210> SEQ ID NO 134
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Ser Gly
            20                  25                  30

Tyr Asp Met Cys Trp Val Arg Gln Pro Pro Gly Lys Gly Leu Glu Trp
        35                  40                  45

Ile Ala Cys Val Val Ala Gly Ser Val Asp Ile Thr Tyr Tyr Ala Ser
    50                  55                  60

Trp Ala Lys Gly Arg Val Thr Ile Ser Lys Asp Ser Ser Lys Asn Gln
65                  70                  75                  80

Val Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
```

100 105 110

Gln Gly Thr Leu Val Thr Val Ser Ser
115 120

<210> SEQ ID NO 135
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 135

Gln Ala Ser Gln Ser Ile Asn Asp Tyr Leu Ala
1 5 10

<210> SEQ ID NO 136
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 136

Lys Ala Ser Thr Leu Ala Ser
1 5

<210> SEQ ID NO 137
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 137

Gln Gln Gly Tyr Ile Ile Thr Asp Ile Asp Asn Val
1 5 10

<210> SEQ ID NO 138
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 138

Ala Ser Gln Ser Ile Asn Asp Tyr
1 5

<210> SEQ ID NO 139
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 139

Lys Ala Ser Thr Leu Ala Ser Gly Val Pro Ser Arg
1 5 10

<210> SEQ ID NO 140
<211> LENGTH: 9
<212> TYPE: PRT

```
<213> ORGANISM: Artificial Sequence
<220> FEATURE:
<223> OTHER INFORMATION: sequence of recombinant antibody or functional
      part thereof

<400> SEQUENCE: 140

Gly Tyr Ile Ile Thr Asp Ile Asp Asn
1               5


<210> SEQ ID NO 141
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 141

Ser Gln Ser Ile Asn Asp Tyr
1               5


<210> SEQ ID NO 142
<211> LENGTH: 3
<212> TYPE: PRT
<213> ORGANISM: Artificial Sequence
<220> FEATURE:
<223> OTHER INFORMATION: sequence of recombinant antibody or functional
      part thereof

<400> SEQUENCE: 142

Lys Ala Ser
1


<210> SEQ ID NO 143
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 143

Gly Tyr Ile Ile Thr Asp Ile Asp Asn
1               5


<210> SEQ ID NO 144
<211> LENGTH: 111
<212> TYPE: PRT
<213> ORGANISM: Artificial Sequence
<220> FEATURE:
<223> OTHER INFORMATION: sequence of recombinant antibody or functional
      part thereof

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
```

```
                85                  90                  95

Ile Asp Asn Val Phe Gly Thr Gly Thr Lys Val Thr Val Leu Gly
            100                 105                 110


<210> SEQ ID NO 145
<211> LENGTH: 111
<212> TYPE: PRT
<213> ORGANISM: Artificial Sequence
<220> FEATURE:
<223> OTHER INFORMATION: sequence of recombinant antibody or functional
      part thereof

<400> SEQUENCE: 145

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly
            100                 105                 110


<210> SEQ ID NO 146
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
```

```
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser
                245                 250


<210> SEQ ID NO 147
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 147

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Ser Gln Leu Gln Glu Ser Gly Pro Gly Leu Val Lys
    130                 135                 140

Pro Ser Glu Thr Leu Ser Leu Thr Cys Lys Ala Ser Gly Phe Ser Phe
145                 150                 155                 160

Ser Ser Gly Tyr Asp Met Cys Trp Val Arg Gln Pro Pro Gly Lys Gly
                165                 170                 175

Leu Glu Trp Ile Ala Cys Val Val Ala Gly Ser Val Asp Ile Thr Tyr
            180                 185                 190

Tyr Ala Ser Trp Ala Lys Gly Arg Val Thr Ile Ser Lys Asp Ser Ser
        195                 200                 205

Lys Asn Gln Val Ser Leu Lys Leu Ser Ser Val Thr Ala Ala Asp Thr
    210                 215                 220

Ala Val Tyr Phe Cys Ala Arg Lys Asp Ala Tyr Ser Asp Ala Phe Asn
225                 230                 235                 240

Leu Trp Gly Gln Gly Thr Leu Val Thr Val Ser Ser
                245                 250


<210> SEQ ID NO 148
<211> LENGTH: 252
```

```
<212> TYPE: PRT
<213> ORGANISM: Artificial Sequence
<220> FEATURE:
<223> OTHER INFORMATION: sequence of recombinant antibody or functional
      part thereof

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Ala Ser Gly Phe Ser Phe
145                 150                 155                 160

Ser Ser Gly Tyr Asp Met Cys Trp Val Arg Gln Pro Pro Gly Lys Gly
                165                 170                 175

Leu Glu Trp Ile Ala Cys Val Val Ala Gly Ser Val Asp Ile Thr Tyr
            180                 185                 190

Tyr Ala Ser Trp Ala Lys Gly Arg Val Thr Ile Ser Lys Asp Ser Ser
        195                 200                 205

Lys Asn Gln Val Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser
                245                 250


<210> SEQ ID NO 149
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 149

Gly Phe Ser Leu Ser Ser Asn Ala Met Gly
1               5                   10


<210> SEQ ID NO 150
<211> LENGTH: 16
<212> TYPE: PRT
<213> ORGANISM: Artificial Sequence
<220> FEATURE:
<223> OTHER INFORMATION: sequence of recombinant antibody or functional
      part thereof
```

<400> SEQUENCE: 150

Ile Ile Ser Val Gly Gly Phe Thr Tyr Tyr Ala Ser Trp Ala Lys Gly
1 5 10 15

<210> SEQ ID NO 151
<211> LENGTH: 14
<212> TYPE: PRT
<213> ORGANISM: Artificial Sequence
<220> FEATURE:
<223> OTHER INFORMATION: sequence of recombinant antibody or functional part thereof

<400> SEQUENCE: 151

Arg Asp Arg His Gly Gly Asp Ser Ser Gly Ala Phe Tyr Leu
1 5 10

<210> SEQ ID NO 152
<211> LENGTH: 10
<212> TYPE: PRT
<213> ORGANISM: Artificial Sequence
<220> FEATURE:
<223> OTHER INFORMATION: sequence of recombinant antibody or functional part thereof

<400> SEQUENCE: 152

Ala Ser Gly Phe Ser Leu Ser Ser Asn Ala
1 5 10

<210> SEQ ID NO 153
<211> LENGTH: 16
<212> TYPE: PRT
<213> ORGANISM: Artificial Sequence
<220> FEATURE:
<223> OTHER INFORMATION: sequence of recombinant antibody or functional part thereof

<400> SEQUENCE: 153

Ile Ser Val Gly Gly Phe Thr Tyr Tyr Ala Ser Trp Ala Lys Gly Arg
1 5 10 15

<210> SEQ ID NO 154
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 154

Asp Arg His Gly Gly Asp Ser Ser Gly Ala Phe Tyr
1 5 10

<210> SEQ ID NO 155
<211> LENGTH: 5
<212> TYPE: PRT
<213> ORGANISM: Artificial Sequence
<220> FEATURE:
<223> OTHER INFORMATION: sequence of recombinant antibody or functional part thereof

<400> SEQUENCE: 155

Ser Asn Ala Met Gly
1 5

<210> SEQ ID NO 156
<211> LENGTH: 16
<212> TYPE: PRT

<213> ORGANISM: Artificial Sequence
<220> FEATURE:
<223> OTHER INFORMATION: sequence of recombinant antibody or functional part thereof

<400> SEQUENCE: 156

Ile Ile Ser Val Gly Gly Phe Thr Tyr Tyr Ala Ser Trp Ala Lys Gly
1 5 10 15

<210> SEQ ID NO 157
<211> LENGTH: 13
<212> TYPE: PRT
<213> ORGANISM: Artificial Sequence
<220> FEATURE:
<223> OTHER INFORMATION: sequence of recombinant antibody or functional part thereof

<400> SEQUENCE: 157

Asp Arg His Gly Gly Asp Ser Ser Gly Ala Phe Tyr Leu
1 5 10

<210> SEQ ID NO 158
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 158

Gly Phe Ser Leu Ser Ser Asn
1 5

<210> SEQ ID NO 159
<211> LENGTH: 3
<212> TYPE: PRT
<213> ORGANISM: Artificial Sequence
<220> FEATURE:
<223> OTHER INFORMATION: sequence of recombinant antibody or functional part thereof

<400> SEQUENCE: 159

Val Gly Gly
1

<210> SEQ ID NO 160
<211> LENGTH: 13
<212> TYPE: PRT
<213> ORGANISM: Artificial Sequence
<220> FEATURE:
<223> OTHER INFORMATION: sequence of recombinant antibody or functional part thereof

<400> SEQUENCE: 160

Arg Asp Arg His Gly Gly Asp Ser Ser Gly Ala Phe Tyr
1 5 10

<210> SEQ ID NO 161
<211> LENGTH: 121
<212> TYPE: PRT
<213> ORGANISM: Artificial Sequence
<220> FEATURE:
<223> OTHER INFORMATION: sequence of recombinant antibody or functional part thereof

<400> SEQUENCE: 161

Glu Val Gln Leu Val Glu Ser Gly Gly Gly Leu Val Gln Pro Gly Gly
1 5 10 15

```
Ser Leu Arg Leu Ser Cys Ala Ala Ser Gly Phe Ser Leu Ser Ser Asn
            20                  25                  30

Ala Met Gly Trp Val Arg Gln Ala Pro Gly Lys Gly Leu Glu Tyr Ile
        35                  40                  45

Gly Ile Ile Ser Val Gly Gly Phe Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Asp Arg His Gly Gly Asp Ser Ser Gly Ala Phe Tyr Leu Trp Gly
            100                 105                 110

Gln Gly Thr Leu Val Thr Val Ser Ser
        115                 120


<210> SEQ ID NO 162
<211> LENGTH: 13
<212> TYPE: PRT
<213> ORGANISM: Artificial Sequence
<220> FEATURE:
<223> OTHER INFORMATION: sequence of recombinant antibody or functional
      part thereof

<400> SEQUENCE: 162

Gln Ser Ser Glu Ser Val Tyr Ser Asn Asn Gln Leu Ser
1               5                   10


<210> SEQ ID NO 163
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 163

Asp Ala Ser Asp Leu Ala Ser
1               5


<210> SEQ ID NO 164
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 164

Ala Gly Gly Phe Ser Ser Ser Ser Asp Thr Ala
1               5                   10


<210> SEQ ID NO 165
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 165

Ser Ser Glu Ser Val Tyr Ser Asn Asn Gln
1               5                   10
```

<210> SEQ ID NO 166
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 166

```
Asp Ala Ser Asp Leu Ala Ser Gly Val Pro Ser Arg
1               5                   10
```

<210> SEQ ID NO 167
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 167

```
Gly Phe Ser Ser Ser Ser Asp Thr
1               5
```

<210> SEQ ID NO 168
<211> LENGTH: 9
<212> TYPE: PRT
<213> ORGANISM: Artificial Sequence
<220> FEATURE:
<223> OTHER INFORMATION: sequence of recombinant antibody or functional part thereof

<400> SEQUENCE: 168

```
Ser Glu Ser Val Tyr Ser Asn Asn Gln
1               5
```

<210> SEQ ID NO 169
<211> LENGTH: 3
<212> TYPE: PRT
<213> ORGANISM: Artificial Sequence
<220> FEATURE:
<223> OTHER INFORMATION: sequence of recombinant antibody or functional part thereof

<400> SEQUENCE: 169

```
Asp Ala Ser
1
```

<210> SEQ ID NO 170
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 170

```
Gly Phe Ser Ser Ser Ser Asp Thr
1               5
```

<210> SEQ ID NO 171
<211> LENGTH: 112
<212> TYPE: PRT
<213> ORGANISM: Artificial Sequence
<220> FEATURE:
<223> OTHER INFORMATION: sequence of recombinant antibody or functional part thereof

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Ser Asn
            20                  25                  30

Asn Gln Leu Ser Trp Tyr Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Phe Ser Ser
                85                  90                  95

Ser Ser Asp Thr Ala Phe Gly Gly Gly Thr Lys Leu Thr Val Leu Gly
            100                 105                 110


<210> SEQ ID NO 172
<211> LENGTH: 253
<212> TYPE: PRT
<213> ORGANISM: Artificial Sequence
<220> FEATURE:
<223> OTHER INFORMATION: sequence of recombinant antibody or functional
      part thereof

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Ser Asn
            20                  25                  30

Asn Gln Leu Ser Trp Tyr Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Phe Ser Ser
                85                  90                  95

Ser Ser Asp Thr Ala Phe Gly Gly Gly Thr Lys Leu Thr Val Leu Gly
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Ser
145                 150                 155                 160

Leu Ser Ser Asn Ala Met Gly Trp Val Arg Gln Ala Pro Gly Lys Gly
                165                 170                 175

Leu Glu Tyr Ile Gly Ile Ile Ser Val Gly Gly Phe Thr Tyr Tyr Ala
            180                 185                 190

Ser Trp Ala Lys Gly Arg Phe Thr Ile Ser Arg Asp Asn Ser Lys Asn
        195                 200                 205

Thr Val Tyr Leu Gln Met Asn Ser Leu Arg Ala Glu Asp Thr Ala Thr
    210                 215                 220

Tyr Phe Cys Ala Arg Asp Arg His Gly Gly Asp Ser Ser Gly Ala Phe
225                 230                 235                 240

Tyr Leu Trp Gly Gln Gly Thr Leu Val Thr Val Ser Ser
```

245 250

<210> SEQ ID NO 173
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 173

Gly Phe Ser Phe Ser Ser Ser Tyr Trp Ile Cys
1 5 10

<210> SEQ ID NO 174
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 174

Cys Val Phe Thr Gly Asp Gly Thr Thr Tyr Tyr Ala Ser Trp Ala Lys
1 5 10 15

Gly

<210> SEQ ID NO 175
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 175

Arg Pro Val Ser Val Tyr Tyr Tyr Gly Met Asp Leu
1 5 10

<210> SEQ ID NO 176
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 176

Ala Ser Gly Phe Ser Phe Ser Ser Ser Tyr Trp
1 5 10

<210> SEQ ID NO 177
<211> LENGTH: 17
<212> TYPE: PRT
<213> ORGANISM: Artificial Sequence
<220> FEATURE:
<223> OTHER INFORMATION: sequence of recombinant antibody or functional part thereof

<400> SEQUENCE: 177

Val Phe Thr Gly Asp Gly Thr Thr Tyr Tyr Ala Ser Trp Ala Lys Gly
1 5 10 15

Arg

<210> SEQ ID NO 178
<211> LENGTH: 10

```
<212> TYPE: PRT
<213> ORGANISM: Artificial Sequence
<220> FEATURE:
<223> OTHER INFORMATION: sequence of recombinant antibody or functional
      part thereof

<400> SEQUENCE: 178

Pro Val Ser Val Tyr Tyr Tyr Gly Met Asp
1               5                   10


<210> SEQ ID NO 179
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 179

Ser Ser Tyr Trp Ile Cys
1               5


<210> SEQ ID NO 180
<211> LENGTH: 17
<212> TYPE: PRT
<213> ORGANISM: Artificial Sequence
<220> FEATURE:
<223> OTHER INFORMATION: sequence of recombinant antibody or functional
      part thereof

<400> SEQUENCE: 180

Cys Val Phe Thr Gly Asp Gly Thr Thr Tyr Tyr Ala Ser Trp Ala Lys
1               5                   10                  15

Gly


<210> SEQ ID NO 181
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 181

Pro Val Ser Val Tyr Tyr Tyr Gly Met Asp Leu
1               5                   10


<210> SEQ ID NO 182
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 182

Gly Phe Ser Phe Ser Ser Ser Tyr Trp
1               5


<210> SEQ ID NO 183
<211> LENGTH: 4
<212> TYPE: PRT
<213> ORGANISM: Artificial Sequence
<220> FEATURE:
<223> OTHER INFORMATION: sequence of recombinant antibody or functional
      part thereof

<400> SEQUENCE: 183
```

```
Thr Gly Asp Gly
1


<210> SEQ ID NO 184
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 184

Val Ser Val Tyr Tyr Tyr Gly Met Asp
1               5


<210> SEQ ID NO 185
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Val Gly Cys Val Phe Thr Gly Asp Gly Thr Thr Tyr Tyr Ala Ser Trp
    50                  55                  60

Ala Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Phe
                85                  90                  95

Cys Ala Arg Pro Val Ser Val Tyr Tyr Tyr Gly Met Asp Leu Trp Gly
            100                 105                 110

Gln Gly Thr Leu Val Thr Val Ser Ser
        115                 120


<210> SEQ ID NO 186
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 186

Gln Ala Ser Gln Ile Ile Ser Ser Arg Ser Ala
1               5                   10


<210> SEQ ID NO 187
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 187

Gln Ala Ser Lys Leu Ala Ser
```

1 5

<210> SEQ ID NO 188
<211> LENGTH: 11
<212> TYPE: PRT
<213> ORGANISM: Artificial Sequence
<220> FEATURE:
<223> OTHER INFORMATION: sequence of recombinant antibody or functional part thereof

<400> SEQUENCE: 188

Gln Cys Thr Tyr Ile Asp Ser Asn Phe Gly Ala
1 5 10

<210> SEQ ID NO 189
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 189

Ala Ser Gln Ile Ile Ser Ser Arg
1 5

<210> SEQ ID NO 190
<211> LENGTH: 12
<212> TYPE: PRT
<213> ORGANISM: Artificial Sequence
<220> FEATURE:
<223> OTHER INFORMATION: sequence of recombinant antibody or functional part thereof

<400> SEQUENCE: 190

Gln Ala Ser Lys Leu Ala Ser Gly Val Pro Ser Arg
1 5 10

<210> SEQ ID NO 191
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 191

Thr Tyr Ile Asp Ser Asn Phe Gly
1 5

<210> SEQ ID NO 192
<211> LENGTH: 7
<212> TYPE: PRT
<213> ORGANISM: Artificial Sequence
<220> FEATURE:
<223> OTHER INFORMATION: sequence of recombinant antibody or functional part thereof

<400> SEQUENCE: 192

Ser Gln Ile Ile Ser Ser Arg
1 5

<210> SEQ ID NO 193
<211> LENGTH: 3
<212> TYPE: PRT
<213> ORGANISM: Artificial Sequence
<220> FEATURE:
<223> OTHER INFORMATION: sequence of recombinant antibody or functional part thereof

<400> SEQUENCE: 193

Gln Ala Ser
1

<210> SEQ ID NO 194
<211> LENGTH: 8
<212> TYPE: PRT
<213> ORGANISM: Artificial Sequence
<220> FEATURE:
<223> OTHER INFORMATION: sequence of recombinant antibody or functional part thereof

<400> SEQUENCE: 194

Thr Tyr Ile Asp Ser Asn Phe Gly
1 5

<210> SEQ ID NO 195
<211> LENGTH: 110
<212> TYPE: PRT
<213> ORGANISM: Artificial Sequence
<220> FEATURE:
<223> OTHER INFORMATION: sequence of recombinant antibody or functional part thereof

<400> SEQUENCE: 195

Asp Val Val Met Thr Gln Ser Pro Ser Ser Leu Ser Ala Ser Val Gly
1 5 10 15

Asp Arg Val Thr Ile Thr Cys Gln Ala Ser Gln Ile Ile Ser Ser Arg
20 25 30

Ser Ala Trp Tyr Gln Gln Lys Pro Gly Gln Pro Pro Lys Leu Leu Ile
35 40 45

Tyr Gln Ala Ser Lys Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Cys Thr Tyr Ile Asp Ser Asn
85 90 95

Phe Gly Ala Phe Gly Gly Gly Thr Lys Leu Thr Val Leu Gly
100 105 110

<210> SEQ ID NO 196
<211> LENGTH: 251
<212> TYPE: PRT
<213> ORGANISM: Artificial Sequence
<220> FEATURE:
<223> OTHER INFORMATION: sequence of recombinant antibody or functional part thereof

<400> SEQUENCE: 196

Asp Val Val Met Thr Gln Ser Pro Ser Ser Leu Ser Ala Ser Val Gly
1 5 10 15

Asp Arg Val Thr Ile Thr Cys Gln Ala Ser Gln Ile Ile Ser Ser Arg
20 25 30

Ser Ala Trp Tyr Gln Gln Lys Pro Gly Gln Pro Pro Lys Leu Leu Ile
35 40 45

Tyr Gln Ala Ser Lys Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Cys Thr Tyr Ile Asp Ser Asn
                85                  90                  95

Phe Gly Ala Phe Gly Gly Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ser Ser Tyr Trp Ile Cys Trp Val Arg Gln Ala Pro Gly Lys Gly Leu
                165                 170                 175

Glu Trp Val Gly Cys Val Phe Thr Gly Asp Gly Thr Thr Tyr Tyr Ala
            180                 185                 190

Ser Trp Ala Lys Gly Arg Phe Thr Ile Ser Arg Asp Asn Ser Lys Asn
        195                 200                 205

Thr Val Tyr Leu Gln Met Asn Ser Leu Arg Ala Glu Asp Thr Ala Thr
    210                 215                 220

Tyr Phe Cys Ala Arg Pro Val Ser Val Tyr Tyr Tyr Gly Met Asp Leu
225                 230                 235                 240

Trp Gly Gln Gly Thr Leu Val Thr Val Ser Ser
                245                 250


<210> SEQ ID NO 197
<211> LENGTH: 255
<212> TYPE: PRT
<213> ORGANISM: Homo sapiens

<400> SEQUENCE: 197

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205
```

```
Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 198
<211> LENGTH: 290
<212> TYPE: PRT
<213> ORGANISM: Homo sapiens

<400> SEQUENCE: 198

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 199
<211> LENGTH: 11
<212> TYPE: PRT
```

<213> ORGANISM: Homo sapiens

<400> SEQUENCE: 199

Phe Gly Thr Gly Thr Lys Val Thr Val Leu Gly
1 5 10

<210> SEQ ID NO 200
<211> LENGTH: 11
<212> TYPE: PRT
<213> ORGANISM: Homo sapiens

<400> SEQUENCE: 200

Phe Gly Gly Gly Thr Lys Leu Thr Val Leu Gly
1 5 10

<210> SEQ ID NO 201
<211> LENGTH: 11
<212> TYPE: PRT
<213> ORGANISM: Homo sapiens

<400> SEQUENCE: 201

Phe Gly Gly Gly Thr Gln Leu Ile Ile Leu Gly
1 5 10

<210> SEQ ID NO 202
<211> LENGTH: 11
<212> TYPE: PRT
<213> ORGANISM: Homo sapiens

<400> SEQUENCE: 202

Phe Gly Glu Gly Thr Glu Leu Thr Val Leu Gly
1 5 10

<210> SEQ ID NO 203
<211> LENGTH: 11
<212> TYPE: PRT
<213> ORGANISM: Homo sapiens

<400> SEQUENCE: 203

Phe Gly Ser Gly Thr Lys Val Thr Val Leu Gly
1 5 10

<210> SEQ ID NO 204
<211> LENGTH: 11
<212> TYPE: PRT
<213> ORGANISM: Homo sapiens

<400> SEQUENCE: 204

Phe Gly Gly Gly Thr Gln Leu Thr Val Leu Gly
1 5 10

<210> SEQ ID NO 205
<211> LENGTH: 11
<212> TYPE: PRT
<213> ORGANISM: Homo sapiens

<400> SEQUENCE: 205

Phe Gly Gly Gly Thr Gln Leu Thr Ala Leu Gly
1 5 10

<210> SEQ ID NO 206
<211> LENGTH: 20
<212> TYPE: PRT
<213> ORGANISM: Artificial Sequence
<220> FEATURE:

```
<223> OTHER INFORMATION: sequence of recombinant antibody or functional
      part thereof

<400> SEQUENCE: 206

Gly Gly Gly Gly Ser Gly Gly Gly Gly Ser Gly Gly Gly Gly Ser Gly
1               5                   10                  15

Gly Gly Gly Ser
            20


<210> SEQ ID NO 207
<211> LENGTH: 5
<212> TYPE: PRT
<213> ORGANISM: Artificial Sequence
<220> FEATURE:
<223> OTHER INFORMATION: sequence of recombinant antibody or functional
      part thereof

<400> SEQUENCE: 207

Gly Gly Gly Gly Ser
1               5


<210> SEQ ID NO 208
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 208

Gly Gly Gly Gly Ser Gly Gly Gly Gly Ser
1               5                   10


<210> SEQ ID NO 209
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160
```

```
Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490


<210> SEQ ID NO 210
<211> LENGTH: 499
<212> TYPE: PRT
<213> ORGANISM: Artificial Sequence
<220> FEATURE:
<223> OTHER INFORMATION: sequence of recombinant antibody or functional
      part thereof

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
```

```
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Ser
    130                 135                 140

Phe Asn Asn Asp Tyr Asp Met Cys Trp Val Arg Gln Ala Pro Gly Lys
145                 150                 155                 160

Gly Leu Glu Trp Ile Gly Cys Ile Asp Thr Gly Asp Gly Ser Thr Tyr
                165                 170                 175

Tyr Ala Ser Trp Ala Lys Gly Arg Phe Thr Ile Ser Arg Asp Asn Ser
            180                 185                 190

Lys Asn Thr Val Tyr Leu Gln Met Asn Ser Leu Arg Ala Glu Asp Thr
        195                 200                 205

Ala Val Tyr Tyr Cys Ala Arg Glu Ala Ala Ser Ser Ser Gly Tyr Gly
    210                 215                 220

Met Gly Tyr Phe Asp Leu Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ser Ser Gln Ser
        275                 280                 285

Val Tyr Asp Asn Asn Trp Leu Ala Trp Tyr Gln Gln Lys Pro Gly Lys
    290                 295                 300

Ala Pro Lys Leu Leu Ile Tyr Arg Ala Ser Asn Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Gly
            340                 345                 350

Thr Tyr Leu Ser Ser Asn Trp Tyr Trp Ala Phe Gly Thr Gly Thr Lys
        355                 360                 365

Val Thr Val Leu Gly Gly Gly Gly Gly Ser Gln Val Gln Leu Gln Glu
    370                 375                 380

Ser Gly Pro Gly Leu Val Lys Pro Ser Glu Thr Leu Ser Leu Thr Cys
385                 390                 395                 400

Lys Val Ser Gly Phe Ser Phe Ser Ser Gly Tyr Asp Met Cys Trp Ile
                405                 410                 415

Arg Gln Pro Pro Gly Lys Gly Leu Glu Trp Ile Gly Cys Val Val Ala
            420                 425                 430

Gly Ser Val Asp Ile Thr Tyr Tyr Ala Ser Trp Ala Lys Gly Arg Val
        435                 440                 445
```

```
Thr Ile Ser Val Asp Ser Ser Lys Asn Gln Phe Ser Leu Lys Leu Ser
    450                 455                 460

Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
                485                 490                 495

Val Ser Ser


<210> SEQ ID NO 211
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Val Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Val Ser Leu Lys Leu Ser Ser Val Thr Ala Ala Asp
        195                 200                 205

Thr Ala Val Tyr Phe Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Pro Pro Lys
    290                 295                 300
```

```
Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490
```

<210> SEQ ID NO 212
<211> LENGTH: 493
<212> TYPE: PRT
<213> ORGANISM: Artificial Sequence
<220> FEATURE:
<223> OTHER INFORMATION: sequence of recombinant antibody or functional part thereof

<400> SEQUENCE: 212

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Ala Ser Gly Phe Ser
    130                 135                 140

Phe Ser Asn Ser Tyr Trp Ile Cys Trp Val Arg Gln Pro Pro Gly Lys
145                 150                 155                 160

Gly Leu Glu Trp Ile Gly Cys Thr Phe Val Gly Ser Ser Asp Ser Thr
```

```
                165                 170                 175

Tyr Tyr Ala Asn Trp Ala Lys Gly Arg Val Thr Ile Ser Lys Asp Ser
            180                 185                 190

Ser Lys Asn Gln Val Ser Leu Lys Leu Ser Ser Val Thr Ala Ala Asp
        195                 200                 205

Thr Ala Val Tyr Phe Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Leu Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Pro Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490


<210> SEQ ID NO 213
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30
```

```
Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
```

```
    450                 455                 460

Thr Ala Val Tyr Phe Cys Ala Arg Lys Asp Ala Tyr Ser Asp Ala Phe
465                 470                 475                 480

Asn Leu Trp Gly Gln Gly Thr Leu Val Thr Val Ser Ser
                485                 490


<210> SEQ ID NO 214
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 214

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320
```

```
Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Ser Gln Leu Gln Glu Ser Gly Pro Gly Leu Val
    370                 375                 380

Lys Pro Ser Glu Thr Leu Ser Leu Thr Cys Lys Ala Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
            420                 425                 430

Tyr Tyr Ala Ser Trp Ala Lys Gly Arg Val Thr Ile Ser Lys Asp Ser
        435                 440                 445

Ser Lys Asn Gln Val Ser Leu Lys Leu Ser Ser Val Thr Ala Ala Asp
    450                 455                 460

Thr Ala Val Tyr Phe Cys Ala Arg Lys Asp Ala Tyr Ser Asp Ala Phe
465                 470                 475                 480

Asn Leu Trp Gly Gln Gly Thr Leu Val Thr Val Ser Ser
                485                 490


<210> SEQ ID NO 215
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 215

Asp Ile Gln Met Thr Gln Ser Pro Ser Ser Leu Ser Ala Ser Val Gly
1               5                   10                  15

Asp Ala Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190
```

```
Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Glu Val Gln Leu Val Glu Ser Gly Gly Gly Leu Val
    370                 375                 380

Gln Pro Gly Gly Ser Leu Arg Leu Ser Cys Ala Ala Ser Gly Phe Ser
385                 390                 395                 400

Phe Ser Ser Gly Tyr Asp Met Cys Trp Val Arg Gln Ala Pro Gly Lys
                405                 410                 415

Gly Leu Glu Trp Val Gly Cys Val Val Ala Gly Ser Val Asp Ile Thr
            420                 425                 430

Tyr Tyr Ala Ser Trp Ala Lys Gly Arg Phe Thr Ile Ser Arg Asp Asn
        435                 440                 445

Ser Lys Asn Thr Val Tyr Leu Gln Met Asn Ser Leu Arg Ala Glu Asp
    450                 455                 460

Thr Ala Thr Tyr Tyr Cys Ala Arg Lys Asp Ala Tyr Ser Asp Ala Phe
465                 470                 475                 480

Asn Leu Trp Gly Pro Gly Thr Leu Val Thr Val Ser Ser
                485                 490


<210> SEQ ID NO 216
<211> LENGTH: 755
<212> TYPE: PRT
<213> ORGANISM: Artificial Sequence
<220> FEATURE:
<223> OTHER INFORMATION: sequence of recombinant antibody or functional
      part thereof

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480
```

```
Asn Leu Trp Gly Gln Gly Thr Leu Val Thr Val Ser Ser Gly Gly Gly
                485                 490                 495

Gly Ser Gly Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
        515                 520                 525

Glu Ser Val Tyr Ser Asn Asn Gln Leu Ser Trp Tyr Gln Gln Lys Pro
    530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Ser Asp Thr Ala Phe Gly Gly Gly Thr
        595                 600                 605

Lys Leu Thr Val Leu Gly Gly Gly Gly Gly Ser Gly Gly Gly Gly Ser
    610                 615                 620

Gly Gly Gly Gly Ser Gly Gly Gly Gly Ser Glu Val Gln Leu Val Glu
625                 630                 635                 640

Ser Gly Gly Gly Leu Val Gln Pro Gly Gly Ser Leu Arg Leu Ser Cys
                645                 650                 655

Ala Ala Ser Gly Phe Ser Leu Ser Ser Asn Ala Met Gly Trp Val Arg
            660                 665                 670

Gln Ala Pro Gly Lys Gly Leu Glu Tyr Ile Gly Ile Ile Ser Val Gly
        675                 680                 685

Gly Phe Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755


<210> SEQ ID NO 217
<211> LENGTH: 761
<212> TYPE: PRT
<213> ORGANISM: Artificial Sequence
<220> FEATURE:
<223> OTHER INFORMATION: sequence of recombinant antibody or functional
      part thereof

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Asn Asn Asp Tyr Asp Met Cys Trp Ile Arg Gln Pro Pro Gly Lys
145                 150                 155                 160

Gly Leu Glu Trp Ile Gly Cys Ile Asp Thr Gly Asp Gly Ser Thr Tyr
                165                 170                 175

Tyr Ala Ser Trp Ala Lys Gly Arg Val Thr Ile Ser Val Asp Ser Ser
            180                 185                 190

Lys Asn Gln Phe Ser Leu Lys Leu Ser Ser Val Thr Ala Ala Asp Thr
        195                 200                 205

Ala Val Tyr Tyr Cys Ala Arg Glu Ala Ala Ser Ser Ser Gly Tyr Gly
    210                 215                 220

Met Gly Tyr Phe Asp Leu Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ser Ser Gln Ser
        275                 280                 285

Val Tyr Asp Asn Asn Trp Leu Ala Trp Tyr Gln Gln Lys Pro Gly Lys
    290                 295                 300

Ala Pro Lys Leu Leu Ile Tyr Arg Ala Ser Asn Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Gly
            340                 345                 350

Thr Tyr Leu Ser Ser Asn Trp Tyr Trp Ala Phe Gly Thr Gly Thr Lys
        355                 360                 365

Val Thr Val Leu Gly Gly Gly Gly Gly Ser Gln Val Gln Leu Gln Glu
    370                 375                 380

Ser Gly Pro Gly Leu Val Lys Pro Ser Glu Thr Leu Ser Leu Thr Cys
385                 390                 395                 400

Lys Val Ser Gly Phe Ser Phe Ser Ser Gly Tyr Asp Met Cys Trp Ile
                405                 410                 415

Arg Gln Pro Pro Gly Lys Gly Leu Glu Trp Ile Gly Cys Val Val Ala
            420                 425                 430

Gly Ser Val Asp Ile Thr Tyr Tyr Ala Ser Trp Ala Lys Gly Arg Val
        435                 440                 445

Thr Ile Ser Val Asp Ser Ser Lys Asn Gln Phe Ser Leu Lys Leu Ser
    450                 455                 460

Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
                485                 490                 495
```

Val Ser Ser Gly Gly Gly Gly Ser Gly Gly Gly Gly Ser Ile Gln Met
500 505 510

Thr Gln Ser Pro Ser Ser Leu Ser Ala Ser Val Gly Asp Arg Val Thr
515 520 525

Ile Thr Cys Gln Ser Ser Glu Ser Val Tyr Ser Asn Asn Gln Leu Ser
530 535 540

Trp Tyr Gln Gln Lys Pro Gly Gln Pro Pro Lys Leu Leu Ile Tyr Asp
545 550 555 560

Ala Ser Asp Leu Ala Ser Gly Val Pro Ser Arg Phe Ser Gly Ser Gly
565 570 575

Ser Gly Thr Asp Phe Thr Leu Thr Ile Ser Ser Leu Gln Pro Glu Asp
580 585 590

Phe Ala Thr Tyr Tyr Cys Ala Gly Gly Phe Ser Ser Ser Ser Asp Thr
595 600 605

Ala Phe Gly Gly Gly Thr Lys Leu Thr Val Leu Gly Gly Gly Gly Gly
610 615 620

Ser Gly Gly Gly Gly Ser Gly Gly Gly Gly Ser Gly Gly Gly Gly Ser
625 630 635 640

Glu Val Gln Leu Val Glu Ser Gly Gly Gly Leu Val Gln Pro Gly Gly
645 650 655

Ser Leu Arg Leu Ser Cys Ala Ala Ser Gly Phe Ser Leu Ser Ser Asn
660 665 670

Ala Met Gly Trp Val Arg Gln Ala Pro Gly Lys Gly Leu Glu Tyr Ile
675 680 685

Gly Ile Ile Ser Val Gly Gly Phe Thr Tyr Tyr Ala Ser Trp Ala Lys
690 695 700

Gly Arg Phe Thr Ile Ser Arg Asp Asn Ser Lys Asn Thr Val Tyr Leu
705 710 715 720

Gln Met Asn Ser Leu Arg Ala Glu Asp Thr Ala Thr Tyr Phe Cys Ala
725 730 735

Arg Asp Arg His Gly Gly Asp Ser Ser Gly Ala Phe Tyr Leu Trp Gly
740 745 750

Gln Gly Thr Leu Val Thr Val Ser Ser
755 760

<210> SEQ ID NO 218
<211> LENGTH: 753
<212> TYPE: PRT
<213> ORGANISM: Artificial Sequence
<220> FEATURE:
<223> OTHER INFORMATION: sequence of recombinant antibody or functional part thereof

<400> SEQUENCE: 218

Asp Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asp Tyr
20 25 30

Leu Ala Trp Tyr Gln Gln Lys Pro Gly Lys Ala Pro Lys Leu Leu Ile
35 40 45

Tyr Lys Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Tyr Ile Ile Thr Asp

```
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser Gly Gly Gly
                485                 490                 495

Gly Ser Gly Gly Gly Gly Ser Val Val Met Thr Gln Ser Pro Ser Ser
            500                 505                 510
```

```
Leu Ser Ala Ser Val Gly Asp Arg Val Thr Ile Thr Cys Gln Ala Ser
        515                 520                 525

Gln Ile Ile Ser Ser Arg Ser Ala Trp Tyr Gln Gln Lys Pro Gly Gln
    530                 535                 540

Pro Pro Lys Leu Leu Ile Tyr Gln Ala Ser Lys Leu Ala Ser Gly Val
545                 550                 555                 560

Pro Ser Arg Phe Ser Gly Ser Gly Ser Gly Thr Asp Phe Thr Leu Thr
                565                 570                 575

Ile Ser Ser Leu Gln Pro Glu Asp Phe Ala Thr Tyr Tyr Cys Gln Cys
            580                 585                 590

Thr Tyr Ile Asp Ser Asn Phe Gly Ala Phe Gly Gly Gly Thr Lys Leu
        595                 600                 605

Thr Val Leu Gly Gly Gly Gly Gly Ser Gly Gly Gly Gly Ser Gly Gly
    610                 615                 620

Gly Gly Ser Gly Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Ser Phe Ser Ser Ser Tyr Trp Ile Cys Trp Val Arg Gln
            660                 665                 670

Ala Pro Gly Lys Gly Leu Glu Trp Val Gly Cys Val Phe Thr Gly Asp
        675                 680                 685

Gly Thr Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Pro Val Ser Val Tyr
                725                 730                 735

Tyr Tyr Gly Met Asp Leu Trp Gly Gln Gly Thr Leu Val Thr Val Ser
            740                 745                 750

Ser


<210> SEQ ID NO 219
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110
```

```
Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Asn Asn Asp Tyr Asp Met Cys Trp Ile Arg Gln Pro Pro Gly Lys
145                 150                 155                 160

Gly Leu Glu Trp Ile Gly Cys Ile Asp Thr Gly Asp Gly Ser Thr Tyr
                165                 170                 175

Tyr Ala Ser Trp Ala Lys Gly Arg Val Thr Ile Ser Val Asp Ser Ser
            180                 185                 190

Lys Asn Gln Phe Ser Leu Lys Leu Ser Ser Val Thr Ala Ala Asp Thr
        195                 200                 205

Ala Val Tyr Tyr Cys Ala Arg Glu Ala Ala Ser Ser Ser Gly Tyr Gly
    210                 215                 220

Met Gly Tyr Phe Asp Leu Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ser Ser Gln Ser
        275                 280                 285

Val Tyr Asp Asn Asn Trp Leu Ala Trp Tyr Gln Gln Lys Pro Gly Lys
    290                 295                 300

Ala Pro Lys Leu Leu Ile Tyr Arg Ala Ser Asn Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Gly
            340                 345                 350

Thr Tyr Leu Ser Ser Asn Trp Tyr Trp Ala Phe Gly Thr Gly Thr Lys
        355                 360                 365

Val Thr Val Leu Gly Gly Gly Gly Gly Ser Gln Val Gln Leu Gln Glu
    370                 375                 380

Ser Gly Pro Gly Leu Val Lys Pro Ser Glu Thr Leu Ser Leu Thr Cys
385                 390                 395                 400

Lys Val Ser Gly Phe Ser Phe Ser Ser Gly Tyr Asp Met Cys Trp Ile
                405                 410                 415

Arg Gln Pro Pro Gly Lys Gly Leu Glu Trp Ile Gly Cys Val Val Ala
            420                 425                 430

Gly Ser Val Asp Ile Thr Tyr Tyr Ala Ser Trp Ala Lys Gly Arg Val
        435                 440                 445

Thr Ile Ser Val Asp Ser Ser Lys Asn Gln Phe Ser Leu Lys Leu Ser
    450                 455                 460

Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
                485                 490                 495

Val Ser Ser Gly Gly Gly Gly Ser Gly Gly Gly Gly Ser Val Val Met
            500                 505                 510

Thr Gln Ser Pro Ser Ser Leu Ser Ala Ser Val Gly Asp Arg Val Thr
        515                 520                 525
```

```
Ile Thr Cys Gln Ala Ser Gln Ile Ile Ser Ser Arg Ser Ala Trp Tyr
    530                 535                 540

Gln Gln Lys Pro Gly Gln Pro Pro Lys Leu Leu Ile Tyr Gln Ala Ser
545                 550                 555                 560

Lys Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590

Thr Tyr Tyr Cys Gln Cys Thr Tyr Ile Asp Ser Asn Phe Gly Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Phe Ser Ser Ser Tyr Trp
            660                 665                 670

Ile Cys Trp Val Arg Gln Ala Pro Gly Lys Gly Leu Glu Trp Val Gly
        675                 680                 685

Cys Val Phe Thr Gly Asp Gly Thr Thr Tyr Tyr Ala Ser Trp Ala Lys
    690                 695                 700

Gly Arg Phe Thr Ile Ser Arg Asp Asn Ser Lys Asn Thr Val Tyr Leu
705                 710                 715                 720

Gln Met Asn Ser Leu Arg Ala Glu Asp Thr Ala Thr Tyr Phe Cys Ala
                725                 730                 735

Arg Pro Val Ser Val Tyr Tyr Tyr Gly Met Asp Leu Trp Gly Gln Gly
            740                 745                 750

Thr Leu Val Thr Val Ser Ser
        755


<210> SEQ ID NO 220
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Gln Val Gln Leu Gln Glu Ser Gly Pro
        115                 120                 125
```

```
Gly Leu Val Lys Pro Ser Glu Thr Leu Ser Leu Thr Cys Lys Val Ser
    130                 135                 140

Gly Phe Ser Phe Ser Asn Ser Tyr Trp Ile Cys Trp Ile Arg Gln Pro
145                 150                 155                 160

Pro Gly Lys Gly Leu Glu Trp Ile Gly Cys Thr Phe Val Gly Ser Ser
                165                 170                 175

Asp Ser Thr Tyr Tyr Ala Asn Trp Ala Lys Gly Arg Val Thr Ile Ser
            180                 185                 190

Val Asp Ser Ser Lys Asn Gln Phe Ser Leu Lys Leu Ser Ser Val Thr
        195                 200                 205

Ala Ala Asp Thr Ala Val Tyr Tyr Cys Ala Arg His Pro Ser Asp Ala
    210                 215                 220

Val Tyr Gly Tyr Ala Asn Asn Leu Trp Gly Gln Gly Thr Leu Val Thr
225                 230                 235                 240

Val Ser Ser Gly Gly Gly Gly Ser Gly Gly Gly Gly Ser Gly Gly Gly
                245                 250                 255

Gly Ser Gly Gly Gly Gly Ser Ile Gln Met Thr Gln Ser Pro Ser Ser
            260                 265                 270

Leu Ser Ala Ser Val Gly Asp Arg Val Thr Ile Thr Cys Gln Ala Ser
        275                 280                 285

Gln Ser Ile Asn Asn Val Leu Ala Trp Tyr Gln Gln Lys Pro Gly Lys
    290                 295                 300

Ala Pro Lys Leu Leu Ile Tyr Arg Ala Ser Thr Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Ser
            340                 345                 350

Ser Tyr Gly Asn Tyr Gly Asp Phe Gly Thr Gly Thr Lys Val Thr Val
        355                 360                 365

Leu Gly Gly Gly Gly Gly Ser Gln Val Gln Leu Gln Glu Ser Gly Pro
    370                 375                 380

Gly Leu Val Lys Pro Ser Glu Thr Leu Ser Leu Thr Cys Lys Val Ser
385                 390                 395                 400

Gly Phe Ser Phe Asn Ser Asp Tyr Trp Ile Tyr Trp Ile Arg Gln Pro
                405                 410                 415

Pro Gly Lys Gly Leu Glu Trp Ile Gly Ser Ile Tyr Gly Gly Ser Ser
            420                 425                 430

Gly Asn Thr Gln Tyr Ala Ser Trp Ala Gln Gly Arg Val Thr Ile Ser
        435                 440                 445

Val Asp Ser Ser Lys Asn Gln Phe Ser Leu Lys Leu Ser Ser Val Thr
    450                 455                 460

Ala Ala Asp Thr Ala Val Tyr Tyr Cys Ala Arg Gly Tyr Val Asp Tyr
465                 470                 475                 480

Gly Gly Ala Thr Asp Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540
```

```
Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590

Thr Tyr Tyr Cys Ala Gly Gly Phe Ser Ser Ser Ser Asp Thr Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685

Ile Ser Val Gly Gly Phe Thr Tyr Tyr Ala Ser Trp Ala Lys Gly Arg
    690                 695                 700

Phe Thr Ile Ser Arg Asp Asn Ser Lys Asn Thr Val Tyr Leu Gln Met
705                 710                 715                 720

Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755


<210> SEQ ID NO 221
<211> LENGTH: 758
<212> TYPE: PRT
<213> ORGANISM: Artificial Sequence
<220> FEATURE:
<223> OTHER INFORMATION: sequence of recombinant antibody or functional
      part thereof

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Gln Val Gln Leu Gln Glu Ser Gly Pro
        115                 120                 125

Gly Leu Val Lys Pro Ser Glu Thr Leu Ser Leu Thr Cys Lys Val Ser
    130                 135                 140
```

```
Gly Phe Ser Phe Ser Asn Ser Tyr Trp Ile Cys Trp Ile Arg Gln Pro
145                 150                 155                 160

Pro Gly Lys Gly Leu Glu Trp Ile Gly Cys Thr Phe Val Gly Ser Ser
                165                 170                 175

Asp Ser Thr Tyr Tyr Ala Asn Trp Ala Lys Gly Arg Val Thr Ile Ser
            180                 185                 190

Val Asp Ser Ser Lys Asn Gln Phe Ser Leu Lys Leu Ser Ser Val Thr
        195                 200                 205

Ala Ala Asp Thr Ala Val Tyr Tyr Cys Ala Arg His Pro Ser Asp Ala
    210                 215                 220

Val Tyr Gly Tyr Ala Asn Asn Leu Trp Gly Gln Gly Thr Leu Val Thr
225                 230                 235                 240

Val Ser Ser Gly Gly Gly Gly Ser Gly Gly Gly Gly Ser Gly Gly Gly
                245                 250                 255

Gly Ser Gly Gly Gly Gly Ser Asp Ile Gln Met Thr Gln Ser Pro Ser
            260                 265                 270

Ser Leu Ser Ala Ser Val Gly Asp Arg Val Thr Ile Thr Cys Gln Ala
        275                 280                 285

Ser Gln Ser Ile Asn Asn Val Leu Ala Trp Tyr Gln Gln Lys Pro Gly
    290                 295                 300

Lys Ala Pro Lys Leu Leu Ile Tyr Arg Ala Ser Thr Leu Ala Ser Gly
305                 310                 315                 320

Val Pro Ser Arg Phe Ser Gly Ser Gly Ser Gly Thr Asp Phe Thr Leu
                325                 330                 335

Thr Ile Ser Ser Leu Gln Pro Glu Asp Phe Ala Thr Tyr Tyr Cys Gln
            340                 345                 350

Ser Ser Tyr Gly Asn Tyr Gly Asp Phe Gly Thr Gly Thr Lys Val Thr
        355                 360                 365

Val Leu Gly Gly Gly Gly Gly Ser Gln Val Gln Leu Gln Glu Ser Gly
    370                 375                 380

Pro Gly Leu Val Lys Pro Ser Glu Thr Leu Ser Leu Thr Cys Lys Val
385                 390                 395                 400

Ser Gly Phe Ser Phe Asn Ser Asp Tyr Trp Ile Tyr Trp Ile Arg Gln
                405                 410                 415

Pro Pro Gly Lys Gly Leu Glu Trp Ile Gly Ser Ile Tyr Gly Gly Ser
            420                 425                 430

Ser Gly Asn Thr Gln Tyr Ala Ser Trp Ala Gln Gly Arg Val Thr Ile
        435                 440                 445

Ser Val Asp Ser Ser Lys Asn Gln Phe Ser Leu Lys Leu Ser Ser Val
    450                 455                 460

Thr Ala Ala Asp Thr Ala Val Tyr Tyr Cys Ala Arg Gly Tyr Val Asp
465                 470                 475                 480

Tyr Gly Gly Ala Thr Asp Leu Trp Gly Gln Gly Thr Leu Val Thr Val
                485                 490                 495

Ser Ser Gly Gly Gly Gly Ser Gly Gly Gly Gly Ser Val Val Met Thr
            500                 505                 510

Gln Ser Pro Ser Ser Leu Ser Ala Ser Val Gly Asp Arg Val Thr Ile
        515                 520                 525

Thr Cys Gln Ala Ser Gln Ile Ile Ser Ser Arg Ser Ala Trp Tyr Gln
    530                 535                 540

Gln Lys Pro Gly Gln Pro Pro Lys Leu Leu Ile Tyr Gln Ala Ser Lys
545                 550                 555                 560
```

```
Leu Ala Ser Gly Val Pro Ser Arg Phe Ser Gly Ser Gly Ser Gly Thr
                565                 570                 575

Asp Phe Thr Leu Thr Ile Ser Ser Leu Gln Pro Glu Asp Phe Ala Thr
            580                 585                 590

Tyr Tyr Cys Gln Cys Thr Tyr Ile Asp Ser Asn Phe Gly Ala Phe Gly
        595                 600                 605

Gly Gly Thr Lys Leu Thr Val Leu Gly Gly Gly Gly Gly Ser Gly Gly
    610                 615                 620

Gly Gly Ser Gly Gly Gly Gly Ser Gly Gly Gly Gly Ser Glu Val Gln
625                 630                 635                 640

Leu Val Glu Ser Gly Gly Gly Leu Val Gln Pro Gly Gly Ser Leu Arg
                645                 650                 655

Leu Ser Cys Ala Ala Ser Gly Phe Ser Phe Ser Ser Ser Tyr Trp Ile
            660                 665                 670

Cys Trp Val Arg Gln Ala Pro Gly Lys Gly Leu Glu Trp Val Gly Cys
        675                 680                 685

Val Phe Thr Gly Asp Gly Thr Thr Tyr Tyr Ala Ser Trp Ala Lys Gly
    690                 695                 700

Arg Phe Thr Ile Ser Arg Asp Asn Ser Lys Asn Thr Val Tyr Leu Gln
705                 710                 715                 720

Met Asn Ser Leu Arg Ala Glu Asp Thr Ala Thr Tyr Phe Cys Ala Arg
                725                 730                 735

Pro Val Ser Val Tyr Tyr Tyr Gly Met Asp Leu Trp Gly Gln Gly Thr
            740                 745                 750

Leu Val Thr Val Ser Ser
        755
```

<210> SEQ ID NO 222
<211> LENGTH: 759
<212> TYPE: PRT
<213> ORGANISM: Artificial Sequence
<220> FEATURE:
<223> OTHER INFORMATION: sequence of recombinant antibody or functional part thereof

<400> SEQUENCE: 222

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Ser Phe Ser Asn Ser Tyr Trp Ile Cys Trp Val Arg Gln Ala
145                 150                 155                 160
```

```
Pro Gly Lys Cys Leu Glu Trp Ile Gly Cys Thr Phe Val Gly Ser Ser
                165                 170                 175

Asp Ser Thr Tyr Tyr Ala Asn Trp Ala Lys Gly Arg Phe Thr Ile Ser
            180                 185                 190

Arg Asp Asn Ser Lys Asn Thr Val Tyr Leu Gln Met Asn Ser Leu Arg
        195                 200                 205

Ala Glu Asp Thr Ala Val Tyr Tyr Cys Ala Arg His Pro Ser Asp Ala
    210                 215                 220

Val Tyr Gly Tyr Ala Asn Asn Leu Trp Gly Gln Gly Thr Leu Val Thr
225                 230                 235                 240

Val Ser Ser Gly Gly Gly Gly Ser Gly Gly Gly Gly Ser Gly Gly Gly
                245                 250                 255

Gly Ser Gly Gly Gly Gly Ser Ile Gln Met Thr Gln Ser Pro Ser Ser
            260                 265                 270

Leu Ser Ala Ser Val Gly Asp Arg Val Thr Ile Thr Cys Gln Ala Ser
        275                 280                 285

Gln Ser Ile Asn Asn Val Leu Ala Trp Tyr Gln Gln Lys Pro Gly Lys
    290                 295                 300

Ala Pro Lys Leu Leu Ile Tyr Arg Ala Ser Thr Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Ser
            340                 345                 350

Ser Tyr Gly Asn Tyr Gly Asp Phe Gly Cys Gly Thr Lys Val Thr Val
        355                 360                 365

Leu Gly Gly Gly Gly Gly Ser Gln Val Gln Leu Gln Glu Ser Gly Pro
    370                 375                 380

Gly Leu Val Lys Pro Ser Glu Thr Leu Ser Leu Thr Cys Lys Val Ser
385                 390                 395                 400

Gly Phe Ser Phe Asn Ser Asp Tyr Trp Ile Tyr Trp Ile Arg Gln Pro
                405                 410                 415

Pro Gly Lys Gly Leu Glu Trp Ile Gly Ser Ile Tyr Gly Gly Ser Ser
            420                 425                 430

Gly Asn Thr Gln Tyr Ala Ser Trp Ala Gln Gly Arg Val Thr Ile Ser
        435                 440                 445

Val Asp Ser Ser Lys Asn Gln Phe Ser Leu Lys Leu Ser Ser Val Thr
    450                 455                 460

Ala Ala Asp Thr Ala Val Tyr Tyr Cys Ala Arg Gly Tyr Val Asp Tyr
465                 470                 475                 480

Gly Gly Ala Thr Asp Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540

Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575
```

```
Thr Asp Phe Thr Leu Thr Ile Ser Ser Leu Gln Pro Glu Asp Phe Ala
            580                 585                 590

Thr Tyr Tyr Cys Ala Gly Gly Phe Ser Ser Ser Ser Asp Thr Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685

Ile Ser Val Gly Gly Phe Thr Tyr Tyr Ala Ser Trp Ala Lys Gly Arg
    690                 695                 700

Phe Thr Ile Ser Arg Asp Asn Ser Lys Asn Thr Val Tyr Leu Gln Met
705                 710                 715                 720

Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755


<210> SEQ ID NO 223
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 223

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Ser Phe Ser Asn Ser Tyr Trp Ile Cys Trp Val Arg Gln Ala
145                 150                 155                 160

Pro Gly Lys Cys Leu Glu Trp Ile Gly Cys Thr Phe Val Gly Ser Ser
                165                 170                 175
```

```
Asp Ser Thr Tyr Tyr Ala Asn Trp Ala Lys Gly Arg Phe Thr Ile Ser
            180                 185                 190

Arg Asp Asn Ser Lys Asn Thr Val Tyr Leu Gln Met Asn Ser Leu Arg
        195                 200                 205

Ala Glu Asp Thr Ala Val Tyr Tyr Cys Ala Arg His Pro Ser Asp Ala
    210                 215                 220

Val Tyr Gly Tyr Ala Asn Asn Leu Trp Gly Gln Gly Thr Leu Val Thr
225                 230                 235                 240

Val Ser Ser Gly Gly Gly Gly Ser Gly Gly Gly Gly Ser Gly Gly Gly
                245                 250                 255

Gly Ser Gly Gly Gly Gly Ser Ile Gln Met Thr Gln Ser Pro Ser Ser
            260                 265                 270

Leu Ser Ala Ser Val Gly Asp Arg Val Thr Ile Thr Cys Gln Ala Ser
        275                 280                 285

Gln Ser Ile Asn Asn Val Leu Ala Trp Tyr Gln Gln Lys Pro Gly Lys
    290                 295                 300

Ala Pro Lys Leu Leu Ile Tyr Arg Ala Ser Thr Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Ser
            340                 345                 350

Ser Tyr Gly Asn Tyr Gly Asp Phe Gly Cys Gly Thr Lys Val Thr Val
        355                 360                 365

Leu Gly Gly Gly Gly Gly Ser Glu Val Gln Leu Val Glu Ser Gly Gly
    370                 375                 380

Gly Leu Val Gln Pro Gly Gly Ser Leu Arg Leu Ser Cys Ala Ala Ser
385                 390                 395                 400

Gly Phe Ser Phe Asn Ser Asp Tyr Trp Ile Tyr Trp Val Arg Gln Ala
                405                 410                 415

Pro Gly Lys Gly Leu Glu Trp Ile Ala Ser Ile Tyr Gly Gly Ser Ser
            420                 425                 430

Gly Asn Thr Gln Tyr Ala Ser Trp Ala Gln Gly Arg Phe Thr Ile Ser
        435                 440                 445

Arg Asp Asn Ser Lys Asn Thr Val Tyr Leu Gln Met Asn Ser Leu Arg
    450                 455                 460

Ala Glu Asp Thr Ala Val Tyr Phe Cys Ala Arg Gly Tyr Val Asp Tyr
465                 470                 475                 480

Gly Gly Ala Thr Asp Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540

Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590
```

```
Thr Tyr Tyr Cys Ala Gly Gly Phe Ser Ser Ser Ser Asp Thr Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685

Ile Ser Val Gly Gly Phe Thr Tyr Tyr Ala Ser Trp Ala Lys Gly Arg
    690                 695                 700

Phe Thr Ile Ser Arg Asp Asn Ser Lys Asn Thr Val Tyr Leu Gln Met
705                 710                 715                 720

Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755


<210> SEQ ID NO 224
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly Gly Gly Gly Gly
            100                 105                 110

Ser Glu Val Gln Leu Val Glu Ser Gly Gly Gly Leu Val Gln Pro Gly
        115                 120                 125

Gly Ser Leu Arg Leu Ser Cys Ala Ala Ser Gly Phe Ser Phe Asn Ser
    130                 135                 140

Asp Tyr Trp Ile Tyr Trp Val Arg Gln Ala Pro Gly Lys Gly Leu Glu
145                 150                 155                 160

Trp Ile Ala Ser Ile Tyr Gly Gly Ser Ser Gly Asn Thr Gln Tyr Ala
                165                 170                 175

Ser Trp Ala Gln Gly Arg Phe Thr Ile Ser Arg Asp Asn Ser Lys Asn
            180                 185                 190
```

```
Thr Val Tyr Leu Gln Met Asn Ser Leu Arg Ala Glu Asp Thr Ala Val
        195                 200                 205

Tyr Phe Cys Ala Arg Gly Tyr Val Asp Tyr Gly Gly Ala Thr Asp Leu
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Ile
                245                 250                 255

Gln Met Thr Gln Ser Pro Ala Ser Leu Ser Ala Ser Val Gly Asp Arg
            260                 265                 270

Val Thr Ile Thr Cys Gln Ala Ser Gln Ser Ile Gly Thr Tyr Leu Ala
        275                 280                 285

Trp Tyr Gln Gln Lys Pro Gly Lys Pro Pro Lys Leu Leu Ile Tyr Arg
    290                 295                 300

Ala Phe Ile Leu Ala Ser Gly Val Pro Ser Arg Phe Ser Gly Ser Gly
305                 310                 315                 320

Ser Gly Thr Asp Phe Thr Leu Thr Ile Ser Ser Leu Gln Pro Glu Asp
                325                 330                 335

Phe Ala Thr Tyr Tyr Cys Gln Ser Asn Phe Tyr Ser Asp Ser Thr Thr
            340                 345                 350

Ile Gly Pro Asn Ala Phe Gly Thr Gly Thr Lys Val Thr Val Leu Gly
        355                 360                 365

Gly Gly Gly Gly Ser Glu Val Gln Leu Val Glu Ser Gly Gly Gly Leu
    370                 375                 380

Val Gln Pro Gly Gly Ser Leu Arg Leu Ser Cys Ala Ala Ser Gly Phe
385                 390                 395                 400

Ser Phe Ser Asn Ser Tyr Trp Ile Cys Trp Val Arg Gln Ala Pro Gly
                405                 410                 415

Lys Cys Leu Glu Trp Ile Gly Cys Thr Phe Val Gly Ser Ser Asp Ser
            420                 425                 430

Thr Tyr Tyr Ala Asn Trp Ala Lys Gly Arg Phe Thr Ile Ser Arg Asp
        435                 440                 445

Asn Ser Lys Asn Thr Val Tyr Leu Gln Met Asn Ser Leu Arg Ala Glu
    450                 455                 460

Asp Thr Ala Val Tyr Tyr Cys Ala Arg His Pro Ser Asp Ala Val Tyr
465                 470                 475                 480

Gly Tyr Ala Asn Asn Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540

Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590

Thr Tyr Tyr Cys Ala Gly Gly Phe Ser Ser Ser Ser Asp Thr Ala Phe
        595                 600                 605
```

```
Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685

Ile Ser Val Gly Gly Phe Thr Tyr Tyr Ala Ser Trp Ala Lys Gly Arg
    690                 695                 700

Phe Thr Ile Ser Arg Asp Asn Ser Lys Asn Thr Val Tyr Leu Gln Met
705                 710                 715                 720

Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755


<210> SEQ ID NO 225
<211> LENGTH: 755
<212> TYPE: PRT
<213> ORGANISM: Artificial Sequence
<220> FEATURE:
<223> OTHER INFORMATION: sequence of recombinant antibody or functional
      part thereof

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Ser
    130                 135                 140

Phe Ser Asn Ser Tyr Trp Ile Cys Trp Val Arg Gln Ala Pro Gly Lys
145                 150                 155                 160

Cys Leu Glu Trp Ile Gly Cys Thr Phe Val Gly Ser Ser Asp Ser Thr
                165                 170                 175

Tyr Tyr Ala Asn Trp Ala Lys Gly Arg Phe Thr Ile Ser Arg Asp Asn
            180                 185                 190

Ser Lys Asn Thr Val Tyr Leu Gln Met Asn Ser Leu Arg Ala Glu Asp
        195                 200                 205
```

```
Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Cys Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Ala Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
            420                 425                 430

Tyr Tyr Ala Ser Trp Ala Lys Gly Arg Val Thr Ile Ser Lys Asp Ser
        435                 440                 445

Ser Lys Asn Gln Val Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser Gly Gly Gly
                485                 490                 495

Gly Ser Gly Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
        515                 520                 525

Glu Ser Val Tyr Ser Asn Asn Gln Leu Ser Trp Tyr Gln Gln Lys Pro
    530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Ser Asp Thr Ala Phe Gly Gly Gly Thr
        595                 600                 605

Lys Leu Thr Val Leu Gly Gly Gly Gly Gly Ser Gly Gly Gly Gly Ser
    610                 615                 620
```

```
Gly Gly Gly Gly Ser Gly Gly Gly Gly Ser Glu Val Gln Leu Val Glu
625                 630                 635                 640

Ser Gly Gly Gly Leu Val Gln Pro Gly Gly Ser Leu Arg Leu Ser Cys
                645                 650                 655

Ala Ala Ser Gly Phe Ser Leu Ser Ser Asn Ala Met Gly Trp Val Arg
            660                 665                 670

Gln Ala Pro Gly Lys Gly Leu Glu Tyr Ile Gly Ile Ile Ser Val Gly
        675                 680                 685

Gly Phe Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755


<210> SEQ ID NO 226
<211> LENGTH: 755
<212> TYPE: PRT
<213> ORGANISM: Artificial Sequence
<220> FEATURE:
<223> OTHER INFORMATION: sequence of recombinant antibody or functional
      part thereof

<400> SEQUENCE: 226

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Ser
    130                 135                 140

Phe Ser Asn Ser Tyr Trp Ile Cys Trp Val Arg Gln Ala Pro Gly Lys
145                 150                 155                 160

Cys Leu Glu Trp Ile Gly Cys Thr Phe Val Gly Ser Ser Asp Ser Thr
                165                 170                 175

Tyr Tyr Ala Asn Trp Ala Lys Gly Arg Phe Thr Ile Ser Arg Asp Asn
            180                 185                 190

Ser Lys Asn Thr Val Tyr Leu Gln Met Asn Ser Leu Arg Ala Glu Asp
        195                 200                 205

Thr Ala Val Tyr Tyr Cys Ala Arg His Pro Ser Asp Ala Val Tyr Gly
    210                 215                 220
```

```
Tyr Ala Asn Asn Leu Trp Gly Gln Gly Thr Leu Val Thr Val Ser Ser
225                 230                 235                 240

Gly Gly Gly Gly Ser Gly Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Cys Gly Thr Lys Val Thr Val Leu Gly Gly
        355                 360                 365

Gly Gly Gly Ser Gln Ser Gln Leu Gln Glu Ser Gly Pro Gly Leu Val
    370                 375                 380

Lys Pro Ser Glu Thr Leu Ser Leu Thr Cys Lys Ala Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
            420                 425                 430

Tyr Tyr Ala Ser Trp Ala Lys Gly Arg Val Thr Ile Ser Lys Asp Ser
        435                 440                 445

Ser Lys Asn Gln Val Ser Leu Lys Leu Ser Ser Val Thr Ala Ala Asp
    450                 455                 460

Thr Ala Val Tyr Phe Cys Ala Arg Lys Asp Ala Tyr Ser Asp Ala Phe
465                 470                 475                 480

Asn Leu Trp Gly Gln Gly Thr Leu Val Thr Val Ser Ser Gly Gly Gly
                485                 490                 495

Gly Ser Gly Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
        515                 520                 525

Glu Ser Val Tyr Ser Asn Asn Gln Leu Ser Trp Tyr Gln Gln Lys Pro
    530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Ser Asp Thr Ala Phe Gly Gly Gly Thr
        595                 600                 605

Lys Leu Thr Val Leu Gly Gly Gly Gly Gly Ser Gly Gly Gly Gly Ser
    610                 615                 620

Gly Gly Gly Gly Ser Gly Gly Gly Gly Ser Glu Val Gln Leu Val Glu
625                 630                 635                 640
```

```
Ser Gly Gly Gly Leu Val Gln Pro Gly Gly Ser Leu Arg Leu Ser Cys
                645                 650                 655

Ala Ala Ser Gly Phe Ser Leu Ser Ser Asn Ala Met Gly Trp Val Arg
            660                 665                 670

Gln Ala Pro Gly Lys Gly Leu Glu Tyr Ile Gly Ile Ile Ser Val Gly
        675                 680                 685

Gly Phe Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755
```

<210> SEQ ID NO 227
<211> LENGTH: 755
<212> TYPE: PRT
<213> ORGANISM: Artificial Sequence
<220> FEATURE:
<223> OTHER INFORMATION: sequence of recombinant antibody or functional part thereof

<400> SEQUENCE: 227

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly Gly Gly Gly Gly
            100                 105                 110

Ser Gln Ser Gln Leu Gln Glu Ser Gly Pro Gly Leu Val Lys Pro Ser
        115                 120                 125

Glu Thr Leu Ser Leu Thr Cys Lys Ala Ser Gly Phe Ser Phe Ser Ser
    130                 135                 140

Gly Tyr Asp Met Cys Trp Val Arg Gln Pro Pro Gly Lys Gly Leu Glu
145                 150                 155                 160

Trp Ile Ala Cys Val Val Ala Gly Ser Val Asp Ile Thr Tyr Tyr Ala
                165                 170                 175

Ser Trp Ala Lys Gly Arg Val Thr Ile Ser Lys Asp Ser Ser Lys Asn
            180                 185                 190

Gln Val Ser Leu Lys Leu Ser Ser Val Thr Ala Ala Asp Thr Ala Val
        195                 200                 205

Tyr Phe Cys Ala Arg Lys Asp Ala Tyr Ser Asp Ala Phe Asn Leu Trp
    210                 215                 220

Gly Gln Gly Thr Leu Val Thr Val Ser Ser Gly Gly Gly Gly Ser Gly
225                 230                 235                 240
```

```
Gly Gly Gly Ser Gly Gly Gly Gly Ser Gly Gly Gly Gly Ser Phe Gln
                245                 250                 255

Leu Thr Gln Ser Pro Ser Ser Leu Ser Ala Ser Val Gly Asp Arg Val
            260                 265                 270

Thr Ile Thr Cys Gln Ala Ser Gln Ser Ile Asn Asp Tyr Leu Ala Trp
        275                 280                 285

Tyr Gln Gln Lys Pro Gly Lys Ser Pro Lys Leu Leu Ile Tyr Lys Ala
    290                 295                 300

Ser Thr Leu Ala Ser Gly Val Pro Ser Arg Phe Ser Gly Ser Gly Ser
305                 310                 315                 320

Gly Thr Asp Phe Thr Leu Thr Ile Ser Ser Leu Gln Pro Glu Asp Phe
                325                 330                 335

Ala Thr Tyr Tyr Cys Gln Gln Gly Tyr Ile Ile Thr Asp Ile Asp Asn
            340                 345                 350

Val Phe Gly Thr Gly Thr Lys Val Thr Val Leu Gly Gly Gly Gly Gly
        355                 360                 365

Ser Glu Val Gln Leu Val Glu Ser Gly Gly Gly Leu Val Gln Pro Gly
    370                 375                 380

Gly Ser Leu Arg Leu Ser Cys Ala Ala Ser Gly Phe Ser Phe Ser Asn
385                 390                 395                 400

Ser Tyr Trp Ile Cys Trp Val Arg Gln Ala Pro Gly Lys Cys Leu Glu
                405                 410                 415

Trp Ile Gly Cys Thr Phe Val Gly Ser Ser Asp Ser Thr Tyr Tyr Ala
            420                 425                 430

Asn Trp Ala Lys Gly Arg Phe Thr Ile Ser Arg Asp Asn Ser Lys Asn
        435                 440                 445

Thr Val Tyr Leu Gln Met Asn Ser Leu Arg Ala Glu Asp Thr Ala Val
    450                 455                 460

Tyr Tyr Cys Ala Arg His Pro Ser Asp Ala Val Tyr Gly Tyr Ala Asn
465                 470                 475                 480

Asn Leu Trp Gly Gln Gly Thr Leu Val Thr Val Ser Ser Gly Gly Gly
                485                 490                 495

Gly Ser Gly Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
        515                 520                 525

Glu Ser Val Tyr Ser Asn Asn Gln Leu Ser Trp Tyr Gln Gln Lys Pro
    530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Ser Asp Thr Ala Phe Gly Gly Gly Thr
        595                 600                 605

Lys Leu Thr Val Leu Gly Gly Gly Gly Gly Ser Gly Gly Gly Gly Ser
    610                 615                 620

Gly Gly Gly Gly Ser Gly Gly Gly Gly Ser Glu Val Gln Leu Val Glu
625                 630                 635                 640

Ser Gly Gly Gly Leu Val Gln Pro Gly Gly Ser Leu Arg Leu Ser Cys
                645                 650                 655
```

```
Ala Ala Ser Gly Phe Ser Leu Ser Ser Asn Ala Met Gly Trp Val Arg
            660                 665                 670

Gln Ala Pro Gly Lys Gly Leu Glu Tyr Ile Gly Ile Ile Ser Val Gly
        675                 680                 685

Gly Phe Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755


<210> SEQ ID NO 228
<211> LENGTH: 755
<212> TYPE: PRT
<213> ORGANISM: Artificial Sequence
<220> FEATURE:
<223> OTHER INFORMATION: sequence of recombinant antibody or functional
      part thereof

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly Gly Gly Gly Gly
            100                 105                 110

Ser Gln Val Gln Leu Gln Glu Ser Gly Pro Gly Leu Val Lys Pro Ser
        115                 120                 125

Glu Thr Leu Ser Leu Thr Cys Lys Ala Ser Gly Phe Ser Phe Ser Ser
    130                 135                 140

Gly Tyr Asp Met Cys Trp Val Arg Gln Pro Pro Gly Lys Gly Leu Glu
145                 150                 155                 160

Trp Ile Ala Cys Val Val Ala Gly Ser Val Asp Ile Thr Tyr Tyr Ala
                165                 170                 175

Ser Trp Ala Lys Gly Arg Val Thr Ile Ser Lys Asp Ser Ser Lys Asn
            180                 185                 190

Gln Val Ser Leu Lys Leu Ser Ser Val Thr Ala Ala Asp Thr Ala Val
        195                 200                 205

Tyr Tyr Cys Ala Arg Lys Asp Ala Tyr Ser Asp Ala Phe Asn Leu Trp
    210                 215                 220

Gly Gln Gly Thr Leu Val Thr Val Ser Ser Gly Gly Gly Gly Ser Gly
225                 230                 235                 240

Gly Gly Gly Ser Gly Gly Gly Gly Ser Gly Gly Gly Gly Ser Ile Gln
                245                 250                 255
```

```
Met Thr Gln Ser Pro Ser Ser Leu Ser Ala Ser Val Gly Asp Arg Val
            260                 265                 270

Thr Ile Thr Cys Gln Ala Ser Gln Ser Ile Asn Asp Tyr Leu Ala Trp
        275                 280                 285

Tyr Gln Gln Lys Pro Gly Lys Ala Pro Lys Leu Leu Ile Tyr Lys Ala
    290                 295                 300

Ser Thr Leu Ala Ser Gly Val Pro Ser Arg Phe Ser Gly Ser Gly Ser
305                 310                 315                 320

Gly Thr Asp Phe Thr Leu Thr Ile Ser Ser Leu Gln Pro Glu Asp Phe
                325                 330                 335

Ala Thr Tyr Tyr Cys Gln Gln Gly Tyr Ile Ile Thr Asp Ile Asp Asn
            340                 345                 350

Val Phe Gly Thr Gly Thr Lys Val Thr Val Leu Gly Gly Gly Gly Gly
        355                 360                 365

Ser Glu Val Gln Leu Val Glu Ser Gly Gly Gly Leu Val Gln Pro Gly
    370                 375                 380

Gly Ser Leu Arg Leu Ser Cys Ala Ala Ser Gly Phe Ser Phe Ser Asn
385                 390                 395                 400

Ser Tyr Trp Ile Cys Trp Val Arg Gln Ala Pro Gly Lys Cys Leu Glu
                405                 410                 415

Trp Ile Gly Cys Thr Phe Val Gly Ser Ser Asp Ser Thr Tyr Tyr Ala
            420                 425                 430

Asn Trp Ala Lys Gly Arg Phe Thr Ile Ser Arg Asp Asn Ser Lys Asn
        435                 440                 445

Thr Val Tyr Leu Gln Met Asn Ser Leu Arg Ala Glu Asp Thr Ala Val
    450                 455                 460

Tyr Tyr Cys Ala Arg His Pro Ser Asp Ala Val Tyr Gly Tyr Ala Asn
465                 470                 475                 480

Asn Leu Trp Gly Gln Gly Thr Leu Val Thr Val Ser Ser Gly Gly Gly
                485                 490                 495

Gly Ser Gly Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
        515                 520                 525

Glu Ser Val Tyr Ser Asn Asn Gln Leu Ser Trp Tyr Gln Gln Lys Pro
    530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Ser Asp Thr Ala Phe Gly Gly Gly Thr
        595                 600                 605

Lys Leu Thr Val Leu Gly Gly Gly Gly Gly Ser Gly Gly Gly Gly Ser
    610                 615                 620

Gly Gly Gly Gly Ser Gly Gly Gly Gly Ser Glu Val Gln Leu Val Glu
625                 630                 635                 640

Ser Gly Gly Gly Leu Val Gln Pro Gly Gly Ser Leu Arg Leu Ser Cys
                645                 650                 655

Ala Ala Ser Gly Phe Ser Leu Ser Ser Asn Ala Met Gly Trp Val Arg
            660                 665                 670
```

```
Gln Ala Pro Gly Lys Gly Leu Glu Tyr Ile Gly Ile Ile Ser Val Gly
        675                 680                 685

Gly Phe Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755


<210> SEQ ID NO 229
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 229

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Ser Phe Ser Ala Asn Tyr Tyr Pro Cys Trp Val Arg Gln Ala
145                 150                 155                 160

Pro Gly Lys Gly Leu Glu Trp Ile Gly Cys Ile Tyr Gly Gly Ser Ser
                165                 170                 175

Asp Ile Thr Tyr Asp Ala Asn Trp Thr Lys Gly Arg Phe Thr Ile Ser
            180                 185                 190

Arg Asp Asn Ser Lys Asn Thr Val Tyr Leu Gln Met Asn Ser Leu Arg
        195                 200                 205

Ala Glu Asp Thr Ala Val Tyr Tyr Cys Ala Arg Ser Ala Trp Tyr Ser
    210                 215                 220

Gly Trp Gly Gly Asp Leu Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Ile Gln Met Thr Gln Ser Pro Ser Ser Leu Ser
            260                 265                 270
```

```
Ala Ser Val Gly Asp Arg Val Thr Ile Thr Cys Gln Ala Ser Gln Ser
        275                 280                 285

Ile Ser Asn Arg Leu Ala Trp Tyr Gln Gln Lys Pro Gly Lys Ala Pro
    290                 295                 300

Lys Leu Leu Ile Tyr Ser Ala Ser Thr Leu Ala Ser Gly Val Pro Ser
305                 310                 315                 320

Arg Phe Ser Gly Ser Gly Ser Gly Thr Asp Phe Thr Leu Thr Ile Ser
                325                 330                 335

Ser Leu Gln Pro Glu Asp Phe Ala Thr Tyr Tyr Cys Gln Ser Thr Tyr
            340                 345                 350

Tyr Gly Asn Asp Gly Asn Ala Phe Gly Thr Gly Thr Lys Val Thr Val
        355                 360                 365

Leu Gly Gly Gly Gly Gly Ser Glu Val Gln Leu Val Glu Ser Gly Gly
    370                 375                 380

Gly Leu Val Gln Pro Gly Gly Ser Leu Arg Leu Ser Cys Ala Ala Ser
385                 390                 395                 400

Gly Phe Ser Phe Asn Ser Asp Tyr Trp Ile Tyr Trp Val Arg Gln Ala
                405                 410                 415

Pro Gly Lys Gly Leu Glu Trp Ile Ala Ser Ile Tyr Gly Gly Ser Ser
            420                 425                 430

Gly Asn Thr Gln Tyr Ala Ser Trp Ala Gln Gly Arg Phe Thr Ile Ser
        435                 440                 445

Arg Asp Asn Ser Lys Asn Thr Val Tyr Leu Gln Met Asn Ser Leu Arg
    450                 455                 460

Ala Glu Asp Thr Ala Val Tyr Phe Cys Ala Arg Gly Tyr Val Asp Tyr
465                 470                 475                 480

Gly Gly Ala Thr Asp Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540

Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590

Thr Tyr Tyr Cys Ala Gly Gly Phe Ser Ser Ser Ser Asp Thr Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685
```

```
Ile Ser Val Gly Gly Phe Thr Tyr Tyr Ala Ser Trp Ala Lys Gly Arg
    690                 695                 700

Phe Thr Ile Ser Arg Asp Asn Ser Lys Asn Thr Val Tyr Leu Gln Met
705                 710                 715                 720

Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755


<210> SEQ ID NO 230
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 230

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Glu Ser Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Ser Phe Ser Ala Asn Tyr Tyr Pro Cys Trp Val Arg Gln Ala
145                 150                 155                 160

Pro Gly Lys Gly Leu Glu Trp Ile Gly Cys Ile Tyr Gly Gly Ser Ser
                165                 170                 175

Asp Ile Thr Tyr Asp Ala Asn Trp Thr Lys Gly Arg Phe Thr Ile Ser
            180                 185                 190

Arg Asp Asn Ser Lys Asn Thr Val Tyr Leu Gln Met Asn Ser Leu Arg
        195                 200                 205

Ala Glu Asp Thr Ala Val Tyr Phe Cys Ala Arg Ser Ala Trp Tyr Ser
    210                 215                 220

Gly Trp Gly Gly Asp Leu Trp Gly Pro Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Phe Gln Leu Thr Gln Ser Pro Ser Ser Leu Ser
            260                 265                 270

Ala Ser Val Gly Asp Arg Val Thr Ile Thr Cys Gln Ala Ser Gln Ser
        275                 280                 285
```

```
Ile Ser Asn Arg Leu Ala Trp Tyr Gln Gln Lys Pro Gly Lys Pro Pro
    290                 295                 300

Lys Leu Leu Ile Tyr Ser Ala Ser Thr Leu Ala Ser Gly Val Pro Ser
305                 310                 315                 320

Arg Phe Ser Gly Ser Gly Ser Gly Thr Asp Phe Thr Leu Thr Ile Ser
                325                 330                 335

Ser Leu Gln Pro Glu Asp Phe Ala Thr Tyr Tyr Cys Gln Ser Thr Tyr
            340                 345                 350

Tyr Gly Asn Asp Gly Asn Ala Phe Gly Thr Gly Thr Lys Val Thr Val
        355                 360                 365

Leu Gly Gly Gly Gly Gly Ser Glu Val Gln Leu Val Glu Ser Gly Gly
    370                 375                 380

Gly Leu Val Gln Pro Gly Gly Ser Leu Arg Leu Ser Cys Ala Ala Ser
385                 390                 395                 400

Gly Phe Ser Phe Asn Ser Asp Tyr Trp Ile Tyr Trp Val Arg Gln Ala
                405                 410                 415

Pro Gly Lys Gly Leu Glu Trp Ile Ala Ser Ile Tyr Gly Gly Ser Ser
            420                 425                 430

Gly Asn Thr Gln Tyr Ala Ser Trp Ala Gln Gly Arg Phe Thr Ile Ser
        435                 440                 445

Arg Asp Asn Ser Lys Asn Thr Val Tyr Leu Gln Met Asn Ser Leu Arg
    450                 455                 460

Ala Glu Asp Thr Ala Val Tyr Phe Cys Ala Arg Gly Tyr Val Asp Tyr
465                 470                 475                 480

Gly Gly Ala Thr Asp Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540

Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590

Thr Tyr Tyr Cys Ala Gly Gly Phe Ser Ser Ser Ser Asp Thr Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685

Ile Ser Val Gly Gly Phe Thr Tyr Tyr Ala Ser Trp Ala Lys Gly Arg
    690                 695                 700
```

```
Phe Thr Ile Ser Arg Asp Asn Ser Lys Asn Thr Val Tyr Leu Gln Met
705                 710                 715                 720

Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755


<210> SEQ ID NO 231
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 231

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Gly Ser Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Ser Phe Ser Ala Asn Tyr Tyr Pro Cys Trp Val Arg Gln Ala
145                 150                 155                 160

Pro Gly Lys Cys Leu Glu Trp Ile Gly Cys Ile Tyr Gly Gly Ser Ser
                165                 170                 175

Asp Ile Thr Tyr Asp Ala Asn Trp Thr Lys Gly Arg Phe Thr Ile Ser
            180                 185                 190

Arg Asp Asn Ser Lys Asn Thr Val Tyr Leu Gln Met Asn Ser Leu Arg
        195                 200                 205

Ala Glu Asp Thr Ala Val Tyr Tyr Cys Ala Arg Ser Ala Trp Tyr Ser
    210                 215                 220

Gly Trp Gly Gly Asp Leu Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ala Ser Gln Ser
        275                 280                 285

Ile Ser Asn Arg Leu Ala Trp Tyr Gln Gln Lys Pro Gly Lys Ala Pro
    290                 295                 300
```

```
Lys Leu Leu Ile Tyr Ser Ala Ser Thr Leu Ala Ser Gly Val Pro Ser
305                 310                 315                 320

Arg Phe Ser Gly Ser Gly Ser Gly Thr Asp Phe Thr Leu Thr Ile Ser
                325                 330                 335

Ser Leu Gln Pro Glu Asp Phe Ala Thr Tyr Tyr Cys Gln Ser Thr Tyr
            340                 345                 350

Tyr Gly Asn Asp Gly Asn Ala Phe Gly Cys Gly Thr Lys Val Thr Val
        355                 360                 365

Leu Gly Gly Gly Gly Gly Ser Glu Val Gln Leu Val Glu Ser Gly Gly
    370                 375                 380

Gly Leu Val Gln Pro Gly Gly Ser Leu Arg Leu Ser Cys Ala Ala Ser
385                 390                 395                 400

Gly Phe Ser Phe Asn Ser Asp Tyr Trp Ile Tyr Trp Val Arg Gln Ala
                405                 410                 415

Pro Gly Lys Gly Leu Glu Trp Ile Ala Ser Ile Tyr Gly Gly Ser Ser
            420                 425                 430

Gly Asn Thr Gln Tyr Ala Ser Trp Ala Gln Gly Arg Phe Thr Ile Ser
        435                 440                 445

Arg Asp Asn Ser Lys Asn Thr Val Tyr Leu Gln Met Asn Ser Leu Arg
    450                 455                 460

Ala Glu Asp Thr Ala Val Tyr Phe Cys Ala Arg Gly Tyr Val Asp Tyr
465                 470                 475                 480

Gly Gly Ala Thr Asp Leu Trp Gly Gln Gly Thr Leu Val Thr Val Ser
                485                 490                 495

Ser Gly Gly Gly Gly Ser Gly Gly Gly Gly Ser Ile Gln Met Thr Gln
            500                 505                 510

Ser Pro Ser Ser Leu Ser Ala Ser Val Gly Asp Arg Val Thr Ile Thr
        515                 520                 525

Cys Gln Ser Ser Glu Ser Val Tyr Ser Asn Asn Gln Leu Ser Trp Tyr
    530                 535                 540

Gln Gln Lys Pro Gly Gln Pro Pro Lys Leu Leu Ile Tyr Asp Ala Ser
545                 550                 555                 560

Asp Leu Ala Ser Gly Val Pro Ser Arg Phe Ser Gly Ser Gly Ser Gly
                565                 570                 575

Thr Asp Phe Thr Leu Thr Ile Ser Ser Leu Gln Pro Glu Asp Phe Ala
            580                 585                 590

Thr Tyr Tyr Cys Ala Gly Gly Phe Ser Ser Ser Ser Asp Thr Ala Phe
        595                 600                 605

Gly Gly Gly Thr Lys Leu Thr Val Leu Gly Gly Gly Gly Gly Ser Gly
    610                 615                 620

Gly Gly Gly Ser Gly Gly Gly Gly Ser Gly Gly Gly Gly Ser Glu Val
625                 630                 635                 640

Gln Leu Val Glu Ser Gly Gly Gly Leu Val Gln Pro Gly Gly Ser Leu
                645                 650                 655

Arg Leu Ser Cys Ala Ala Ser Gly Phe Ser Leu Ser Ser Asn Ala Met
            660                 665                 670

Gly Trp Val Arg Gln Ala Pro Gly Lys Gly Leu Glu Tyr Ile Gly Ile
        675                 680                 685

Ile Ser Val Gly Gly Phe Thr Tyr Tyr Ala Ser Trp Ala Lys Gly Arg
    690                 695                 700

Phe Thr Ile Ser Arg Asp Asn Ser Lys Asn Thr Val Tyr Leu Gln Met
705                 710                 715                 720
```

```
Asn Ser Leu Arg Ala Glu Asp Thr Ala Thr Tyr Phe Cys Ala Arg Asp
                725                 730                 735

Arg His Gly Gly Asp Ser Ser Gly Ala Phe Tyr Leu Trp Gly Gln Gly
            740                 745                 750

Thr Leu Val Thr Val Ser Ser
        755
```

<210> SEQ ID NO 232
<211> LENGTH: 478
<212> TYPE: PRT
<213> ORGANISM: Artificial Sequence
<220> FEATURE:
<223> OTHER INFORMATION: sequence of recombinant antibody or functional part thereof

<400> SEQUENCE: 232

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Ile Gln Met Thr Gln Ser Pro Ser Ser Leu Ser Ala Ser
225                 230                 235                 240

Val Gly Asp Arg Val Thr Ile Thr Cys Gln Ala Ser Gln Ser Ile Asn
                245                 250                 255

Asn Val Leu Ala Trp Tyr Gln Gln Lys Pro Gly Lys Ala Pro Lys Leu
            260                 265                 270

Leu Ile Tyr Arg Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300

Gln Pro Glu Asp Phe Ala Thr Tyr Tyr Cys Gln Ser Ser Tyr Gly Asn
305                 310                 315                 320
```

Tyr Gly Asp Phe Gly Thr Gly Thr Lys Val Thr Val Leu Gly Gly Gly
325 330 335

Gly Gly Ser Gly Gly Gly Gly Ser Gly Gly Gly Gly Ser Gly Gly Gly
340 345 350

Gly Ser Gln Val Gln Leu Gln Glu Ser Gly Pro Gly Leu Val Lys Pro
355 360 365

Ser Glu Thr Leu Ser Leu Thr Cys Lys Val Ser Gly Phe Ser Phe Ser
370 375 380

Asn Ser Tyr Trp Ile Cys Trp Ile Arg Gln Pro Pro Gly Lys Gly Leu
385 390 395 400

Glu Trp Ile Gly Cys Thr Phe Val Gly Ser Ser Asp Ser Thr Tyr Tyr
405 410 415

Ala Asn Trp Ala Lys Gly Arg Val Thr Ile Ser Val Asp Ser Ser Lys
420 425 430

Asn Gln Phe Ser Leu Lys Leu Ser Ser Val Thr Ala Ala Asp Thr Ala
435 440 445

Val Tyr Tyr Cys Ala Arg His Pro Ser Asp Ala Val Tyr Gly Tyr Ala
450 455 460

Asn Asn Leu Trp Gly Gln Gly Thr Leu Val Thr Val Ser Ser
465 470 475

<210> SEQ ID NO 233
<211> LENGTH: 451
<212> TYPE: PRT
<213> ORGANISM: Artificial Sequence
<220> FEATURE:
<223> OTHER INFORMATION: sequence of recombinant antibody or functional part thereof

<400> SEQUENCE: 233

Gln Val Gln Leu Gln Glu Ser Gly Pro Gly Leu Val Lys Pro Ser Glu
1 5 10 15

Thr Leu Ser Leu Thr Cys Lys Val Ser Gly Phe Ser Phe Ser Ser Gly
20 25 30

Tyr Asp Met Cys Trp Ile Arg Gln Pro Pro Gly Lys Gly Leu Glu Trp
35 40 45

Ile Gly Cys Val Val Ala Gly Ser Val Asp Ile Thr Tyr Tyr Ala Ser
50 55 60

Trp Ala Lys Gly Arg Val Thr Ile Ser Val Asp Ser Ser Lys Asn Gln
65 70 75 80

Phe Ser Leu Lys Leu Ser Ser Val Thr Ala Ala Asp Thr Ala Val Tyr
85 90 95

Tyr Cys Ala Arg Lys Asp Ala Tyr Ser Asp Ala Phe Asn Leu Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His

```
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 234
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95
```

```
Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 235
<211> LENGTH: 712
<212> TYPE: PRT
<213> ORGANISM: Artificial Sequence
<220> FEATURE:
<223> OTHER INFORMATION: sequence of recombinant antibody or functional
      part thereof

<400> SEQUENCE: 235

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Ile Gln Met
    450                 455                 460

Thr Gln Ser Pro Ser Ser Leu Ser Ala Ser Val Gly Asp Arg Val Thr
465                 470                 475                 480

Ile Thr Cys Gln Ala Ser Gln Ser Ile Asn Asn Val Leu Ala Trp Tyr
                485                 490                 495

Gln Gln Lys Pro Gly Lys Ala Pro Lys Leu Leu Ile Tyr Arg Ala Ser
            500                 505                 510

Thr Leu Ala Ser Gly Val Pro Ser Arg Phe Ser Gly Ser Gly Ser Gly
        515                 520                 525

Thr Asp Phe Thr Leu Thr Ile Ser Ser Leu Gln Pro Glu Asp Phe Ala
    530                 535                 540

Thr Tyr Tyr Cys Gln Ser Ser Tyr Gly Asn Tyr Gly Asp Phe Gly Thr
545                 550                 555                 560

Gly Thr Lys Val Thr Val Leu Gly Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Gln Glu Ser Gly Pro Gly Leu Val Lys Pro Ser Glu Thr Leu Ser Leu
        595                 600                 605

Thr Cys Lys Val Ser Gly Phe Ser Phe Ser Asn Ser Tyr Trp Ile Cys
    610                 615                 620

Trp Ile Arg Gln Pro Pro Gly Lys Gly Leu Glu Trp Ile Gly Cys Thr
625                 630                 635                 640

Phe Val Gly Ser Ser Asp Ser Thr Tyr Tyr Ala Asn Trp Ala Lys Gly
                645                 650                 655
```

```
Arg Val Thr Ile Ser Val Asp Ser Ser Lys Asn Gln Phe Ser Leu Lys
            660                 665                 670

Leu Ser Ser Val Thr Ala Ala Asp Thr Ala Val Tyr Tyr Cys Ala Arg
        675                 680                 685

His Pro Ser Asp Ala Val Tyr Gly Tyr Ala Asn Asn Leu Trp Gly Gln
    690                 695                 700

Gly Thr Leu Val Thr Val Ser Ser
705                 710


<210> SEQ ID NO 236
<211> LENGTH: 478
<212> TYPE: PRT
<213> ORGANISM: Artificial Sequence
<220> FEATURE:
<223> OTHER INFORMATION: sequence of recombinant antibody or functional
      part thereof

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Ile Gln Met Thr Gln Ser Pro Ser Ser Leu Ser Ala Ser
225                 230                 235                 240

Val Gly Asp Arg Val Thr Ile Thr Cys Gln Ala Ser Gln Ser Ile Asn
                245                 250                 255

Asn Val Leu Ala Trp Tyr Gln Gln Lys Pro Gly Lys Ala Pro Lys Leu
            260                 265                 270

Leu Ile Tyr Arg Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300
```

```
Gln Pro Glu Asp Phe Ala Thr Tyr Tyr Cys Gln Ser Ser Tyr Gly Asn
305                 310                 315                 320

Tyr Gly Asp Phe Gly Thr Gly Thr Lys Val Thr Val Leu Gly Gly Gly
                325                 330                 335

Gly Gly Ser Gly Gly Gly Gly Ser Gly Gly Gly Gly Ser Gly Gly Gly
            340                 345                 350

Gly Ser Gln Val Gln Leu Gln Glu Ser Gly Pro Gly Leu Val Lys Pro
        355                 360                 365

Ser Glu Thr Leu Ser Leu Thr Cys Lys Val Ser Gly Phe Ser Phe Ser
    370                 375                 380

Asn Ser Tyr Trp Ile Cys Trp Ile Arg Gln Pro Pro Gly Lys Gly Leu
385                 390                 395                 400

Glu Trp Ile Gly Cys Thr Phe Val Gly Ser Ser Asp Ser Thr Tyr Tyr
                405                 410                 415

Ala Asn Trp Ala Lys Gly Arg Val Thr Ile Ser Val Asp Ser Ser Lys
            420                 425                 430

Asn Gln Phe Ser Leu Lys Leu Ser Ser Val Thr Ala Ala Asp Thr Ala
        435                 440                 445

Val Tyr Tyr Cys Ala Arg His Pro Ser Asp Ala Val Tyr Gly Tyr Ala
    450                 455                 460

Asn Asn Leu Trp Gly Gln Gly Thr Leu Val Thr Val Ser Ser
465                 470                 475
```

<210> SEQ ID NO 237
<211> LENGTH: 451
<212> TYPE: PRT
<213> ORGANISM: Artificial Sequence
<220> FEATURE:
<223> OTHER INFORMATION: sequence of recombinant antibody or functional part thereof

<400> SEQUENCE: 237

```
Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 238
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 239
<211> LENGTH: 712
<212> TYPE: PRT
<213> ORGANISM: Artificial Sequence
<220> FEATURE:
<223> OTHER INFORMATION: sequence of recombinant antibody or functional
      part thereof

<400> SEQUENCE: 239

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

```
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Ile Gln Met
    450                 455                 460

Thr Gln Ser Pro Ser Ser Leu Ser Ala Ser Val Gly Asp Arg Val Thr
465                 470                 475                 480

Ile Thr Cys Gln Ala Ser Gln Ser Ile Asn Asn Val Leu Ala Trp Tyr
                485                 490                 495

Gln Gln Lys Pro Gly Lys Ala Pro Lys Leu Leu Ile Tyr Arg Ala Ser
            500                 505                 510

Thr Leu Ala Ser Gly Val Pro Ser Arg Phe Ser Gly Ser Gly Ser Gly
        515                 520                 525

Thr Asp Phe Thr Leu Thr Ile Ser Ser Leu Gln Pro Glu Asp Phe Ala
    530                 535                 540

Thr Tyr Tyr Cys Gln Ser Ser Tyr Gly Asn Tyr Gly Asp Phe Gly Thr
545                 550                 555                 560

Gly Thr Lys Val Thr Val Leu Gly Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Gln Glu Ser Gly Pro Gly Leu Val Lys Pro Ser Glu Thr Leu Ser Leu
        595                 600                 605

Thr Cys Lys Val Ser Gly Phe Ser Phe Ser Asn Ser Tyr Trp Ile Cys
    610                 615                 620

Trp Ile Arg Gln Pro Pro Gly Lys Gly Leu Glu Trp Ile Gly Cys Thr
625                 630                 635                 640
```

```
Phe Val Gly Ser Ser Asp Ser Thr Tyr Tyr Ala Asn Trp Ala Lys Gly
            645                 650                 655

Arg Val Thr Ile Ser Val Asp Ser Ser Lys Asn Gln Phe Ser Leu Lys
        660                 665                 670

Leu Ser Ser Val Thr Ala Ala Asp Thr Ala Val Tyr Tyr Cys Ala Arg
    675                 680                 685

His Pro Ser Asp Ala Val Tyr Gly Tyr Ala Asn Asn Leu Trp Gly Gln
    690                 695                 700

Gly Thr Leu Val Thr Val Ser Ser
705                 710


<210> SEQ ID NO 240
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 240

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 241
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 241
```

```
Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
            420                 425                 430

His Glu Ala Leu His Asn His Tyr Thr Gln Lys Ser Leu Ser Leu Ser
        435                 440                 445

Pro Gly Lys
    450


<210> SEQ ID NO 242
<211> LENGTH: 220
<212> TYPE: PRT
<213> ORGANISM: Artificial Sequence
<220> FEATURE:
<223> OTHER INFORMATION: sequence of recombinant antibody or functional
      part thereof

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 243
<211> LENGTH: 452
<212> TYPE: PRT
<213> ORGANISM: Artificial Sequence
<220> FEATURE:
<223> OTHER INFORMATION: sequence of recombinant antibody or functional
      part thereof

<400> SEQUENCE: 243

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Ser Asp
            20                  25                  30

Tyr Trp Ile Tyr Trp Ile Arg Gln Pro Pro Gly Lys Gly Leu Glu Trp
```

-continued

```
        35                  40                  45

Ile Gly Ser Ile Tyr Gly Gly Ser Ser Gly Asn Thr Gln Tyr Ala Ser
    50                  55                  60

Trp Ala Gln Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Tyr Val Asp Tyr Gly Gly Ala Thr Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 244
<211> LENGTH: 214
<212> TYPE: PRT
<213> ORGANISM: Artificial Sequence
<220> FEATURE:
<223> OTHER INFORMATION: sequence of recombinant antibody or functional part thereof

<400> SEQUENCE: 244

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 245
<211> LENGTH: 451
<212> TYPE: PRT
<213> ORGANISM: Artificial Sequence
<220> FEATURE:
<223> OTHER INFORMATION: sequence of recombinant antibody or functional part thereof

<400> SEQUENCE: 245

```
Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Ile Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80
```

```
Phe Ser Leu Lys Leu Ser Ser Val Thr Ala Ala Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450
```

<210> SEQ ID NO 246
<211> LENGTH: 5
<212> TYPE: PRT
<213> ORGANISM: Artificial sequence
<220> FEATURE:

<223> OTHER INFORMATION: artificial antibody-based sequence
<220> FEATURE:
<221> NAME/KEY: Repeat
<222> LOCATION: (1)..(5)
<223> OTHER INFORMATION: (GSGGS)n linker with n being an integer of at least 1

<400> SEQUENCE: 246

Gly Ser Gly Gly Ser
1               5

<210> SEQ ID NO 247
<211> LENGTH: 5
<212> TYPE: PRT
<213> ORGANISM: Artificial sequence
<220> FEATURE:
<223> OTHER INFORMATION: artificial antibody-based sequence
<220> FEATURE:
<221> NAME/KEY: Repeat
<222> LOCATION: (1)..(5)
<223> OTHER INFORMATION: (GGGGS)n linker with n being an integer of at least 1

<400> SEQUENCE: 247

Gly Gly Gly Gly Ser
1               5

<210> SEQ ID NO 248
<211> LENGTH: 4
<212> TYPE: PRT
<213> ORGANISM: Artificial sequence
<220> FEATURE:
<223> OTHER INFORMATION: artificial antibody-based sequence
<220> FEATURE:
<221> NAME/KEY: Repeat
<222> LOCATION: (1)..(4)
<223> OTHER INFORMATION: (GGGS)n linker with n being an integer of at least 1

<400> SEQUENCE: 248

Gly Gly Gly Ser
1

<210> SEQ ID NO 249
<211> LENGTH: 5
<212> TYPE: PRT
<213> ORGANISM: Artificial sequence
<220> FEATURE:
<223> OTHER INFORMATION: artificial antibody-based sequence
<220> FEATURE:
<221> NAME/KEY: Repeat
<222> LOCATION: (1)..(5)
<223> OTHER INFORMATION: (GGGGS)n linker with n being selected from 1 and 2

<400> SEQUENCE: 249

Gly Gly Gly Gly Ser
1               5

<210> SEQ ID NO 250
<211> LENGTH: 5
<212> TYPE: PRT
<213> ORGANISM: Artificial sequence
<220> FEATURE:
<223> OTHER INFORMATION: artificial antibody-based sequence
<220> FEATURE:
<221> NAME/KEY: Repeat
<222> LOCATION: (1)..(5)
<223> OTHER INFORMATION: (GGGGS)n linker with n being selected from 1, 2, 3, 4, 5, 6, 7, and 8

-continued

```
<400> SEQUENCE: 250

Gly Gly Gly Gly Ser
1               5
```

MULTISPECIFIC ANTIBODY COMPRISING CD137 BINDING DOMAIN AND PDL1 BINDING DOMAIN

CROSS-REFERENCE TO RELATED APPLICATIONS

This application is a 371 National Phase of International Patent Application No. PCT/EP2018/077509 filed on Oct. 9, 2018, which claims priority to EP 17195779.8 filed on Oct. 10, 2017, EP 18150465.5 filed on Jan. 5, 2018, EP 18167093.6 filed on Apr. 12, 2018 and EP 18180814.8 filed on Jun. 29, 2018, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRNT7NP-replacement-seqlist.txt", which was created on Dec. 19, 2023, which is 303,995 bytes in size, and which is herein incorporated by reference in its entirety.

FIELD OF THE INVENTION

The present invention relates to a multispecific antibody comprising at least one CD137 binding domain and at least one PDL1 binding domain, and pharmaceutical compositions and methods of use thereof. The present invention further relates to a nucleic acid encoding said multispecific antibody, a vector comprising said nucleic acid, a host cell comprising said nucleic acid or said vector, and a method of producing said multispecific antibody.

BACKGROUND OF THE INVENTION

The tumor necrosis factor receptor superfamily (TNFRSF) is a protein superfamily of receptors characterized by their ability to bind tumor necrosis factors (TNFs) via cysteine-rich pseudorepeats in the extracellular domain (Locksley et al., 2001, Cell. 104: 487-501). At present, 27 TNF family members have been identified. TNFRSF members and their ligands are expressed mostly on immune cells, where they are playing a role of immunomodulators in T-cell-mediated immune responses. TNFRSF members play a role in enhancement of dendric cell survival and priming capacity of T cells, optimal generation of effector T cells, optimal antibody responses, and amplification of inflammatory reactions.

CD137 (4-1BB, TNF-receptor superfamily 9, TNFRSF9) is a surface glycoprotein of the TNFR superfamily. It is an inducible costimulatory T cell receptor. CD137 expression is activation-dependent, and encompasses a broad subset of immune cells including activated NK and NKT cells, regulatory T cells, dendritic cells (DC) including follicular DC, stimulated mast cells, differentiating myeloid cells, monocytes, neutrophils, eosinophils (Wang et al, Immunol Rev. 229(1): 192-215 (2009)), and activated B cells (Zhang et al, J Immunol. 184(2):787-795 (2010)). In addition, CD137 expression has also been demonstrated on tumor vasculature (Broil K et al., Am J Clin Pathol. 115(4):543-549 (2001); Seaman et al, Cancer Cell 11(6):539-554 (2007)) and atherosclerotic endothelium (Olofsson et al, Circulation 117 (10): 1292 1301 (2008)).

CD137-Ligand (CD137L, 4-1BBL or tnfsf9), a molecule of the TNF family, is an intercellular natural ligand known for CD137 (Alderson, M. R., et al., Eur. J. Immunol. 24:2219-2227 (1994); Pollok K., et al., Eur. J. Immunol. 24:367-374 (1994); Goodwin, R. G., et al., Eur. J. Immunol. 23: 2631-2641 (1993)). The ligand for CD137 forms a homotrimer, and the signaling via CD137 proceeds from ligated molecules at the cell surface, which become cross-linked by trimerized ligand (Won, E. Y., et al., J. Biol. Chem. 285: 9202-9210 (2010)). The higher order clustering of CD137 was thus suggested to be necessary for mediating the signaling. CD137 associates with the adaptors TRAF-2 and TRAF-1 in its cytoplasmic tail, resulting in coimmunoprecipitation, which is enhanced upon CD137 activation in T cells (Saoulli, K., et al., J. Exp. Med. 187: 1849-1862 (1998); Sabbagh, L., et al., J. Immunol. 180: 8093-8101 (2008)). Recruitment of TRAF-1 and TRAF-2 by CD137 results in downstream activation of NFKB and the Mitogen Activated Protein (MAP) Kinase cascade including ERK, JNK, and p38 MAP kinases. NFkB activation leads to upregulation of Bfl-1 and Bcl-XL, pro-survival members of the Bcl-2 family. The pro-apoptotic protein Bim is downregulated in a TRAF-1 and ERK dependent manner (Sabbagh et al., J Immunol. 180(12):8093-8101 (2008)). It has been suggested that the main action of CD137 is to place two or more TRAF-2 molecules in close molecular proximity to each other (Sanchez-Paulete, A. R., et al., Eur. J. Immunology 46(3): 513-522 (2016)). Based on this it was postulated that the major factor driving CD137 signaling is the relative density of TRAF-2-assembled CD137 moieties in micropatches of plasma membrane (Sanchez-Paulete, A. R., et al., Eur. J. Immunology 46(3): 513-522 (2016)). Overall, CD137 signaling is fostered by multimerization, and it was proposed that cross-linking CD137 molecules is the key factor in CD137 co-stimulatory activity.

CD137 co-stimulates T cells to carry out effector functions such as eradication of established tumors, broadening primary $CD8^+$ T cell responses, and enhancing the memory pool of antigen-specific $CD8^+$ T cells, induction of interferon-gamma (IFN-γ) synthesis. The critical role of CD137 stimulation in $CD8^+$ T-cell function and survival could be potentially utilized for the treatment of tumors through manipulation of the CD137/CD137L function. In fact, in vivo efficacy studies in mice have demonstrated that treatment with anti-CD137 antibodies led to tumor regressions in multiple tumor models. For example, agonistic anti-mouse CD137 antibody were demonstrated to induce an immune response against P815 mastocytoma tumors, and low immunogenic tumor model Ag104 (I. Melero et al., Nat. Med., 3(6):682-5 (1997)). The efficacy of CD137 agonist mAbs in prophylactic and therapeutic settings for both monotherapy and combination therapy and anti-tumor protective T cell memory responses have been reported in several studies (Lynch et al., Immunol Rev. 222:277-286 (2008)). CD137 agonists also inhibit autoimmune reactions in a variety of autoimmunity models (Vinay et al, J Mol Med 84(9):726-736 (2006)).

Two anti-CD137 antibodies currently in the clinic are urelumab (Bristol-Myers Squibb), a fully humanized IgG4 mAb, and utomilumab (PF-05082566, Pfizer), a fully human IgG2 mAb (Chester C., et al., Cancer Immunol Immunother Oct; 65(10):1243-8 (2016)). Although utilization of therapeutic antibodies agonizing CD137 is a very promising treatment strategy, it is coupled to such difficulties as low efficacy of anti-CD137 agonist antibodies, high toxicities and adverse events.

CD137 agonist antibodies were shown to lead to alterations in immune system and organ function increasing risks of toxicities. High doses of CD137 agonist antibodies in naïve and tumor-bearing mice have been reported to induce T-cell infiltration to the liver and elevations of aspartate aminotransferase and alanine aminotransferase consistent with liver inflammation (Niu L, et al. J Immunol 178(7): 4194-4213 (2007); Dubrot J, et al., Int J Cancer 128(1):105-118 (2011)). Initial clinical studies into the human therapeutic use of CD137 agonist antibody have also demonstrated elevations of liver enzymes and increased incidence of hepatitis (Sznol M., et al., J Clin Oncol 26(1155):3007 (2008); Ascierto P A, et al., Semin Oncol 37(5):508-516 (2010); Chester C., et al., Cancer Immunol Immunother Oct; 65(10):1243-8 (2016)). Potentially fatal hepatitis was observed in a Bristol-Myers Squibb (BMS) phase II anti-CD137 study for previously treated stage III/IV melanoma, National Clinical Trial (NCT) 00612664. This study and several others (NCT00803374, NCT00309023, NCT00461110, NCT00351325) were terminated due to adverse events (Chester C., et al., Cancer Immunol Immunother Oct; 65(10):1243-8 (2016)). Such adverse events are most probably due to systemic overstimulation of T-cells.

Further to the above, bivalent CD137 antibodies were shown in vitro to be generally weak in their ability to induce the signaling in the absence of an exogenous clustering. To illustrate, anti-CD137 antibody utomilumab is only capable to activate CD137 signaling when either cross-linked to anti-human F(ab')2 secondary antibody or immobilized to tissue culture plastic (Fisher at al., Cancer Immunol Immunother 61:1721-1733 (2012)). Studies in rodent agonistic antibodies to CD40 (TNFRSF5), another member of TNFRSF, have suggested that the exogenous clustering can be partially achieved through the interaction with Fcγ-receptor (Li F, Ravetch J V, Science 333(6045):1030-10 (2011); White A L, et al., J Immunol 187(4):1754-1763 (2011)). The interaction with Fcγ-receptor can however deplete the CD137-expressing cells through effector mechanisms. The current bivalent antibodies targeting CD137 have the limitations that a) they have limited CD137 stimulation capacity in absence of Fcγ-receptor interaction, b) such interaction with Fcγ-receptor can induce depletion of CD137 expressing cells, which likely affects activity, and c) their activity is not restricted to the target tissue, thereby causing systemic adverse effects.

To gain additional cross-linking function and achieve certain levels of TNRSF, in particular CD137, activation, it has been recently suggested to use multivalent and multispecific fusion polypeptides that bind PDL1 and TNRSF members, or folate receptor alpha (FRα) and TNRSF members, wherein the binding to PDL1 or FRα is capable of providing additional crosslinking function (WO 2017/123650). Eckelman et al. have demonstrated that bivalent engagement of CD137, as in the case of INBRX-105, a multispecific and multivalent polypeptide having two PDL1 binding domains, two CD137 binding domains and an Fc region, is insufficient to effectively cluster and mediate productive CD137 signaling in absence of an exogenous clustering event, using an assay isolating the effects of the molecule on a reporter T cell-line. In contrast, engagement for a second cell surface antigen PDL1 in the presence of PDL1-positive cells enables further clustering of CD137 and productive signaling (WO 2017/123650).

PDL1 (CD274, B7-H1) is a 40 kDa type I transmembrane protein. PDL1 is a surface glycoprotein ligand for PD-1, a key immune checkpoint receptor expressed by activated T and B cells and mediates immunosuppression. PDL1 is implicated in the suppression of immune system responses during chronic infections, pregnancy, tissue allografts, autoimmune diseases, and cancer. PDL1 is found on both antigen-presenting cells and human cancer cells, such as squamous cell carcinoma of the head and neck, melanoma, and brain tumor, thyroid, thymus, esophagus, lung, breast, gastrointestinal tract, colorectum, liver, pancreas, kidney, adrenal cortex, bladder, urothelium, ovary, and skin (Katsuya Y, et al., Lung Cancer. 88(2):154-159 (2015); Nakanishi J, et al., Cancer Immunol Immunother. 56(8):1173-1182 (2007); Nomi T, et al., Clin Cancer Res. 13(7):2151-2157 (2007); Fay A P, et al., J Immunother Cancer. 3:3 (2015); Strome S E, et al., Cancer Res. 63(19):6501-6505 (2003); Jacobs J F, et al. Neuro Oncol. 11(4):394-402 (2009); Wilmotte R, et al. Neuroreport. 16(10):1081-1085 (2005)). PDL1 is rarely expressed on normal tissues but inducibly expressed on tumor site (Dong H, et al., Nat Med. 8(8):793-800 (2002); Wang et al., Onco Targets Ther. 9: 5023-5039 (2016)). PDL1 downregulates T cell activation and cytokine secretion by binding to PD-1 (Freeman et al., 2000; Latchman et al, 2001). PD-1, activated by PDL1, potentially provides an immune-tolerant environment for tumor development and growth. PDL1 also negatively regulates T-cell function through interaction with another receptor, B7.1 (B7-1, CD80).

Inhibition of the PDL1/PD-1 interaction allows for potent anti-tumor activity. A number of antibodies that disrupt the PD-1 signaling have entered clinical development.

These antibodies belong to the following two main categories: those that target PD-1 (nivolumab, Bristol-Myers Squibb; pembrolizumab, Merck, Whitehouse Station, NJ; pidilizumab, CureTech, Yavne, Israel) and those that target PDL1 (MPDL3280A, Genentech, South San Francisco, CA; MED14736, MedImmune/AstraZeneca; BMS-936559, Bristol-Myers Squibb; MSB0010718C, EMD Serono, Rockland, MA) (for review see Postow M A et al., J Clin Oncol. June 10; 33(17):1974-82 (2015)). Targeting PDL1 versus targeting PD-1 may result in different biologic effects. PD-1 antibodies prevent interaction of PD-1 with both its ligands, PDL1 and PDL2. PDL1 antibodies do not prevent PD-1 from interacting with PDL2, although the effect of this interaction remains unknown. PDL1 antibodies however prevent interaction of PDL1 with not only PD-1, but also B7-1 (Butte M J, et al., Immunity 27:111-122, (2007)), which is believed to exert negative signals on T cells. Blocking PDL1 has demonstrated promising early data, and currently, four clinical anti-PDL1 mAbs are in the testing: atezolizumab and MEDI4736 (both are Fc null variants of human IgG1), MSB001078C (IgG1), and BMS-936559 (IgG4) (Chester C., et al., Cancer Immunol Immunother Oct; 65(10):1243-8 (2016)).

The combination of anti-PDL1 and anti-CD137 antibodies increased overall survival and enhanced T-cell effector function in the ID-8 ovarian adenocarcinoma model (Duraiswamy J, et al., Cancer Res 73:6900-6912 (2013)). The combination of urelumab (anti-CD137) with nivolumab (anti-PD-1) in both solid tumors and B-cell non-Hodgkin's lymphoma is being tested in a phase I/II trial (NCT02253992), while PF-05082566 (anti-CD137) is being tested in a phase Ib trial with pembrolizumab (anti-PD-1) in patients with solid tumors (NCT02179918) (Chester C., et al., Cancer Immunol Immunother Oct; 65(10):1243-8 (2016)).

Recently, the effect of multivalent and multispecific fusion polypeptides that bind PDL1 and CD137 has been evaluated in vitro on T-cell activation and proliferation. Using an autologous in vitro co-culture system implementing immature DC and donor matched T-cells, it has been demonstrated that INBRX-105, a multispecific and multivalent polypeptide having two PDL1 binding domains, two CD137 binding domains and an Fc region, is superior in stimulating interferon-gamma production, when compared to the monospecific PDL1 sd-Ab-Fc fusion protein, the CD137 sdAb-Fc fusion protein, the combination of the two, the anti-PDL1 antibody atezolizumab, the anti-CD137 antibody utomilumab (PF-05082566), or the anti-PDL1 antibody prembrolizumab, and combinations thereof, at inducing INFγ or mediating $CD8^+$ T-cell proliferation and activation (WO 2017/123650). Additionally, WO 2016/149201 discloses certain antibodies directed against PDL1 and suggests creating bispecific antibody constructs further comprising a T-cell engaging antibody, with CD137 being contained in a non-exclusive list of more than 20 potential T-cell targets.

In spite of numerous treatment options for patients suffering from cancer, there remains a need for effective and safe therapeutic agents and a need for their preferential use in a more targeted manner. Immune-modulating biologics offer promising approaches in treatment of cancers due to their modes of actions, however global immunostimulation and lack of any restriction of this immunomodulation to pathologically relevant cells and sites causes numerous side effects and significant toxicities, which potentially may lead to increased morbidity and mortality of patients. It is therefore an object of the present invention to provide a medicament to improve treatment of a proliferative disease, particularly a cancer.

SUMMARY OF THE INVENTION

It is an object of the present invention to provide a medicament to improve treatment of a proliferative disease, particularly a cancer. The present invention addresses the need for precision therapeutics for immuno-oncology that target only the disease-colocalized T cells for upregulation.

In one aspect, the present invention relates to a multispecific antibody comprising at least one CD137 binding domain and at least one PDL1 binding domain. The present invention further relates to a multispecific antibody comprising at least one CD137 binding domain, at least one PDL1 binding domain, and at least one human serum albumin domain.

In one aspect, the present invention relates to a pharmaceutical composition comprising the multispecific antibody of the invention and a pharmaceutically acceptable carrier.

In a further aspect, the present invention provides the multispecific antibody of the invention or the pharmaceutical composition of the invention for use as a medicament.

In a further aspect, the present invention provides the multispecific antibody of the invention or the pharmaceutical composition of the invention for use in treatment of cancer in a subject in need thereof.

In one aspect, the present invention provides use of the multispecific antibody of the invention or the pharmaceutical composition of the invention for treating cancer in a subject in need thereof.

In one aspect, the present invention provides use of the multispecific antibody of the invention or the pharmaceutical composition of the invention in the manufacture of a medicament for treatment of a cancer, in a subject in need thereof.

In yet another aspect, the present invention provides a method of treating a cancer in a subject in need thereof comprising administering to the subject a therapeutically effective amount of the multispecific antibody of the invention or the pharmaceutical composition of the invention.

In a further aspect, the present invention provides a nucleic acid comprising a nucleotide sequence encoding the multispecific antibody of the invention. In a further aspect, the present invention provides a vector comprising said nucleic acid. In a further aspect, the present invention provides a host cell comprising said nucleic or said vector.

In yet another aspect, the present invention provides a method of producing the multispecific antibody of the invention or a binding domain thereof or a fragment thereof, the method comprising the step of culturing a host cell comprising a nucleic acid or a vector encoding the multispecific antibody of the invention or a binding domain thereof or a fragment thereof.

The aspects, advantageous features and preferred embodiments of the present invention summarized in the following items, respectively alone or in combination, further contribute to solving the object of the invention:

1. A multispecific antibody comprising:
   a) at least one CD137 binding domain (CD137-BD); and
   b) at least one PDL1 binding domain (PDL1-BD).
2. The multispecific antibody of item 1, wherein said antibody is monovalent, bivalent or multivalent for CD137 specificity, preferably monovalent.
3. The multispecific antibody of item 1 or 2, wherein said antibody is monovalent, bivalent or multivalent for PDL1 specificity, preferably monovalent.
4. The multispecific antibody of item 1, wherein said antibody comprises one CD137-BD and one PDL1-BD.
5. The multispecific antibody of item 1, wherein said antibody consists of one CD137-BD and one PDL1-BD.
6. The multispecific antibody of any one of items 1 to 4, wherein said antibody is trispecific.
7. The multispecific antibody of any one of items 1 to 4, wherein said antibody further comprises at least one human serum albumin binding domain, preferably one human serum albumin binding domain.
8. The multispecific antibody of item 7, wherein said antibody comprises one CD137-BD, one PDL1-BD and one HSA-BD.
9. The multispecific antibody of any of the preceding items, wherein said antibody does not comprise an immunoglobulin Fc region polypeptide.
10. The multispecific antibody of any of the preceding items, wherein said binding domains are capable of binding to their respective antigen or receptor simultaneously.
11. The multispecific antibody of any of the preceding items, wherein each of said binding domain, e.g., PDL1-BD, CD137-BD, or HSA-BD, is independently selected from the group consisting of a Fab, an Fv, an scFv, dsFv, a scAb, STAB, a single domain antibody (sdAb or dAb), a single domain heavy chain antibody, and a single domain light chain antibody, a VHH, a VNAR, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology (F-star's Modular Antibody Technology™).

12. The multispecific antibody of any of the preceding items, wherein said PDL1-BD and/or said CD137-BD and/or said HSA-BD is/are independently selected from Fv and scFv.
13. The multispecific antibody of any of the preceding items, wherein said CD137-BD can agonize CD137 upon clustering.
14. The multispecific antibody of item 13, wherein said CD137-BD:
   a) binds to human CD137 with a dissociation constant (KD) of less than 50 nM, particularly less than 10 nM, particularly less than 5 nM, particularly less than 1 nM, particularly less than 500 pM, more particularly less than 100 pM, more particularly less than 50 pM, in particular as measured by SPR), particularly wherein said antibody is an scFv (monovalent affinity);
   b) binds to human CD137 with a $K_{off}$ rate of $10^{-3}$ $s^{-1}$ or less, or $10^{-4}$ $s^{-1}$ or less, or $10^{-5}$ $s^{-1}$ or less as measured by SPR, particularly wherein said antibody is an scFv;
   c) binds to human CD137 with a $K_{on}$ rate of at least $10^4$ $M^{-1}s^{-1}$ or greater, at least $10^5$ $M^{-1}s^{-1}$ or greater, at least $10^6$ $M^{-1}s^{-1}$ or greater, as measured by SPR, particularly wherein said antibody is an scFv;
   d) optionally, does not cross-compete with urelumab;
   e) optionally, does not cross-compete with utomilumab; and/or
   f) is cross-reactive with *Macaca fascicularis* (Cynomolgus) CD137; and/or
   g) when in scFv format, has a melting temperature (Tm), determined by differential scanning fluorimetry, of at least 50° C., preferably of at least 55° C., more preferably at least 60° C., in particular wherein said antibody or antigen-binding fragment thereof is formulated in phosphate-citrate buffer at pH 6.4, 150 mM NaCl, in particular wherein said antibody is formulated in 50 mM phosphate citrate buffer with 150 mM NaCl at pH 6.4;
   h) when in scFv format, has a loss in monomer content, after storage for at least two weeks, particularly for at least four weeks, at 4° C., of less than 7%, e.g. less than 6%, less than 5%, less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH 6.4; and/or
   i) when in scFv format, has a loss in monomer content, after storage for at least two weeks, particularly for at least four weeks, at 40° C., of less than 5%, e.g. less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH 6.4.
15. The multispecific antibody of item 13 or item 14, wherein said CD137-BD comprises a heavy chain variable region comprising a CDR having the sequence of SEQ ID NO: 1 for HCDR1, SEQ ID NO: 2 for HCDR2, and SEQ ID NO: 3 for HCDR3, and a light chain variable region comprising a CDR having the sequence SEQ ID NO: 18 for LCDR1, SEQ ID NO: 19 for LCDR2, and SEQ ID NO: 20 for LCDR3.
16. The multispecific antibody of item 15, wherein said CD137-BD comprises a heavy chain variable region comprising an amino acid sequence that is at least 90 percent identical to the amino acid sequence selected from the group consisting of SEQ ID NOs: 14, 15, 16 and 17; and a light chain variable region comprising an amino acid sequence that is at least 90 percent identical to the amino acid sequence selected from the group consisting of SEQ ID NOs: 27, 28, 29 and 30.
17. The multispecific antibody of item 16, wherein said CD137-BD comprises: a heavy chain variable region comprising an amino acid sequence selected from any of SEQ ID NOs: 14, 15, 16 and 17; and a light chain variable region comprising an amino acid sequence selected from any of SEQ ID NOs: 27, 28, 29 and 30.
18. The multispecific antibody of item 16, wherein said CD137-BD comprises (a) a VH sequence of SEQ ID NO: 14 and a VL sequence of SEQ ID NO: 27; (b) a VH sequence of SEQ ID NO: 15 and a VL sequence of SEQ ID NO: 28; (c) a VH sequence of SEQ ID NO: 16 and a VL sequence of SEQ ID NO: 29; or (d) a VH sequence of SEQ ID NO: 17 and a VL sequence of SEQ ID NO: 30.
19. The multispecific antibody of item 15, wherein said CD137-BD a heavy chain variable region comprising an amino acid sequence that is at least 90 percent identical to the amino acid sequence SEQ ID NO: 17; and a light chain variable region comprising an amino acid sequence that is at least 90 percent identical to the amino acid sequence SEQ ID NO: 30, wherein said heavy chain variable region comprises a G51C mutation (AHo numbering) and said light chain variable region comprises T141C mutation (AHo numbering).
20. The multispecific antibody of item 13 or item 14, wherein said CD137-BD comprises a heavy chain variable region comprising a CDR having the sequence of SEQ ID NO: 59 for HCDR1, SEQ ID NO: 60 for HCDR2, and SEQ ID NO: 61 for HCDR3, and a light chain variable region comprising a CDR having the sequence SEQ ID NO: 74 for LCDR1, SEQ ID NO: 75 for LCDR2, and SEQ ID NO: 76 for LCDR3.
21. The multispecific antibody of item 20, wherein said CD137-BD comprises a heavy chain variable region comprising an amino acid sequence that is at least 90 percent identical to the amino acid sequence selected from the group consisting of SEQ ID NOs: 71, 72 and 73; and a light chain variable region comprising an amino acid sequence that is at least 90 percent identical to the amino acid sequence selected from the group consisting of SEQ ID NOs: 83, 84 and 85.
22. The multispecific antibody of item 21, wherein said CD137-BD comprises: a heavy chain variable region comprising an amino acid sequence selected from any of SEQ ID NOs: 71, 72 and 73; and a light chain variable region comprising an amino acid sequence selected from any of SEQ ID NOs: 83, 84 and 85.
23. The multispecific antibody of item 21, wherein said CD137-BD comprises (a) a VH sequence of SEQ ID NO: 71 and a VL sequence of SEQ ID NO: 83; (b) a VH sequence of SEQ ID NO: 72 and a VL sequence of SEQ ID NO: 84; or (c) a VH sequence of SEQ ID NO: 73 and a VL sequence of SEQ ID NO: 85.
24. The multispecific antibody of item 21, wherein said CD137-BD a heavy chain variable region comprising an amino acid sequence that is at least 90 percent identical to the amino acid sequence SEQ ID NO: 73; and a light chain variable region comprising an amino acid sequence that is at least 90 percent identical to the amino acid sequence SEQ ID NO: 85, wherein said heavy chain variable region comprises a G51C mutation (AHo numbering) and said light chain variable region comprises T141C mutation (AHo numbering).

25. The multispecific antibody of any of the preceding items, wherein said PDL1-BD is a blocker of PDL1.

26. The multispecific antibody of item 25, wherein said PDL1-BD:

a) binds to human PDL1 with a dissociation constant (KD) of less than 50 nM, particularly less than 10 nM, particularly less than 5 nM, particularly less than 1 nM, particularly less than 500 pM, more particularly less than 100 pM, preferably less than 10 pM, more preferably 5 pM, in particular as measured by SPR, particularly wherein said antibody is an scFv (monovalent affinity);

b) binds to human PDL1 with a $K_{off}$ rate of $10^{-3}$ $s^{-1}$ or less, or $10^{4}$ $s^{-1}$ or less, or $10^{-5}$ $s^{-1}$ or less as measured by SPR, particularly wherein said antibody is an scFv;

c) binds to human PDL1 with a $K_{on}$ rate of at least 103 $M^{-1}s^{-1}$ or greater, at least 104 $M^{-1}s^{-1}$ or greater, at least 105 $M^{-1}s^{-1}$ or greater, at least $10^{6}$ $M^{-1}s^{-1}$ or greater as measured by SPR, particularly wherein said antibody is an scFv;

d) is cross-reactive with *Macaca fascicularis* (Cynomolgus) PDL1; and/or e) is non-cross reactive to *Mus musculus* PDL1; and/or f) when in scFv format, has a melting temperature (Tm), determined by differential scanning fluorimetry, of at least 55° C., e.g. at least 60° C., preferably at least 65° C., more preferably at least 70° C., in particular wherein said antibody or antigen-binding fragment thereof is formulated in phosphate-citrate buffer at pH 6.4, 150 mM NaCl, in particular wherein said antibody is formulated in 50 mM phosphate citrate buffer with 150 mM NaCl at pH 6.4;

g) when in scFv format, has a loss in monomer content, after five consecutive freeze-thaw cycles, of less than 5%, preferably less than 3%, more preferably less than 1%, when the antibody of the invention is at a starting concentration of 10 mg/ml, in particular wherein said antibody is formulated in 50 mM phosphate citrate buffer with 150 mM NaCl at pH 6.4; and/or h) when in scFv format, has a loss in monomer content, after storage for at least two weeks, particularly for at least four weeks, at 4° C., of less than 15%, e.g. less than 12%, less than 10%, less than 7%, less than 5%, less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH 6.4.

27. The multispecific antibody of item 25 or item 26, wherein said PDL1-BD comprises: (a) a HCDR1 comprising the amino acid sequence of SEQ ID NO: 89; (b) a HCDR2 comprising the amino acid sequence of SEQ ID NO: 90; (c) a HCDR3 comprising the amino acid sequence of SEQ ID NO: 91; (d) a LCDR1 comprising the amino acid sequence of SEQ ID NO: 105; (e) a LCDR2 comprising the amino acid sequence of SEQ ID NO: 106; and (f) a LCDR3 comprising the amino acid sequence of SEQ ID NO: 107.

28. The multispecific antibody of item 25 or item 26, wherein said PDL1-BD comprises: (a) a HCDR1 comprising the amino acid sequence of SEQ ID NO: 119; (b) a HCDR2 comprising the amino acid sequence of SEQ ID NO: 120; (c) a HCDR3 comprising the amino acid sequence of SEQ ID NO: 121; (d) a LCDR1 comprising the amino acid sequence of SEQ ID NO: 135; (e) a LCDR2 comprising the amino acid sequence of SEQ ID NO: 136; and (f) a LCDR3 comprising the amino acid sequence of SEQ ID NO: 137.

29. The multispecific antibody of any one of items 25 to 28, wherein said PDL1-BD comprises: a heavy chain variable region comprising an amino acid sequence that is at least 90 percent identical to the amino acid sequence selected from the group consisting of SEQ ID NOs: 102, 103, 104, 132, 133 and 134; and a light chain variable region comprising an amino acid sequence that is at least 90 percent identical to the amino acid sequence selected from the group consisting of SEQ ID NOs: 114, 115, 144 and 145.

30. The multispecific antibody of any one of items 25 to 28, wherein said PDL1-BD comprises: a heavy chain variable region comprising an amino acid sequence selected from any of SEQ ID NOs: 102, 103, 104, 132, 133 and 134; and a light chain variable region comprising an amino acid sequence selected from any of SEQ ID NOs: 114, 115, 144 and 145.

31. The multispecific antibody of any one of items 25 to 28, wherein said PDL1-BD comprises: (a) a VH sequence of SEQ ID NO: 102 and a VL sequence of SEQ ID NO: 114; (b) a VH sequence of SEQ ID NO: 103 and a VL sequence of SEQ ID NO: 114; (c) a VH sequence of SEQ ID NO: 104 and a VL sequence of SEQ ID NO: 115; (d) a VH sequence of SEQ ID NO: 132 and a VL sequence of SEQ ID NO: 144; (e) a VH sequence of SEQ ID NO: 133 and a VL sequence of SEQ ID NO: 145; or (f) a VH sequence of SEQ ID NO: 134 and a VL sequence of SEQ ID NO: 144.

32. The multispecific antibody of item 27, wherein said PDL1-BD comprises: (a) a VH sequence of SEQ ID NO: 102 and a VL sequence of SEQ ID NO: 114; or (b) a VH sequence of SEQ ID NO: 104 and a VL sequence of SEQ ID NO: 115.

33. The multispecific antibody of item 28, wherein said PDL1-BD comprises: (a) a VH sequence of SEQ ID NO: 133 and a VL sequence of SEQ ID NO: 145; or (b) a VH sequence of SEQ ID NO: 134 and a VL sequence of SEQ ID NO: 144.

34. The multispecific antibody of any of the preceding items, wherein said CD137-BD binds to human CD137 with a dissociation constant (KD) of at least 5 times, preferably at least 10 times, e.g., at least 50, at least 100, at least 200, at least 300, at least 400, more preferably at least 500 times, e.g., at least 600, at least 700, at least 800, at least 900, at least 1,000 times higher relative to a dissociation constant (KD) of binding to human PDL1 of said PDL1-BD.

35. The multispecific antibody of claim 34, wherein said CD137-BD binds to human CD137 with a dissociation constant (KD) between 10 nM and 10 pM, e.g., between 10 nM and 0.1 nM, preferably between 5 nM and 0.1 nM more preferably between 5 nM and 1 nM.

36. The multispecific antibody of any one of items 7 to 35, wherein said HSA-BD comprises: (a) a heavy chain variable region CDR1 comprising an amino acid sequence selected from any one of SEQ ID NOs: 149 and 173; (b) a heavy chain variable region CDR2 comprising an amino acid sequence selected from any of SEQ ID NOs: 150 and 174; (c) a heavy chain variable region CDR3 comprising an amino acid sequence selected from any of SEQ ID NOs: 151 and 175; (d) a light chain variable region CDR1 comprising an amino acid sequence selected from any of SEQ ID NOs: 162 and 186; (e) a light chain variable region CDR2 comprising an amino acid sequence selected from any of SEQ ID NOs: 163 and 187; and (f) a light chain variable region CDR3 comprising an amino acid sequence selected from any of SEQ ID NOs: 164 and 188.

37. The multispecific antibody of item 36, wherein said HSA-BD comprises: a heavy chain variable region comprising an amino acid sequence that is at least 90 percent identical to the amino acid sequence selected from the group consisting of SEQ ID NOs: 161 and 185; and a light chain variable region comprising an amino acid sequence that is at least 90 percent identical to the amino acid sequence selected from the group consisting of SEQ ID NOs: 171 and 195.

38. The multispecific antibody of item 36, wherein said HSA-BD comprises: a heavy chain variable region comprising an amino acid sequence selected from any of SEQ ID NOs: 161, and 185; and a light chain variable region comprising an amino acid sequence selected from any of SEQ ID NOs: 171 and 195.

39. The multispecific antibody of item 36, wherein said HSA-BD comprises: (a) a VH sequence of SEQ ID NO: 161 and a VL sequence of SEQ ID NO: 171; or (b) a VH sequence of SEQ ID NO: 185 and a VL sequence of SEQ ID NO: 195.

40. The multispecific antibody of item 36, wherein said HSA-BD comprises: (a) HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively, and a heavy chain variable region comprising an amino acid sequence that is at least 90 percent identical to the amino acid sequence SEQ ID NO: 161, and a light chain variable region comprising an amino acid sequence that is at least 90 percent identical to the amino acid sequence SEQ ID NO: 171; or (b) HCDR1, HCDR2, and HCDR3 sequences of SEQ ID NOs: 173, 174, and 175, respectively, and LCDR1, LCDR2, and LCDR3 sequences of SEQ ID NOs: 186, 187, and 188, respectively, and a heavy chain variable region comprising an amino acid sequence that is at least 90 percent identical to the amino acid sequence SEQ ID NO: 185; and a light chain variable region comprising an amino acid sequence that is at least 90 percent identical to the amino acid sequence SEQ ID NO: 195.

41. The multispecific antibody of item 1, wherein said antibody is in a format selected from the group consisting of a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH3-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs); an Fv, scFv, scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH and DuoBodies.

42. The multispecific antibody of item 1, wherein said antibody is a scDb comprising an amino acid sequence selected from any of SEQ ID NOs: 209, 210, 211, 212, 213, 214, and 215.

43. The multispecific antibody of item 1, wherein said antibody is a scDb-scFv comprising an amino acid sequence selected from any of SEQ ID NOs: 216, 217, 218, 219, 220, 221, 222, 223, 224, 225, 226, 227, 228, 229, 230 and 231, preferably wherein said antibody is a scDb-scFv comprising an amino acid sequence SEQ ID NO: 229 or SEQ ID NO: 231, more preferably wherein said antibody is a scDb-scFv comprising an amino acid sequence SEQ ID NO: 231.

44. A pharmaceutical composition comprising the multispecific antibody of any one of the preceding items and a pharmaceutically acceptable carrier.

45. The multispecific antibody of any one of items 1 to 43 or the pharmaceutical composition of item 44 for use as a medicament.

46. The multispecific antibody of any one of items 1 to 43 or the pharmaceutical composition of item 44 for use in treatment of a cancer in a subject in need thereof.

47. Use of the multispecific antibody of any one of items 1 to 43 or the pharmaceutical composition of item 44 for treating a cancer in a subject in need thereof.

48. Use of the multispecific antibody of any one of items 1 to 43 or the pharmaceutical composition of item 44 in the manufacture of a medicament for treatment of a cancer, in a subject in need thereof.

49. A method of treating a cancer in a subject in need thereof comprising administering to the subject a therapeutically effective amount of the multispecific antibody of any one of items 1 to 43 or the pharmaceutical composition of item 44.

50. The multispecific antibody of any one of items 45 to 46 or the use of any one of items 47 to 48 or the method of item 49, wherein said cancer is a PDL1-positive cancer, preferably wherein said cancer expresses high levels of PDL1 in comparison to a healthy tissue.

51. A nucleic acid encoding the multispecific antibody according to any one of items 1 to 43 or a binding domain thereof or a fragment thereof.

52. A vector comprising the nucleic acid of item 51.

53. A host cell comprising the nucleic acid of item 51 or the vector of item 52.

54. A method of producing the multispecific antibody according to any one of items 1 to 43, the method comprising the step of culturing a host cell comprising a nucleic acid according to item 51 or a vector according to item 52.

55. A kit comprising the multispecific antibody according to any one of items 1 to 43, or the composition of item 44.

BRIEF DESCRIPTION OF THE DRAWINGS

FIG. 5 Neutralization potency of the PDL1/PD-1 interaction in the reporter gene assay by scDb-scFvs PR0963 and PRO1057 (A), PRO1186 and PRO1430 (B), PRO1431 and PRO1432 (C), PRO1473 (D), PRO1476 (E), PRO1479 (F), PRO1482 (G), PRO1480 and PRO1481 (H) in presence of recombinant human serum albumin. % inhibition proportional to the luminescence signal obtained in the assay is represented in function of the scFvs concentrations in ng/ml. Avelumab was used as reference.

Luminescence was read 6 h after addition of Jurkat reporter cells and data were fitted using sigmoidal 4PL fit (GraphPad Prism).

Figure 18:
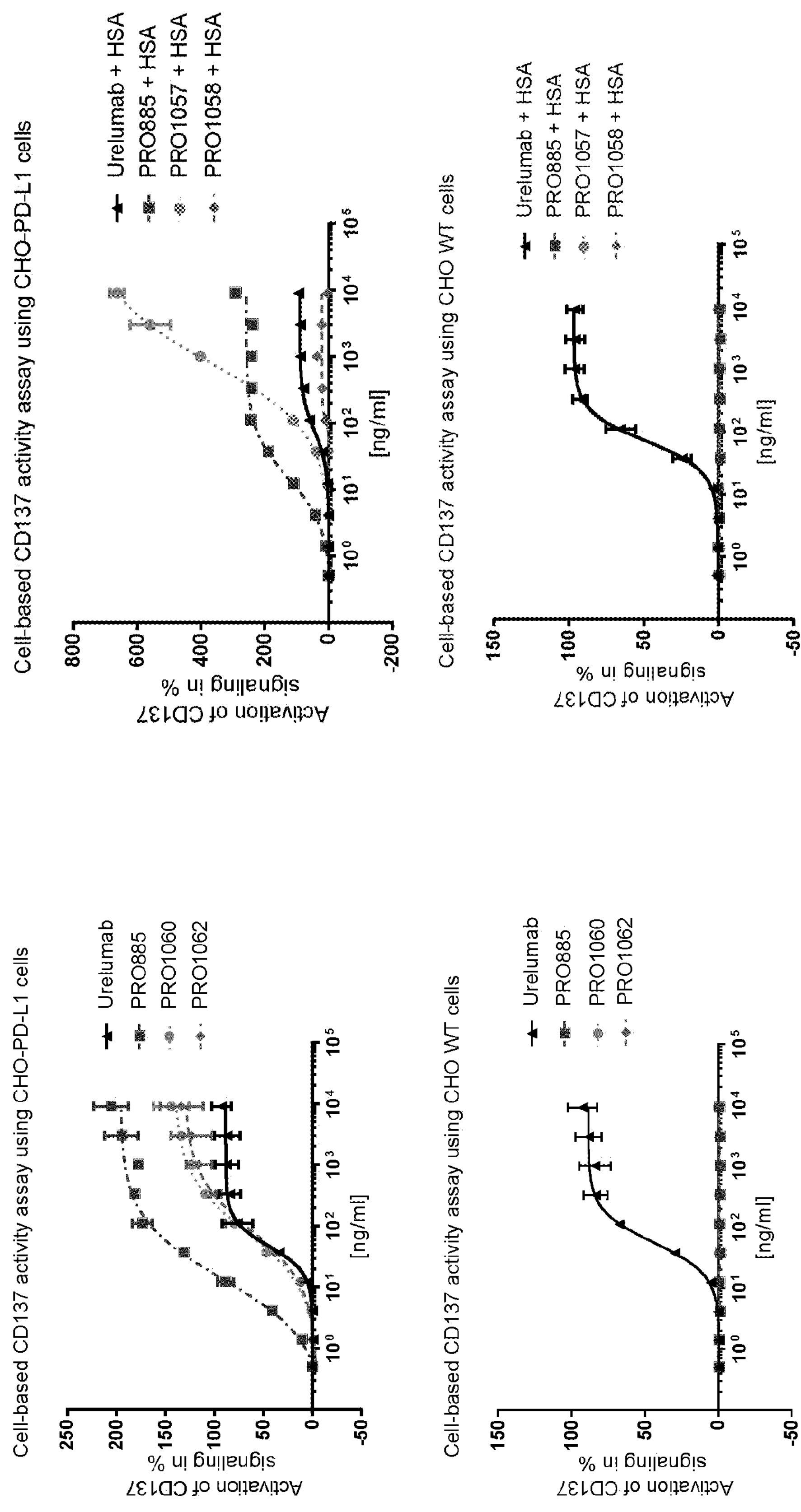

FIG. 18 CD137 activation by molecules with prolonged serum half-life in the NFkB-Luciferase reporter gene assay after 24 h. In the presence of PDL1 expressing CHO cells, long half-life molecules activated CD137 signaling in Jurkat cells whereas no activation was observed when CHO WT cells were tested. Urelumab activated CD137 signaling independently of PDL1 expression. Interestingly, despite similar affinities to both targets, PRO1057 showed a much higher maximal signal than PRO1058, which after 24 hours exceeded even the activity of the scDb Pro885. And further, the monovalent scDb-scFv PRO1057 showed much stronger activation than the respective bivalent Morrison format PRO1060. Luminscence was read 24 h after addition of Jurkat reporter cells and data were fitted using sigmoidal 4PL fit (GraphPad Prism).

FIG. 19 (A) CD137 activation by molecules with prolonged half-life, after 24 h. In the presence of HCC827 cells either unstimulated or stimulated with IFNy at 10 ng/ml for 24 h, long half-life molecules activated CD137 signaling in Jurkat cells. Urelumab served as reference molecule to assess the relative activation of CD137 signaling. The monovalent scDb-scFv PRO1057 showed higher maximal activation than the respective bivalent Morrison format PRO1060. Luminescence was read 24 h after addition of Jurkat reporter cells and data were fitted using sigmoidal 4PL fit (GraphPad Prism). (B) Tri-specific scDb-scFv molecules PRO1430, PRO1431, PRO1432, PRO1473, PRO1476, PRO1479, PRO1480, PRO1481 and PRO1482 were tested in CD137 activity assay in the presence of IFNy (10 ng/ml) stimulated HCC827 for 6 h and 24 h. In this experiment, PRO885 served as reference molecule to assess the relative activation of CD137 signaling. Tri-specific scDb-scFv molecule PRO1186 was taken along on each plate to compare its activity with the other scDb-scFv molecules. Luminescence was read 6 h or 24 h after addition of Jurkat reporter cells and concentrations of tested molecules with increasing RLU values only were fitted using sigmoidal 4PL fit (GraphPad Prism).

Figure 20:
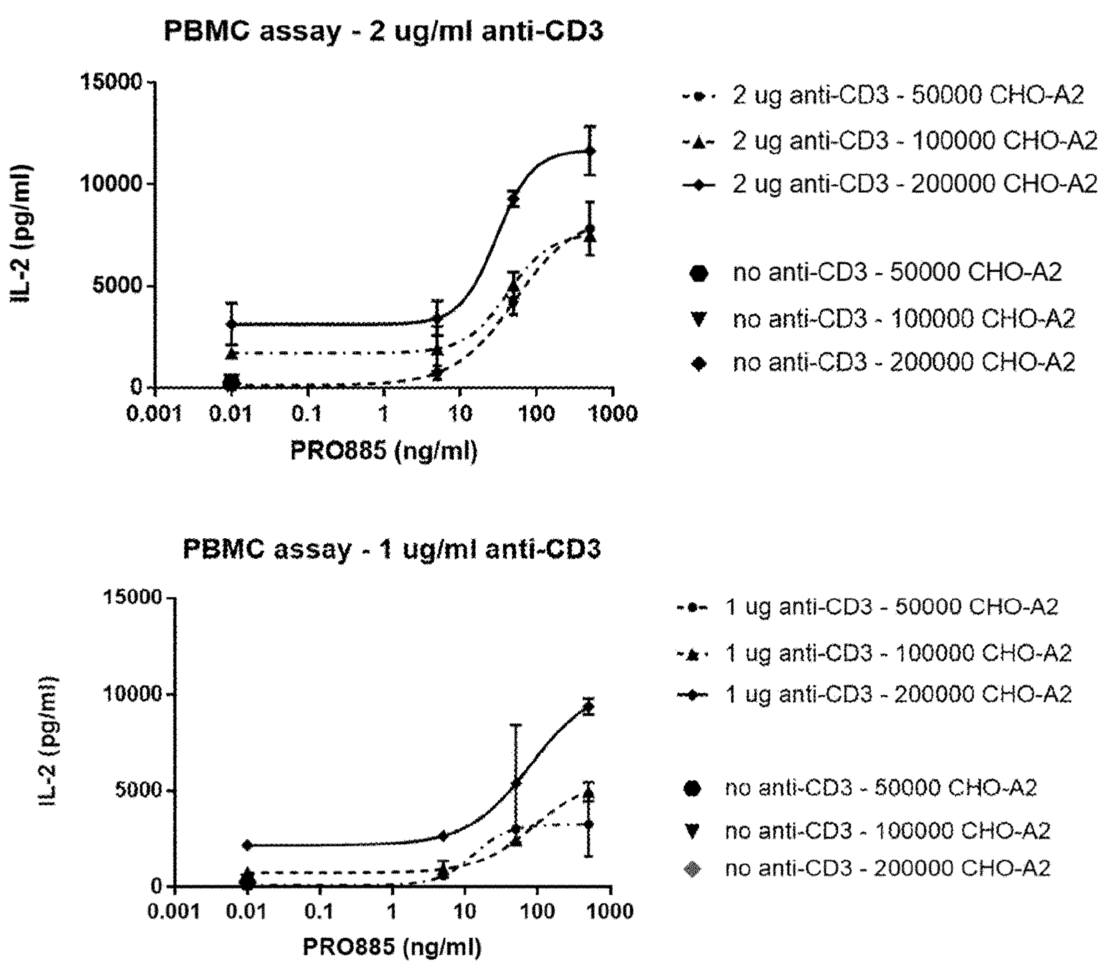

FIG. 20 Ex vivo T cell activation. The costimulatory engagement of PDL1 and CD137 by PRO885 is shown, leading to IL-2 production clearly above background IL-2 levels. CHO-A2 cells are transgenic CHO cells expressing PDL1.

Figure 21:
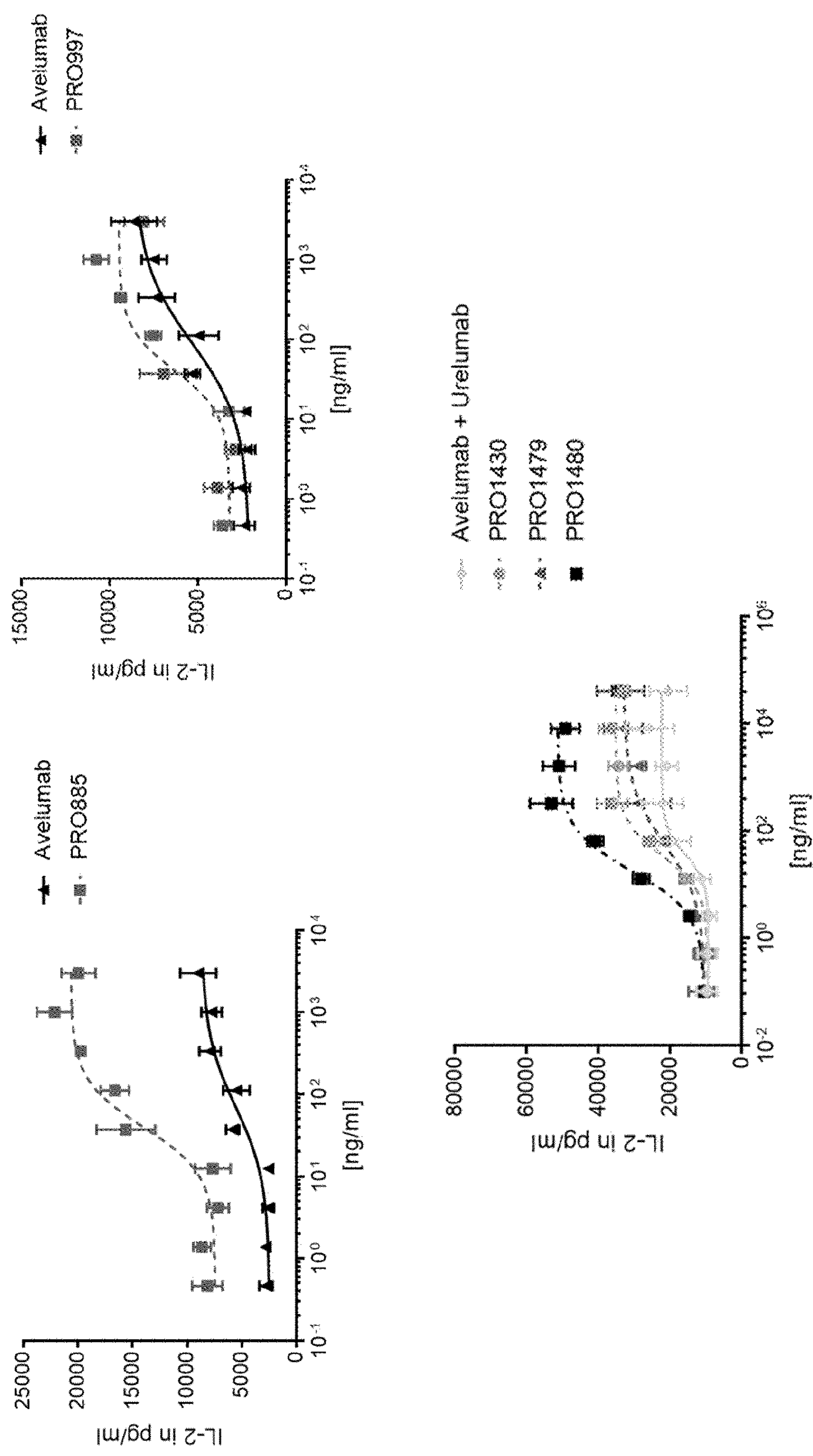

FIG. 21 Ex vivo T cell activation assay. PBMC were stimulated with 10 ng/ml SEA and treated with serial dilutions of the reference molecule avelumab, a cocktail of the reference molecules avelumab and urelumab, or scFv PRO997, the scDb PRO885 or the scDb-scFvs PRO1430, PRO1479 and PRO1480 for 96 h. Activation of T-cells was assessed by quantification of IL-2 in harvested supernatants by ELISA. Treatment with PRO885, PRO997, PRO1430, PRO1479 and PRO1480 resulted in pronounced IL-2 secretion. PRO997 showed higher potency than Aavelumab. PRO885 showed much increased effect size when compared to avelumab. Treatment with scDb-scFvs resulted in pronounced IL-2 secretion when compared to the cocktail of the reference molecules. PRO1480 showed much increased effect size when compared to the other scDb-scFvs. Data were fitted using sigmoidal 4PL fit (GraphPad Prism).

Figure 22:
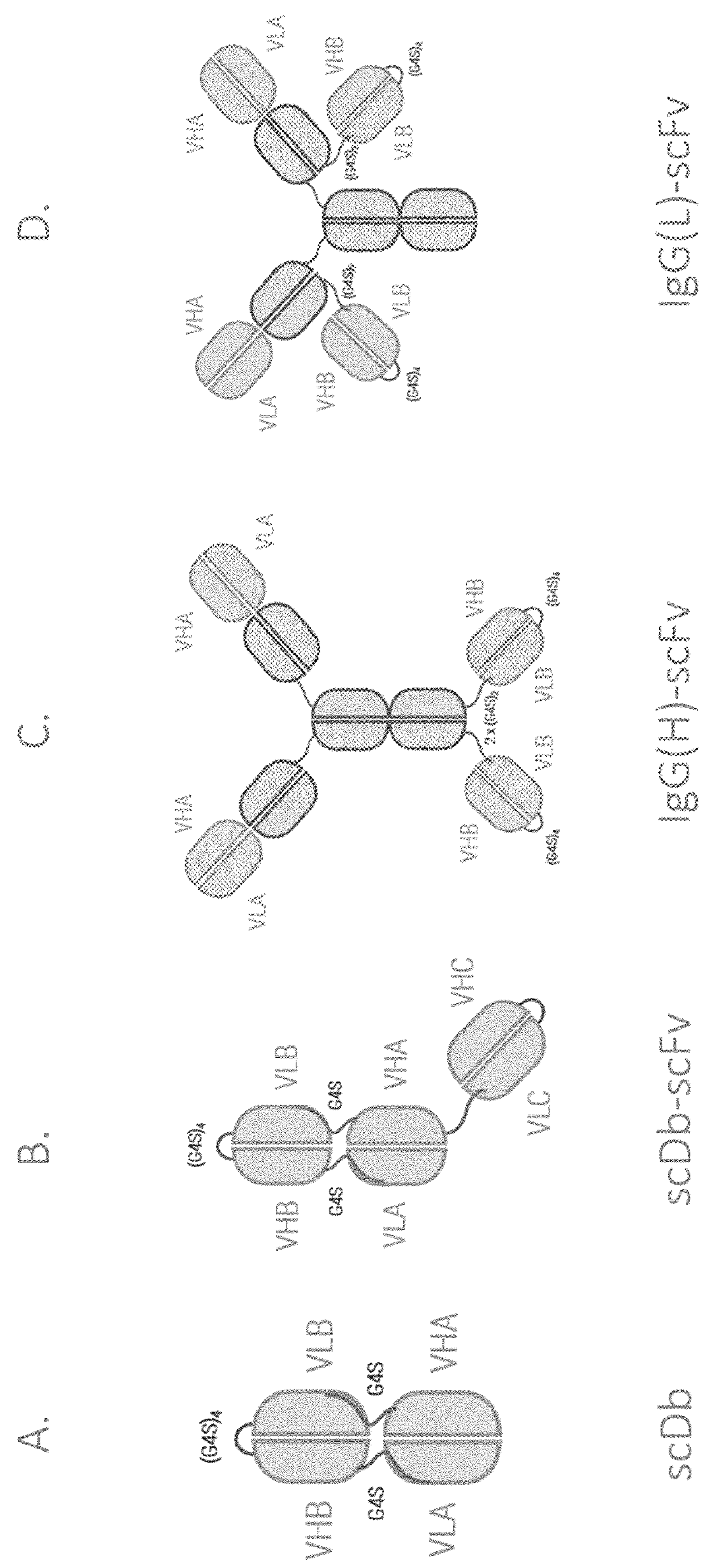

FIG. 22 Schematic representation of the exemplary formats of the multispecific antibodies of the disclosure: single chain diabodies (scDb) (A), scDb-scFvs (B), IgG-scFv molecules (C and D).

FIG. 23 Ex vivo T cell activation assay. (A)-(D) PBMC were stimulated with 10 ng/ml SEA (Staphylococcal Enterotoxin A) and treated with serial dilutions of avelumab, urelumab, the combination of avelumab and urelumab, the scDb PRO885, and the scDb-scFv PRO1175 or PRO1186 for 96 h. Activation of T-cells was assessed by quantification of IL-2 in harvested supernatants by ELISA. PRO1175 and PRO1186 showed superior potency to stimulate IL-2 production in PMBCs when compared to the combination of avelumab and urelumab. Data were fitted using sigmoidal 4PL fit (GraphPad Prism). (E)-(I) PBMC stimulated with 10 ng/ml SEA were treated with serial dilutions of the scDb-scFv molecules PRO1430, PRO1431, PRO1476, PRO1479, PRO1482 for 96 h. Tri-specific scDb-scFv molecule PRO 1186 served as reference molecule to assess the relative IL-2 production in PBMCs on each plate. PRO1430, PRO1479, and PRO1482 demonstrated superior potency to stimulate IL-2 production in PMBCs when compared to the others scDb-scFv molecules. Concentrations of tested molecules with increasing IL-2 values only were fitted using sigmoidal 4PL fit (GraphPad Prism). (J)-(K) PBMCs from healthy donors were incubated for 3 days in presence of an anti-CD3 antibody. Human PDL1 expressing CHO cells and serial dilutions of avelumab, urelumab, avelumab/urelumab combination or anti-PDL1×CD137 PRO 1186 (scDb-scFv2) were added to the culture. IFNy secretion was assessed by ELISA. PRO 1186 was more potent to induce IL-2 (J) and IFNy (K) production than avelumab or urelumab, or the combination of the two. In absence of anti-CD3 antibodies, IL-2 and IFNy levels were comparable to basal cytokine secretion at all concentrations tested, showing the requirement of TCR signaling or CD3 engagement for productive CD137 signaling. (L) Stimulation of T-cells ex vivo in SEA PBMC assay by scDb-scFv molecule PRO1186 and combinations of anti-human CD137 and anti-human PDL1 IgGs. Measured RLUs normalized to Urelumab are represented in function of the molecules concentrations in ng/ml. (M) Maximum IL-2 secretion of T-cells ex vivo in SEA PBMC assay by scDb-scFv molecule PRO1186 and combinations of anti-human CD137 and anti-human PDL1 IgGs. The average of IL-2 levels at high concentrations of the molecules tested (8000, 1600, 320 ng/ml) were calculated and compared. PRO 1186 showed statistically significant higher IL-2 levels than the combinations of the IgGs ($p<0.0001$). Statistical analysis by 1way ANOVA and Tukey's multiple comparisons test.

Figure 24:
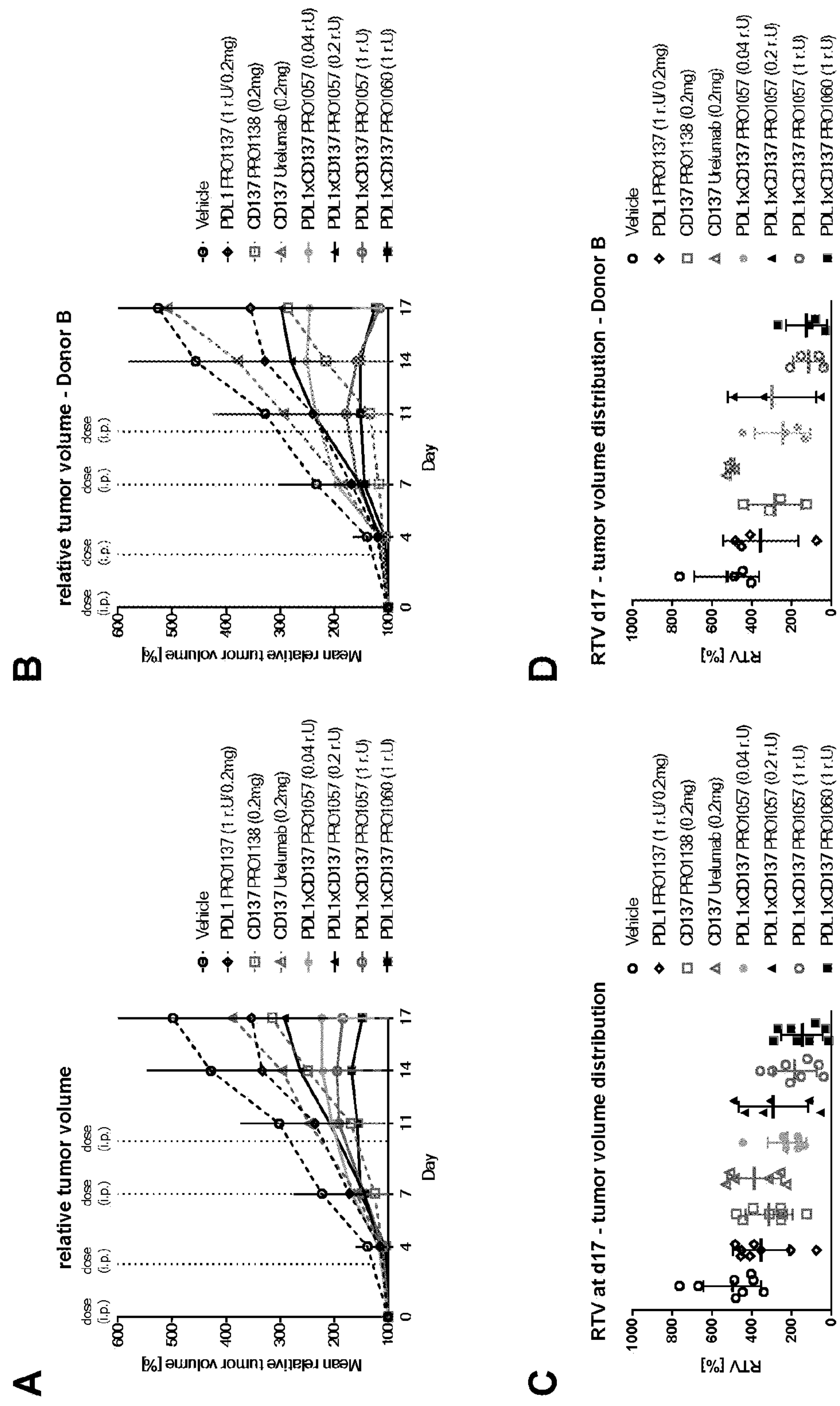

FIG. 24 Anti-tumor activity of the multispecific antibodies PRO1057 (scDb-scFv anti-PDL1×CD137×HSA) and PRO1060 (Morrison format anti-PDL1×CD137) compared to anti-PDL1 (PRO1137) and anti-CD137 (PRO1138 or urelumab) therapy in human HCC827 NSCLC xenografts using the immunodeficient NOG mice strain and allogeneic human peripheral blood mononuclear cells (hPBMC). Mice were treated with the multispecific antibodies (PRO1057 and PRO1060), anti-PDL1 (PRO1037), anti-CD137 (PRO1038 or urelumab) or vehicle i.p. on days 0, 3, 7 and 10. The relative activity compared to a 0.1 mg dose of avelumab is indicated in brackets as relative units (r.U). Tumor volumes were measured twice per week until mice were sacrificed on day 17 and 18. Tumor volumes are normalized to the tumor volume at the start of the treatment (relative tumor volume). (A) Mean relative tumor volumes ($n=8$ mice per group) of mice reconstituted with PBMCs from two donors. The dotted line indicates the time of treatment. (B) Mean relative tumor volumes from mice reconstituted with PBMCs from donor B ($n=4$ mice per group). (C) Individual relative tumor volumes of mice reconstituted with PBMCs from two donors. Each symbol represents an individual animal within the same treatment group. (D) Individual relative tumor volumes of mice reconstituted with PBMCs from donor B. Each symbol represents an individual animal within the same treatment group.

Figure 25:
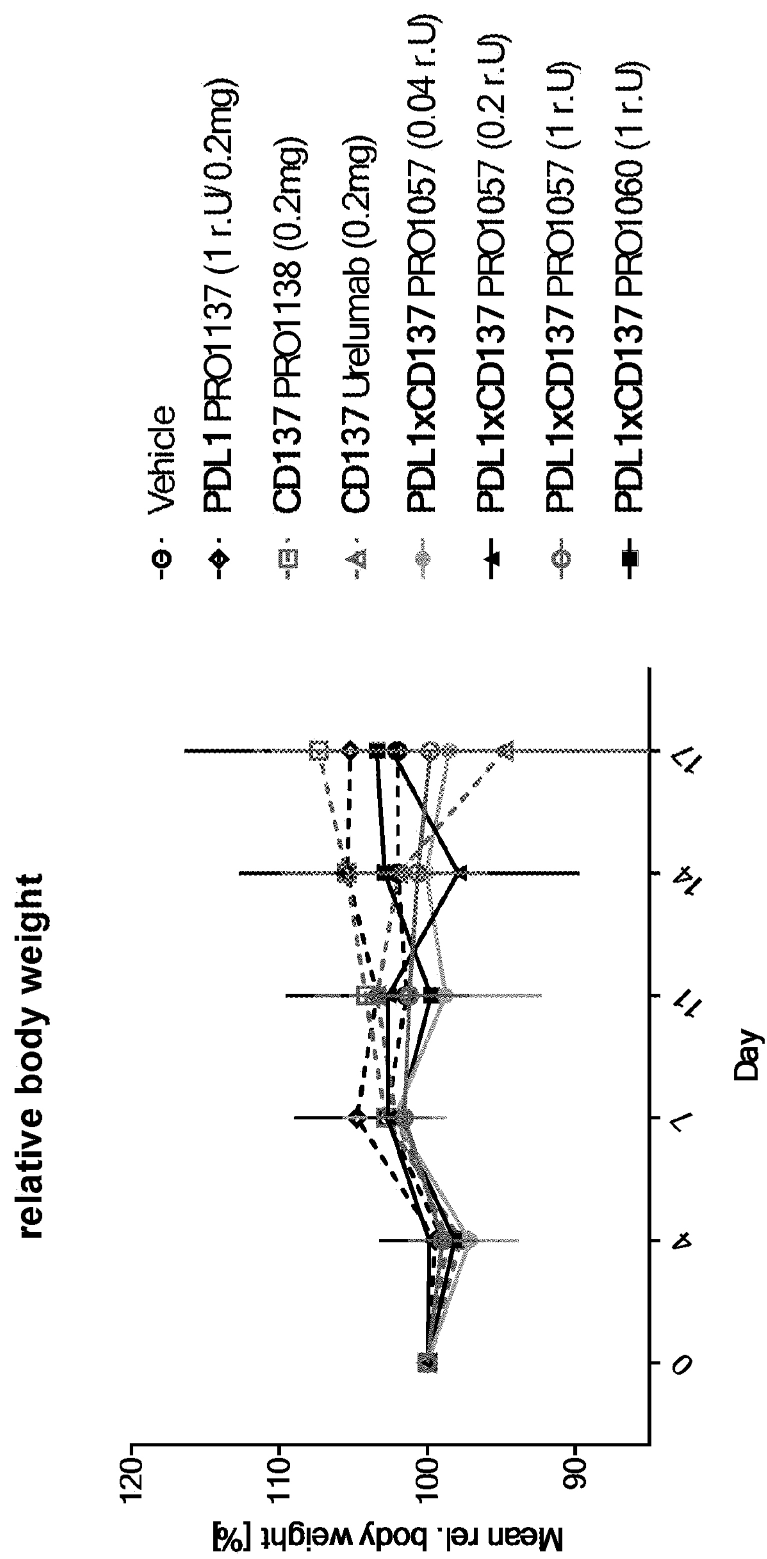

FIG. 25 HCC827 xenograft in hPBMC substituted NOG mice. Body weight of HCC827 challenged NOG mice upon treatment with multispecific antibodies PRO1057 (scDb-scFv anti-PDL1×CD137×HSA) and PRO1060 (Morrison format anti-PDL1×CD137) compared to anti-PDL1 (PRO1137) and anti-CD137 (PRO 1138 or urelumab) therapy. Body weight was measured twice per week until mice were sacrificed on day 17 and 18.

FIG. 26 HCC827 xenograft in hPBMC substituted NOG mice. Tumor infiltrating lymphocytes of HCC827 challenged NOG mice treated with multispecific antibodies PRO1057 (scDb-scFv anti-PDL1×CD137×HSA) and PRO1060 (Morrison format anti-PDL1×CD137) and anti-PDL1 (PRO1137) or anti-CD137 (PRO1138 or urelumab) antibodies, respectively, were studied by flow cytometry. (A) Frequency of human regulatory T cells (CD4+, FoxP3+) is shown as percentage of CD45+ cells. (B). Ratio of frequency of human CD8+ T cells and frequency of human regulatory T cells (Treg) in the tumor microenvironment (TME) is depicted. Each symbol represents an individual animal within the same treatment group.

Figure 27:
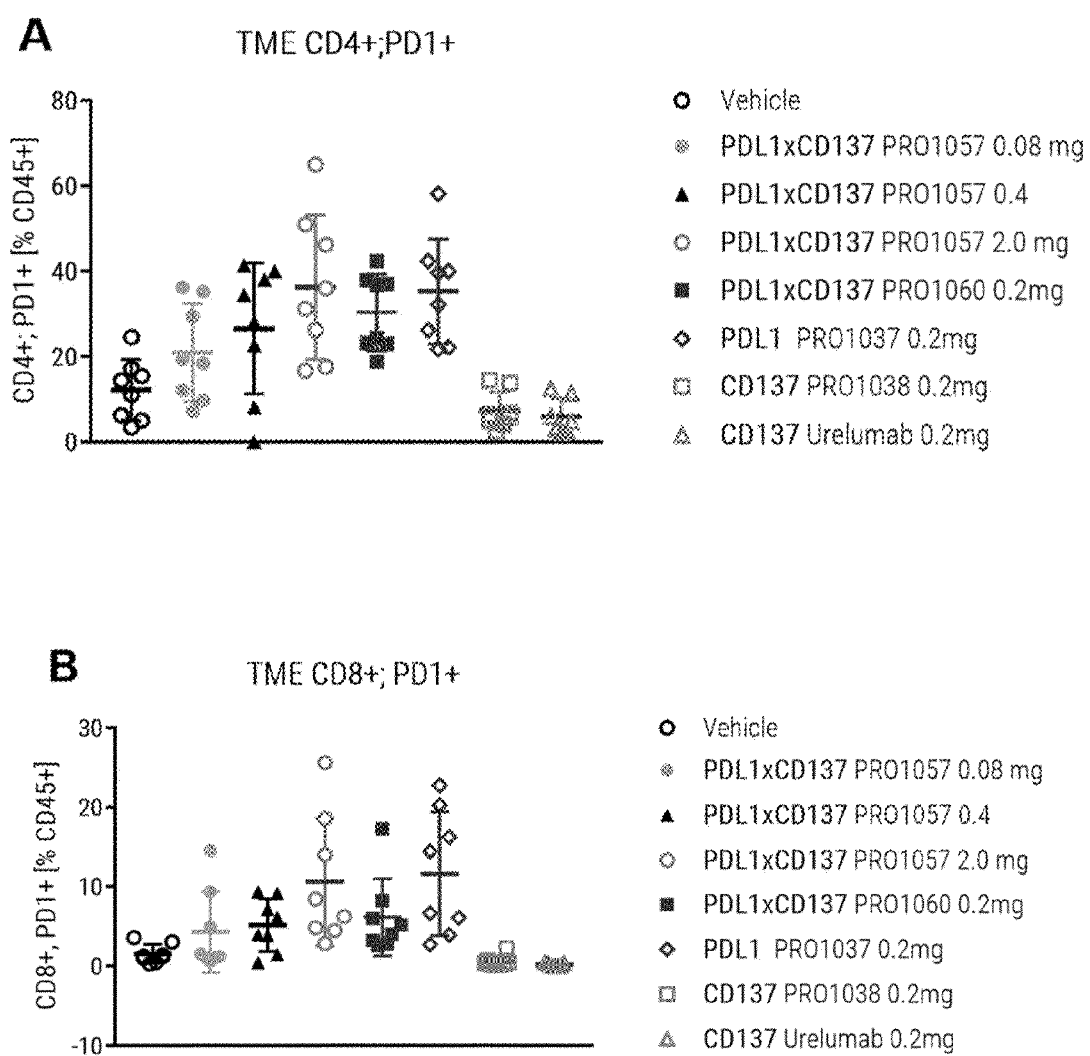

FIG. 27 HCC827 xenograft in hPBMC substituted NOG mice. Tumor infiltrating lymphocytes of HCC827 challenged NOG mice treated with multispecific antibodies PRO1057 (scDb-scFv anti-PDL1×CD137×HSA) and PRO1060 (Morrison format anti-PDL1×CD137) and anti-PDL1 (PRO1137) or anti-CD137 (PRO1138 or urelumab) antibodies, respectively, were studied by flow cytometry. (A) Frequency of human activated CD4+ T cells (CD4+, PD-1+) is shown as percentage of CD45+ cells. (B). Frequency of human activated CD8+ T cells (CD8+, PD-1+) is shown as percentage of CD45+ cells. Each symbol represents an individual animal within the same treatment group.

Figure 28:
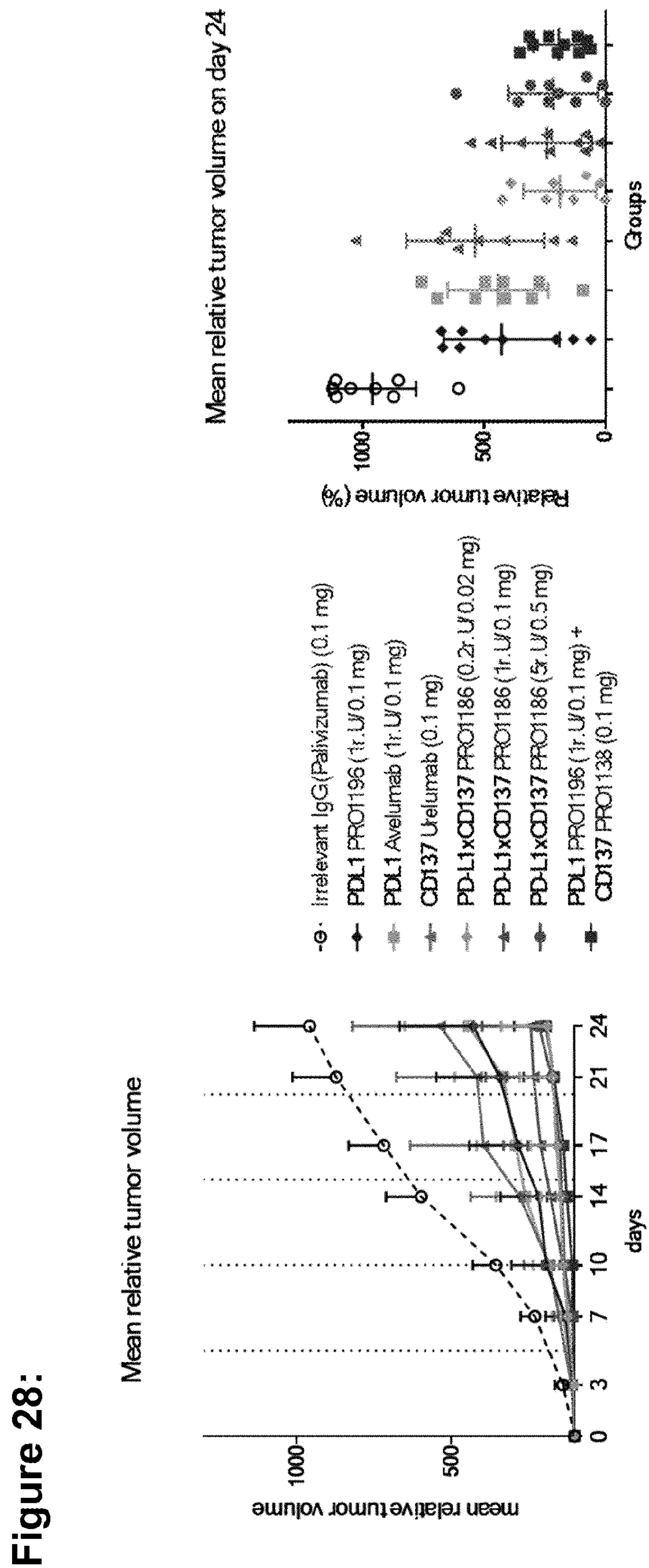

FIG. 28 Assessment of the anti-tumor efficacy of PDL1 blockade and concomitant localized stimulation of CD137 in NOG mice engrafted with human umbilical cord blood-derived CD34+ hematopoietic stem cells (UCB HSCs). Anti-tumor activity of the multispecific antibody PRO1186 (scDb-scFv anti-PDL1×CD137×HSA) was compared to treatment with anti-PDL1 IgG1 (PRO 1196 or avelumab) and anti-CD137 IgG4 (urelumab) therapy or the combination of the anti-PDL1 IgG1 (PRO 1196) with the anti-CD137 IgG4 (PRO 1138). Mice were treated with Palivizumab (0.1 mg), anti-PDL1 IgG1 (0.1 mg PRO1196, or 0.1 mg avelumab), anti-CD137 IgG4 (0.1 mg urelumab), PRO1186 at 3 different dose levels (0.02 mg, 0.1 mg and 0.5 mg), or a combination of anti-PDL1 IgG1 (PRO1196) and anti-CD137 IgG4 (PRO1138) (0.1 mg each) on day 0, 5, 10, 15 and 20 (dotted vertical lines). Tumor growth and body weight was recorded twice weekly.

Figure 29:
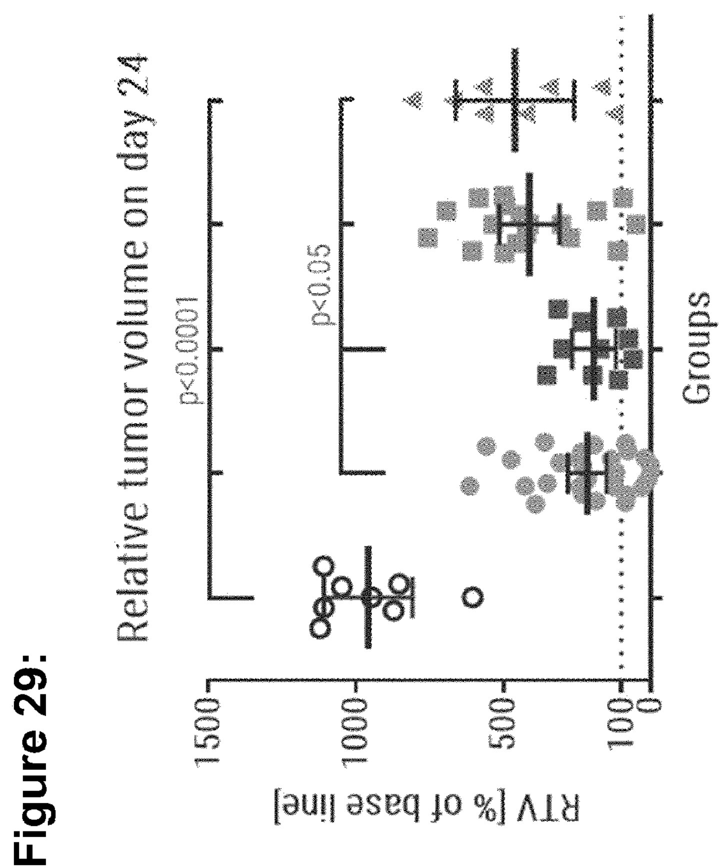

FIG. 29 Assessment of the anti-tumor efficacy of PDL1 blockade and concomitant localized stimulation of CD137 in NOG mice engrafted with human umbilical cord blood-derived CD34+ hematopoietic stem cells (UCB HSCs). Anti-tumor activity of the multispecific antibody PRO1186 (scDb-scFv anti-PDL1×CD137×HSA; all dose levels combined) was compared to treatment with anti-PDL1 IgG1 (PRO1196 and avelumab combined) and anti-CD137 IgG4 (urelumab) therapy or the combination of the anti-PDL1 IgG1 (PRO 1196) with the anti-CD137 IgG4 (PRO1138). All statistics were calculated using GraphPad Prism Version 6. Statistical significance was determined using One-way ANOVA test applying Bonferroni correction. Graphs show mean with 95% CI (confidence interval). Tumor growth and body weight was recorded twice weekly.

Figure 30:
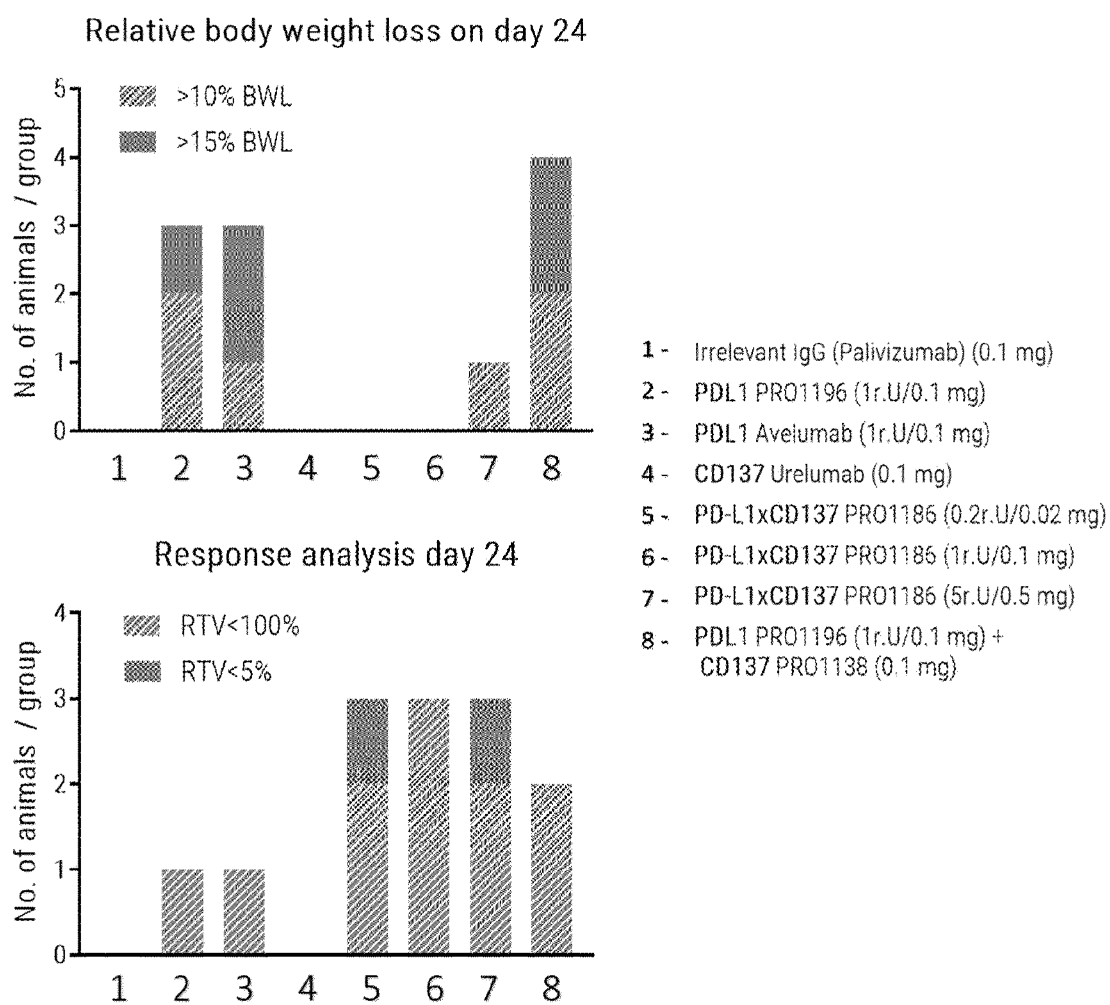

FIG. 30 Assessment of the anti-tumor efficacy in NOG mice engrafted with human umbilical cord blood-derived CD34+ hematopoietic stem cells (UCB HSCs). Body weight and relative tumor volume upon treatment with the multispecific antibody PRO1186 (scDb-scFv anti-PDL1×CD137×HSA) was compared to treatment with anti-PDL1 IgG1 (PRO1196 or avelumab) and anti-CD137 IgG4 (urelumab) therapy or the combination of the anti-PDL1 IgG1 (PRO1196) with the anti-CD137 IgG4 (PRO1138).

Figure 31:
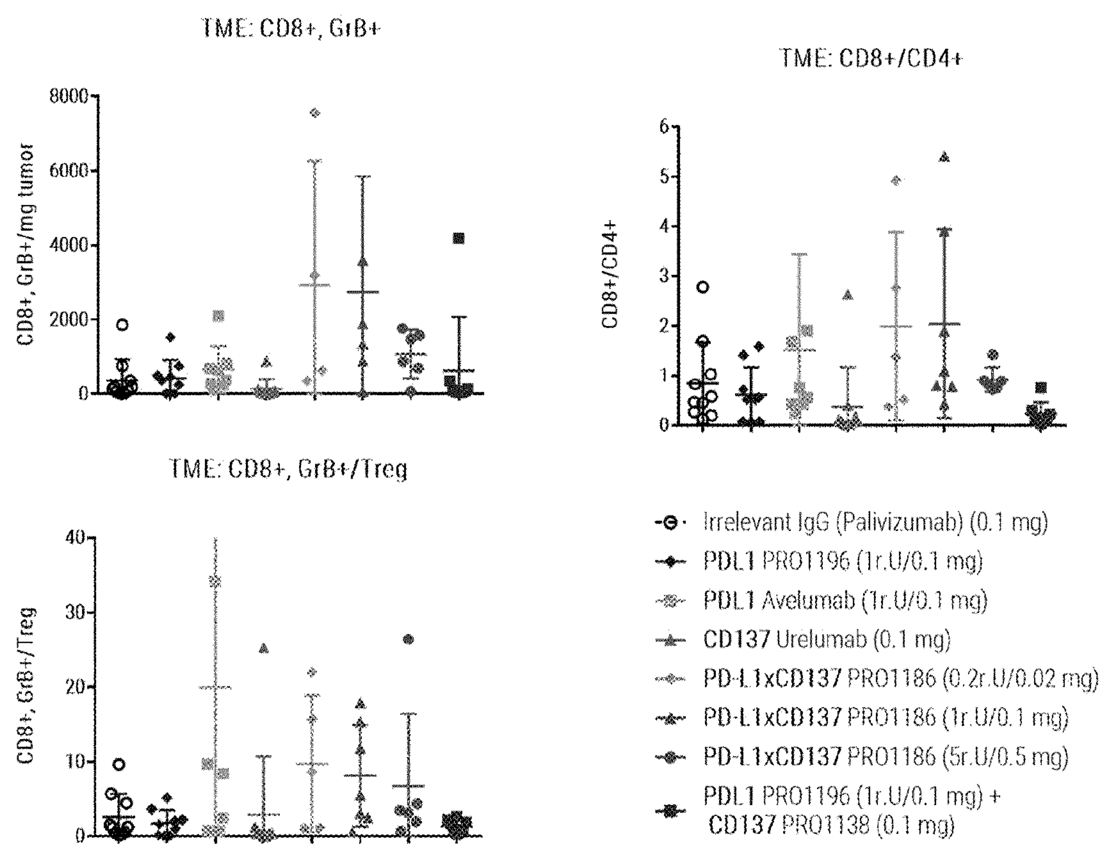

FIG. 31 Tumor infiltrating lymphocytes of HCC827 challenged NOG mice engrafted with human umbilical cord blood-derived CD34+ hematopoietic stem cells (UCB HSCs) were analyzed after the treatment with multispecific antibody PRO1186 (scDb-scFv anti-PDL1×CD137×HSA), or anti-PDL1 IgG1 (PRO 1196 or avelumab) or anti-CD137 IgG4 (urelumab) alone, or the combination of the anti-PDL1 IgG1 (PRO1196) with the anti-CD137 IgG4 (PRO 1138). Anti-PDL1×CD137 therapy led to higher frequency of cytotoxic T cells (CD8+, GrB+) and increased CD8+/CD4+ and CD8+, GrB+/Treg ratio in the tumor.

Figure 32:
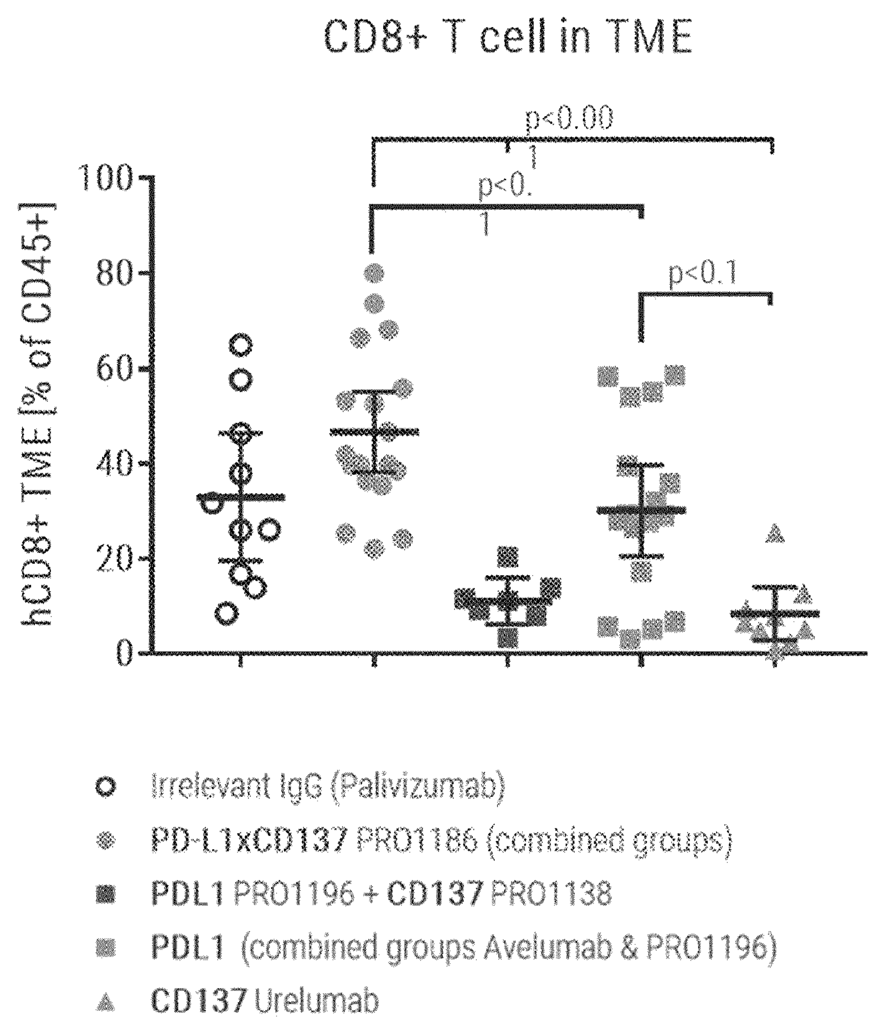

FIG. 32 Tumor infiltrating lymphocytes of HCC827 challenged NOG mice engrafted with human umbilical cord blood-derived CD34+ hematopoietic stem cells (UCB HSCs) and treated with the multispecific antibody PRO1186 (scDb-scFv anti-PDL1×CD137×HSA) were analyzed. Treatment with the multispecific antibody PRO1186 (scDb-scFv anti-PDL1×CD137×HSA; all dose levels combined) was compared to treatments with anti-PDL1 IgG1 alone (PRO1196 and avelumab combined, anti-CD137 IgG4 alone (urelumab), or the combination of the anti-PDL1 IgG1 (PRO 1196) with the anti-CD137 IgG4 (PRO 1138). All statistics were calculated using GraphPad Prism Version 6. Statistical significance was determined using One-way ANOVA test applying Bonferroni correction. Graphs show mean with 95% CI (confidence interval). Anti-PDL1×CD137 therapy led to higher frequency of cytotoxic T cells (CD8+) in the tumor.

Figure 33:
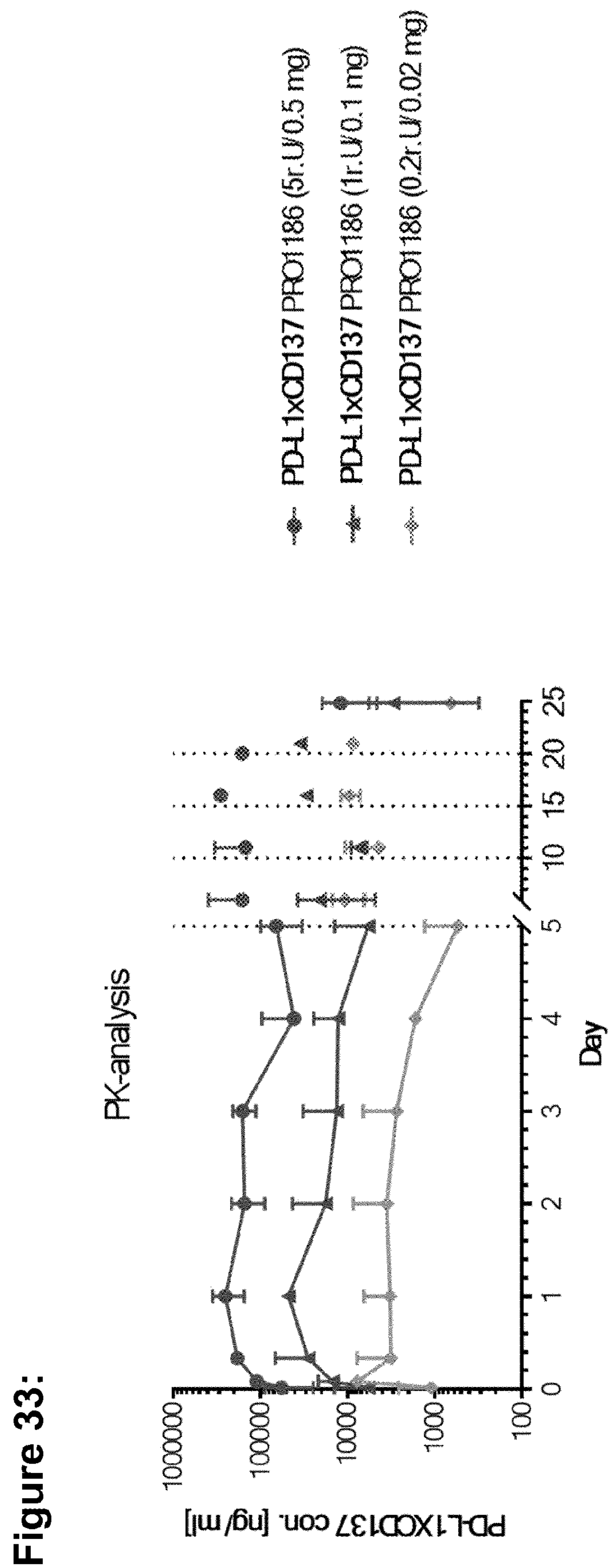

FIG. 33 Pharmacokinetic analysis to quantify the multispecific antibody PRO1186 (scDb-scFv anti-PDL1×CD137×HSA) in serum samples from animals in HCC827 xenograft study using human CD34+ stem cell substituted NOG mice. PRO1186 (scDb-scFv anti-PDL1×CD137×HSA) concentrations in diluted serum samples were interpolated from the calibration curve. Pharmacokinetic parameters were estimated by means of PK solver software add-in using a non-compartmental approach.

DETAILED DESCRIPTION OF THE INVENTION

Even though utilization of therapeutic antibodies agonizing CD137 is a very promising treatment strategy, it is coupled to such difficulties as low efficacy of anti-CD137 agonist antibodies, and their high toxicities and adverse events. Cross-linking of T cell co-stimulatory receptors by, for example, a full-length bivalent IgG, as in the case of urelumab, supports global stimulation of T cells, resulting in dose-limiting toxicities (FIG. 1A). There is thus a need in the medical field for novel anti-CD137 agonist antibodies, which are capable of potently inducing CD137 signaling without systemic overstimulation of T-cells, and thus which have lower rate of dose-limiting toxicities and adverse events than the currently available antibodies.

The present invention provides a multispecific antibody comprising: (a) at least one CD137 binding domain (CD137-BD), and (b) at least one PDL1 binding domain (PDL1-BD).

The multispecific antibody of the present disclosure are capable of agonizing CD137 signaling in a targeted manner, e.g. at a site of interest, namely in PDL1-positive tumor microenviroment. The multispecific antibody of the present invention is capable of mediating, e.g. agonizing, potent CD137 signaling without any need for as cross-linkage by anti-human F(ab')2 secondary antibody or immobilization to tissue culture plastic as in the case of PF-05082566 (Fisher at al., Cancer Immunol Immunother 61:1721-1733 (2012)), or Fcγ-receptor interaction. Thus, the multispecific antibody of the present invention due to its ability to mediate, e.g. agonize, potent CD137 signaling without interacting with Fcγ-receptor, does not lead to depletion of CD137-expressing cells. Further, it was surprisingly found that the multispecific antibody of the present disclosure, even when monovalent for CD137, in particular when comprising the novel CD137 binding domain of the present disclosure, is able to cluster and to agonize CD137, however solely in the presence of PDL1-positive cells, thus avoiding systemic activation of CD137. The monovalent CD137 binding and Fc-less structure of the multispecific antibody ensures that agonism of CD137 on effector cells can only arise when the antibody concomitantly binds to PDL1 on the surface of target cells.

In addition, it has been surprisingly found that, the multispecific antibody of the present disclosure comprising (a) at least one CD137 binding domain (CD137-BD), (b) at least one PDL1 binding domain (PDL1-BD), and (c) at least one human serum albumin binding domain (HSA-BD) demonstrated further beneficial properties such as (i) enhanced clustering of CD137 compared to non-cross-linked bivalent antibodies, (ii) increased half-life of the antibodies while retaining the ability to block PDL1 and to agonize CD137, and (iii) beneficial kinetics (e.g., higher levels of CD137 activation). Furthermore, the addition of a half-life-extending anti-HSA domain not only enables convenient dosing but also should promote delivery of the molecule to tumor microenvironments.

The multispecific antibodies of the present invention thus provide distinct therapeutic advantages over conventional compositions and therapies.

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In a first aspect, the present invention relates to a multispecific antibody comprising: (a) at least one CD137 binding domain (CD137-BD), and (b) at least one PDL1 binding domain (PDL1-BD).

The term "antibody" and the like, as used herein, includes whole antibodies or single chains thereof; and any antigen-binding fragment (i.e., "antigen-binding portion") or single chains thereof; and molecules comprising antibody CDRs, VH regions or VL regions (including without limitation multispecific antibodies). A naturally occurring "whole antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "binding domain", "antigen-binding fragment thereof", "antigen binding portion" of an antibody, and the like, as used herein, refer to one or more fragments of an intact antibody that retain the ability to specifically bind to a given antigen (e.g., CD137, PDL1, HSA). Antigen binding functions of an antibody can be performed by fragments of an intact antibody. In some embodiments, a binding domain of a multispecific antibody of the present invention is selected from the group consisting of a Fab fragment, a monovalent fragment consisting of the VL, VH, CL and CH1 domains; a F (ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain; an isolated complementarity determining region (CDR), dsFv, a scAb, STAB, a single domain antibody (sdAb or dAb), a single domain heavy chain antibody, and a single domain light chain antibody, a VHH, a VNAR, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology (F-star's Modular Antibody Technology™)). Suitably, a binding domain of the present invention is a single-chain Fv fragment (scFv) or single antibody variable domains. In a preferred embodiment, a binding domain of the present invention is a single-chain Fv fragment (scFv).

The term "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme) and numbering scheme described in Honegger & Plückthun, J. Mol. Biol. 309 (2001) 657-670 ("AHo" numbering). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align.

In the context of the present invention, the numbering system suggested by Honegger & Pluckthun ("AHo) is used (Honegger & Pluckthun, J. Mol. Biol. 309 (2001) 657-670), unless specifically mentioned otherwise. Furthermore, the following residues are defined as CDRs according to AHo numbering scheme: LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Pluckthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue.

The term "binding specificity" as used herein refers to the ability of an individual antibody to react with one antigenic determinant and not with a different antigenic determinant. As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In its most general form (and when no defined reference is mentioned), "specific binding" is referring to the ability of the antibody to discriminate between the target of interest and an unrelated molecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference molecule, but a set of about three to five unrelated molecules, such as milk powder, transferrin or the like.

Suitably, the antibody of the invention is an isolated antibody. The term "isolated antibody", as used herein, refers to an antibody that is substantially free of other antibodies having different antigenic specificities (e.g., an isolated antibody that specifically binds CD137 and PDL1 is substantially free of antibodies that specifically bind antigens other than CD137 and PDL1, e.g., an isolated antibody that specifically binds CD137, PDL1 and human serum albumin is substantially free of antibodies that specifically bind antigens other than CD137, PDL1 and human serum albumin). Moreover, an isolated antibody may be substantially free of other cellular material and/or chemicals.

Suitably, the antibody of the invention is a monoclonal antibody. The term "monoclonal antibody" or "monoclonal antibody composition" as used herein refers to antibodies that are substantially identical to amino acid sequence or are derived from the same genetic source. A monoclonal antibody composition displays a binding specificity and affinity for a particular epitope, or binding specificities and affinities for specific epitopes.

Antibodies of the invention include, but are not limited to, the chimeric, human and humanized.

The term "chimeric antibody" (or antigen-binding fragment thereof) is an antibody molecule (or antigen-binding fragment thereof) in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "human antibody" (or antigen-binding fragment thereof), as used herein, is intended to include antibodies (and antigen-binding fragments thereof) having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies and antigen-binding fragments thereof of the invention may include amino acid residues not encoded by human sequences (e.g., mutations introduced by random or site-specific mutagenesis in vitro or by somatic mutation in vivo). This definition of a human antibody specifically excludes a humanized antibody comprising non-human antigen-binding residues. Human antibodies can be produced using various techniques known in the art, including phage-display libraries (Hoogenboom and Winter, J. Mol. Biol, 227:381 (1991); Marks et al, J. Mol. Biol, 222:581 (1991)). Also available for the preparation of human monoclonal antibodies are methods described in Cole et al, Monoclonal Antibodies and Cancer Therapy, Alan R. Liss, p. 77 (1985); Boemer et al, J. Immunol, 147(1):86-95 (1991). See also van Dijk and van de Winkel, Curr. Opin. Pharmacol, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-3562 (2006) regarding human antibodies generated via a human B-cell hybridoma technology.

A "humanized" antibody (or antigen-binding fragment thereof), as used herein, is an antibody (or antigen-binding fragment thereof) that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). Additional framework region modifications may be made within the human framework sequences as well as within the CDR sequences derived from the germline of another mammalian species. The humanized antibodies of the invention may include amino acid residues not encoded by human sequences (e.g., mutations introduced by random or site-specific mutagenesis in vitro or by somatic mutation in vivo, or a conservative substitution to promote stability or manufacturing). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239: 1534-1536, 1988; Padlan, Molec. Immun., 28:489-498, 1991; and Padlan, Molec. Immun., 31: 169-217, 1994. Other examples of human engineering technology include, but is not limited to Xoma technology disclosed in U.S. Pat. No. 5,766,886.

The term "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

Suitably, the antibody of the invention or antigen-binding fragment thereof is humanized. Suitably, the antibody of the invention or antigen-binding fragment thereof is humanized and comprises rabbit-derived CDRs.

The term "multispecific antibody" as used herein, refers to an antibody that binds to two or more different epitopes on at least two or more different targets (e.g., CD137 and PDL1). The term "multispecific antibody" includes bispecific, trispecific, tetraspecific, pentaspecific and hexaspecific. The term "bispecific antibody" as used herein, refers to an antibody that binds to two different epitopes on at least two different targets (e.g., CD137 and PDL1). The term "trispecific antibody" as used herein, refers to an antibody that binds to three different epitopes on at least three different targets (e.g., CD137, PDL1 and HSA).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. "Conformational" and "linear" epitopes are distinguished in that the binding to the former but not the latter is lost in the presence of denaturing solvents.

The term "conformational epitope" as used herein refers to amino acid residues of an antigen that come together on the surface when the polypeptide chain folds to form the native protein, and show a significantly reduced rate of HD exchange due to Fab binding. The conformation epitope contains, but is not limited to, the functional epitope.

The term "linear epitope" refers to an epitope with all of the points of interaction between the protein and the interacting molecule (such as an antibody) occurring linearly along the primary amino acid sequence of the protein (continuous).

The term "recognize" as used herein refers to an antibody antigen-binding fragment thereof that finds and interacts (e.g., binds) with its conformational epitope.

Suitably, the multispecific antibody of the present invention is monovalent, bivalent or multivalent for CD137 specificity. In one embodiment, the multispecific antibody of the present invention is bivalent for CD137 specificity. In a preferred embodiment, the multispecific antibody of the present invention is monovalent for CD137 specificity.

Suitably, the multispecific antibody of the present invention is monovalent, bivalent or multivalent for PDL1 specificity. In one embodiment, the multispecific antibody of the present invention is bivalent for PDL1 specificity. In a preferred embodiment, the multispecific antibody of the present invention is monovalent for PDL1 specificity.

The term "multivalent antibody" refers to a single binding molecule with more than one valency, where "valency" is described as the number of antigen-binding moieties that binds to epitopes on identical target molecules. As such, the single binding molecule can bind to more than one binding site on a target molecule. Examples of multivalent antibodies include, but are not limited to bivalent antibodies, trivalent antibodies, tetravalent antibodies, pentavalent antibodies, and the like.

The term "monovalent antibody", as used herein, refers to an antibody that binds to a single epitope on a target molecule, such as CD137. Also, the term "binding domain" or "monovalent binding domain", as used herein, refers to a binding domain that binds to a single epitope on a target molecule such as CD137.

The term "bivalent antibody" as used herein, refers to an antibody that binds to two epitopes on at least two identical target molecules, such as CD137 target molecules.

Recently, in order to gain additional cross-linking function and achieve certain levels of CD137 activation, use of multivalent and multispecific fusion polypeptides that bind PDL1 and CD137 was proposed. Eckelman et al. have demonstrated that while bivalent engagement of CD137 in the case of INBRX-105 (a multispecific and multivalent polypeptide having two PDL1 binding domains, two CD137 binding domains and an Fc region) is insufficient to effectively cluster and mediate productive CD137 signaling, engagement of a second cell surface antigen PDL1 in the presence of PDL1-positive cells enables further clustering of CD137 and productive signaling (WO 2017/123650).

Figure 1C:
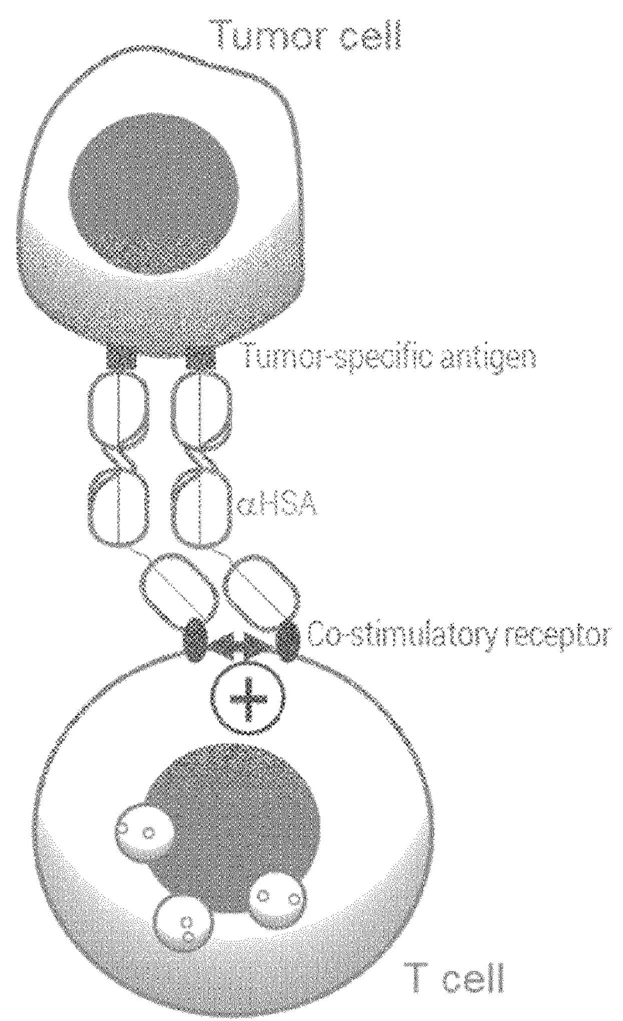
FIG. 1 Cross-linking of T cell co-stimulatory receptors by, for example, a full-length bivalent IgG supports global stimulation of T cells, resulting in dose-limiting toxicities (A). The stable bi-/trispecific monovalent molecules of the present invention cannot cross-link (or, by extension, agonize) co-stimulatory receptors on T cells in the absence of the cell-type being targeted for depletion (B). The stable bi-/trispecific monovalent molecules of the present invention cross-link (or, by extension, agonize) co-stimulatory receptors on T cells in the presence of the cell-type being targeted for depletion (C).
Figure 2:
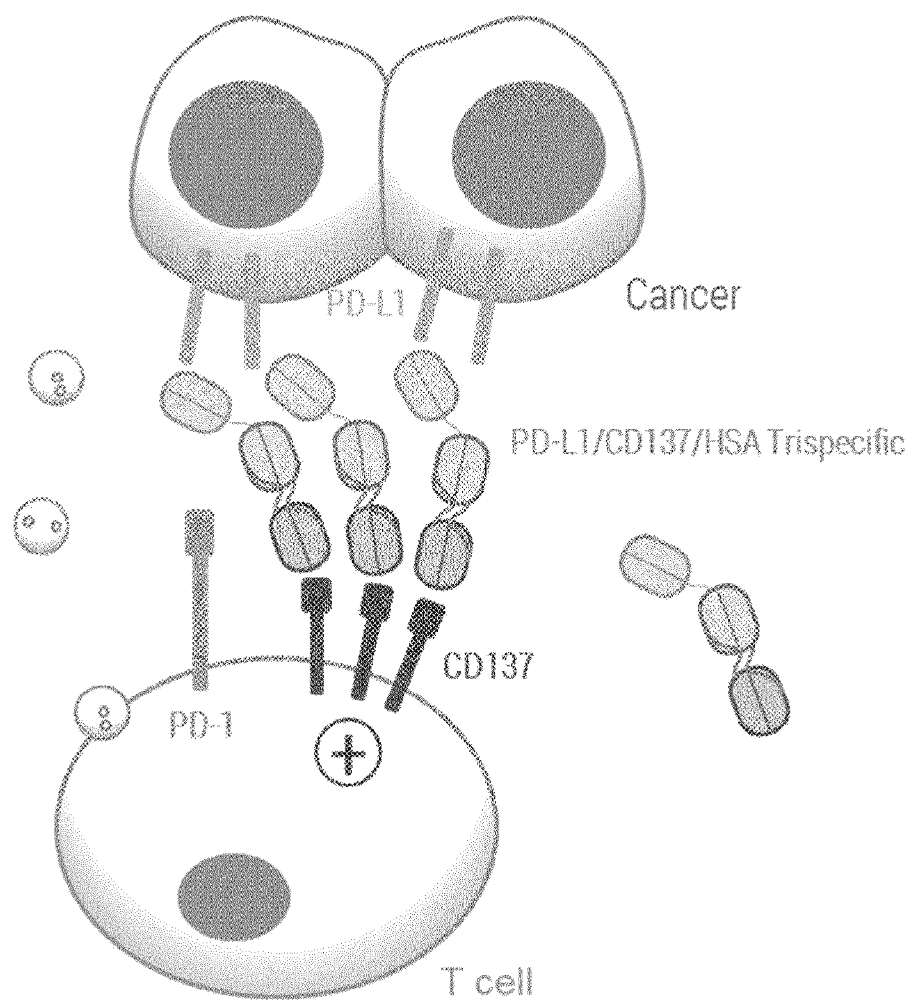
FIG. 2 Concomitant binding to PDL1 and CD137 triggers selective activation of tumor-reactive T cells and simultaneously blocks PD-1 signaling.

The inventors of the present invention have now surprisingly found that a multispecific antibody comprising (a) only one CD137 binding domain (CD137-BD); and (b) at least one PDL1 binding domain (PDL1-BD) is able to effectively activate CD137 signaling in a targeted manner. The stable multispecific (e.g., bi-/trispecific) monovalent for CD137 molecules of the present invention are shown to be not capable of agonizing CD137 on T cells in the absence of another cell-type, which is recognized by PDL1 binding domain (FIG. 1B). The effective activation of CD137 takes place only in the presence of PDL1-positive cells due to binding of anti-PDL1 domains of the multispecific antibodies of the invention to PDL1 molecules exposed on the surface of PDL1-positive cells (FIG. 1C and FIG. 2). This leads to increased density of the multispecific antibodies of the present invention in a specific location, and thus increased density of CD137 binding domains. The CD137-BDs thus can effectively cluster and agonize CD137. This concomitant binding to PDL1 and CD137 triggers selective activation of tumor-reactive T cells and simultaneously blocks PD-1 signaling (FIG. 2). Due to high overexpression of PDL1 on tumor cells, CD137 signaling is activated only locally in the presence of said tumor cells, which leads to reduced systemic toxicity. The antibody of the invention thus is expected to have several beneficial effects in comparison to current treatment options. The antibody of the invention is predicted to have (i) lower rate of immune-related adverse events, and (ii) lower rate of dose-limiting toxicities.

In a preferred embodiment, the multispecific antibody of the present invention is monovalent for CD137 specificity. Importantly, the monovalent for CD137 specificity multispecific antibody of the present invention is not capable of inducing CD137 signaling systemically due to a lack of CD137 activation in the absence of clustering, which is caused by binding of PDL1-BD to its antigen. In one embodiment, the present invention relates to a multispecific antibody comprising (a) one CD137-BD; and (b) at least one PDL1-BD, preferably one or two PDL1-BDs, more preferably one PDL1-BD. Thus, the multispecific antibody of the invention is monovalent, bivalent or multivalent for PDL1 specificity, preferably monovalent for PDL1 specificity. In one embodiment, the multispecific antibody of the present invention comprises one CD137-BD and one PDL1-BD. In one embodiment, the multispecific antibody of the present invention consist of one CD137-BD and one PDL1-BD.

The term "CD137" refers in particular to human CD137 with UniProt ID number Q07011, reproduced herein as SEQ ID NO: 197. Suitably, the CD137-BD of the present invention targets CD137, in particular human CD137 as shown in UniProt ID number Q07011, reproduced herein as SEQ ID NO: 197. Suitably, the multispecific antibody of the invention comprising a CD137-BD targets human and cynomoglous (*Macaca fascicularis*) CD137. Preferably, the multispecific antibody of the invention comprising a CD137-BD does not block CD137/CD137L interaction.

The CD137-BD of the invention specifically binds CD137. Suitably, the multispecific antibodies of the invention comprise a CD137-BD, wherein said CD137-BD specifically binds CD137. In a specific embodiment, said CD137-BD has a binding specificity for human CD137 and does not bind to human CD40 and/or does not bind to human OX40, in particular as determined by SPR.

Suitably, the CD137-BD of the invention is CD137 agonist. An "activator" or "activating antibody" or "agonist" or "agonist antibody" or "agonist binding domains" or "activating binding domain" is one that enhances or initiates signaling by the antigen to which it binds. In the context of the present invention, the term "CD137 agonist" encompasses the CD137 binding domains of the invention that are capable to activate CD137 signaling upon their clustering, e.g., wherein binding of at least two of said CD137-BDs allow for multimerization of the bound CD137 molecules and their activation. In some embodiments, agonist antibodies activate signaling without the presence of the natural ligand.

In some embodiments, the CD137-BD of the invention is derived from a monoclonal antibody or antibody fragment.

Suitable CD137-BDs for use in the multispecific antibody of the present invention are novel binding domains provided in the present disclosure. The novel CD137-BDs of the invention include, but are not limited to, the humanized monoclonal antibodies isolated as described herein, including in the Examples. Examples of such CD137-BDs are antibodies or binding domains thereof whose sequences are listed in Table 1. Additional details regarding the generation and characterization of the antibodies and binding domains described herein are provided in the Examples. The novel CD137-BDs of the present invention are particularly suitable for the purposes of the present invention. The multispecific antibodies of the present invention comprising at least one said CD137-BD, e.g. monovalent for CD137 binding specificity, are capable of activating CD137 in the presence of PDL1 positive cells.

Suitably, the CD137-BD specifically binds to CD137 and is characterized by one or more of the following parameters:

(i) binds to human CD137 with a dissociation constant (KD) of less than 50 nM, particularly less than 10 nM, particularly less than 5 nM, particularly less than 1 nM, particularly less than 500 pM, more particularly less than 100 pM, more particularly less than 50 pM, particularly wherein said antibody is an scFv (monovalent affinity);

(ii) binds to human CD137 with a $K_{off}$ rate of $10^{-3}$ $s^{-1}$ or less, or $10^{-4}$ $s^{-1}$ or less, or $10^{-5}$ $s^{-1}$ or less as measured by SPR, particularly wherein said antibody is an scFv;

(iii) binds to human CD137 with a $K_{on}$ rate of at least $10^4$ $M^{-1}s^{-1}$ or greater, at least $10^5$ $M^{-1}s^{-1}$ or greater, at least $10^6$ $M^{-1}s^{-1}$ or greater, as measured by SPR, particularly wherein said antibody is an scFv;

(iv) optionally, does not cross-compete with urelumab;

(v) optionally, does not cross-compete with utomilumab;

(vi) optionally, is cross-reactive with *Macaca fascicularis* (Cynomolgus) CD137; and (vii) optionally, does not inhibit the interaction between CD137 and its ligand CD137L, in particular as measured by the competition ELISA.

The term "avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to"

or "binding to" refers to intrinsic binding affinity that reflects a 1:1 interaction between members of a binding pair (e.g., an antibody fragment and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity, i.e. binding strength are described in the following.

The term "$K_{assoc}$", "Ka" or "$K_{on}$", as used herein, is intended to refer to the association rate of a particular antibody-antigen interaction, whereas the term "$K_{dis}$", "Kd" or "$K_{off}$", as used herein, is intended to refer to the dissociation rate of a particular antibody-antigen interaction. In one embodiment, the term "KD", as used herein, is intended to refer to the dissociation constant, which is obtained from the ratio of Kd to Ka (i.e. Kd/Ka) and is expressed as a molar concentration (M). The "KD" or "KD value" or "$K_D$" or "$K_D$ value" according to this invention is in one embodiment measured by using surface-plasmon resonance assays using a MASS-1 SPR instrument (Sierra Sensors). To measure affinity, an antibody specific for the Fc region of rabbit IgGs (Bethyl Laboratories, Cat. No. A120-111A) is immobilized on a sensor chip (SPR-2 Affinity Sensor, High Capacity Amine, Sierra Sensors) using a standard amine-coupling procedure. Rabbit monoclonal antibodies in B-cell supernatants are captured by the immobilized anti-rabbit IgG antibody. A minimal IgG concentration in the B-cell supernatants is required to allow sufficient capture. After capturing of the monoclonal antibodies, human CD137 ECD (Peprotech, cat. 310-15-1MG) or, as in the case of PDL1-BD, human PDL1 (Peprotech) is injected into the flow cells for 3 min at a concentration of 90 nM, and dissociation of the protein from the IgG captured on the sensor chip was allowed to proceed for 5 min. After each injection cycle, surfaces are regenerated with two injections of 10 mM Glycine-HCl. The apparent dissociation (kd) and association (ka) rate constants and the apparent dissociation equilibrium constant (KD) are calculated with the MASS-1 analysis software (Analyzer, Sierra Sensors) using one-to-one Langmuir binding model and quality of the fits is monitored based on relative $Chi^2$ ($Chi^2$ normalized to the extrapolated maximal binding level of the analyte), which is a measure for the quality of the curve fitting. The smaller the value for the $Chi^2$ the more accurate is the fitting to the one-to-one Langmuir binding model. Results are deemed valid if the response units (RU) for ligand binding are at least 2% of the RUs for antibody capturing. Samples with RUs for ligand binding with less than 2% of the RUs for antibody capturing are considered to show no specific binding of CD137 or PDL1 to the captured antibody. The equilibrium dissociation constant ($K_D$) is calculated as the ratio $k_{off}/k_{on}$. See, e.g., Chen et al, J. Mol. Biol. 293:865-881 (1999).

Suitably, the affinity of the multispecific antibody of the invention to CD137 may be comparable to or higher than the affinity of CD137L to CD137. Suitably, the affinity of the multispecific antibody of the invention to CD137 may be comparable to or higher than the affinity of urelumab to CD137. It will be appreciated that the higher affinity of the CD137 binding domain may be particularly suitable for use in the multispecific antibody of the invention, wherein said antibody is monovalent for CD137. The binding affinity of an antibody or binding fragment thereof, may be determined, for example, by the dissociation constant (KD). A stronger affinity is represented by a lower KD, while a weaker affinity is represented by a higher KD.

Thus, in a suitable embodiment, the multispecific antibody of the invention or the CD137-BD of the invention binds to human CD137 with a KD of between 5 to 50,000 pM, 5 to 40,000 pM, 5 to 30,000 pM, 5 to 20,000 pM, 5 to 10,000 pM, 5 to 9,000 pM, 5 to 8,000 pM, 5 to 7,000 pM, 5 to 6,000 pM, 5 to 5,000 pM, 5 to 2,500 pM, 5 to 1,000 pM, 5 to 750 pM, 5 to 500 pM, 5 to 250 pM, 5 to 100 pM, 5 to 75 pM, 5 to 50 pM, 5 to 30 pM, in particular as measured by SPR. In a further embodiment, the multispecific antibody of the invention or the CD137-BD of the invention binds to human CD137 with a KD of between 10 nM and 10 pM, preferably between 10 nM and 0.1 nM, e.g., between 5 nM and 0.1 nM, more preferably between 5 nM and 1 nM, in particular as measured by SPR.

In a suitable embodiment, the multispecific antibody of the invention or the CD137-BD of the invention binds to human CD137 with a KD of less than approximately 50 nM, less than approximately 45 nM, less than approximately 40 nM, less than approximately 35 nM, less than approximately 30 nM, less than approximately 25 nM, less than 20 nM, less than approximately 15 nM, less than approximately 10 nM, less than approximately 9 nM, less than approximately 8 nM, less than approximately 7 nM, less than approximately 6 nM, less than approximately 5 nM, less than approximately 4 nM, less than approximately 3 nM, less than 2 nM, less than 1 nM, less than 0.5 nM, less than 0.25 nM, or less than 0.1 nM, less than 50 pM, less than 40 pM, less than 30 pM, less than 20 pM, in particular as measured by SPR. Suitably, the multispecific antibody of the invention or the CD137-BD of the invention binds to human CD137 with a KD of less than 10 nM, in particular as measured by SPR.

Preferably, the multispecific antibody of the invention or the CD137-BD of the invention binds to human CD137 with a KD of less than 5 nM, in particular as measured by SPR. Suitably, the multispecific antibody of the invention or the CD137-BD of the invention binds to human CD137 with a KD of less than 1 nM, in particular as measured by SPR. Suitably, the multispecific antibody of the invention or the CD137-BD of the invention binds to human CD137 with a KD of less than 50 pM, in particular as measured by SPR.

Suitably, the multispecific antibody of the invention or the CD137-BD of the invention binds to human CD137 with a $K_{on}$ rate of at least $10^3$ $M^{-1}s^{-1}$ or greater, at least $10^4$ $M^{-1}s^{-1}$ or greater, at least $5\times10^4$ $M^{-1}s^{-1}$ or greater, at least $10^5$ $M^{-1}s^{-1}$ or greater, at least $5\times10^5$ $M^{-1}s^{-1}$ or greater, at least $10^6$ $M^{-1}s^{-1}$ or greater, at least $5\times10^6$ $M^{-1}s^{-1}$ or greater, at least 107 MS-1 or greater, at least $5\times10^7$ $M^{-1}s^{-1}$ or greater as measured by surface plasmon resonance (SPR). Suitably, the multispecific antibody of the invention or the CD137-BD of the invention binds to human CD137 with a $K_{on}$ rate of at least $10^4$ $M^{-1}s^{-1}$ or greater, in particular at least $10^5$ $M^{-1}s^{-1}$ or greater, as measured by SPR, particularly wherein said antibody is an scFv (monovalent affinity).

Suitably, the multispecific antibody of the invention or the CD137-BD of the invention binds to human CD137 with a $K_{off}$ rate of $10^{-3}$ $s^{-1}$ or less, $3\times10^{-3}$ $s^{-1}$ or less, $5\times10^{-3}$ $s^{-1}$ or less, $10^{-4}$ $s^{-1}$ or less, $5\times10^{-4}$ $s^{-1}$ or less, $10^{-5}$ $s^{-1}$ or less, $5\times10^{-5}$ $s^{-1}$ or less, $10^{-6}$ $s^{-1}$ or less, or $10^{-7}$ $s^{-1}$ or less as measured by surface plasmon resonance (SPR). Suitably, the multispecific antibody of the invention or the CD137-BD of the invention binds to human CD137 with a $K_{off}$ rate of $10^{-4}$ $s^{-1}$ or less, in particular $10^{-5}$ $s^{-1}$ or less as measured by SPR.

Suitably the multispecific antibody of the invention or the CD137-BD of the invention has a binding to human CD137 of at least 60% or greater, at least 70% or greater, at least 75% or greater, at least 80% of greater, at least 85% or greater, at least 90% or greater, at least 95% or greater, as measured with SPR and normalized to binding levels obtained for urelumab.

In one embodiment, the CD137-BD of the invention does not cross-compete for binding with urelumab. The present invention thus provides the CD137-BD that binds to a different epitope than urelumab. Urelumab, also referred to as BMS-663513, is a fully humanized IgG4 mAb from Bristol-Myers Squibb, and is described in WO 2004/010947, U.S. Pat. Nos. 6,887,673 and 7,214,493, which are hereby incorporated into the present application by reference in their entirety. In another embodiment, the CD137-BD of the invention cross-competes for binding with urelumab.

In one embodiment, the CD137-BD of the invention does not cross-compete for binding with utomilumab. The present invention thus provides the CD137-BD that binds to a different epitope than utomilumab. Utomilumab, also referred to as PF-05082566, is a fully human IgG2 mAb from Pfizer, and is described in WO 2012/032433 and U.S. Pat. No. 8,821,867, which is hereby incorporated into the present application by reference in its entirety. In another embodiment, the CD137-BD of the invention cross-competes for binding with utomilumab.

In a further embodiment, the CD137-BD of the invention does not cross-compete for binding neither with urelumab nor with utomilumab. The present invention thus provides the CD137-BD of the invention that binds to a different epitope than urelumab and utomilumab.

The terms "compete" or "cross-compete" and related terms are used interchangeably herein to mean the ability of an antibody or other binding agent to interfere with the binding of other antibodies or binding agents to CD137 in a standard competitive binding assay.

The ability or extent to which an antibody or other binding agent is able to interfere with the binding of another antibody or binding molecule to a target of interest, e.g., CD137, PDL1, and therefore whether it can be said to cross-compete according to the invention, can be determined using standard competition binding assays. Suitable quantitative cross-competition assay uses a FACS- or an AlphaScreen-based approach to measure competition between the labelled (e.g. His tagged, biotinylated or radioactive labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% to 100%. For the purposes of this invention, a competition ELISA was utilized, the corresponding protocol is described in details in the "Examples" section of the present disclosure. In one embodiment, the CD137-BD of the invention does not inhibit the binding of urelumab and/or utomilumab to CD137 protein, which demonstrates that the CD137-BD of the invention cannot compete with urelumab and/or utomilumab, respectively for binding to CD137; such CD137-BD or an antibody comprising said domain may, according to non-limiting theory, bind to a different (e.g., a structurally different or a spatially remote) epitope on CD137 as urelumab or utomilumab, respectively. In one embodiment, the CD137-BD of the invention inhibits the binding of urelumab or utomilumab to CD137 protein, which demonstrates that the CD137-BD of the invention can compete with urelumab or utomilumab, respectively for binding to CD137; such CD137-BD or an antibody comprising said domain may, according to non-limiting theory, bind to the same or an overlapping (e.g., a structurally similar or spatially proximal) epitope on CD137 as urelumab or utomilumab, respectively.

The present invention also provides binding domains that bind to the same epitope as do the CD137-BDs listed in Table 1. Additional binding domains can therefore be identified based on their ability to cross-compete (e.g., to competitively inhibit the binding of, in a statistically significant manner) with other antibodies and antigen-binding fragments thereof of the invention in CD137 binding assays.

The ability of a test binding domain to inhibit the binding of the CD137-BD of the invention to CD137 protein demonstrates that the test binding domain can compete with that CD137-BD for binding to CD137; such binding domain may, according to non-limiting theory, bind to the same or a related (e.g., a structurally similar or spatially proximal) epitope on CD137 as the CD137-BD with which it competes. In a certain embodiment, the binding domain that binds to the same epitope on CD137 as the CD137-BD of the present invention is a human or humanized monoclonal antibody. Such human or humanized monoclonal antibodies can be prepared and isolated as described herein.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in WO 2003/48731. As will be appreciated by one of skill in the art, practically anything to which an antibody can specifically bind could be an epitope. An epitope can comprise those residues to which the antibody binds.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, New Jersey. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids CD137 such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157: 105-132; for hydropathy plots.

Suitably, the CD137-BD specifically binds to CD137 and is characterized by one or more of the following parameters:

a) when in scFv format, has a melting temperature (Tm), determined by differential scanning fluorimetry (DSF), of at least 50° C., preferably of at least 55° C., more preferably at least 60° C., in particular wherein said antibody or antigen-binding fragment thereof is formulated in phosphate-citrate buffer at pH 6.4, 150 mM NaCl, in particular in 50 mM phosphate-citrate buffer at pH 6.4, 150 mM NaCl;

b) when in scFv format, has a loss in monomer content, after storage for at least two weeks, particularly for at least four weeks, at 4° C., of less than 7%, e.g. less than 6%, less than 5%, less than 4%, less than 3%, less than 2%, preferably less than 1%, when the antibody of the invention is at a starting concentration of 10 mg/ml, and in particular wherein the antibody of the invention, e.g., said antibody or antigen-binding fragment thereof, is formulated in 50 mM phosphate citrate buffer with 150 mM NaCl at pH 6.4; and/or c) when in scFv format, has a loss in monomer content, after storage for at least two weeks, particularly for at least four weeks, at 40° C., of less than 5%, e.g. less than 4%, less than 3%, less than 2%, preferably less than 1%, when the antibody of the invention is at a starting concentration of 10 mg/ml, and in particular wherein the antibody of the invention, e.g., said antibody or antigen-binding fragment thereof, is formulated in 50 mM phosphate citrate buffer with 150 mM NaCl at pH 6.4.

DSF is described earlier (Egan, et al., MAbs, 9(1) (2017), 68-84; Niesen, et al., Nature Protocols, 2(9) (2007) 2212-2221). The midpoint of transition for the thermal unfolding of the scFv constructs is determined by Differential Scanning Fluorimetry using the fluorescence dye SYPRO® Orange (see Wong & Raleigh, Protein Science 25 (2016) 1834-1840). Samples in phosphate-citrate buffer at pH 6.4 are prepared at a final protein concentration of 50 μg/mL and containing a final concentration of 5×SYPRO® Orange in a total volume of 100 μl. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about two hours. The Tm is calculated by the software GraphPad Prism using a mathematical second derivative method to calculate the inflection point of the curve. The reported Tm is an average of three measurements.

The loss in monomer content is as determined by area under the curve calculation of SE-HPLC chromatograms. SE-HPLC is a separation technique based on a solid stationary phase and a liquid mobile phase as outlined by the USP chapter 621. This method separates molecules based on their size and shape utilizing a hydrophobic stationary phase and aqueous mobile phase. The separation of molecules is occurring between the void volume (VO) and the total permeation volume (VT) of a specific column. Measurements by SE-HPLC are performed on a Chromaster HPLC system (Hitachi High-Technologies Corporation) equipped with automated sample injection and a UV detector set to the detection wavelength of 280 nm. The equipment is controlled by the software EZChrom Elite (Agilent Technologies, Version 3.3.2 SP2) which also supports analysis of resulting chromatograms. Protein samples are cleared by centrifugation and kept at a temperature of 4-6° C. in the autosampler prior to injection. For the analysis of scFv samples the column Shodex KW403-4F (Showa Denko Inc., #F6989202) is employed with a standardized buffered saline mobile phase (50 mM sodium-phosphate pH 6.5, 300 mM sodium chloride) at the recommended flow rate of 0.35 mL/min. The target sample load per injection was 5 pg. Samples are detected by an UV detector at a wavelength of 280 nm and the data recorded by a suitable software suite. The resulting chromatograms are analyzed in the range of V0 to VT thereby excluding matrix associated peaks with >10 min elution time.

The present invention provides the CD137-BDs that specifically bind to CD137 protein, said binding domains comprising a VH CDR having an amino acid sequence of any one of the VH CDRs listed in Table 1. In particular, the invention provides CD137-BDs that specifically bind to CD137 protein, said CD137-BDs comprising (or alternatively, consisting of) one, two, three, or more VH CDRs having an amino acid sequence of any of the VH CDRs listed in Table 1.

The present invention also provides CD137-BDs that specifically bind to CD137 protein, said CD137-BDs comprising a VL CDR having an amino acid sequence of any one of the VL CDRs listed in Table 1. In particular, the invention provides CD137-BDs that specifically bind to CD137 protein, said CD137-BDs comprising (or alternatively, consisting of) one, two, three or more VL CDRs having an amino acid sequence of any of the VL CDRs listed in Table 1.

Other CD137-BDs of the invention include amino acids that have been mutated, yet have at least 60, 70, 80, 90, 91, 92, 93, 94, 95, 96, 97, 98 or 99 percent identity in the CDR regions with the CDR regions depicted in the sequences described in Table 1. In one aspect, other CD137-BDs of the invention include mutant amino acid sequences wherein no more than 1, 2, 3, 4 or 5 amino acids have been mutated in the CDR regions when compared with the CDR regions depicted in the sequence described in Table 1.

The terms "identical" or "identity", in the context of two or more nucleic acids or polypeptide sequences, refer to two or more sequences or subsequences that are the same. "Percent (%) sequence identity" and "homology" with respect to nucleic acid, a peptide, a polypeptide or an antibody sequence are defined as the percentage of nucleotides or amino acid residues in a candidate sequence that are identical with the nucleotides or amino acid residues in the specific nucleic acid, peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2 or ALIGN software. Those skilled in the art can determine appropriate parameters for measuring alignment, including any algorithms needed to achieve maximal alignment over the full length of the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information.

The percent identity between two amino acid sequences can also be determined using the algorithm of E. Meyers and W. Miller (Comput. Appl. Biosci., 4: 11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at gcg.com), using either a Blossom 62 matrix or a PAM250 matrix, and a gap weight of 16, 14, 12, 10, 8, 6, or 4 and a length weight of 1, 2, 3, 4, 5, or 6.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

Suitably, the CD137-BD of the multispecific antibody of the present invention comprises: (a) a heavy chain variable region CDR1 (HCDR1) comprising, preferably consisting of, an amino acid sequence selected from any one of SEQ ID NOs: 1, 4, 5, 8, 11, 35, 38, 41 and 44, preferably SEQ ID NO: 1; (b) a heavy chain variable region CDR2 (HCDR2) comprising, preferably consisting of, an amino acid sequence selected from any of SEQ ID NOs: 2, 6, 9, 12, 36, 39, 42 and 45, preferably SEQ ID NO: 2; (c) a heavy chain variable region CDR3 (HCDR3) comprising, preferably consisting of, an amino acid sequence selected from any of SEQ ID NOs: 3, 7, 10, 13, 37, 40, 43 and 46, preferably SEQ ID NO: 3; (d) a light chain variable region CDR1 (LCDR1) comprising, preferably consisting of, an amino acid sequence selected from any of SEQ ID NOs: 18, 21, 24, 48, 51, and 54, preferably SEQ ID NO: 18; (e) a light chain variable region CDR2 (LCDR2) comprising, preferably consisting of, an amino acid sequence selected from any of SEQ ID NOs: 19, 22, 25, 49, 52, and 55, preferably SEQ ID NO: 19; and (f) a light chain variable region CDR3 (LCDR3) comprising, preferably consisting of, an amino acid sequence selected from any of SEQ ID NOs: 20, 23, 26, 50, 53, and 56, preferably SEQ ID NO: 20. Suitably, the CD137-BD of the multispecific antibody of the present invention comprises: (a) a heavy chain variable region CDR1 (HCDR1) comprising, preferably consisting of, an amino acid sequence having at least 60, 70, 80, 90, 91, 92, 93, 94, 95, 96, 97, 98 or 99 percent identity to any one of SEQ ID NOs: 1, 4, 5, 8, 11, 35, 38, 41 and 44, preferably SEQ ID NO: 1; (b) a heavy chain variable region CDR2 (HCDR2) having at least 60, 70, 80, 90, 91, 92, 93, 94, 95, 96, 97, 98 or 99 percent identity to any of SEQ ID NOs: 2, 6, 9, 12, 36, 39, 42 and 45, preferably SEQ ID NO: 2; (c) a heavy chain variable region CDR3 (HCDR3) having at least 60, 70, 80, 90, 91, 92, 93, 94, 95, 96, 97, 98 or 99 percent identity to any of SEQ ID NOs: 3, 7, 10, 13, 37, 40, 43 and 46, preferably SEQ ID NO: 3; (d) a light chain variable region CDR1 (LCDR1) having at least 60, 70, 80, 90, 91, 92, 93, 94, 95, 96, 97, 98 or 99 percent identity to any of SEQ ID NOs: 18, 21, 24, 48, 51, and 54, preferably SEQ ID NO: 18; (e) a light chain variable region CDR2 (LCDR2) having at least 60, 70, 80, 90, 91, 92, 93, 94, 95, 96, 97, 98 or 99 percent identity to any of SEQ ID NOs: 19, 22, 25, 49, 52, and 55, preferably SEQ ID NO: 19; and (f) a light chain variable region CDR3 (LCDR3) having at least 60, 70, 80, 90, 91, 92, 93, 94, 95, 96, 97, 98 or 99 percent identity to any of SEQ ID NOs: 20, 23, 26, 50, 53, and 56, preferably SEQ ID NO: 20.

In one embodiment, the CD137-BD of the multispecific antibody of the present invention comprises: (a) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively; (b) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively; (c) HCDR1, HCDR2, and HCDR3 sequences of SEQ ID NOs: 5, 6, and 7, respectively, and LCDR1, LCDR2, and LCDR3 sequences of SEQ ID NOs: 21, 22, and 23, respectively; (d) HCDR1, HCDR2, and HCDR3 sequences of SEQ ID NOs: 8, 9, and 10, respectively, and LCDR1, LCDR2, and LCDR3 sequences of SEQ ID NOs: 18, 19, and 20, respectively; (e) HCDR1, HCDR2, and HCDR3 sequences of SEQ ID NOs: 11, 12, and 13, respectively, and LCDR1, LCDR2, and LCDR3 sequences of SEQ ID NOs: 24, 25, and 26, respectively; (f) HCDR1, HCDR2, and HCDR3 sequences of SEQ ID NOs: 35, 36, and 37, respectively, and LCDR1, LCDR2, and LCDR3 sequences of SEQ ID NOs: 48, 49, and 50, respectively; (g) HCDR1, HCDR2, and HCDR3 sequences of SEQ ID NOs: 38, 39, and 40, respectively, and LCDR1, LCDR2, and LCDR3 sequences of SEQ ID NOs: 51, 52, and 53, respectively; (h) HCDR1, HCDR2, and HCDR3 sequences of SEQ ID NOs: 41, 42, and 43, respectively, and LCDR1, LCDR2, and LCDR3 sequences of SEQ ID NOs: 48, 49, and 50, respectively; (i) HCDR1, HCDR2, and HCDR3 sequences of SEQ ID NOs: 44, 45, and 46, respectively, and LCDR1, LCDR2, and LCDR3 sequences of SEQ ID NOs: 54, 55, and 56, respectively. In a preferred embodiment, the CD137-BD of the multispecific antibody of the present invention comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively.

Suitably, the CD137-BD of the multispecific antibody of the present invention comprises: (a) HCDR1, HCDR2, and HCDR3 sequences having at least 60, 70, 80, 90, 91, 92, 93, 94, 95, 96, 97, 98 or 99 percent identity to SEQ ID NOs: 1, 2, and 3, respectively, and LCDR1, LCDR2, and LCDR3 sequences having at least 60, 70, 80, 90, 91, 92, 93, 94, 95, 96, 97, 98 or 99 percent identity to SEQ ID NOs: 18, 19, and 20, respectively; (b) HCDR1, HCDR2, and HCDR3 sequences having at least 60, 70, 80, 90, 91, 92, 93, 94, 95, 96, 97, 98 or 99 percent identity to SEQ ID NOs: 4, 6, and 7, respectively, and LCDR1, LCDR2, and LCDR3 sequences having at least 60, 70, 80, 90, 91, 92, 93, 94, 95, 96, 97, 98 or 99 percent identity to SEQ ID NOs: 21, 22, and 23, respectively; (c) HCDR1, HCDR2, and HCDR3 sequences having at least 60, 70, 80, 90, 91, 92, 93, 94, 95, 96, 97, 98 or 99 percent identity to SEQ ID NOs: 5, 6, and 7, respectively, and LCDR1, LCDR2, and LCDR3 sequences having at least 60, 70, 80, 90, 91, 92, 93, 94, 95, 96, 97, 98 or 99 percent identity to SEQ ID NOs: 21, 22, and 23, respectively; (d) HCDR1, HCDR2, and HCDR3 sequences having at least 60, 70, 80, 90, 91, 92, 93, 94, 95, 96, 97, 98 or 99 percent identity to SEQ ID NOs: 8, 9, and 10, respectively, and LCDR1, LCDR2, and LCDR3 sequences having at least 60, 70, 80, 90, 91, 92, 93, 94, 95, 96, 97, 98 or 99 percent identity to SEQ ID NOs: 18, 19, and 20, respectively; (e) HCDR1, HCDR2, and HCDR3 sequences having at least 60, 70, 80, 90, 91, 92, 93, 94, 95, 96, 97, 98 or 99 percent identity to SEQ ID NOs: 11, 12, and 13, respectively, and LCDR1, LCDR2, and LCDR3 sequences having at least 60, 70, 80, 90, 91, 92, 93, 94, 95, 96, 97, 98 or 99 percent identity to SEQ ID NOs: 24, 25, and 26, respectively; (f) HCDR1, HCDR2, and HCDR3 sequences having at least 60, 70, 80, 90, 91, 92, 93, 94, 95, 96, 97, 98 or 99 percent identity to SEQ ID NOs: 35, 36, and 37, respectively, and LCDR1, LCDR2, and LCDR3 sequences having at least 60, 70, 80, 90, 91, 92, 93, 94, 95, 96, 97, 98 or 99 percent identity to SEQ ID NOs: 48, 49, and 50, respectively; (g) HCDR1, HCDR2, and HCDR3 sequences having at least 60, 70, 80, 90, 91, 92, 93, 94, 95, 96, 97, 98 or 99 percent identity to SEQ ID NOs: 38, 39, and 40, respectively, and LCDR1, LCDR2, and LCDR3 sequences having at least 60, 70, 80, 90, 91, 92, 93, 94, 95, 96, 97, 98 or 99 percent identity to SEQ ID NOs: 51, 52, and 53, respectively; (h) HCDR1, HCDR2, and HCDR3 sequences having at least 60, 70, 80, 90, 91, 92, 93, 94, 95, 96, 97, 98 or 99 percent identity to SEQ ID NOs: 41, 42, and 43, respectively, and LCDR1, LCDR2, and LCDR3 sequences having at least 60, 70, 80, 90, 91, 92, 93, 94, 95, 96, 97, 98 or 99 percent identity to SEQ ID NOs: 48, 49, and 50, respectively; (i) HCDR1, HCDR2, and HCDR3 sequences having at least 60, 70, 80, 90, 91, 92, 93, 94, 95, 96, 97, 98 or 99 percent identity to SEQ ID NOs: 44, 45, and 46, respectively, and LCDR1, LCDR2, and LCDR3 sequences having at least 60, 70, 80, 90, 91, 92, 93, 94, 95, 96, 97, 98 or 99 percent identity to SEQ ID NOs: 54, 55, and 56, respectively. In a preferred embodiment, the CD137-BD of the multispecific antibody of the present invention comprises HCDR1, HCDR2, and HCDR3 sequences having at least 60, 70, 80, 90, 91, 92, 93, 94, 95, 96, 97, 98 or 99 percent identity to SEQ ID NOs: 1, 2, and 3, respectively, and LCDR1, LCDR2, and LCDR3 sequences having at least 60, 70, 80, 90, 91, 92, 93, 94, 95, 96, 97, 98 or 99 percent identity to SEQ ID NOs: 18, 19, and 20, respectively. Suitably, the CD137-BD of the multispecific antibody of the present invention comprises: (a) a HCDR1 comprising the amino acid sequence having at least 60, 70, 80, 90, 91, 92, 93, 94, 95, 96, 97, 98 or 99 percent identity to SEQ ID NO: 1; (b) a HCDR2 comprising the amino acid sequence having at least 60, 70, 80, 90, 91, 92, 93, 94, 95, 96, 97, 98 or 99 percent identity to SEQ ID NO: 2; (c) a HCDR3 comprising the amino acid sequence having at least 60, 70, 80, 90, 91, 92, 93, 94, 95, 96, 97, 98 or 99 percent identity to SEQ ID NO: 3; (d) a LCDR1 comprising the amino acid sequence having at least 60, 70, 80, 90, 91, 92, 93, 94, 95, 96, 97, 98 or 99 percent identity to SEQ ID NO: 18; (e) a LCDR2 comprising the amino acid sequence having at least 60, 70, 80, 90, 91, 92, 93, 94, 95, 96, 97, 98 or 99 percent identity to SEQ ID NO: 19; and (f) a LCDR3 comprising the amino acid sequence having at least 60, 70, 80, 90, 91, 92, 93, 94, 95, 96, 97, 98 or 99 percent identity to SEQ ID NO: 20.

In a further embodiment, the CD137-BD of the multispecific antibody of the present invention comprises: (a) a HCDR1 comprising, preferably consisting of, the amino acid sequence of SEQ ID NO: 4 or SEQ ID NO: 5; (b) a HCDR2 comprising, preferably consisting of, the amino acid sequence of SEQ ID NO: 6; (c) a HCDR3 comprising, preferably consisting of, the amino acid sequence of SEQ ID NO: 7; (d) a LCDR1 comprising, preferably consisting of, the amino acid sequence of SEQ ID NO: 21; (e) a LCDR2 comprising, preferably consisting of, the amino acid sequence of SEQ ID NO: 22; and (f) a LCDR3 comprising, preferably consisting of, the amino acid sequence of SEQ ID NO: 23. Suitably, the CD137-BD of the multispecific antibody of the present invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 4 or SEQ ID NO: 5; (b) a HCDR2 comprising, preferably consisting of, the amino acid sequence having at least 60, 70, 80, 90, 91, 92, 93, 94, 95, 96, 97, 98 or 99 percent identity to SEQ ID NO: 6; (c) a HCDR3 comprising, preferably consisting of, the amino acid sequence having at least 60, 70, 80, 90, 91, 92, 93, 94, 95, 96, 97, 98 or 99 percent identity to SEQ ID NO: 7; (d) a LCDR1 comprising, preferably consisting of, the amino acid sequence having at least 60, 70, 80, 90, 91, 92, 93, 94, 95, 96, 97, 98 or 99 percent identity to SEQ ID NO: 21; (e) a LCDR2 comprising, preferably consisting of, the amino acid sequence having at least 60, 70, 80, 90, 91, 92, 93, 94, 95, 96, 97, 98 or 99 percent identity to SEQ ID NO: 22; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 23.

In yet a further embodiment, the CD137-BD of the multispecific antibody of the present invention comprises: (a) a HCDR1 comprising, preferably consisting of, the amino acid sequence of SEQ ID NO: 35; (b) a HCDR2 comprising, preferably consisting of, the amino acid sequence of SEQ ID NO: 36; (c) a HCDR3 comprising, preferably consisting of, the amino acid sequence of SEQ ID NO: 37; (d) a LCDR1 comprising, preferably consisting of, the amino acid sequence of SEQ ID NO: 48; (e) a LCDR2 comprising, preferably consisting of, the amino acid sequence of SEQ ID NO: 49; and (f) a LCDR3 comprising, preferably consisting of, the amino acid sequence of SEQ ID NO: 50. Suitably, the CD137-BD of the multispecific antibody of the present invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 35; (b) a HCDR2 comprising, preferably consisting of, the amino acid sequence having at least 60, 70, 80, 90, 91, 92, 93, 94, 95, 96, 97, 98 or 99 percent identity to SEQ ID NO: 36; (c) a HCDR3 comprising, preferably consisting of, the amino acid sequence having at least 60, 70, 80, 90, 91, 92, 93, 94, 95, 96, 97, 98 or 99 percent identity to SEQ ID NO: 37; (d) a LCDR1 comprising, preferably consisting of, the amino acid sequence having at least 60, 70, 80, 90, 91, 92, 93, 94, 95, 96, 97, 98 or 99 percent identity to SEQ ID NO: 48; (e) a LCDR2 comprising, preferably consisting of, the amino acid sequence having at least 60, 70, 80, 90, 91, 92, 93, 94, 95, 96, 97, 98 or 99 percent identity to SEQ ID NO: 49; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 50.

In a further embodiment, the CD137-BD of the multispecific antibody of the present invention comprises: (a) a HCDR1 comprising, preferably consisting of, the amino acid sequence of SEQ ID NO: 38; (b) a HCDR2 comprising, preferably consisting of, the amino acid sequence of SEQ ID NO: 39; (c) a HCDR3 comprising, preferably consisting of, the amino acid sequence of SEQ ID NO: 40; (d) a LCDR1 comprising, preferably consisting of, the amino acid sequence of SEQ ID NO: 51; (e) a LCDR2 comprising, preferably consisting of, the amino acid sequence of SEQ ID NO: 52; and (f) a LCDR3 comprising, preferably consisting of, the amino acid sequence of SEQ ID NO: 53. Suitably, the CD137-BD of the multispecific antibody of the present invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 38; (b) a HCDR2 comprising, preferably consisting of, the amino acid sequence having at least 60, 70, 80, 90, 91, 92, 93, 94, 95, 96, 97, 98 or 99 percent identity to SEQ ID NO: 39; (c) a HCDR3 comprising, preferably consisting of, the amino acid sequence having at least 60, 70, 80, 90, 91, 92, 93, 94, 95, 96, 97, 98 or 99 percent identity to SEQ ID NO: 40; (d) a LCDR1 comprising, preferably consisting of, the amino acid sequence having at least 60, 70, 80, 90, 91, 92, 93, 94, 95, 96, 97, 98 or 99 percent identity to SEQ ID NO: 51; (e) a LCDR2 comprising, preferably consisting of, the amino acid sequence having at least 60, 70, 80, 90, 91, 92, 93, 94, 95, 96, 97, 98 or 99 percent identity to SEQ ID NO: 52; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 53.

In a preferred embodiment, the multispecific antibody of the present invention comprises a CD137-BD, wherein said CD137-BD comprises: (a) a heavy chain variable region CDR1 comprising, preferably consisting of, an amino acid sequence selected from any one of SEQ ID NOs: 59, 62, 65 and 68, preferably SEQ ID NO: 59; (b) a heavy chain variable region CDR2 comprising, preferably consisting of, an amino acid sequence selected from any of SEQ ID NOs: 60, 63, 66 and 69, preferably SEQ ID NO: 60; (c) a heavy chain variable region CDR3 comprising, preferably consisting of, an amino acid sequence selected from any of SEQ ID NOs: 61, 64, 67 and 70, preferably SEQ ID NO: 61; (d) a light chain variable region CDR1 comprising, preferably consisting of, an amino acid sequence selected from any of SEQ ID NOs: 74, 77 and 80, preferably SEQ ID NO: 74; (e) a light chain variable region CDR2 comprising, preferably consisting of, an amino acid sequence selected from any of SEQ ID NOs: 75, 78 and 81, preferably SEQ ID NO: 75; and (f) a light chain variable region CDR3 comprising, preferably consisting of, an amino acid sequence selected from any of SEQ ID NOs: 76, 79 and 82, preferably SEQ ID NO: 76. Suitably, the CD137-BD of the multispecific antibody of the present invention comprises: (a) a heavy chain variable region CDR1 having at least 60, 70, 80, 90, 91, 92, 93, 94, 95, 96, 97, 98 or 99 percent identity to any one of SEQ ID NOs: 59, 62, 65 and 68, preferably SEQ ID NO: 59; (b) a heavy chain variable region CDR2 having at least 60, 70, 80, 90, 91, 92, 93, 94, 95, 96, 97, 98 or 99 percent identity to any of SEQ ID NOs: 60, 63, 66 and 69, preferably SEQ ID NO: 60; (c) a heavy chain variable region CDR3 having at least 60, 70, 80, 90, 91, 92, 93, 94, 95, 96, 97, 98 or 99 percent identity to any of SEQ ID NOs: 61, 64, 67 and 70, preferably SEQ ID NO: 61; (d) a light chain variable region CDR1 having at least 60, 70, 80, 90, 91, 92, 93, 94, 95, 96, 97, 98 or 99 percent identity to any of SEQ ID NOs: 74, 77 and 80, preferably SEQ ID NO: 74; (e) a light chain variable region CDR2 having at least 60, 70, 80, 90, 91, 92, 93, 94, 95, 96, 97, 98 or 99 percent identity to any of SEQ ID NOs: 75, 78 and 81, preferably SEQ ID NO: 75; and (f) a light chain variable region CDR3 having at least 60, 70, 80, 90, 91, 92, 93, 94, 95, 96, 97, 98 or 99 percent identity to any of SEQ ID NOs: 76, 79 and 82, preferably SEQ ID NO: 76.

In one embodiment, the CD137-BD of the multispecific antibody of the present invention comprises: (a) HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively; (b) HCDR1, HCDR2, and HCDR3 sequences of SEQ ID NOs: 62, 63 and 64, respectively, and LCDR1, LCDR2, and LCDR3 sequences of SEQ ID NOs: 77, 78 and 79, respectively; (c) HCDR1, HCDR2, and HCDR3 sequences of SEQ ID NOs: 65, 66 and 67, respectively, and LCDR1, LCDR2, and LCDR3 sequences of SEQ ID NOs: 74, 75 and 76, respectively; (d) HCDR1, HCDR2, and HCDR3 sequences of SEQ ID NOs: 68, 69 and 70, respectively, and LCDR1, LCDR2, and LCDR3 sequences of SEQ ID NOs: 80, 81 and 82, respectively. In a preferred embodiment, the CD137-BD of the multispecific antibody of the present invention comprises HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively.

Suitably, the CD137-BD of the multispecific antibody of the present invention comprises: (a) HCDR1, HCDR2, and HCDR3 sequences having at least 60, 70, 80, 90, 91, 92, 93, 94, 95, 96, 97, 98 or 99 percent identity to SEQ ID NOs: 59, 60 and 61, respectively, and LCDR1, LCDR2, and LCDR3 sequences having at least 60, 70, 80, 90, 91, 92, 93, 94, 95, 96, 97, 98 or 99 percent identity to SEQ ID NOs: 74, 75 and 76, respectively; (b) HCDR1, HCDR2, and HCDR3 sequences having at least 60, 70, 80, 90, 91, 92, 93, 94, 95, 96, 97, 98 or 99 percent identity to SEQ ID NOs: 62, 63 and 64, respectively, and LCDR1, LCDR2, and LCDR3 sequences having at least 60, 70, 80, 90, 91, 92, 93, 94, 95, 96, 97, 98 or 99 percent identity to SEQ ID NOs: 77, 78 and 79, respectively; (c) HCDR1, HCDR2, and HCDR3 sequences having at least 60, 70, 80, 90, 91, 92, 93, 94, 95, 96, 97, 98 or 99 percent identity to SEQ ID NOs: 65, 66 and 67, respectively, and LCDR1, LCDR2, and LCDR3 sequences having at least 60, 70, 80, 90, 91, 92, 93, 94, 95, 96, 97, 98 or 99 percent identity to SEQ ID NOs: 74, 75 and 76, respectively; (d) HCDR1, HCDR2, and HCDR3 sequences having at least 60, 70, 80, 90, 91, 92, 93, 94, 95, 96, 97, 98 or 99 percent identity to SEQ ID NOs: 68, 69 and 70, respectively, and LCDR1, LCDR2, and LCDR3 sequences having at least 60, 70, 80, 90, 91, 92, 93, 94, 95, 96, 97, 98 or 99 percent identity to SEQ ID NOs: 80, 81 and 82, respectively. In a preferred embodiment, the CD137-BD of the multispecific antibody of the present invention comprises HCDR1, HCDR2, and HCDR3 sequences having at least 60, 70, 80, 90, 91, 92, 93, 94, 95, 96, 97, 98 or 99 percent identity to SEQ ID NOs: 59, 60 and 61, respectively, and LCDR1, LCDR2, and LCDR3 sequences having at least 60, 70, 80, 90, 91, 92, 93, 94, 95, 96, 97, 98 or 99 percent identity to SEQ ID NOs: 74, 75 and 76, respectively. Suitably, the CD137-BD of the multispecific antibody of the present invention comprises: (a) a HCDR1 comprising the amino acid sequence having at least 60, 70, 80, 90, 91, 92, 93, 94, 95, 96, 97, 98 or 99 percent identity to SEQ ID NO: 59; (b) a HCDR2 comprising the amino acid sequence having at least 60, 70, 80, 90, 91, 92, 93, 94, 95, 96, 97, 98 or 99 percent identity to SEQ ID NO: 60; (c) a HCDR3 comprising the amino acid sequence having at least 60, 70, 80, 90, 91, 92, 93, 94, 95, 96, 97, 98 or 99 percent identity to SEQ ID NO: 61; (d) a LCDR1 comprising the amino acid sequence having at least 60, 70, 80, 90, 91, 92, 93, 94, 95, 96, 97, 98 or 99 percent identity to SEQ ID NO: 74; (e) a LCDR2 comprising the amino acid sequence having at least 60, 70, 80, 90, 91, 92, 93, 94, 95, 96, 97, 98 or 99 percent identity to SEQ ID NO: 75; and (f) a LCDR3 comprising the amino acid sequence having at least 60, 70, 80, 90, 91, 92, 93, 94, 95, 96, 97, 98 or 99 percent identity to SEQ ID NO: 76.

In a further embodiment, the CD137-BD of the multispecific antibody of the present invention comprises a VH domain and a VL domain. In the context of the present invention the terms "VH" (variable heavy chain), "VL" (variable light chain), "Vκ" and "Vλ" refer to families of antibody heavy and light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For VH, Vκ and Vλ different subfamilies can be identified, as shown, for example, in Knappik et al., J. Mol. Biol. 296 (2000) 57-86, which groups VH in VH1A, VH1B and VH2 to VH6, Vκ in Vκ1 to Vκ4 and Vλ in Vλ1 to Vλ3. In vivo, antibody Vκ chains, Vλ chains, and VH chains are the result of the random rearrangement of germline x chain V and J segments, germline λ chain V and J segments, and heavy chain V, D and J segments, respectively. To which subfamily a given antibody variable chain belongs is determined by the corresponding V segment, and in particular by the framework regions FR1 to FR3. Thus, any VH sequence that is characterized in the present application by a particular set of framework regions HFR1 to HFR3 only, may be combined with any HFR4 sequence, for example a HFR4 sequence taken from one of the heavy chain germline J segments, or a HFR4 sequence taken from a rearranged VH sequence.

Suitably, the CD137-BD of the multispecific antibody of the present invention comprises VH4 or VH3 domain framework sequences, preferably VH4 domain framework sequences, more preferably VH3 domain framework sequences.

A specific example of a VH belonging to VH3 family is represented under SEQ ID NO: 71. In particular, framework regions FR1 to FR4 taken from SEQ ID NO: 71 belong to VH3 family (Table 1, regions marked in non-bold). Suitably, a VH belonging to VH3 family, as used herein, is a VH comprising FR1 to FR4 having at least 85%, preferably at least 90%, more preferably at least 95% sequence identity to FR1 to FR4 of SEQ ID NO: 71.

A specific example of a VH belonging to VH4 family is represented under SEQ ID NO: 14. In particular, framework regions FR1 to FR4 taken from SEQ ID NO: 14 belong to VH4 family (Table 1, regions marked in non-bold). Suitably, a VH belonging to VH4 family, as used herein, is a VH comprising FR1 to FR4 having at least 85%, preferably at least 90%, more preferably at least 95% sequence identity to FR1 to FR4 of SEQ ID NO: 14.

Suitably, the CD137-BD of the multispecific antibody of the present invention comprises Vκ frameworks FR1, FR2 and FR3, particularly Vκ1 or Vκ3 frameworks, preferably Vκ1 frameworks FR1 to 3, and a framework FR4, which is selected from a Vκ FR4, particularly Vκ1 FR4, Vκ3 FR4, and a Vλ FR4. Suitable Vκ1 frameworks FR1 to 3 are set forth in SEQ ID NO: 27 or SEQ ID NO: 83 (Table 1, FR regions are marked in non-bold). Suitable Vκ1 frameworks FR1 to 3 comprise the amino acid sequences having at least 60, 70, 80, 90 percent identity to amino acid sequences corresponding to FR1 to 3 and taken from SEQ ID NO: 27 or SEQ ID NO: 83 (Table 1, FR regions are marked in non-bold). Suitable Vλ FR4 are as set forth in SEQ ID NO: 199 to SEQ ID NO: 205. In one embodiment, the CD137-BD of the multispecific antibody of the present invention comprises Vλ FR4 comprising the amino acid sequence having at least 60, 70, 80, 90 percent identity to comprising an amino acid sequence selected from any of SEQ ID NO: 199 to SEQ ID NO: 205.

In one embodiment, the CD137-BD of the multispecific antibody of the present invention comprises:

(i) the HCDR1, HCDR2, and HCDR3 sequences of:
  a. SEQ ID NOs: 1, 2, and 3, respectively, and the LCDR1, LCDR2, and LCDR3 sequences of SEQ ID NOs: 18, 19, and 20, respectively; or
  b. SEQ ID NOs: 35, 36, and 37, respectively, and the LCDR1, LCDR2, and LCDR3 sequences of SEQ ID NOs: 48, 49, and 50, respectively; or
  c. SEQ ID NOs: 59, 60 and 61, respectively, and the LCDR1, LCDR2, and LCDR3 sequences of SEQ ID NOs: 74, 75 and 76, respectively;

(ii) VH3 or VH4 domain framework sequences FR1 to FR4; preferably VH4 domain framework sequences FR1 to FR4, more preferably VH3 domain framework sequences FR1 to FR4; and (iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to comprising an amino acid sequence selected from any of SEQ ID NO: 199 to SEQ ID NO: 205, more particularly Vλ FR4 comprising an amino acid sequence selected from any of SEQ ID NO: 199 to SEQ ID NO: 205, preferably Vλ FR4 comprising an amino acid sequence SEQ ID NO: 199.

In a preferred embodiment, said the CD137-BD of the multispecific antibody of the present invention comprises the HCDR1, HCDR2, and HCDR3 sequences of SEQ ID NOs: 59, 60 and 61, respectively, and the LCDR1, LCDR2, and LCDR3 sequences of SEQ ID NOs: 74, 75 and 76, respectively.

In one embodiment, the CD137-BD of the multispecific antibody of the present invention comprises:

(i) the HCDR1, HCDR2, and HCDR3 sequences of:

a. SEQ ID NOs: 4, 6, and 7, respectively, and the LCDR1, LCDR2, and LCDR3 sequences of SEQ ID NOs: 21, 22, and 23, respectively;

b. SEQ ID NOs: 5, 6, and 7, respectively, and the LCDR1, LCDR2, and LCDR3 sequences of SEQ ID NOs: 21, 22, and 23, respectively; or c. SEQ ID NOs: 38, 39, and 40, respectively, and the LCDR1, LCDR2, and LCDR3 sequences of SEQ ID NOs: 51, 52, and 53, respectively;

(ii) VH3 or VH4 domain framework sequences FR1 to FR4; preferably VH4 domain framework sequences FR1 to FR4, more preferably VH3 domain framework sequences FR1 to FR4; and (iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vλ FR4, particularly Vκ1 FR4, Vκ3 FR4, and a Vλ FR4, particularly Vλ FR4 comprising the amino acid sequence having at least 60, 70, 80, 90 percent identity to comprising an amino acid sequence selected from any of SEQ ID NO: 199 to SEQ ID NO: 205, more particularly Vλ FR4 comprising an amino acid sequence selected from any of SEQ ID NO: 199 to SEQ ID NO: 205, preferably Vλ FR4 comprising an amino acid sequence SEQ ID NO: 199.

In one embodiment, the CD137-BD of the multispecific antibody of the present invention comprises a VL comprising:

(i) CDR domains CDR1, CDR2 and CDR3;

(ii) human Vκ framework regions FR1 to FR3, particularly human Vκ1 framework regions FR1 to FR3;

(iii) FR4, which is selected from (a) a human Vλ germ line sequence for FR4, particularly a Vλ germ line sequence selected from the list of: SEQ ID NO: 199 to 205, preferably Vλ FR4 comprising an amino acid sequence SEQ ID NO: 199; and (b) a Vλ-based sequence, which has one or two mutations, particularly one mutation, compared to the closest human Vλ germ line sequence for FR4 comprising an amino acid sequence selected from any of SEQ ID NO: 199 to SEQ ID NO: 205, preferably Vλ FR4 comprising an amino acid sequence SEQ ID NO: 199.

In a preferred embodiment, the CD137-BD of the multispecific antibody of the present invention comprises:

(i) the HCDR1, HCDR2, and HCDR3 sequences of:

a. SEQ ID NOs: 4, 6, and 7, respectively, and the LCDR1, LCDR2, and LCDR3 sequences of SEQ ID NOs: 21, 22, and 23, respectively;

b. SEQ ID NOs: 5, 6, and 7, respectively, and the LCDR1, LCDR2, and LCDR3 sequences of SEQ ID NOs: 21, 22, and 23, respectively; or c. SEQ ID NOs: 38, 39, and 40, respectively, and the LCDR1, LCDR2, and LCDR3 sequences of SEQ ID NOs: 51, 52, and 53, respectively (ii) VH4 domain framework sequences FR1 to FR4; and (iii) a VL domain comprising a VL framework comprising Vλ1 frameworks FR1, FR2 and FR3, and a Vλ FR4 comprising the amino acid sequence having at least 60, 70, 80, 90 percent identity to comprising an amino acid sequence selected from any of SEQ ID NO: 199 to SEQ ID NO: 205, particularly Vλ FR4 as set forth in SEQ ID NO: 199 to SEQ ID NO: 205, preferably SEQ ID NO: 199.

In another preferred embodiment, the CD137-BD of the multispecific antibody of the present invention comprises:

(i) the HCDR1, HCDR2, and HCDR3 sequences of SEQ ID NOs: 1, 2, and 3, respectively, and the LCDR1, LCDR2, and LCDR3 sequences of SEQ ID NOs: 18, 19, and 20, respectively;

(ii) VH3 domain framework sequences FR1 to FR4; and (iii) a VL domain comprising a VL framework comprising Vλ1 frameworks FR1, FR2 and FR3, and a Vλ FR4 comprising the amino acid sequence having at least 60, 70, 80, 90 percent identity to comprising an amino acid sequence selected from any of SEQ ID NO: 199 to SEQ ID NO: 205, particularly Vλ FR4 as set forth in SEQ ID NO: 199 to SEQ ID NO: 205, preferably SEQ ID NO: 199.

In a more preferred embodiment, the CD137-BD of the multispecific antibody of the present invention comprises:

(i) the HCDR1, HCDR2, and HCDR3 sequences of SEQ ID NOs: 59, 60 and 61, respectively, and the LCDR1, LCDR2, and LCDR3 sequences of SEQ ID NOs: 74, 75 and 76, respectively;

(ii) VH3 domain framework sequences FR1 to FR4; and (iii) a VL domain comprising a VL framework comprising Vλ1 frameworks FR1, FR2 and FR3, and a Vλ FR4 comprising the amino acid sequence having at least 60, 70, 80, 90 percent identity to comprising an amino acid sequence selected from any of SEQ ID NO: 199 to SEQ ID NO: 205, particularly Vλ FR4 as set forth in SEQ ID NO: 199 to SEQ ID NO: 205, preferably SEQ ID NO: 199.

Suitably, the CD137-BD of the invention comprises a VH domain listed in Table 1.

Suitably, the CD137-BD of the invention comprises (a VH amino acid sequence listed in Table 1, wherein no more than about 10 amino acids in a framework sequence (for example, a sequence which is not a CDR) have been mutated (wherein a mutation is, as various non-limiting examples, an addition, substitution or deletion). Suitably, the CD137-BD of the invention comprises a VH amino acid sequence listed in Table 1, wherein no more than about 20 amino acids in a framework sequence (for example, a sequence which is not a CDR) have been mutated (wherein a mutation is, as various non-limiting examples, an addition, substitution or deletion). Other CD137-BD of the invention include amino acids that have been mutated, yet have at least 60, 70, 80, 90, 91, 92, 93, 94, 95, 96, 97, 98 or 99 percent identity in the VH regions with the VH regions depicted in the sequences described in Table 1.

Suitably, the CD137-BD of the invention comprises a VL domain listed in Table 1. Suitably, the CD137-BD of the invention comprises a VL amino acid sequence listed in Table 1, wherein no more than about 10 amino acids in a framework sequence (for example, a sequence which is not a CDR) have been mutated (wherein a mutation is, as various non-limiting examples, an addition, substitution or deletion). Suitably, the CD137-BD of the invention comprises a VL amino acid sequence listed in Table 1, wherein no more than about 20 amino acids in a framework sequence (for example, a sequence which is not a CDR) have been mutated (wherein a mutation is, as various non-limiting examples, an addition, substitution or deletion). Other CD137-BD of the invention include amino acids that have been mutated, yet have at least 60, 70, 80, 90, 91, 92, 93, 94, 95, 96, 97, 98 or 99 percent identity in the VL regions with the VL regions depicted in the sequences described in Table 1.

Suitably, the CD137-BD of the invention comprises a heavy chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 14, 15, 16, 17 and 47, preferably SEQ ID NO: 17; and a light chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 27, 28, 29, 30 and 57, preferably SEQ ID NO: 30.

Suitably, the CD137-BD of the present invention comprises: a heavy chain variable region comprising an amino acid sequence selected from any of SEQ ID NOs: 14, 15, 16, 17 and 47, preferably SEQ ID NO: 17; and a light chain variable region comprising an amino acid sequence selected from any of SEQ ID NOs: 27, 28, 29, 30 and 57, preferably SEQ ID NO: 30.

In a further embodiment, the CD137-BD of the present invention comprises: (a) a VH sequence of SEQ ID NO: 14 and a VL sequence of SEQ ID NO: 27; (b) a VH sequence of SEQ ID NO: 15 and a VL sequence of SEQ ID NO: 28; (c) a VH sequence of SEQ ID NO: 16 and a VL sequence of SEQ ID NO: 29; (d) a VH sequence of SEQ ID NO: 17 and a VL sequence of SEQ ID NO: 30; or (e) a VH sequence of SEQ ID NO: 47 and a VL sequence of SEQ ID NO: 57. In a preferred embodiment, the CD137-BD of the present invention comprises a VH sequence of SEQ ID NO: 17 and a VL sequence of SEQ ID NO: 30.

In one embodiment, the CD137-BD of the present invention comprises:

(a) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, a VH sequence at least 60, 70, 80, 90, 91, 92, 93, 94, 95, 96, 97, 98 or 99 percent identical to the amino acid sequence SEQ ID NO: 14, and a VL sequence at least 60, 70, 80, 90, 91, 92, 93, 94, 95, 96, 97, 98 or 99 percent identical to the amino acid sequence SEQ ID NO: 27;

(b) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, a VH sequence at least 60, 70, 80, 90, 91, 92, 93, 94, 95, 96, 97, 98 or 99 percent identical to the amino acid sequence SEQ ID NO: 15, and a VL sequence at least 60, 70, 80, 90, 91, 92, 93, 94, 95, 96, 97, 98 or 99 percent identical to the amino acid sequence SEQ ID NO: 28;

(c) HCDR1, HCDR2, and HCDR3 sequences of SEQ ID NOs: 5, 6, and 7, respectively, and LCDR1, LCDR2, and LCDR3 sequences of SEQ ID NOs: 21, 22, and 23, respectively, a VH sequence at least 60, 70, 80, 90, 91, 92, 93, 94, 95, 96, 97, 98 or 99 percent identical to the amino acid sequence SEQ ID NO: 16, and a VL sequence at least 60, 70, 80, 90, 91, 92, 93, 94, 95, 96, 97, 98 or 99 percent identical to the amino acid sequence SEQ ID NO: 29;

(d) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, a VH sequence at least 60, 70, 80, 90, 91, 92, 93, 94, 95, 96, 97, 98 or 99 percent identical to the amino acid sequence SEQ ID NO: 17, and a VL sequence at least 60, 70, 80, 90, 91, 92, 93, 94, 95, 96, 97, 98 or 99 percent identical to the amino acid sequence SEQ ID NO: 30, preferably wherein said VH comprises a G51C mutation (AHo numbering) and said VL comprises T141C mutation (AHo numbering); or (e) HCDR1, HCDR2, and HCDR3 sequences of SEQ ID NOs: 38, 39, and 40, respectively, and LCDR1, LCDR2, and LCDR3 sequences of SEQ ID NOs: 51, 52, and 53, respectively, a VH sequence at least 60, 70, 80, 90, 91, 92, 93, 94, 95, 96, 97, 98 or 99 percent identical to the amino acid sequence SEQ ID NO: 47, and a VL sequence at least 60, 70, 80, 90, 91, 92, 93, 94, 95, 96, 97, 98 or 99 percent identical to the amino acid sequence SEQ ID NO: 57.

In one embodiment, the CD137-BD of the present invention comprises:

(a) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 14, and a VL sequence at least 60, 70, 80, 90, 91, 92, 93, 94, 95, 96, 97, 98 or 99 percent identical to the amino acid sequence SEQ ID NO: 27;

(b) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 15, and a VL sequence at least 60, 70, 80, 90, 91, 92, 93, 94, 95, 96, 97, 98 or 99 percent identical to the amino acid sequence SEQ ID NO: 28;

(c) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 16, and a VL sequence at least 60, 70, 80, 90, 91, 92, 93, 94, 95, 96, 97, 98 or 99 percent identical to the amino acid sequence SEQ ID NO: 29;

(d) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 17, and a VL sequence at least 60, 70, 80, 90, 91, 92, 93, 94, 95, 96, 97, 98 or 99 percent identical to the amino acid sequence SEQ ID NO: 30, preferably wherein said VH comprises a G51C mutation (AHo numbering) and said VL comprises T141C mutation (AHo numbering); or (e) HCDR1, HCDR2, and HCDR3 sequences of SEQ ID NOs: 35, 36, and 37, respectively, and LCDR1, LCDR2, and LCDR3 sequences of SEQ ID NOs: 48, 49, and 50, respectively, a VH sequence at least 60, 70, 80, 90, 91, 92, 93, 94, 95, 96, 97, 98 or 99 percent identical to the amino acid sequence SEQ ID NO: 47, and a VL sequence at least 60, 70, 80, 90, 91, 92, 93, 94, 95, 96, 97, 98 or 99 percent identical to the amino acid sequence SEQ ID NO: 57.

In a preferred embodiment, the CD137-BD of the present invention comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 17, and a VL sequence at least 60, 70, 80, 90, 91, 92, 93, 94, 95, 96, 97, 98 or 99 percent identical to the amino acid sequence SEQ ID NO: 30, preferably wherein said VH comprises a G51C mutation (AHo numbering) and said VL comprises T141C mutation (AHo numbering). Suitably, said CD137-BD of the present invention is mutated to form an artificial interdomain disulfide bridge within the framework region, in particular wherein the pair of cysteins replaces Gly 51 (AHo numbering) on said VH and Thr 141 (AHo numbering) on said VL. It was surprisingly found that such CD137-BD comprising an interdomain disulfide bridge has a significantly increased thermostability.

The term "artificial" with reference to a disulfide bridge ("S—S bridge" or "diS") means that the S—S bridge is not naturally formed by the wild-type antibody, but is formed by an engineered mutant of a parent molecule, wherein at least one foreign amino acid contributes to the disulfide bonding. The site-directed engineering of artificial disulfide bridges clearly differentiates from those naturally available in native immunoglobulins or in modular antibodies, such as those described in WO 2009/000006, because at least one of the sites of bridge piers of an artificial disulfide bridge is typically located aside from the positions of Cys residues in the wild-type antibody, thus, providing for an alternative or additional disulfide bridge within the framework region. The artificial disulfide bridge of the present invention may be engineered within an antibody domain ("intradomain bridge"), which would stabilize the beta-sheet structure or bridging the domains ("interdomain bridge") or chains of domains ("interchain bridge"), to constrain the structure of the multispecific antibody according to the invention and support its interaction with potential binding partners.

In one embodiment, the CD137-BD of the present invention comprises:

(a) a VH sequence of SEQ ID NO: 14 and a VL sequence of SEQ ID NO: 27;
(b) a VH sequence of SEQ ID NO: 15 and a VL sequence of SEQ ID NO: 28;
(c) a VH sequence of SEQ ID NO: 16 and a VL sequence of SEQ ID NO: 29;
(d) a VH sequence of SEQ ID NO: 17, and a VL sequence of SEQ ID NO: 30; or
(e) a VH sequence of SEQ ID NO: 47 and a VL sequence of SEQ ID NO: 57.

In one embodiment, the CD137-BD of the present invention comprises:

(a) a VH sequence of SEQ ID NO: 14 and a VL sequence of SEQ ID NO: 27;
(b) a VH sequence of SEQ ID NO: 15 and a VL sequence of SEQ ID NO: 28;
(c) a VH sequence of SEQ ID NO: 16 and a VL sequence of SEQ ID NO: 29;
(d) a VH sequence of SEQ ID NO: 17, and a VL sequence of SEQ ID NO: 30; or
(e) a VH sequence of SEQ ID NO: 47 and a VL sequence of SEQ ID NO: 57.

In a preferred embodiment, the CD137-BD of the present invention comprises a VH sequence of SEQ ID NO: 17, and a VL of SEQ ID NO: 30.

In one embodiment, the CD137-BD of the present invention is described in Table 1. In one embodiment, the CD137-BD of the present invention is at least 60, 70, 80, 90, 91, 92, 93, 94, 95, 96, 97, 98 or 99 percent identical to the amino acid sequence selected from the group consisting of SEQ ID NO: 31, SEQ ID NO: 32, SEQ ID NO: 33, SEQ ID NO: 34 or SEQ ID NO: 58. In one embodiment, the CD137-BD of the present invention is as set forth in SEQ ID NO: 31, SEQ ID NO: 32, SEQ ID NO: 33, SEQ ID NO: 34 or SEQ ID NO: 58. In one embodiment, the CD137-BD of the present invention is as set forth in SEQ ID NO: 31 or SEQ ID NO: 33 or SEQ ID NO: 34. In a preferred embodiment, the CD137-BD of the present invention is as set forth in SEQ ID NO: 33. In a more preferred embodiment, the CD137-BD of the present invention is as set forth in SEQ ID NO: 34.

In a preferred embodiment, the CD137-BD of the invention comprises a heavy chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 71, 72 and 73, preferably SEQ ID NO: 71, more preferably SEQ ID NO: 73; and a light chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 83, 84 and 85, preferably SEQ ID NO: 83, more preferably SEQ ID NO: 85. In a particular embodiment, the CD137-BD of the present invention comprises: a heavy chain variable region comprising an amino acid sequence selected from any of SEQ ID NOs: 71, 72 and 73, preferably SEQ ID NO: 71, more preferably SEQ ID NO: 73; and a light chain variable region comprising an amino acid sequence selected from any of SEQ ID NOs: 83, 84 and 85, preferably SEQ ID NO: 83, more preferably SEQ ID NO: 85.

In a further embodiment, the CD137-BD of the present invention comprises: (a) a VH sequence of SEQ ID NO: 71 and a VL sequence of SEQ ID NO: 83; (b) a VH sequence of SEQ ID NO: 72 and a VL sequence of SEQ ID NO: 84; or (c) a VH sequence of SEQ ID NO: 73 and a VL sequence of SEQ ID NO: 85. In a preferred embodiment, the CD137-BD of the present invention comprises a VH sequence of SEQ ID NO: 71 and a VL sequence of SEQ ID NO: 83. In a more preferred embodiment, the CD137-BD of the present invention comprises a VH sequence of SEQ ID NO: 73 and a VL sequence of SEQ ID NO: 85.

In a preferred embodiment, the CD137-BD of the present invention comprises:

(a) HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, a VH sequence at least 60, 70, 80, 90, 91, 92, 93, 94, 95, 96, 97, 98 or 99 percent identical to the amino acid sequence SEQ ID NO: 71, and a VL sequence at least 60, 70, 80, 90, 91, 92, 93, 94, 95, 96, 97, 98 or 99 percent identical to the amino acid sequence SEQ ID NO: 83, preferably wherein said VH comprises a G51C mutation (AHo numbering) and said VL comprises T141C mutation (AHo numbering);
(b) HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, a VH sequence at least 60, 70, 80, 90, 91, 92, 93, 94, 95, 96, 97, 98 or 99 percent identical to the amino acid sequence SEQ ID NO: 72, and a VL sequence at least 60, 70, 80, 90, 91, 92, 93, 94, 95, 96, 97, 98 or 99 percent identical to the amino acid sequence SEQ ID NO: 84; or
(c) HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, a VH sequence at least 60, 70, 80, 90, 91, 92, 93, 94, 95, 96, 97, 98 or 99 percent identical to the amino acid sequence SEQ ID NO: 73, and a VL sequence at least 60, 70, 80, 90, 91, 92, 93, 94, 95, 96, 97, 98 or 99 percent identical to the amino acid sequence SEQ ID NO: 85, preferably wherein said VH comprises a G51C mutation (AHo numbering) and said VL comprises T141C mutation (AHo numbering).

In a preferred embodiment, the CD137-BD of the present invention comprises HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, a VH sequence at least 60, 70, 80, 90, 91, 92, 93, 94, 95, 96, 97, 98 or 99 percent identical to the amino acid sequence SEQ ID NO: 71, and a VL sequence at least 60, 70, 80, 90, 91, 92, 93, 94, 95, 96, 97, 98 or 99 percent identical to the amino acid sequence SEQ ID NO: 83, preferably wherein said VH comprises a G51C mutation (AHo numbering) and said VL comprises T141C mutation (AHo numbering). Suitably, said CD137-BD of the present invention is mutated to form an artificial interdomain disulfide bridge within the framework region, in particular wherein the pair of cysteins replaces Gly 51 (AHo numbering) on said VH and Thr 141 (AHo numbering) on said VL. It was surprisingly found that such CD137-BD comprising an interdomain disulfide bridge has a significantly increased thermostability.

In a preferred embodiment, the CD137-BD of the present invention comprises a VH sequence of SEQ ID NO: 71, and a VL of SEQ ID NO: 83. In a more preferred embodiment, the CD137-BD of the present invention comprises a VH sequence of SEQ ID NO: 73, and a VL of SEQ ID NO: 85.

In one embodiment, the CD137-BD of the present invention is described in Table 1. In one embodiment, the CD137-BD of the present invention is at least 60, 70, 80, 90, 91, 92, 93, 94, 95, 96, 97, 98 or 99 percent identical to the amino acid sequence selected from the group consisting of SEQ ID NOs: 86, 87 and 88. In one embodiment, the CD137-BD of the present invention is as set forth in SEQ ID NO: 86, SEQ ID NO: 87, or SEQ ID NO: 88. In a preferred embodiment, the CD137-BD of the present invention is as set forth in SEQ ID NO: 86. In a more preferred embodiment, the CD137-BD of the present invention is as set forth in SEQ ID NO: 88.

Other CD137-BD of the present invention include those wherein the amino acids or nucleic acids encoding the amino acids have been mutated, yet have at least 60, 70, 80, 90 or 95 percent identity to the sequences described in Table 1. In one embodiment, it includes mutant amino acid sequences wherein no more than 1, 2, 3, 4 or 5 amino acids have been mutated in the variable regions when compared with the variable regions depicted in the sequence described in Table 1, while retaining substantially the same therapeutic activity. The term "substantially the same activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent CD137-BD, in particular the CD137-BD of the invention described in Table 1.

Given that each of these binding domains or antibodies can bind to CD137 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different binding domains or antibodies can be mixed and match, although each binding domains or each antibody must contain a VH CDR1, 2 and 3 and a VL CDR1, 2 and 3 to create other CD137-binding molecules of the invention. Such "mixed and matched" CD137-BD can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by mutating one or more VH and/or VL CDR region sequences with structurally similar sequences from the CDR sequences shown herein for monoclonal antibodies or binding domains of the present invention.

In yet another embodiment, the present invention provides a CD137-BD comprising amino acid sequences that are homologous to the sequences described in Table 1, and said binding domain binds to CD137, and retains the desired functional properties of those binding domains described in Table 1.

For example, the invention provides a CD137-BD comprising a heavy chain variable region and a light chain variable region, wherein the heavy chain variable region comprises an amino acid sequence that is at least 80 percent, at least 90 percent, or at least 95 percent identical to an amino acid sequence selected from the group consisting of SEQ ID NOs: 14, 15, 16, 17, 47, 71, 72 and 73, preferably SEQ ID NO: 17, more preferably SEQ ID NO: 71; the light chain variable region comprises an amino acid sequence that is at least 80 percent, at least 90 percent, or at least 95 percent identical to an amino acid sequence selected from the group consisting of SEQ ID NOs: 27, 28, 29, 30, 57, 83, 84 and 85, preferably SEQ ID NO: 30, more preferably SEQ ID NO: 85; wherein the binding domain specifically binds to human CD137 protein.

In one embodiment, the VH and/or VL amino acid sequences may be 50 percent, 60 percent, 70 percent, 80 percent, 90 percent, 95 percent, 96 percent, 97 percent, 98 percent or 99 percent identical to the sequences set forth in Table 1. In one embodiment, the VH and/or VL amino acid sequences may be identical except an amino acid substitution in no more than 1, 2, 3, 4 or 5 amino acid positions.

In one embodiment, the CD137-BD of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the CD137-BDs described herein or conservative modifications thereof, and wherein the CD137-BD retains the desired functional properties of the CD137-BD of the invention.

The term "conservatively modified variant" or "conservative variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" or "conservative variants" include individual substitutions, deletions or additions to a polypeptide sequence which result in the substitution of an amino acid with a chemically similar amino acid.

Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In one embodiment, the term "conservative sequence modifications" are used to refer to amino acid modifications that do not significantly affect or alter the binding characteristics of the antibody containing the amino acid sequence.

Accordingly, the invention provides a CD137-BD consisting of a heavy chain variable region comprising CDR1, CDR2, and CDR3 sequences and a light chain variable region comprising CDR1, CDR2, and CDR3 sequences, wherein: the heavy chain variable region CDR1 comprises, preferably consists of, an amino acid sequence selected from any of SEQ ID NOs: 1, 4, 5, 8, 11, 35, 38, 41, 44, 59, 62, 65, and 68, preferably SEQ ID NO: 1, more preferably SEQ ID NO: 59, or conservative variants thereof; the heavy chain variable region CDR2 comprises, preferably consists of, an amino acid sequence selected from any of SEQ ID NOs: 2, 6, 9, 12, 36, 39, 42, 45, 60, 63, 66 and 69, preferably SEQ ID NO: 2, more preferably SEQ ID NO: 60, or conservative variants thereof; the heavy chain variable region CDR3 comprises, preferably consists of, an amino acid sequence selected from any of SEQ ID NOs: 3, 7, 10, 13, 37, 40, 43, 46, 61, 64, 67 and 70, preferably SEQ ID NO: 3, more preferably SEQ ID NO: 61, or conservative variants thereof; the light chain variable region CDR1 comprises, preferably consists of, an amino acid sequence selected from any of SEQ ID NOs: 18, 21, 24, 48, 51, 54, 74, 77 and 80, preferably SEQ ID NO: 18, more preferably SEQ ID NO: 74, or conservative variants thereof; the light chain variable region CDR2 comprises, preferably consists of, an amino acid sequence selected from any of SEQ ID NOs: 19, 22, 25, 49, 52, 55, 75, 78 and 81, preferably SEQ ID NO: 19, more preferably SEQ ID NO: 75, or conservative variants thereof; and the light chain variable region CDR3 comprises, preferably consists of, an amino acid sequence selected from any of SEQ ID NOs: 20, 23, 26, 50, 53, 56, 76, 79 and 82, preferably SEQ ID NO: 20, more preferably SEQ ID NO: 76, or conservative variants thereof; wherein said CD137-BD is capable of activating CD137 signaling with or without additional cross-linking.

In one embodiment, the CD137-BD or the multispecific antibody comprising said CD137-BD of the invention optimized for expression in a mammalian cell has a heavy chain variable region and a light chain variable region, wherein one or more of these sequences have specified amino acid sequences based on the CD137-BDs described herein or conservative modifications thereof, and wherein the CD137-BD or the multispecific antibody comprising said CD137-BD retains the desired functional properties of the CD137-BD of the invention. Accordingly, the invention provides the CD137-BD or the multispecific antibody comprising said CD137-BD of the invention optimized for expression in a mammalian cell comprising a heavy chain variable region and a light chain variable region wherein: the heavy chain variable region comprises an amino acid sequence selected from any of SEQ ID NOs: 14, 15, 16, 17, 47, 71, 72 and 73, preferably SEQ ID NO: 17, more preferably SEQ ID NO: 71, and conservative modifications thereof; and the light chain variable region comprises an amino acid sequence selected from any of SEQ ID NOs: 27, 28, 29, 30, 57, 83, 84 and 85, preferably SEQ ID NO: 30, more preferably SEQ ID NO: 83, and conservative modifications thereof; wherein said CD137-BD is capable of activating CD137 signaling with or without additional cross-linking.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation (s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

An "affinity-matured" antibody or binding domain is one with one or more alterations in one or more variable domains thereof that result in an improvement in the affinity of the antibody or binding domain for antigen, compared to a parent antibody or binding domain that does not possess those alteration(s). In one embodiment, an affinity-matured antibody or binding domain has nanomolar or even picomolar affinities for the target antigen. Affinity-matured antibodies or domains are produced by procedures known in the art. For example, Marks et al, Bio/Technology 10:779-783 (1992) describes affinity maturation by VH- and VL-domain shuffling. Random mutagenesis of hypervariable region (HVR) and/or framework residues is described by, for example: Barbas et al. Proc Nat. Acad. Sci. USA 91:3809-3813 (1994); Schier et al. Gene 169:147-155 (1995); Jackson et al, J. Immunol. 154(7):3310-9 (1995); and Hawkins et al, J. Mol. Biol. 226:889-896 (1992).

In one embodiment, an "affinity-matured" CD137-BD of the invention comprises: a VH4 comprising I44V; F89V; Y105F mutations, in particular comprising an amino acid sequence according to SEQ ID NO: 15; and a VL comprising A51P mutation, in particular comprising an amino acid sequence according to SEQ ID NO: 28.

In another embodiment, an "affinity-matured" CD137-BD of the invention comprises: a VH4 comprising V25A; I44V; V82K; F89V; Y105F mutations, in particular comprising an amino acid sequence according to SEQ ID NO: 16; and a VL comprising I2L; A51P mutations, in particular comprising an amino acid sequence according to SEQ ID NO: 29.

A CD137-BD of the invention can be prepared using an antibody or a binding domain thereof having one or more of the VH and/or VL sequences shown herein as starting material to engineer a modified binding domain, which may have altered properties from the starting binding domain. A binding domain can be engineered by modifying one or more residues within one or both variable regions (i.e., VH and/or VL), for example within one or more CDR regions and/or within one or more framework regions.

One type of variable region engineering that can be performed is CDR grafting. Antibodies or binding domains thereof interact with target antigens predominantly through amino acid residues that are located in the six heavy and light chain complementarity determining regions (CDRs). For this reason, the amino acid sequences within CDRs are more diverse between individual antibodies or binding domains thereof than sequences outside of CDRs. Because CDR sequences are responsible for most antibody-antigen interactions, it is possible to express recombinant antibodies or binding domains that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86: 10029-10033; U.S. Pat. No. 5,225,539 to Winter, and U.S. Pat. Nos. 5,530,101; 5,585,089; 5,693,762 and 6,180,370 to Queen et al.).

Such framework sequences can be obtained from public DNA databases or published references that include germine antibody gene sequences or rearranged antibody sequences. For example, germine DNA sequences for human heavy and light chain variable region genes can be found in the "VBase" human germline sequence database (available on the Internet at mrc-cpe.cam.ac.uk), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference. For example, germline DNA sequences for human heavy and light chain variable region genes and rearranged antibody sequences can be found in "IMGT" database (available on the Internet at imgt.org; see Lefranc, M. P. et al., 1999 Nucleic Acids Res. 27:209-212; the contents of each of which are expressly incorporated herein by reference).

An example of framework sequences for use in the CD137-BD of the invention are those that are structurally similar to the framework sequences used by selected CD137-BDs the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody or binding domain thereof (see e.g., U.S. Pat. Nos. 5,530,101; 5,585,089; 5,693,762 and 6,180,370 to Queen et al).

Suitably, the CD137-BD of the invention is selected from the group consisting of: a Fab, an Fv, an scFv, dsFv, a scAb, STAB, a single domain antibody (sdAb or dAb), a single domain heavy chain antibody, and a single domain light chain antibody, a VHH, a VNAR, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology (F-star's Modular Antibody Technology™)).

Suitably, the CD137-BD of the invention is scFv antibody fragment. "Single-chain Fv" or "scFv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding. "Single-chain Fv" or "scFv" antibody fragments comprise the VH and VL domains of antibody, wherein these domains are present in a single polypeptide chain. Generally, the scFv polypeptides further comprises a polypeptide linker between the VH and VL domains which enables the scFv to form the desired structure for antigen binding (see, for example, Plückthun, The pharmacology of Monoclonal Antibodies, vol. 113, Rosenburg and Moore eds., (Springer-Verlag, New York, 1994), pp. 269-315).

In particular embodiments, said CD137-BD is an scFv comprising the linker according to SEQ ID NO: 206.

In a further embodiment, the CD137-BD of the invention is a single-chain variable fragment (scFv) as shown in SEQ ID NO: 31, SEQ ID NO: 32, SEQ ID NO: 33, SEQ ID NO: 34 and SEQ ID NO: 58, preferably SEQ ID NO: 34. In one embodiment, the CD137-BD of the invention is a single-chain variable fragment (scFv) as shown in SEQ ID NO: 32. In another embodiment, the CD137-BD of the invention is a single-chain variable fragment (scFv) as shown in SEQ ID NO: 33. In a preferred embodiment, the CD137-BD of the invention is a single-chain variable fragment (scFv) as shown in SEQ ID NO: 34. In a further preferred embodiment, the CD137-BD of the invention is a single-chain variable fragment (scFv) as shown in SEQ ID NO: 86, 87 or 88, preferably SEQ ID NO: 86, more preferably SEQ ID NO: 88.

Other suitable CD137 binding domain for use in the multispecific antibody of the present invention comprises or is derived from an antibody selected from the group consisting of: (i) urelumab (BMS-663513; a fully humanized IgG4 mAb; Bristol-Myers Squibb; described in WO 2004/010947, U.S. Pat. Nos. 6,887,673 and 7,214,493, which are hereby incorporated into the present application by reference in their entirety); and (ii) utomilumab (PF-05082566; a fully human IgG2 mAb; Pfizer; described in WO 2012/032433 and U.S. Pat. No. 8,821,867, which is hereby incorporated into the present application by reference in its entirety).

The multispecific antibody of the present invention comprises at least one PDL1 binding domain (PDL1-BD).

The term "PDL1" refers in particular to human PDL1 with UniProt ID number Q9NZQ7, reproduced herein as SEQ ID NO: 198. Suitably, the PDL1-BD of the present invention targets PDL1, in particular human PDL1 as shown in UniProt ID number Q9NZQ7, reproduced herein as SEQ ID NO: 198. Suitably, the antibodies of the present invention or antigen-binding fragments thereof comprising a PDL1-BD target human and cynomoglous (*Macaca fascicularis*) PDL1, and preferably does not cross-react with *Mus musculus* PDL1. The PDL1-BD of the present invention specifically binds to human PDL1 protein.

The PDL1-BD of the present invention is a PDL1 inhibitor. The term "blocker" or "blocking antibody" or "inhibitor" or "inhibiting antibody" or "antagonist" or "antagonist antibody" or "blocking binding domains" or "inhibiting binding domain" refers to an antibody or binding domain thereof that inhibits or reduces a biological activity of the antigen it binds to. In some embodiments, blocking antibodies or blocking binding domains or antagonist antibodies or antagonist binding domains substantially or completely inhibit the biological activity of the antigen. The PDL1-BD of the present invention targets, decreases, inhibits the binding ability of PDL1 to its binding partners, thereby interfering with the PDL1 function. In particular, the PDL1-BD of the present invention blocks the interaction of PDL1 with its receptor, specifically with PD-1. In some embodiments, the PDL1-BD of the present invention blocks the interaction of PDL1 with its receptor or receptors, specifically with PD-1 and/or B7-1.

In some embodiments, the PDL1-BD is derived from a monoclonal antibody or antibody fragment.

Suitable PDL1-BDs for use in the multispecific antibody of the present invention are novel binding domains provided in the present disclosure. The novel PDL1 binding domains of the present invention include, but are not limited to, the humanized monoclonal antibodies isolated as described herein, including in the Examples. Examples of such PDL1-BDs are antibodies or binding domains thereof whose sequences are listed in Table 2.

Suitably, the PDL1-BD of the present invention specifically binds to PDL1 and is characterized by one or more of the following parameters:

(i) binds to human PDL1 with a dissociation constant (KD) of less than 10 nM, particularly less than 5 nM, particularly less than 1 nM, particularly less than 500 pM, more particularly less than 100 pM, preferably less than 50 pM, more preferably less than 10 pM, more preferably 5 pM, in particular as measured by surface plasmon resonance (SPR), particularly wherein said antibody is an scFv (monovalent affinity);

(ii) binds to human PDL1 with a $K_{off}$ rate of $10^{-3}$ $s^{-1}$ or less, or $10^{-4}$ $s^{-1}$ or less, or $10^{-5}$ $s^{-1}$ or less as measured by SPR, particularly wherein said antibody is an scFv;

(iii) binds to human PDL1 with a $K_{on}$ rate of at least $10^3$ $M^{-1}s^{-1}$ or greater, at least $10^4$ $M^{-1}s^{-1}$ or greater, at least $10^5$ $M^{-1}s^{-1}$ or greater, at least $10^6$ $M^{-1}s^{-1}$ or greater as measured by SPR, particularly wherein said antibody is an scFv;

(iv) is cross-reactive with *Macaca fascicularis* (Cynomolgus) PDL1, in particular binds to Cynomolgus PDL1 with a KD of less than 10 nM, less than 5 nM, particularly less than 1 nM, particularly less than 500 pM, more particularly less than 100 pM, preferably less than 10 pM as measured by surface plasmon resonance;

(v) is non-cross-reactive to *Mus musculus* PDL1, in particular as measured by SPR; and/or (vi) does not bind to human PDL2, in particular as measured by SPR.

In one embodiment, the PDL1-BD of the present invention has a high affinity to PDL1, e.g., human PDL1. In a suitable embodiment, the PDL1-BD of the invention binds to human PDL1 with a KD of between 1 to 50,000 pM, 1 to 40,000 pM, 1 to 30,000 pM, 1 to 20,000 pM, 1 to 10,000 pM, 1 to 5,000 pM, 1 to 2,500 pM, 1 to 1,000 pM, 1 to 750 pM, 1 to 500 pM, 1 to 250 pM, 1 to 100 pM, in particular as measured by surface plasmon resonance (SPR). In a suitable embodiment, the PDL1-BD of the invention binds to human PDL1 with a KD of less than approximately 50 nM, less than approximately 45 nM, less than approximately 40 nM, less than approximately 35 nM, less than approximately 30 nM, less than approximately 25 nM, less than 20 nM, less than approximately 15 nM, less than approximately 10 nM, less than approximately 9 nM, less than approximately 8 nM, less than approximately 7 nM, less than approximately 6 nM, less than approximately 5 nM, less than approximately 4 nM, less than approximately 3 nM, less than 2 nM, less than 1 nM, less than 0.5 nM, less than 0.25 nM, less than 100 pM, less than 10 pM, or less than 5 pM, in particular as measured by SPR. Suitably, the PDL1-BD of the invention binds to human PDL1 with a KD of less than 1 nM. Suitably, the PDL1-BD of the invention binds to human PDL1 with a KD of less than 0.5 nM, in particular as measured by SPR. Suitably, the PDL1-BD of the invention binds to human PDL1 with a KD of less than 100 pM, in particular as measured by SPR. Preferably, the PDL1-BD of the invention binds to human PDL1 with a KD of less than 10 pM, in particular as measured by SPR. More preferably, the PDL1-BD of the invention binds to human PDL1 with a KD of less than 5 pM, in particular as measured by SPR.

Suitably, the PDL1-BD of the invention binds to human PDL1 with a $K_{on}$ rate of at least $10^3$ $M^{-1}s^{-1}$ or greater, at least $10^4$ $M^{-1}s^{-1}$ or greater, at least $5\times10^4$ $M^{-1}s^{-1}$ or greater, at least $10^5$ $M^{-1}s^{-1}$ or greater, at least $5\times10^5$ $M^{-1}s^{-1}$ or greater, at least $10^6$ $M^{-1}s^{-1}$ or greater, at least $5\times10^6$ $M^{-1}s^{-1}$ or greater, at least $10^7$ $M^{-1}s^{-1}$ or greater, at least $5\times10^7$ $M^{-1}s^{-1}$ or greater as measured by surface plasmon resonance (SPR). Preferably, the PDL1-BD of the invention binds to human PDL1 with a $K_{on}$ rate of at least $10^5$ $M^{-1}s^{-1}$ or greater, in particular at least $10^6$ $M^{-1}s^{-1}$ or greater, as measured by SPR, particularly wherein said antibody is an scFv (monovalent affinity).

Suitably, the PDL1-BD of the invention binds to human PDL1 with a $K_{off}$ rate of $10^{-3}$ $s^{-1}$ or less, $3\times10^{-3}$ $s^{-1}$ or less, $5\times10^{-3}$ $s^{-1}$ or less, $10^{-4}$ $s^{-1}$ or less, $5\times10^{-4}$ $s^{-1}$ or less, $10^{-5}$ $s^{-1}$ or less, $5\times10^{-5}$ $s^{-1}$ or less, $10^{-6}$ $s^{-1}$ or less, or $10^{-7}$ $s^{-1}$ or less as measured by surface plasmon resonance (SPR). Preferably, the PDL1-BD of the invention binds to human PDL1 with a $K_{off}$ rate of $10^{-3}$ $s^{-1}$ or less, $10^{-4}$ $s^{-1}$ or less, in particular $10^{-5}$ $s^{-1}$ or less as measured by SPR.

Suitably, the PDL1-BD of the present invention specifically binds to PDL1 and is characterized by one or more of the following parameters:

(i) when in scFv format, has a melting temperature (Tm), determined by differential scanning fluorimetry, of at least 55° C., e.g. at least 60° C., preferably at least 65° C., more preferably at least 70° C., in particular wherein said antibody or antigen-binding fragment thereof is formulated in phosphate-citrate buffer at pH 6.4, 150 mM NaCl, in particular wherein said antibody or antigen-binding fragment thereof is formulated in 50 mM phosphate citrate buffer with 150 mM NaCl at pH 6.4;

(ii) when in scFv format, has a loss in monomer content, after five consecutive freeze-thaw cycles, of less than 5%, preferably less than 3%, more preferably less than 1%, when the antibody of the invention is at a starting concentration of 10 mg/ml, in particular wherein said antibody or antigen-binding fragment thereof is formulated in 50 mM phosphate citrate buffer with 150 mM NaCl at pH 6.4; and/or (iii) when in scFv format, has a loss in monomer content, after storage for at least two weeks, particularly for at least four weeks, at 4° C., of less than 15%, e.g. less than 12%, less than 10%, less than 7%, less than 5%, less than 4%, less than 3%, less than 2%, preferably less than 1%, when the antibody of the invention is at a starting concentration of 10 mg/ml, and in particular wherein the antibody of the invention, e.g., said antibody or antigen-binding fragment thereof, is formulated in 50 mM phosphate citrate buffer with 150 mM NaCl at pH 6.4.

Suitably, the PDL1-BD of the invention comprises a VH CDR having an amino acid sequence of any one of the VH CDRs listed in Table 2. In particular, the PDL1-BD of the invention comprises one, two, three, or more VH CDRs having an amino acid sequence of any of the VH CDRs listed in Table 2.

Suitably, the PDL1-BD of the invention comprises a VL CDR having an amino acid sequence of any one of the VL CDRs listed in Table 2. In particular, the PDL1-BD of the invention comprises one, two, three or more VL CDRs having an amino acid sequence of any of the VL CDRs listed in Table 2.

Other PDL1-BDs of the invention include amino acids that have been mutated, yet have at least 60, 70, 80, 90, 91, 92, 93, 94, 95, 96, 97, 98 or 99 percent identity in the CDR regions with the CDR regions depicted in the sequences described in Table 2. Other PDL1-BDs of the invention include mutant amino acid sequences wherein no more than 1, 2, 3, 4 or 5 amino acids have been mutated in the CDR regions when compared with the CDR regions depicted in the sequence described in Table 2.

The present invention provides a PDL1-BD, which comprises (a) a heavy chain variable region CDR1 comprising, preferably consisting of, an amino acid sequence selected from any one of SEQ ID NOs: 89, 92, 93, 96, 99, 119, 122, 123, 126 and 129, preferably SEQ ID NO: 89 or 119, more preferably SEQ ID NO: 89; (b) a heavy chain variable region CDR2 comprising, preferably consisting of, an amino acid sequence selected from any of SEQ ID NOs: 90, 94, 97, 100, 120, 124, 127 and 130, preferably SEQ ID NO: 90 or 120, more preferably SEQ ID NO: 90; (c) a heavy chain variable region CDR3 comprising, preferably consisting of, an amino acid sequence selected from any of SEQ ID NOs: 91, 95, 98, 101, 121, 125, 128 and 131, preferably SEQ ID NO: 91 or 121, more preferably SEQ ID NO: 91; (d) a light chain variable region CDR1 comprising, preferably consisting of, an amino acid sequence selected from any of SEQ ID NOs: 105, 108, 111, 135, 138 and 141, preferably SEQ ID NO: 105 or 135, more preferably SEQ ID NO: 105; (e) a light chain variable region CDR2 comprising, preferably consisting of, an amino acid sequence selected from any of SEQ ID NOs: 106, 109, 112, 136, 139 and 142, preferably SEQ ID NO: 106 or 136, more preferably SEQ ID NO: 106; and (f) a light chain variable region CDR3 comprising, preferably consisting of, an amino acid sequence selected from any of SEQ ID NOs: 107, 110, 113, 137, 140 and 143, preferably SEQ ID NO: 107 or 137, more preferably SEQ ID NO: 107.

Suitably, the isolated antibody of the invention or antigen-binding fragment thereof comprises: (a) a heavy chain variable region CDR1 comprising, preferably consisting of, an amino acid sequence having at least 60, 70, 80, 90, 91, 92, 93, 94, 95, 96, 97, 98 or 99 percent identity to any one of SEQ ID NOs: 89, 92, 93, 96, 99, 119, 122, 123, 126 and 129, preferably SEQ ID NO: 89 or 119, more preferably SEQ ID NO: 89; (b) a heavy chain variable region CDR2 comprising, preferably consisting of, an amino acid sequence having at least 60, 70, 80, 90, 91, 92, 93, 94, 95, 96, 97, 98 or 99 percent identity to any of SEQ ID NOs: 90, 94, 97, 100, 120, 124, 127 and 130, preferably SEQ ID NO: 90 or 120, more preferably SEQ ID NO: 90; (c) a heavy chain variable region CDR3 comprising, preferably consisting of, an amino acid sequence having at least 60, 70, 80, 90, 91, 92, 93, 94, 95, 96, 97, 98 or 99 percent identity to any of SEQ ID NOs: 91, 95, 98, 101, 121, 125, 128 and 131, preferably SEQ ID NO: 91 or 121, more preferably SEQ ID NO: 91; (d) a light chain variable region CDR1 comprising, preferably consisting of, an amino acid sequence having at least 60, 70, 80, 90, 91, 92, 93, 94, 95, 96, 97, 98 or 99 percent identity to any of SEQ ID NOs: 105, 108, 111, 135, 138 and 141, preferably SEQ ID NO: 105 or 135, more preferably SEQ ID NO: 105; (e) a light chain variable region CDR2 comprising, preferably consisting of, an amino acid sequence having at least 60, 70, 80, 90, 91, 92, 93, 94, 95, 96, 97, 98 or 99 percent identity to any of SEQ ID NOs: 106, 109, 112, 136, 139 and 142, preferably SEQ ID NO: 106 or 136, more preferably SEQ ID NO: 106; and (f) a light chain variable region CDR3 comprising, preferably consisting of, an amino acid sequence having at least 60, 70, 80, 90, 91, 92, 93, 94, 95, 96, 97, 98 or 99 percent identity to any of SEQ ID NOs: 107, 110, 113, 137, 140 and 143, preferably SEQ ID NO: 107 or 137, more preferably SEQ ID NO: 107.

In one embodiment, the PDL1-BD of the invention comprises: (a) HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively; (b) HCDR1, HCDR2, and HCDR3 sequences of SEQ ID NOs: 92, 94, and 95, respectively, and LCDR1, LCDR2, and LCDR3 sequences of SEQ ID NOs: 108, 109, and 110, respectively; (c) HCDR1, HCDR2, and HCDR3 sequences of SEQ ID NOs: 93, 94, and 95, respectively, and LCDR1, LCDR2, and LCDR3 sequences of SEQ ID NOs: 108, 109, and 110, respectively; (d) HCDR1, HCDR2, and HCDR3 sequences of SEQ ID NOs: 96, 97, and 98, respectively, and LCDR1, LCDR2, and LCDR3 sequences of SEQ ID NOs: 105, 106, and 107, respectively; (e) HCDR1, HCDR2, and HCDR3 sequences of SEQ ID NOs: 99, 100, and 101, respectively, and LCDR1, LCDR2, and LCDR3 sequences of SEQ ID NOs: 111, 112, and 113, respectively; (f) HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively; (g) HCDR1, HCDR2, and HCDR3 sequences of SEQ ID NOs: 122, 124, and 125, respectively, and LCDR1, LCDR2, and LCDR3 sequences of SEQ ID NOs: 138, 139, and 140, respectively; (h) HCDR1, HCDR2, and HCDR3 sequences of SEQ ID NOs: 123, 124, and 125, respectively, and LCDR1, LCDR2, and LCDR3 sequences of SEQ ID NOs: 138, 139, and 140, respectively; (i) HCDR1, HCDR2, and HCDR3 sequences of SEQ ID NOs: 126, 127, and 128, respectively, and LCDR1, LCDR2, and LCDR3 sequences of SEQ ID NOs: 135, 136, and 137, respectively; (j) HCDR1, HCDR2, and HCDR3 sequences of SEQ ID NOs: 129, 130, and 131, respectively, and LCDR1, LCDR2, and LCDR3 sequences of SEQ ID NOs: 141, 142, and 143, respectively. In one embodiment, the PDL1-BD of the invention comprises HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively. In another embodiment, the PDL1-BD of the invention comprises HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively.

Suitably, the PDL1-BD of the invention comprises: (a) HCDR1, HCDR2, and HCDR3 sequences having at least 60, 70, 80, 90, 91, 92, 93, 94, 95, 96, 97, 98 or 99 percent identity to SEQ ID NOs: 89, 90, and 91, respectively, and LCDR1, LCDR2, and LCDR3 sequences having at least 60, 70, 80, 90, 91, 92, 93, 94, 95, 96, 97, 98 or 99 percent identity to SEQ ID NOs: 105, 106, and 107, respectively; (b) HCDR1, HCDR2, and HCDR3 sequences having at least 60, 70, 80, 90, 91, 92, 93, 94, 95, 96, 97, 98 or 99 percent identity to SEQ ID NOs: 92, 94, and 95, respectively, and LCDR1, LCDR2, and LCDR3 sequences having at least 60, 70, 80, 90, 91, 92, 93, 94, 95, 96, 97, 98 or 99 percent identity to SEQ ID NOs: 108, 109, and 110, respectively; (c) HCDR1, HCDR2, and HCDR3 sequences having at least 60, 70, 80, 90, 91, 92, 93, 94, 95, 96, 97, 98 or 99 percent identity to SEQ ID NOs: 93, 94, and 95, respectively, and LCDR1, LCDR2, and LCDR3 sequences having at least 60, 70, 80, 90, 91, 92, 93, 94, 95, 96, 97, 98 or 99 percent identity to SEQ ID NOs: 108, 109, and 110, respectively; (d) HCDR1, HCDR2, and HCDR3 sequences having at least 60, 70, 80, 90, 91, 92, 93, 94, 95, 96, 97, 98 or 99 percent identity to SEQ ID NOs: 96, 97, and 98, respectively, and LCDR1, LCDR2, and LCDR3 sequences having at least 60, 70, 80, 90, 91, 92, 93, 94, 95, 96, 97, 98 or 99 percent identity to SEQ ID NOs: 105, 106, and 107, respectively; (e) HCDR1, HCDR2, and HCDR3 sequences having at least 60, 70, 80, 90, 91, 92, 93, 94, 95, 96, 97, 98 or 99 percent identity to SEQ ID NOs: 99, 100, and 101, respectively, and LCDR1, LCDR2, and LCDR3 sequences having at least 60, 70, 80, 90, 91, 92, 93, 94, 95, 96, 97, 98 or 99 percent identity to SEQ ID NOs: 111, 112, and 113, respectively; (f) HCDR1, HCDR2, and HCDR3 sequences having at least 60, 70, 80, 90, 91, 92, 93, 94, 95, 96, 97, 98 or 99 percent identity to SEQ ID NOs: 119, 120, and 121, respectively, and LCDR1, LCDR2, and LCDR3 sequences having at least 60, 70, 80, 90, 91, 92, 93, 94, 95, 96, 97, 98 or 99 percent identity to SEQ ID NOs: 135, 136, and 137, respectively; (g) HCDR1, HCDR2, and HCDR3 sequences having at least 60, 70, 80, 90, 91, 92, 93, 94, 95, 96, 97, 98 or 99 percent identity to SEQ ID NOs: 122, 124, and 125, respectively, and LCDR1, LCDR2, and LCDR3 sequences having at least 60, 70, 80, 90, 91, 92, 93, 94, 95, 96, 97, 98 or 99 percent identity to SEQ ID NOs: 138, 139, and 140, respectively; (h) HCDR1, HCDR2, and HCDR3 sequences having at least 60, 70, 80, 90, 91, 92, 93, 94, 95, 96, 97, 98 or 99 percent identity to SEQ ID NOs: 123, 124, and 125, respectively, and LCDR1, LCDR2, and LCDR3 sequences having at least 60, 70, 80, 90, 91, 92, 93, 94, 95, 96, 97, 98 or 99 percent identity to SEQ ID NOs: 138, 139, and 140, respectively; (i) HCDR1, HCDR2, and HCDR3 sequences having at least 60, 70, 80, 90, 91, 92, 93, 94, 95, 96, 97, 98 or 99 percent identity to SEQ ID NOs: 126, 127, and 128, respectively, and LCDR1, LCDR2, and LCDR3 sequences having at least 60, 70, 80, 90, 91, 92, 93, 94, 95, 96, 97, 98 or 99 percent identity to SEQ ID NOs: 135, 136, and 137, respectively; (j) HCDR1, HCDR2, and HCDR3 sequences having at least 60, 70, 80, 90, 91, 92, 93, 94, 95, 96, 97, 98 or 99 percent identity to SEQ ID NOs: 129, 130, and 131, respectively, and LCDR1, LCDR2, and LCDR3 sequences having at least 60, 70, 80, 90, 91, 92, 93, 94, 95, 96, 97, 98 or 99 percent identity to SEQ ID NOs: 141, 142, and 143, respectively. In one embodiment, the PDL1-BD of the invention comprises HCDR1, HCDR2, and HCDR3 sequences having at least 60, 70, 80, 90, 91, 92, 93, 94, 95, 96, 97, 98 or 99 percent identity to SEQ ID NOs: 89, 90, and 91, respectively, and LCDR1, LCDR2, and LCDR3 sequences having at least 60, 70, 80, 90, 91, 92, 93, 94, 95, 96, 97, 98 or 99 percent identity to SEQ ID NOs: 105, 106, and 107, respectively. In another embodiment, the PDL1-BD of the invention comprises HCDR1, HCDR2, and HCDR3 sequences having at least 60, 70, 80, 90, 91, 92, 93, 94, 95, 96, 97, 98 or 99 percent identity to SEQ ID NOs: 119, 120, and 121, respectively, and LCDR1, LCDR2, and LCDR3 sequences having at least 60, 70, 80, 90, 91, 92, 93, 94, 95, 96, 97, 98 or 99 percent identity to SEQ ID NOs: 135, 136, and 137, respectively.

Suitably, the PDL1-BD of the invention comprises: (a) a HCDR1 comprising, preferably consisting of, the amino acid sequence of SEQ ID NO: 89; (b) a HCDR2 comprising, preferably consisting of, the amino acid sequence of SEQ ID NO: 90; (c) a HCDR3 comprising, preferably consisting of, the amino acid sequence of SEQ ID NO: 91; (d) a LCDR1 comprising, preferably consisting of, the amino acid sequence of SEQ ID NOs: 105; (e) a LCDR2 comprising, preferably consisting of, the amino acid sequence of SEQ ID NOs: 106; and (f) a LCDR3 comprising, preferably consisting of, the amino acid sequence of SEQ ID NO: 107. Suitably, the PDL1-BD of the invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 89; (b) a HCDR2 comprising, preferably consisting of, the amino acid sequence having at least 60, 70, 80, 90, 91, 92, 93, 94, 95, 96, 97, 98 or 99 percent identity to SEQ ID NO: 90; (c) a HCDR3 comprising, preferably consisting of, the amino acid sequence having at least 60, 70, 80, 90, 91, 92, 93, 94, 95, 96, 97, 98 or 99 percent identity to SEQ ID NO: 91; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 105; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 106; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 107.

In a further embodiment, the PDL1-BD of the invention comprises: (a) a HCDR1 comprising, preferably consisting of, the amino acid sequence of SEQ ID NO: 92 or SEQ ID NO: 93; (b) a HCDR2 comprising, preferably consisting of, the amino acid sequence of SEQ ID NO: 94; (c) a HCDR3 comprising, preferably consisting of, the amino acid sequence of SEQ ID NO: 95; (d) a LCDR1 comprising, preferably consisting of, the amino acid sequence of SEQ ID NOs: 108; (e) a LCDR2 comprising, preferably consisting of, the amino acid sequence of SEQ ID NOs: 109; and (f) a LCDR3 comprising, preferably consisting of, the amino acid sequence of SEQ ID NO: 110. Suitably, the PDL1-BD of the invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 92 or SEQ ID NO: 93; (b) a HCDR2 comprising, preferably consisting of, the amino acid sequence having at least 60, 70, 80, 90, 91, 92, 93, 94, 95, 96, 97, 98 or 99 percent identity to SEQ ID NO: 94; (c) a HCDR3 comprising, preferably consisting of, the amino acid sequence having at least 60, 70, 80, 90, 91, 92, 93, 94, 95, 96, 97, 98 or 99 percent identity to SEQ ID NO: 95; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 108; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 109; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 110.

Suitably, the PDL1-BD of the invention comprises: (a) a HCDR1 comprising, preferably consisting of, the amino acid sequence of SEQ ID NO: 119; (b) a HCDR2 comprising, preferably consisting of, the amino acid sequence of SEQ ID NO: 120; (c) a HCDR3 comprising, preferably consisting of, the amino acid sequence of SEQ ID NO: 121; (d) a LCDR1 comprising, preferably consisting of, the amino acid sequence of SEQ ID NOs: 135; (e) a LCDR2 comprising, preferably consisting of, the amino acid sequence of SEQ ID NOs: 136; and (f) a LCDR3 comprising, preferably consisting of, the amino acid sequence of SEQ ID NO: 137. Suitably, the PDL1-BD of the invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 119; (b) a HCDR2 comprising, preferably consisting of, the amino acid sequence having at least 60, 70, 80, 90, 91, 92, 93, 94, 95, 96, 97, 98 or 99 percent identity to SEQ ID NO: 120; (c) a HCDR3 comprising, preferably consisting of, the amino acid sequence having at least 60, 70, 80, 90, 91, 92, 93, 94, 95, 96, 97, 98 or 99 percent identity to SEQ ID NO: 121; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 135; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 136; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 137.

In a further embodiment, the PDL1-BD of the invention comprises: (a) a HCDR1 comprising, preferably consisting of, the amino acid sequence of SEQ ID NO: 122 or SEQ ID NO: 123; (b) a HCDR2 comprising, preferably consisting of, the amino acid sequence of SEQ ID NO: 124; (c) a HCDR3 comprising, preferably consisting of, the amino acid sequence of SEQ ID NO: 125; (d) a LCDR1 comprising, preferably consisting of, the amino acid sequence of SEQ ID NOs: 138; (e) a LCDR2 comprising, preferably consisting of, the amino acid sequence of SEQ ID NOs: 139; and (f) a LCDR3 comprising, preferably consisting of, the amino acid sequence of SEQ ID NO: 140. Suitably, the PDL1-BD of the invention comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 122 or SEQ ID NO: 123; (b) a HCDR2 comprising, preferably consisting of, the amino acid sequence having at least 60, 70, 80, 90, 91, 92, 93, 94, 95, 96, 97, 98 or 99 percent identity to SEQ ID NO: 124; (c) a HCDR3 comprising, preferably consisting of, the amino acid sequence having at least 60, 70, 80, 90, 91, 92, 93, 94, 95, 96, 97, 98 or 99 percent identity to SEQ ID NO: 125; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 138; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 139; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 140.

In a further embodiment, the present invention provides a PDL1-BD that specifically binds PDL1 (e.g., human PDL1 protein), wherein said binding domain comprises a VH domain and a VL domain.

Suitably, the PDL1-BD of the present invention comprises a VH1A, VH1B, VH3 or VH4. In one embodiment, the PDL1-BD of the present invention comprises VH3 domain. In one embodiment, the PDL1-BD of the present invention comprises VH4 domain. In another embodiment, the PDL1-BD of the present invention comprises VH1A or VH1B domain.

A specific example of a VH belonging to VH1 family is represented under SEQ ID NO: 103. In particular, framework regions FR1 to FR4 taken from SEQ ID NO: 103 belong to VH1 family (Table 1, regions marked in non-bold). Suitably, a VH belonging to VH1 family, as used herein, is a VH comprising FR1 to FR4 having at least 85%, preferably at least 90%, more preferably at least 95% sequence identity to FR1 to FR4 of SEQ ID NO: 103.

A specific example of a VH belonging to VH3 family is represented under SEQ ID NO: 104. In particular, framework regions FR1 to FR4 taken from SEQ ID NO: 104 belong to VH3 family (Table 2, regions marked in non-bold). Suitably, a VH belonging to VH3 family, as used herein, is a VH comprising FR1 to FR4 having at least 85%, preferably at least 90%, more preferably at least 95% sequence identity to FR1 to FR4 of SEQ ID NO: 104.

A specific example of a VH belonging to VH4 family is represented under SEQ ID NO: 102. In particular, framework regions FR1 to FR4 taken from SEQ ID NO: 102 belong to VH4 family (Table 2, regions marked in non-bold). Suitably, a VH belonging to VH4 family, as used herein, is a VH comprising FR1 to FR4 having at least 85%, preferably at least 90%, more preferably at least 95% sequence identity to FR1 to FR4 of SEQ ID NO: 102.

Suitably, the PDL1-BD of the present invention comprises: Vκ frameworks FR1, FR2 and FR3, particularly Vκ1 or Vκ3 frameworks, preferably Vκ1 frameworks FR1 to 3, and a framework FR4, which is selected from a Vκ FR4, particularly Vκ1 FR4, Vκ3 FR4, and a Vλ FR4. Suitable Vκ1 frameworks FR1 to 3 are set forth in SEQ ID NO: 114 (Table 2, FR regions are marked in non-bold). Suitable Vλ1 frameworks FR1 to 3 comprise the amino acid sequences having at least 60, 70, 80, 90 percent identity to amino acid sequences corresponding to FR1 to 3 and taken from SEQ ID NO: 114 (Table 2, FR regions are marked in non-bold). Suitable Vλ FR4 are as set forth in SEQ ID NO: 199 to SEQ ID NO: 205. In one embodiment, the PDL1-BD of the present invention comprises Vλ FR4 comprising the amino acid sequence having at least 60, 70, 80, 90 percent identity to comprising an amino acid sequence selected from any of SEQ ID NO: 199 to SEQ ID NO: 205.

Thus, in one embodiment, the PDL1-BD of the present invention comprises:

(i) the HCDR1, HCDR2, HCDR3, LCDR1, LCDR2, and LCDR3 sequences of:

a. the HCDR1, HCDR2, and HCDR3 sequences of SEQ ID NOs: 92, 94, and 95, respectively, and the LCDR1, LCDR2, and LCDR3 sequences of SEQ ID NOs: 108, 109, and 110, respectively;

b. the HCDR1, HCDR2, and HCDR3 sequences of SEQ ID NOs: 122, 124, and 125, respectively, and the LCDR1, LCDR2, and LCDR3 sequences of SEQ ID NOs: 138, 139, and 140, respectively; or c. the HCDR1, HCDR2, and HCDR3 sequences of SEQ ID NOs: 123, 124, and 125, respectively, and the LCDR1, LCDR2, and LCDR3 sequences of SEQ ID NOs: 138, 139, and 140, respectively;

(ii) a VH3 or VH4 domain, preferably VH4 domain; and (iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, preferably Vλ FR4 comprising the amino acid sequence having at least 60, 70, 80, 90 percent identity to comprising an amino acid sequence selected from any of SEQ ID NO: 199 to SEQ ID NO: 205, preferably Vλ FR4 is as set forth in SEQ ID NO: 199 to SEQ ID NO: 205, more preferably Vλ FR4 is as set forth in SEQ ID NO: 199.

In another embodiment, the PDL1-BD of the present invention comprises:

(i) the HCDR1, HCDR2, and HCDR3 sequences of: SEQ ID NOs: 93, 94, and 95, respectively, and the LCDR1, LCDR2, and LCDR3 sequences of SEQ ID NOs: 108, 109, and 110, respectively;

(ii) a VH1A, VH1B, VH3 or VH4 domain, preferably VH1A or VH1B domain; and (iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, preferably Vλ FR4 comprising the amino acid sequence having at least 60, 70, 80, 90 percent identity to comprising an amino acid sequence selected from any of SEQ ID NO: 199 to SEQ ID NO: 205, preferably Vλ FR4 comprising an amino acid sequence selected from any of SEQ ID NO: 199 to SEQ ID NO: 205, more preferably Vλ FR4 is as set forth in SEQ ID NO: 199.

In a specific embodiment, the PDL1-BD of the present invention comprises:

(i) the HCDR1, HCDR2, and HCDR3 sequences of: SEQ ID NOs: 119, 120, and 121, respectively, and the LCDR1, LCDR2, and LCDR3 sequences of SEQ ID NOs: 135, 136, and 137, respectively;

(ii) a VH3 or VH4 domain, preferably VH4 domain; and (iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, preferably Vλ FR4 comprising the amino acid sequence having at least 60, 70, 80, 90 percent identity to comprising an amino acid sequence selected from any of SEQ ID NO: 199 to SEQ ID NO: 205, preferably Vλ FR4 comprising an amino acid sequence selected from any of SEQ ID NO: 199 to SEQ ID NO: 205, more preferably Vλ FR4 is as set forth in SEQ ID NO: 199.

In a preferred embodiment, the PDL1-BD of the present invention comprises:

(i) the HCDR1, HCDR2, and HCDR3 sequences of SEQ ID NOs: 89, 90, and 91, respectively, and the LCDR1, LCDR2, and LCDR3 sequences of SEQ ID NOs: 105, 106, and 107, respectively;

(ii) VH3 or VH4 domain framework sequences FR1 to FR4; preferably VH3 domain framework sequences FR1 to FR4; and (iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, preferably Vλ FR4 comprising the amino acid sequence having at least 60, 70, 80, 90 percent identity to comprising an amino acid sequence selected from any of SEQ ID NO: 199 to SEQ ID NO: 205, preferably Vλ FR4 is as set forth in SEQ ID NO: 199 to SEQ ID NO: 205, more preferably Vλ FR4 is as set forth in SEQ ID NO: 199.

In one embodiment, the PDL1-BD of the present invention comprises a VL comprising:

(i) CDR domains CDR1, CDR2 and CDR3;

(ii) human Vκ framework regions FR1 to FR3, particularly human Vκ1 framework regions FR1 to FR3;

(iii) FR4, which is selected from (a) a human Vλ germ line sequence for FR4, particularly a Vλ germ line sequence selected from the list of: SEQ ID NO: 199 to 205, preferably Vλ FR4 is as set forth in SEQ ID NO: 199; and (b) a Vλ-based sequence, which has one or two mutations, particularly one mutation, compared to the closest human Vλ germ line sequence for FR4 comprising an amino acid sequence selected from any of SEQ ID NO: 199 to SEQ ID NO: 205, preferably SEQ ID NO: 199.

The PDL1-BD of the invention comprises a VH domain listed in Table 2. Suitably, the PDL1-BD of the invention comprises a VH amino acid sequence listed in Table 2, wherein no more than about 10 amino acids in a framework sequence (for example, a sequence which is not a CDR) have been mutated (wherein a mutation is, as various non-limiting examples, an addition, substitution or deletion). Suitably, the PDL1-BD of the invention comprises a VH amino acid sequence listed in Table 2, wherein no more than about 20 amino acids in a framework sequence (for example, a sequence which is not a CDR) have been mutated (wherein a mutation is, as various non-limiting examples, an addition, substitution or deletion). Other PDL1-BDs of the invention include amino acids that have been mutated, yet have at least 60, 70, 80, 90, 91, 92, 93, 94, 95, 96, 97, 98 or 99 percent identity in the VH regions with the VH regions depicted in the sequences described in Table 2.

The PDL1-BD of the invention comprises a VL domain listed in Table 2. Suitably, the PDL1-BD of the invention comprises a VL amino acid sequence listed in Table 2, wherein no more than about 10 amino acids in a framework sequence (for example, a sequence which is not a CDR) have been mutated (wherein a mutation is, as various non-limiting examples, an addition, substitution or deletion). Suitably, the PDL1-BD of the invention comprises a VL amino acid sequence listed in Table 2, wherein no more than about 20 amino acids in a framework sequence (for example, a sequence which is not a CDR) have been mutated (wherein a mutation is, as various non-limiting examples, an addition, substitution or deletion). Other PDL1-BDs of the invention include amino acids that have been mutated, yet have at least 60, 70, 80, 90, 91, 92, 93, 94, 95, 96, 97, 98 or 99 percent identity in the VL regions with the VL regions depicted in the sequences described in Table 2.

Suitably, the PDL1-BD of the invention comprises a heavy chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 102, 103, 104, 132, 133 and 134, preferably SEQ ID NO: 102 or 104, more preferably SEQ ID NO: 104; and a light chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs:114, 115, 144 and 145, preferably SEQ ID NO: 114 or 115, more preferably SEQ ID NO: 115.

In one embodiment, the PDL1-BD of the invention comprises: a heavy chain variable region comprising an amino acid sequence selected from any of SEQ ID NOs: 102, 103, 104, 132, 133 and 134, preferably SEQ ID NO: 102 or 104, more preferably SEQ ID NO: 104; and a light chain variable region comprising an amino acid sequence selected from any of SEQ ID NOs:114, 115, 144 and 145, preferably SEQ ID NO: 114 or 115, more preferably SEQ ID NO: 115.

In a further embodiment, the PDL1-BD of the invention comprises: (a) a VH sequence of SEQ ID NO: 102 and a VL sequence of SEQ ID NO: 114; (b) a VH sequence of SEQ ID NO: 103 and a VL sequence of SEQ ID NO: 114; (c) a VH sequence of SEQ ID NO: 104 and a VL sequence of SEQ ID NO: 115; (d) a VH sequence of SEQ ID NO: 132 and a VL sequence of SEQ ID NO: 144; (e) a VH sequence of SEQ ID NO: 133 and a VL sequence of SEQ ID NO: 145; or (f) a VH sequence of SEQ ID NO: 134 and a VL sequence of SEQ ID NO: 144. In a preferred embodiment, the PDL1-BD of the invention comprises a VH sequence of SEQ ID NO: 102 and a VL sequence of SEQ ID NO: 114. In a more preferred embodiment, the PDL1-BD of the invention comprises a VH sequence of SEQ ID NO: 104 and a VL sequence of SEQ ID NO: 115.

In one embodiment, the PDL1-BD of the present invention comprises:

(a) HCDR1, HCDR2, and HCDR3 sequences of SEQ ID NOs: 92, 94, and 95, respectively, and the LCDR1, LCDR2, and LCDR3 sequences of SEQ ID NOs: 108, 109, and 110, respectively, a VH sequence at least 60, 70, 80, 90, 91, 92, 93, 94, 95, 96, 97, 98 or 99 percent identical to SEQ ID NO: 102, and a VL sequence at least 60, 70, 80, 90, 91, 92, 93, 94, 95, 96, 97, 98 or 99 percent identical to SEQ ID NO: 114;

(b) the HCDR1, HCDR2, and HCDR3 sequences of: SEQ ID NOs: 93, 94, and 95, respectively, and the LCDR1, LCDR2, and LCDR3 sequences of SEQ ID NOs: 108, 109, and 110, respectively, a VH sequence at least 60, 70, 80, 90, 91, 92, 93, 94, 95, 96, 97, 98 or 99 percent identical to SEQ ID NO: 103, and a VL sequence at least 60, 70, 80, 90, 91, 92, 93, 94, 95, 96, 97, 98 or 99 percent identical to SEQ ID NO: 114;

(c) the HCDR1, HCDR2, and HCDR3 sequences of: SEQ ID NOs: 92, 93 and 94, respectively, and the LCDR1, LCDR2, and LCDR3 sequences of SEQ ID NOs: 108. 109 and 110, respectively, a VH sequence at least 60, 70, 80, 90, 91, 92, 93, 94, 95, 96, 97, 98 or 99 percent identical to SEQ ID NO: 104, and a VL sequence at least 60, 70, 80, 90, 91, 92, 93, 94, 95, 96, 97, 98 or 99 percent identical to SEQ ID NO: 115, preferably wherein said VH comprises G56A and Y105F mutations (AHo numbering) and said VL comprises S9A and A51P mutations (AHo numbering);

(d) HCDR1, HCDR2, and HCDR3 sequences of SEQ ID NOs: 122, 124, and 125, respectively, and the LCDR1, LCDR2, and LCDR3 sequences of SEQ ID NOs: 138, 139, and 140, respectively, a VH sequence at least 60, 70, 80, 90, 91, 92, 93, 94, 95, 96, 97, 98 or 99 percent identical to SEQ ID NO: 132, and a VL sequence at least 60, 70, 80, 90, 91, 92, 93, 94, 95, 96, 97, 98 or 99 percent identical to SEQ ID NO: 144;

(e) HCDR1, HCDR2, and HCDR3 sequences of SEQ ID NOs: 123, 124, and 125, respectively, and the LCDR1, LCDR2, and LCDR3 sequences of SEQ ID NOs: 138, 139, and 140, respectively, a VH sequence at least 60, 70, 80, 90, 91, 92, 93, 94, 95, 96, 97, 98 or 99 percent identical to SEQ ID NO: 133, and a VL sequence at least 60, 70, 80, 90, 91, 92, 93, 94, 95, 96, 97, 98 or 99 percent identical to SEQ ID NO: 145, preferably wherein said VH comprises V2S, V25A, I44V, G56A, V82K, F89V and Y105F mutations (AHo numbering) and said VL comprises 12F, M4L and A51P mutations (AHo numbering); or (f) HCDR1, HCDR2, and HCDR3 sequences of SEQ ID NOs: 122, 124 and 125, respectively, and the LCDR1, LCDR2, and LCDR3 sequences of SEQ ID NOs: 138, 139 and 140, respectively, a VH sequence at least 60, 70, 80, 90, 91, 92, 93, 94, 95, 96, 97, 98 or 99 percent identical to SEQ ID NO: 134, and a VL sequence at least 60, 70, 80, 90, 91, 92, 93, 94, 95, 96, 97, 98 or 99 percent identical to SEQ ID NO: 144, preferably wherein said VH comprises V25A, I44V, G56A, V82K and F89V mutation (AHo numbering).

In one embodiment, the PDL1-BD of the present invention comprises:

(a) HCDR1, HCDR2, and HCDR3 sequences of SEQ ID NOs: 89, 90, and 91, respectively, and the LCDR1, LCDR2, and LCDR3 sequences of SEQ ID NOs 105, 106, and 107, respectively, a VH sequence at least 60, 70, 80, 90, 91, 92, 93, 94, 95, 96, 97, 98 or 99 percent identical to SEQ ID NO: 102, and a VL sequence at least 60, 70, 80, 90, 91, 92, 93, 94, 95, 96, 97, 98 or 99 percent identical to SEQ ID NO: 114;

(b) the HCDR1, HCDR2, and HCDR3 sequences of: SEQ ID NOs: 89, 90, and 91, respectively, and the LCDR1, LCDR2, and LCDR3 sequences of SEQ ID NOs:105, 106, and 107, respectively, a VH sequence at least 60, 70, 80, 90, 91, 92, 93, 94, 95, 96, 97, 98 or 99 percent identical to SEQ ID NO: 103, and a VL sequence at least 60, 70, 80, 90, 91, 92, 93, 94, 95, 96, 97, 98 or 99 percent identical to SEQ ID NO: 114;

(c) the HCDR1, HCDR2, and HCDR3 sequences of: SEQ ID NOs: 89, 90, and 91, respectively, and the LCDR1, LCDR2, and LCDR3 sequences of SEQ ID NOs:105, 106, and 107, respectively, a VH sequence at least 60, 70, 80, 90, 91, 92, 93, 94, 95, 96, 97, 98 or 99 percent identical to SEQ ID NO: 104, and a VL sequence at least 60, 70, 80, 90, 91, 92, 93, 94, 95, 96, 97, 98 or 99 percent identical to SEQ ID NO: 115, preferably wherein said VH comprises G56A and Y105F mutations (AHo numbering) and said VL comprises S9A and A51P mutations (AHo numbering);

(d) HCDR1, HCDR2, and HCDR3 sequences of SEQ ID NOs: 119, 120, and 121, respectively, and the LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to SEQ ID NO: 132, and a VL sequence at least 60, 70, 80, 90, 91, 92, 93, 94, 95, 96, 97, 98 or 99 percent identical to SEQ ID NO: 144;

(e) HCDR1, HCDR2, and HCDR3 sequences of SEQ ID NOs:119, 120, and 121, respectively, and the LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to SEQ ID NO: 133, and a VL sequence at least 60, 70, 80, 90, 91, 92, 93, 94, 95, 96, 97, 98 or 99 percent identical to SEQ ID NO: 145, preferably wherein said VH comprises V2S, V25A, I44V, G56A, V82K, F89V and Y105F mutations (AHo numbering) and said VL comprises 12F, M4L and A51P mutations (AHo numbering); or (f) HCDR1, HCDR2, and HCDR3 sequences of SEQ ID NOs:119, 120, and 121, respectively, and the LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to SEQ ID NO: 134, and a VL sequence at least 60, 70, 80, 90, 91, 92, 93, 94, 95, 96, 97, 98 or 99 percent identical to SEQ ID NO: 144, preferably wherein said VH comprises V25A, I44V, G56A, V82K and F89V mutation (AHo numbering).

In a preferred embodiment, the PDL1-BD of the present invention comprises the HCDR1, HCDR2, and HCDR3 sequences of SEQ ID NOs: 89, 90, and 91, respectively, and the LCDR1, LCDR2, and LCDR3 sequences of SEQ ID NOs:105, 106, and 107, respectively, a VH sequence at least 60, 70, 80, 90, 91, 92, 93, 94, 95, 96, 97, 98 or 99 percent identical to SEQ ID NO: 104, and a VL sequence at least 60, 70, 80, 90, 91, 92, 93, 94, 95, 96, 97, 98 or 99 percent identical to SEQ ID NO: 115, preferably wherein said VH comprises G56A and Y105F mutations (AHo numbering) and said VL comprises S9A and A51P mutations (AHo numbering).

In one embodiment, a PDL1-BD that specifically binds to PDL1 is a binding domain that is described in Table 2. In one embodiment, the PDL1-BD of the invention that specifically binds to PDL1 is as set forth in SEQ ID NO: 116, SEQ ID NO: 117, SEQ ID NO: 118, SEQ ID NO: 146, SEQ ID NO: 147, or SEQ ID NO: 148. In one embodiment, the PDL1-BD of the invention that specifically binds to PDL1 is as set forth in SEQ ID NO: 116 or SEQ ID NO: 117, or SEQ ID NO: 118, preferably SEQ ID NO: 116, more preferably SEQ ID NO: 118. In one embodiment, the PDL1-BD of the invention that specifically binds to PDL1 is as set forth in SEQ ID NO: 146 or SEQ ID NO: 147 or SEQ ID NO: 148, preferably SEQ ID NO: 146, more preferably SEQ ID NO: 148.

Other PDL1-BDs of the invention include those wherein the amino acids or nucleic acids encoding the amino acids have been mutated, yet have at least 60, 70, 80, 90 or 95 percent identity to the sequences described in Table 2. In one embodiment, it includes mutant amino acid sequences wherein no more than 1, 2, 3, 4 or 5 amino acids have been mutated in the variable regions when compared with the variable regions depicted in the sequence described in Table 2, while retaining substantially the same activity. The term "substantially the same activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent PDL1-BD, in particular the PDL1-BD of the invention described in Table 2.

Given that each of these binding domains can bind to PDL1 and that antigen-binding specificity is provided primarily by the CDR1, 2 and 3 regions, the VH CDR1, 2 and 3 sequences and VL CDR1, 2 and 3 sequences can be "mixed and matched". Such "mixed and matched" PDL1-BDs can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s).

In yet another embodiment, the PDL1-BD of the invention comprises amino acid sequences that are homologous to the sequences described in Table 2, and said BD binds to PDL1, and retains the desired functional properties of those antibodies described in Table 2.

For example, the invention provides a PDL1-BD comprising a heavy chain variable region and a light chain variable region, wherein the heavy chain variable region comprises an amino acid sequence that is at least 80 percent, at least 90 percent, or at least 95 percent identical to an amino acid sequence selected from the group consisting of SEQ ID NOs: 102, 103, 104, 132, 133 and 134, preferably SEQ ID NO: 102 or 104, more preferably SEQ ID NO: 104; the light chain variable region comprises an amino acid sequence that is at least 80 percent, at least 90 percent, or at least 95 percent identical to an amino acid sequence selected from the group consisting of SEQ ID NOs: 114, 115, 144 and 145, preferably SEQ ID NO: 114 or 115, more preferably SEQ ID NO: 115.

In one embodiment, the VH and/or VL amino acid sequences may be 50 percent, 60 percent, 70 percent, 80 percent, 90 percent, 95 percent, 96 percent, 97 percent, 98 percent or 99 percent identical to the sequences set forth in Table 2. In one embodiment, the VH and/or VL amino acid sequences may be identical except an amino acid substitution in no more than 1, 2, 3, 4 or 5 amino acid positions.

In one embodiment, the invention provides a PDL1-BD comprising a heavy chain variable region comprising CDR1, CDR2, and CDR3 sequences and a light chain variable region comprising CDR1, CDR2, and CDR3 sequences, wherein one or more of these CDR sequences have specified amino acid sequences based on the PDL1-BDs described herein or conservative modifications thereof, and wherein the PDL1-BDs retain the desired functional properties of the PDL1-BDs of the invention.

Accordingly, the invention provides a PDL1-BD comprising a heavy chain variable region comprising CDR1, CDR2, and CDR3 sequences and a light chain variable region comprising CDR1, CDR2, and CDR3 sequences, wherein: the heavy chain variable region CDR1 comprises an amino acid sequence selected from any of SEQ ID NOs: 89, 92, 93, 96, 99, 119, 122, 123, 126 and 129, preferably SEQ ID NO: 89 or 119, more preferably SEQ ID NO: 89, or conservative variants thereof; the heavy chain variable region CDR2 comprises an amino acid sequence selected from any of SEQ ID NOs: 90, 94, 97, 100, 120, 124, 127 and 130, preferably SEQ ID NO: 90 or 120, more preferably SEQ ID NO: 90, or conservative variants thereof; the heavy chain variable region CDR3 comprises an amino acid sequence selected from any of SEQ ID NOs: 91, 95, 98, 101, 121, 125, 128 and 131, preferably SEQ ID NO: 91 or 121, more preferably SEQ ID NO: 91, or conservative variants thereof; the light chain variable region CDR1 comprises an amino acid sequence selected from any of SEQ ID NOs: 105, 108, 111, 135, 138, and 141, preferably SEQ ID NO: 105 or 135, more preferably SEQ ID NO: 105, or conservative variants thereof; the light chain variable region CDR2 comprises an amino acid sequence selected from any of SEQ ID NOs: 106, 109, 112, 136, 139 and 142, preferably SEQ ID NO: 106 or 136, more preferably SEQ ID NO: 106, or conservative variants thereof; and the light chain variable region CDR3 comprises an amino acid sequence selected from any of SEQ ID NOs: 107, 110, 113, 137, 140, and 143, preferably SEQ ID NO: 107 or 137, more preferably SEQ ID NO: 107, or conservative variants thereof; wherein the PDL1-BD specifically binds to PDL1 and is capable of blocking PD-1/PDL1 interaction.

In one embodiment, a PDL1-BD of the invention is optimized for expression in a mammalian cell has a heavy chain variable region and a light chain variable region, wherein one or more of these sequences have specified amino acid sequences based on the binding domains described herein or conservative modifications thereof, and wherein the binding domains retain the desired functional properties of the PDL1-BD of the invention. Accordingly, the invention provides a PDL1-BD optimized for expression in a mammalian cell comprising a heavy chain variable region and a light chain variable region wherein: the heavy chain variable region comprises an amino acid sequence selected from any of SEQ ID NOs: 102, 103, 104, 132, 133 and 134, preferably SEQ ID NO: 102 or 104, more preferably SEQ ID NO: 104, and conservative modifications thereof; and the light chain variable region comprises an amino acid sequence selected from any of SEQ ID NOs: 114, 115, 144 and 145, preferably SEQ ID NO: 114 or 115, more preferably SEQ ID NO: 115, and conservative modifications thereof; wherein the PDL1-BD specifically binds to PDL1 and is capable of blocking PD-1/PDL1 interaction.

In one embodiment, a PDL1-BD of the invention comprises: a VH3 comprising G56A and Y105F mutations, in particular comprising an amino acid sequence according to SEQ ID NO: 104; and preferably a VL comprising S9A; A51P mutations, in particular comprising an amino acid sequence according to SEQ ID NO: 115.

In one embodiment, an "affinity-matured" PDL1-BD of the invention comprises: a VH4 comprising V25A; I44V; G56A; V82K; F89V mutations, in particular comprising an amino acid sequence according to SEQ ID NO: 134; and preferably a VL comprising an amino acid sequence according to SEQ ID NO: 144. In a further embodiment, an "affinity-matured" PDL1-BD of the invention comprises: a VH4 comprising V2S; V25A; I44V; G56A; V82K; F89V; Y105F mutations, in particular comprising an amino acid sequence according to SEQ ID NO: 133; and a VL comprising I2F; M4L; A51P mutations, in particular comprising an amino acid sequence according to SEQ ID NO: 145.

A PDL1-BD of the invention further can be prepared using an antibody or binding domain having one or more of the VH and/or VL sequences shown herein as starting material to engineer a modified binding domain, which modified binding domain may have altered properties from the starting antibody or binding domain. A binding domain can be engineered by modifying one or more residues within one or both variable regions (i.e., VH and/or VL), for example within one or more CDR regions and/or within one or more framework regions.

Suitably, the PDL1-BD of the invention is selected from the group consisting of: Fab, an Fv, an scFv, dsFv, a scAb, STAB, and binding domains based on alternative scaffolds including but limited to ankyrin-based domains, fynomers, avimers, anticalins, fibronectins, and binding sites being built into constant regions of antibodies (e.g. f-star technology (F-star's Modular Antibody Technology™)).

Suitably, the PDL1-BD of the invention is an scFv antibody fragment. In particular embodiments, said PDL1-BD is an scFv comprising the linker according to SEQ ID NO: 206.

In a further embodiment, the PDL1-BD of the invention is a single-chain variable fragment (scFv) as shown in SEQ ID NO: 116, SEQ ID NO: 117, SEQ ID NO: 118, SEQ ID NO: 146, SEQ ID NO: 147 and SEQ ID NO: 148. In one embodiment, the PDL1-BD of the invention is an scFv as shown in SEQ ID NO: 116 or SEQ ID NO: 117 or SEQ ID NO: 118, preferably SEQ ID NO: 116 or 118, more preferably SEQ ID NO: 118. In one embodiment, the PDL1-BD of the invention is an scFv as shown in SEQ ID NO: 146 or SEQ ID NO: 147 or SEQ ID NO: 148, preferably SEQ ID NO: 147 or 148, more preferably SEQ ID NO: 148.

Other suitable PDL1-BDs comprise or are derived from an antibody selected from the group consisting of: (i) avelumab (MSB0010718C; human IgG1 anti-PDL1 monoclonal antibody; Merck-Serono; described in WO 2013/079174, which is hereby incorporated into the present application by reference in its entirety); (ii) atezolizumab (MPDL3280A, RG7446; human IgG anti-PDL1 monoclonal antibody; Hoffmann-La Roche); (iii) MDX-1105 (BMS-936559; human IgG4 anti-PDL1 monoclonal antibody; Bristol-Myers Squibb; described in WO 2007/005874, which is hereby incorporated into the present application by reference in its entirety); (iv) durvalumab (MEDI4736; humanized IgG1 anti-PDL1 monoclonal antibody; AstraZeneca; described in WO 2011/066389 and US 2013/034559, which are hereby incorporated into the present application by reference in their entirety); (v) KN035 (anti-PDL1 monoclonal antibody; 3D Medicines); (vi) LY3300054 (anti-PDL1 monoclonal antibody; Eli Lilly); and (vii) YW243.55.570 (described in WO 2010/077634 and U.S. Pat. No. 8,217,149, the entirety of each of which is incorporated herein by reference).

The inventors have further surprisingly found that at certain ratios between affinities or avidities of the CD137-BD(s) and PDL1-BD(s), the concentration window of maximal activity is extended, which is predicted to be beneficial for therapeutic applications and allows higher flexibility in dosing the multispecific antibody of the invention or pharmaceutical compositions comprising thereof. Thus, in one embodiment, the multispecific antibody of the present invention comprises at least one CD137-BD and at least one PDL1-BD, the affinity of said CD137-BD relative to the affinity of said PDL1-BD is at least 5.0, preferably at least 10 times, e.g., at least 50, at least 100, at least 200, at least 300, at least 400, more preferably at least 500 times, e.g., at least 600, at least 700, at least 800, at least 900, at least 1,000 times weaker, in particular when measured by SPR. In other words, the multispecific antibody of the present invention comprises at least one CD137-BD and at least one PDL1-BD, wherein said CD137-BD binds to human CD137 with a dissociation constant (KD) of at least 5.0, preferably at least 10 times, e.g., at least 50, at least 100, at least 200, at least 300, at least 400, more preferably at least 500 times, e.g., at least 600, at least 700, at least 800, at least 900, at least 1,000 times higher relative to a dissociation constant (KD) of binding to human PDL1 of said PDL1-BD, in particular when measured by SPR. Thus, suitably, the multispecific antibody of the present invention comprises at least one CD137-BD and at least one PDL1-BD, wherein said CD137-BD binds to human CD137 with a dissociation constant (KD) of 5 to 1,000 times, e.g. of 10 to 1,000 times, preferably 50 to 1,000 times, more preferably 100 to 1,000 times, e.g. 200 to 1,000 times, 300 to 1,000 times, 400 to 1,000 times, 500 to 1,000 times, 600 to 1,000 times, 700 to 1,000 times, 800 to 1,000 times, 900 to 1,000 times higher relative to a dissociation constant (KD) of binding to human PDL1 of said PDL1-BD, in particular when measured by SPR. In a further embodiment, said CD137-BD binds to human CD137 with a dissociation constant (KD) between 10 nM and 10 pM, preferably between 10 nM and 0.1 nM, e.g., between 5 nM and 0.1 nM, more preferably between 5 nM and 1 nM, in particular wherein said PDL1-BD binds to human PDL1 with a dissociation constant (KD) between 1 nM and 1 pM, preferably between 0.5 nM and 1 pM, more preferably between 100 pM and 1 pM, in particular when measured by SPR. In another embodiment, the multispecific antibody of the present invention comprises at least one CD137-BD and at least one PDL1-BD, wherein said CD137-BD has the avidity of at least 5.0, preferably at least 10 times, e.g., at least 50, at least 100, at least 200, at least 300, at least 400, more preferably at least 500 times, e.g., at least 600, at least 700, at least 800, at least 900, at least 1,000 times weaker (lower) relative to the avidity of said PDL1-BD.

In one embodiment, the multispecific antibody of the present invention comprises at least one CD137-BD and at least one PDL1-BD, wherein the affinity of said PDL1-BD relative to the affinity of said CD137-BD is at least 5.0, preferably at least 10 times, e.g., at least 50, at least 100, at least 200, at least 300, at least 400, more preferably at least 500 times, e.g., at least 600, at least 700, at least 800, at least 900, at least 1,000 times stronger, in particular when measured by SPR. In one embodiment, the multispecific antibody of the present invention comprises at least one CD137-BD and at least one PDL1-BD, wherein said PDL1-BD binds to human PDL1 with a dissociation constant (KD) of at least 5.0, preferably at least 10 times, e.g., at least 50, at least 100, at least 200, at least 300, at least 400, more preferably at least 500 times, e.g., at least 600, at least 700, at least 800, at least 900, at least 1,000 times lower relative to a dissociation constant (KD) of binding to human CD137 of said CD137-BD, in particular when measured by SPR. In another embodiment, the multispecific antibody of the present invention comprises at least one CD137-BD and at least one PDL1-BD, wherein said PDL1-BD has the avidity of at least 5.0, preferably at least 10 times, e.g., at least 50, at least 100, at least 200, at least 300, at least 400, more preferably at least 500 times, e.g., at least 600, at least 700, at least 800, at least 900, at least 1,000 times stronger (higher) relative to the avidity of said CD137-BD, in particular when measured by SPR.

In one embodiment, the multispecific antibody of the present invention comprises: (i) at least one CD137-BD, wherein said CD137-BD comprises an amino acid sequence that is at least 80 percent, at least 90 percent, or at least 95 percent identical to an amino acid sequence of SEQ ID NO: 31 or 34, preferably SEQ ID NO: 34; and (ii) at least one PDL1-BD, wherein said PDL1-BD comprises an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 116 or 118, more preferably SEQ ID NO: 118. In a further embodiment, the multispecific antibody of the present invention comprises: (i) at least one CD137-BD, wherein said CD137-BD comprises an amino acid sequence of SEQ ID NO: 31 or 34, preferably SEQ ID NO: 34; and (ii) at least one PDL1-BD, wherein said PDL1-BD comprises an amino acid sequence selected from the list consisting of SEQ ID NO: 116, 117, 118, 146, 147, and 148, preferably SEQ ID NO: 116 or 118, more preferably SEQ ID NO: 118. In one embodiment, the multispecific antibody of the present invention comprises: (i) at least one CD137-BD, wherein said CD137-BD is an scFv comprising an amino acid sequence that is at least 80 percent, at least 90 percent, or at least 95 percent identical to an amino acid sequence of SEQ ID NO: 31 or 34, preferably SEQ ID NO: 34; and (ii) at least one PDL1-BD, wherein said PDL1-BD is an scFv comprising an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 116 or 118, more preferably SEQ ID NO: 118. In a further embodiment, the multispecific antibody of the present invention comprises: (i) at least one CD137-BD, wherein said CD137-BD is an scFv comprising an amino acid sequence of SEQ ID NO: 31 or 34, preferably SEQ ID NO: 34; and (ii) at least one PDL1-BD, wherein said PDL1-BD is an scFv comprising an amino acid sequence selected from the list consisting of SEQ ID NO: 116, 117, 118, 146, 147, and 148, preferably SEQ ID NO: 116 or 118, more preferably SEQ ID NO: 118.

In one embodiment, the multispecific antibody of the present invention comprises: (i) at least one CD137-BD, wherein said CD137-BD comprises an amino acid sequence that is at least 80 percent, at least 90 percent, or at least 95 percent identical to an amino acid sequence of SEQ ID NO: 32; and (ii) at least one PDL1-BD, wherein said PDL1-BD comprises an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 118. In a further embodiment, the multispecific antibody of the present invention comprises: (i) at least one CD137-BD, wherein said CD137-BD comprises an amino acid sequence of SEQ ID NO: 32; and (ii) at least one PDL1-BD, wherein said PDL1-BD comprises an amino acid sequence selected from the list consisting of SEQ ID NO: 116, 117, 118, 146, 147, and 148, preferably SEQ ID NO: 118. In one embodiment, the multispecific antibody of the present invention comprises: (i) at least one CD137-BD, wherein said CD137-BD is a Fv comprising an amino acid sequence that is at least 80 percent, at least 90 percent, or at least 95 percent identical to an amino acid sequence of SEQ ID NO: 32; and (ii) at least one PDL1-BD, wherein said PDL1-BD is a Fv comprising an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 118. In a further embodiment, the multispecific antibody of the present invention comprises: (i) at least one CD137-BD, wherein said CD137-BD is a Fv comprising an amino acid sequence of SEQ ID NO: 32; and (ii) at least one PDL1-BD, wherein said PDL1-BD is a Fv comprising an amino acid sequence selected from the list consisting of SEQ ID NO: 116, 117, 118, 146, 147, and 148, preferably SEQ ID NO: 118.

In one embodiment, the multispecific antibody of the present invention comprises: (i) at least one CD137-BD, wherein said CD137-BD comprises an amino acid sequence that is at least 80 percent, at least 90 percent, or at least 95 percent identical to an amino acid sequence of SEQ ID NO: 33; and (ii) at least one PDL1-BD, wherein said PDL1-BD comprises an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 118. In a further embodiment, the multispecific antibody of the present invention comprises: (i) at least one CD137-BD, wherein said CD137-BD comprises an amino acid sequence of SEQ ID NO: 33; and (ii) at least one PDL1-BD, wherein said PDL1-BD comprises an amino acid sequence selected from the list consisting of SEQ ID NO: 116, 117, 118, 146, 147, and 148, preferably SEQ ID NO: 118. In one embodiment, the multispecific antibody of the present invention comprises: (i) at least one CD137-BD, wherein said CD137-BD is a Fv comprising an amino acid sequence that is at least 80 percent, at least 90 percent, or at least 95 percent identical to an amino acid sequence of SEQ ID NO: 33; and (ii) at least one PDL1-BD, wherein said PDL1-BD is a Fv comprising an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 118. In a further embodiment, the multispecific antibody of the present invention comprises: (i) at least one CD137-BD, wherein said CD137-BD is a Fv comprising an amino acid sequence of SEQ ID NO: 33; and (ii) at least one PDL1-BD, wherein said PDL1-BD is a Fv comprising an amino acid sequence selected from the list consisting of SEQ ID NO: 116, 117, 118, 146, 147, and 148, preferably SEQ ID NO: 118.

In a preferred embodiment, the multispecific antibody of the present invention comprises: (i) at least one CD137-BD, wherein said CD137-BD comprises an amino acid sequence that is at least 80 percent, at least 90 percent, or at least 95 percent identical to an amino acid sequence of SEQ ID NO: 86 or SEQ ID NO: 87 or SEQ ID NO: 88, preferably SEQ ID NO: 86, more preferably SEQ ID NO: 88; and (ii) at least one PDL1-BD, wherein said PDL1-BD comprises an amino acid sequence that is at least 80 percent, at least 90 percent, or at least 95 percent identical to an amino acid sequence selected from the list consisting of SEQ ID NO: 116, 117, 118, 146, 147, and 148, preferably SEQ ID NO: 118. In a further embodiment, the multispecific antibody of the present invention comprises: (i) at least one CD137-BD, wherein said CD137-BD comprises an amino acid sequence of SEQ ID NO: 86 or SEQ ID NO: 87 or SEQ ID NO: 88, preferably SEQ ID NO: 86, more preferably SEQ ID NO: 88; and (ii) at least one PDL1-BD, wherein said PDL1-BD comprises an amino acid sequence selected from the list consisting of SEQ ID NO: 116, 117, 118, 146, 147, and 148, preferably SEQ ID NO: 118.

In a preferred embodiment, the multispecific antibody of the present invention comprises:

(i) at least one CD137-BD, wherein said CD137-BD comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 17, preferably a VH sequence of SEQ ID NO: 17, and a VL sequence at least 60, 70, 80, 90, 91, 92, 93, 94, 95, 96, 97, 98 or 99 percent identical to the amino acid sequence SEQ ID NO:30, preferably a VL sequence of SEQ ID NO: 30; and (ii) at least one PDL1-BD, wherein said PDL1-BD comprises:

(a) HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively, a VH sequence at least 60, 70, 80, 90, 91, 92, 93, 94, 95, 96, 97, 98 or 99 percent identical to the amino acid sequence SEQ ID NO: 102, preferably a VH sequence of SEQ ID NO: 102, and a VL sequence at least 60, 70, 80, 90, 91, 92, 93, 94, 95, 96, 97, 98 or 99 percent identical to the amino acid sequence SEQ ID NO: 114, preferably a VL sequence of SEQ ID NO: 114; or (b) HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively, a VH sequence at least 60, 70, 80, 90, 91, 92, 93, 94, 95, 96, 97, 98 or 99 percent identical to the amino acid sequence SEQ ID NO: 104, preferably a VH sequence of SEQ ID NO: 104, and a VL sequence at least 60, 70, 80, 90, 91, 92, 93, 94, 95, 96, 97, 98 or 99 percent identical to the amino acid sequence SEQ ID NO: 115, preferably a VL sequence of SEQ ID NO: 115; or (c) HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to the amino acid sequence SEQ ID NO: 133, preferably a VH sequence of SEQ ID NO: 133, and a VL sequence at least 60, 70, 80, 90, 91, 92, 93, 94, 95, 96, 97, 98 or 99 percent identical to the amino acid sequence SEQ ID NO: 145, preferably a VL sequence of SEQ ID NO: 145; or (d) HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to the amino acid sequence SEQ ID NO: 134, preferably a VH sequence of SEQ ID NO: 134, and a VL sequence at least 60, 70, 80, 90, 91, 92, 93, 94, 95, 96, 97, 98 or 99 percent identical to the amino acid sequence SEQ ID NO: 144, preferably a VL sequence of SEQ ID NO: 144.

In a more preferred embodiment, the multispecific antibody of the present invention comprises:

(i) at least one CD137-BD, wherein said CD137-BD comprises HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, a VH sequence at least 60, 70, 80, 90, 91, 92, 93, 94, 95, 96, 97, 98 or 99 percent identical to the amino acid sequence SEQ ID NO: 71, preferably a VH sequence of SEQ ID NO: 71, and a VL sequence at least 60, 70, 80, 90, 91, 92, 93, 94, 95, 96, 97, 98 or 99 percent identical to the amino acid sequence SEQ ID NO: 83, preferably a VL sequence of SEQ ID NO: 83; and (ii) at least one PDL1-BD, wherein said PDL1-BD comprises:

(a) HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively, a VH sequence at least 60, 70, 80, 90, 91, 92, 93, 94, 95, 96, 97, 98 or 99 percent identical to the amino acid sequence SEQ ID NO: 102, preferably a VH sequence of SEQ ID NO: 102, and a VL sequence at least 60, 70, 80, 90, 91, 92, 93, 94, 95, 96, 97, 98 or 99 percent identical to the amino acid sequence SEQ ID NO: 114, preferably a VL sequence of SEQ ID NO: 114; or (b) HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively, a VH sequence at least 60, 70, 80, 90, 91, 92, 93, 94, 95, 96, 97, 98 or 99 percent identical to the amino acid sequence SEQ ID NO: 104, preferably a VH sequence of SEQ ID NO: 104, and a VL sequence at least 60, 70, 80, 90, 91, 92, 93, 94, 95, 96, 97, 98 or 99 percent identical to the amino acid sequence SEQ ID NO: 115, preferably a VL sequence of SEQ ID NO: 115; or (c) HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to the amino acid sequence SEQ ID NO: 133, preferably a VH sequence of SEQ ID NO: 133, and a VL sequence at least 60, 70, 80, 90, 91, 92, 93, 94, 95, 96, 97, 98 or 99 percent identical to the amino acid sequence SEQ ID NO: 145, preferably a VL sequence of SEQ ID NO: 145; or (d) HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively, a VH sequence at least 60, 70, 80, 90, 91, 92, 93, 94, 95, 96, 97, 98 or 99 percent identical to the amino acid sequence SEQ ID NO: 134, preferably a VH sequence of SEQ ID NO: 134, and a VL sequence at least 60, 70, 80, 90, 91, 92, 93, 94, 95, 96, 97, 98 or 99 percent identical to the amino acid sequence SEQ ID NO: 144, preferably a VL sequence of SEQ ID NO: 144.

Suitably, the multispecific antibody of the invention has two different specificities (PDL1 and CD137). Suitably, the multispecific antibody of the invention is a bispecific antibody. The multispecific antibody of the present invention may comprise a further specificity (trispecific) or specificities (tetraspecific, pentaspecific or hexaspecific antibody).

In one embodiment, the multispecific antibody is trispecific.

In one embodiment, the multispecific antibody of the invention comprises an immunoglobulin Fc region polypeptide. The term "Fc region" herein is used to define a C-terminal region of an immunoglobulin heavy chain, including native-sequence Fc regions and variant Fc regions. Suitable native-sequence Fc regions include human lgG1, lgG2 (lgG2A, JgG2B), lgG3 and lgG4. "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRI IB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see M. Daeron, Annu. Rev. Immunol. 5:203-234 (1997). FcRs are reviewed in Ravetch and Kinet, Annu. Rev. Immunol. 9: 457-92 (1991); Capet et al, Immunomethods 4: 25-34 (1994); and de Haas et al, J. Lab. Clin. Med. 126: 330-41 (1995). Other FcRs, including those to be identified in the future, are encompassed by the term "FcR" herein. The term "Fc receptor" or "FcR" also includes the neonatal receptor, FcRn, which is responsible for the transfer of maternal IgGs to the fetus. Guyer et al., J. Immunol. 117: 587 (1976) and Kim et al., J. Immunol. 24: 249 (1994). Methods of measuring binding to FcRn are known (see, e.g., Ghetie and Ward, Immunol. Today 18: (12): 592-8 (1997); Ghetie et al., Nature Biotechnology 15 (7): 637-40 (1997); Hinton et al., J. Biol. Chem. TJI (8): 6213-6 (2004); WO 2004/92219 (Hinton et al). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., J. Biol. Chem. 9(2): 6591-6604 (2001).

In another embodiment, the antibody of the invention does not comprise an immunoglobulin Fc region polypeptide.

In order to increase the number of specificities/functionalities at the same or lower molecular weight, it is advantageous to use antibodies comprising antibody fragments, such as Fv, Fab, Fab' and F(ab')2 fragments and other antibody fragments. These smaller molecules retain the antigen binding activity of the whole antibody and can also exhibit improved tissue penetration and pharmacokinetic properties in comparison to the whole immunoglobulin molecules. Whilst such fragments appear to exhibit a number of advantages over whole immunoglobulins, they also suffer from an increased rate of clearance from serum since they lack the Fc domain that imparts a long half-life in vivo (Medasan et al., 1997, J. Immunol. 158:2211-2217). Molecules with lower molecular weights penetrate more efficiently into target tissues (e.g. solid cancers) and thus hold the promise for improved efficacy at the same or lower dose.

The inventors have surprisingly found that an addition of human serum albumin binding domain (HSA-BD) to the multispecific antibody of the invention comprising (a) at least one CD137-BD, and (b) at least one PDL1-BD has the following beneficial effects:

(i) a serum half-life of the multispecific antibody of the invention comprising at least one human serum albumin domain is comparable to that of an IgG;

(ii) addition of a human serum albumin binding domain to the multispecific antibody of the invention is compatible with the functionalities of other binding domains, e.g., the PDL1-BD retains its blocking activity and CD137-BD retains its ability to activate CD137 signaling upon clustering;

(iii) even though, human serum albumin binding domain increases the EC50 of the multispecific antibody of the invention to activate CD137, it unexpectedly improves the maximal effect size, e.g., the maximal activation of CD137 signaling is significantly higher.

Suitably, the multispecific antibody of the present invention may comprise a further binding domain having a specificity to human serum albumin. In one embodiment, the multispecific antibody comprises: (i) at least one CD137-BD; (ii) at least one PDL1-BD; and (iii) at least one HSA-BD. Suitably, the multispecific antibody of the present invention comprises: (i) one CD137-BD; (ii) at least one PDL1-BD, preferably one PDL1-BD or two PDL1-BDs, more preferably one PDL1-BD; and (iii) at least one HSA-BD, preferably one HSA-BD.

The term "HSA" refers in particular to human serum albumin with UniProt ID number P02768. Human Serum Albumin (HSA) is 66.4 kDa abundant protein in human serum (50% of total protein) composing of 585 amino acids (Sugio, Protein Eng, Vol. 12, 1999, 439-446). Multifunctional HSA protein is associated with its structure that allowed to bind and transport a number of metabolizes such as fatty acids, metal ions, bilirubin and some drugs (Fanali, Molecular Aspects of Medicine, Vol. 33, 2012, 209-290). HSA concentration in serum is around 3.5-5 g/dL. Albumin binding antibodies and fragments thereof may be used for example, for extending the in vivo serum half-life of drugs or proteins conjugated thereto.

In some embodiments, the HSA-BD is derived from a monoclonal antibody or antibody fragment.

Suitable HSA-BDs for use in the multispecific antibody of the invention are binding domains provided in the present disclosure. The HSA-BDs of the invention include, but are not limited to, the humanized monoclonal antibodies whose sequences are listed in Table 3.

The HSA-BDs of the invention specifically bind to human serum albumin. The HSA-BDs of the invention comprise a VH CDR having an amino acid sequence of any one of the VH CDRs listed in Table 3. In particular, the invention provides HSA-BDs comprising (one, two, three, or more VH CDRs having an amino acid sequence of any of the VH CDRs listed in Table 3.

The invention also provides HSA-BDs comprising a VL CDR having an amino acid sequence of any one of the VL CDRs listed in Table 3. In particular, the invention provides HSA-BDs comprising one, two, three or more VL CDRs having an amino acid sequence of any of the VL CDRs listed in Table 3.

Other HSA-BDs of the invention include amino acids that have been mutated, yet have at least 60, 70, 80, 90, 91, 92, 93, 94, 95, 96, 97, 98 or 99 percent identity in the CDR regions with the CDR regions depicted in the sequences described in Table 3. Other HSA-BDs of the invention include mutant amino acid sequences wherein no more than 1, 2, 3, 4 or 5 amino acids have been mutated in the CDR regions when compared with the CDR regions depicted in the sequence described in Table 3.

The HSA-BD of the present invention comprises: (a) a heavy chain variable region CDR1 comprising, preferably consisting of, an amino acid sequence selected from any one of SEQ ID NOs: 149, 152, 155, 158, 173, 176, 179 and 182, preferably SEQ ID NO: 149 or 173, more preferably SEQ ID NO: 149; (b) a heavy chain variable region CDR2 comprising, preferably consisting of, an amino acid sequence selected from any of SEQ ID NOs: 150, 153, 156, 159, 174, 177, 180 and 183, preferably SEQ ID NO: 150 or 174, more preferably SEQ ID NO: 150; (c) a heavy chain variable region CDR3 comprising, preferably consisting of, an amino acid sequence selected from any of SEQ ID NOs: 151, 154, 157, 160, 175, 178, 181 and 184, preferably SEQ ID NO: 151 or 175, more preferably SEQ ID NO: 151; (d) a light chain variable region CDR1 comprising, preferably consisting of, an amino acid sequence selected from any of SEQ ID NOs: 162, 165, 168, 186, 189, and 192, preferably SEQ ID NO: 162 or 186, more preferably SEQ ID NO: 162; (e) a light chain variable region CDR2 comprising, preferably consisting of, an amino acid sequence selected from any of SEQ ID NOs: 163, 166, 169, 187, 190, and 193, preferably SEQ ID NO: 163 or 187, more preferably SEQ ID NO: 163; and (f) a light chain variable region CDR3 comprising, preferably consisting of, an amino acid sequence selected from any of SEQ ID NOs: 164, 167, 170, 188, 191, and 194, preferably SEQ ID NO: 164 or 188, more preferably SEQ ID NO: 164. Suitably, the HSA-BD of the present invention comprises: (a) a heavy chain variable region CDR1 comprising, preferably consisting of, an amino acid sequence having at least 60, 70, 80, 90, 91, 92, 93, 94, 95, 96, 97, 98 or 99 percent identity to any one of SEQ ID NOs: 149, 152, 155, 158, 173, 176, 179 and 182, preferably SEQ ID NO: 149 or 173, more preferably SEQ ID NO: 149; (b) a heavy chain variable region CDR2 comprising, preferably consisting of, an amino acid sequence having at least 60, 70, 80, 90, 91, 92, 93, 94, 95, 96, 97, 98 or 99 percent identity to any of SEQ ID NOs: 150, 153, 156, 159, 174, 177, 180 and 183, preferably SEQ ID NO: 150 or 174, more preferably SEQ ID NO: 150; (c) a heavy chain variable region CDR3 comprising, preferably consisting of, an amino acid sequence having at least 60, 70, 80, 90, 91, 92, 93, 94, 95, 96, 97, 98 or 99 percent identity to any of SEQ ID NOs: 151, 154, 157, 160, 175, 178, 181 and 184, preferably SEQ ID NO: 151 or 175, more preferably SEQ ID NO: 151; (d) a light chain variable region CDR1 comprising, preferably consisting of, an amino acid sequence selected having at least 60, 70, 80, 90, 91, 92, 93, 94, 95, 96, 97, 98 or 99 percent identity to any of SEQ ID NOs: 162, 165, 168, 186, 189, and 192, preferably SEQ ID NO: 162 or 186, more preferably SEQ ID NO: 162; (e) a light chain variable region CDR2 comprising, preferably consisting of, an amino acid sequence having at least 60, 70, 80, 90, 91, 92, 93, 94, 95, 96, 97, 98 or 99 percent identity to any of SEQ ID Nos: 163, 166, 169, 187, 190, and 193, preferably SEQ ID NO: 163 or 187, more preferably SEQ ID NO: 163; and (f) a light chain variable region CDR3 comprising, preferably consisting of, an amino acid sequence having at least 60, 70, 80, 90, 91, 92, 93, 94, 95, 96, 97, 98 or 99 percent identity to any of SEQ ID NOs: 164, 167, 170, 188, 191, and 194, preferably SEQ ID NO: 164 or 188, more preferably SEQ ID NO: 164.

In one embodiment, the HSA-BD of the invention comprises: (a) HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively; (b) HCDR1, HCDR2, and HCDR3 sequences of SEQ ID NOs: 152, 153, and 154, respectively, and LCDR1, LCDR2, and LCDR3 sequences of SEQ ID NOs: 165, 166, and 167, respectively; or (c) HCDR1, HCDR2, and HCDR3 sequences of SEQ ID NOs: 173, 174, and 175, respectively, and LCDR1, LCDR2, and LCDR3 sequences of SEQ ID NOs: 186, 187, and 188, respectively; or (d) HCDR1, HCDR2, and HCDR3 sequences of SEQ ID NOs: 176, 177, and 178, respectively, and LCDR1, LCDR2, and LCDR3 sequences of SEQ ID NOs: 189, 190, and 191, respectively. In a preferred embodiment, the HSA-BD of the invention comprises HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively. Suitably, the HSA-BD of the invention comprises: (a) HCDR1, HCDR2, and HCDR3 sequences having at least 60, 70, 80, 90, 91, 92, 93, 94, 95, 96, 97, 98 or 99 percent identity to SEQ ID NOs: 149, 150, and 151, respectively, and LCDR1, LCDR2, and LCDR3 sequences having at least 60, 70, 80, 90, 91, 92, 93, 94, 95, 96, 97, 98 or 99 percent identity to SEQ ID NOs: 162, 163, and 164, respectively; or (b) HCDR1, HCDR2, and HCDR3 sequences having at least 60, 70, 80, 90, 91, 92, 93, 94, 95, 96, 97, 98 or 99 percent identity to SEQ ID NOs: 152, 153, and 154, respectively, and LCDR1, LCDR2, and LCDR3 sequences having at least 60, 70, 80, 90, 91, 92, 93, 94, 95, 96, 97, 98 or 99 percent identity to SEQ ID NOs: 165, 166, and 167, respectively; or (c) HCDR1, HCDR2, and HCDR3 sequences having at least 60, 70, 80, 90, 91, 92, 93, 94, 95, 96, 97, 98 or 99 percent identity to SEQ ID NOs: 173, 174, and 175, respectively, and LCDR1, LCDR2, and LCDR3 sequences having at least 60, 70, 80, 90, 91, 92, 93, 94, 95, 96, 97, 98 or 99 percent identity to SEQ ID NOs: 186, 187, and 188, respectively; or (c) HCDR1, HCDR2, and HCDR3 sequences having at least 60, 70, 80, 90, 91, 92, 93, 94, 95, 96, 97, 98 or 99 percent identity to SEQ ID NOs: 176, 177, and 178, respectively, and LCDR1, LCDR2, and LCDR3 sequences having at least 60, 70, 80, 90, 91, 92, 93, 94, 95, 96, 97, 98 or 99 percent identity to SEQ ID NOs: 189, 190, and 191, respectively. In a preferred embodiment, the HSA-BD of the invention comprises: (a) HCDR1, HCDR2, and HCDR3 sequences having at least 60, 70, 80, 90, 91, 92, 93, 94, 95, 96, 97, 98 or 99 percent identity to SEQ ID NOs: 149, 150, and 151, respectively, and LCDR1, LCDR2, and LCDR3 sequences having at least 60, 70, 80, 90, 91, 92, 93, 94, 95, 96, 97, 98 or 99 percent identity to SEQ ID NOs: 162, 163, and 164, respectively.

In a further embodiment, the invention provides a HSA-BD that specifically binds human serum albumin, wherein said binding domain comprises a VH domain and a VL domain.

Suitably, the HSA-BD of the invention comprises a VH3 or VH4. In one embodiment, the HSA-BD of the invention comprises VH3 domain framework sequences. A specific example of a VH belonging to VH3 family is represented under SEQ ID NO: 161. In particular, framework regions FR1 to FR4 taken from SEQ ID NO: 161 belong to VH3 family (Table 3, regions marked in non-bold). Suitably, a VH belonging to VH3 family, as used herein, is a VH comprising FR1 to FR4 having at least 85%, preferably at least 90%, more preferably at least 95% sequence identity to FR1 to FR4 of SEQ ID NO: 161. Alternative examples of VH3 sequences, and examples of VH4 sequences, may be found in Knappik et al., J. Mol. Biol. 296 (2000) 57-86. Suitably, the HSA-BD of the invention comprises: Vκ frameworks FR1, FR2 and FR3, particularly Vκ1 or Vκ3 frameworks, preferably Vκ1 frameworks FR1 to 3, and a framework FR4, which is selected from a Vκ FR4, particularly Vκ1 FR4, Vκ3 FR4, and a Vλ FR4. Suitable Vκ1 frameworks FR1 to 3 are set forth in SEQ ID NO: 171 (Table 3, FR regions are marked in non-bold). Alternative examples of V κ1 sequences, and examples of Vκ2, Vκ3 or Vκ4 sequences, may be found in Knappik et al., J. Mol. Biol. 296 (2000) 57-86. Suitable Vκ1 frameworks FR1 to 3 comprise the amino acid sequences having at least 60, 70, 80, 90 percent identity to amino acid sequences corresponding to FR1 to 3 and taken from SEQ ID NO: 171 (Table 3, FR regions are marked in non-bold). Suitable Vλ FR4 are as set forth in SEQ ID NO: 199 to SEQ ID NO: 205. In one embodiment, the HSA-BD of the present invention comprises Vλ FR4 comprising the amino acid sequence having at least 60, 70, 80, 90 percent identity to an amino acid sequence selected from any of SEQ ID NO: 199 to SEQ ID NO: 205, preferably to SEQ ID NO: 199.

Thus, in one embodiment, the HSA-BD of the present invention comprises:

(i) the HCDR1, HCDR2, HCDR3, LCDR1, LCDR2, and LCDR3 sequences of:
  (a) HCDR1, HCDR2, and HCDR3 sequences of SEQ ID NOs: 152, 153, and 154, respectively, and LCDR1, LCDR2, and LCDR3 sequences of SEQ ID NOs: 165, 166, and 167, respectively; or
  (b) HCDR1, HCDR2, and HCDR3 sequences of SEQ ID NOs: 176, 177, and 178, respectively, and LCDR1, LCDR2, and LCDR3 sequences of SEQ ID NOs: 189, 190, and 191, respectively;
(ii) VH3 or VH4 domain framework sequences FR1 to FR4; preferably VH3 domain framework sequences FR1 to FR4; and d
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vλ FR4, particularly Vκ1 FR4, Vκ3 FR4, and a Vλ FR4, preferably Vλ FR4 comprising the amino acid sequence having at least 60, 70, 80, 90 percent identity to comprising an amino acid sequence selected from any of SEQ ID NO: 199 to SEQ ID NO: 205, preferably Vλ FR4 is as set forth in an amino acid sequence selected from any of SEQ ID NO: 199 to SEQ ID NO: 205, more preferably Vλ FR4 is as set forth in SEQ ID NO: 199.

Thus, in a preferred embodiment, the HSA-BD of the present invention comprises:

(i) the HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively;
(ii) VH3 or VH4 domain framework sequences FR1 to FR4; preferably VH3 domain framework sequences FR1 to FR4; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vλ FR4, particularly Vκ1 FR4, Vκ3 FR4, and a Vλ FR4, preferably Vλ FR4 comprising the amino acid sequence having at least 60, 70, 80, 90 percent identity to comprising an amino acid sequence selected from any of SEQ ID NO: 199 to SEQ ID NO: 205, preferably Vλ FR4 is as set forth in an amino acid sequence selected from any of SEQ ID NO: 199 to SEQ ID NO: 205, more preferably Vλ FR4 is as set forth in SEQ ID NO: 199.

In one embodiment, the HSA-BD of the present invention comprises a VL comprising:

(iv) CDR domains CDR1, CDR2 and CDR3;
(v) human Vκ framework regions FR1 to FR3, particularly human Vκ1 framework regions FR1 to FR3;
(vi) FR4, which is selected from (a) a human Vλ germ line sequence for FR4, particularly a Vλ germ line sequence selected from the list of: SEQ ID NO: 199 to 205, preferably SEQ ID NO: 199; and (b) a V-based sequence, which has one or two mutations, particularly one mutation, compared to the closest human Vλ germ line sequence for FR4 comprising an amino acid sequence selected from any of SEQ ID NO: 199 to SEQ ID NO: 205, preferably SEQ ID NO: 199.

The HSA-BD of the invention comprises a VH domain listed in Table 3. Suitably, the HSA-BD of the invention comprises a VH amino acid sequence listed in Table 3, wherein no more than about 10 amino acids in a framework sequence (for example, a sequence which is not a CDR) have been mutated (wherein a mutation is, as various non-limiting examples, an addition, substitution or deletion). Suitably, the HSA-BD of the present invention comprises a VH amino acid sequence listed in Table 3, wherein no more than about 20 amino acids in a framework sequence (for example, a sequence which is not a CDR) have been mutated (wherein a mutation is, as various non-limiting examples, an addition, substitution or deletion). Other HSA-BDs of the invention include amino acids that have been mutated, yet have at least 60, 70, 80, 90, 91, 92, 93, 94, 95, 96, 97, 98 or 99 percent identity in the VH regions with the VH regions depicted in the sequences described in Table 3.

The HSA-BD of the invention comprises a VL domain listed in Table 3. Suitably, the HSA-BD of the invention comprises a VL amino acid sequence listed in Table 3, wherein no more than about 10 amino acids in a framework sequence (for example, a sequence which is not a CDR) have been mutated (wherein a mutation is, as various non-limiting examples, an addition, substitution or deletion). Suitably, the HSA-BD of the invention comprises a VL amino acid sequence listed in Table 3, wherein no more than about 20 amino acids in a framework sequence (for example, a sequence which is not a CDR) have been mutated (wherein a mutation is, as various non-limiting examples, an addition, substitution or deletion). Other HSA-BDs of the invention include amino acids that have been mutated, yet have at least 60, 70, 80, 90, 91, 92, 93, 94, 95, 96, 97, 98 or 99 percent identity in the VL regions with the VL regions depicted in the sequences described in Table 3.

Suitably, the HSA-BD of the invention comprises a heavy chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 161 and 185, preferably SEQ ID NO: 161; and a light chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 171 and 195, preferably SEQ ID NO: 171.

In one embodiment, the HSA-BD of the invention comprises: a heavy chain variable region comprising an amino acid sequence selected from any of SEQ ID NOs: 161 and 185, preferably SEQ ID NO: 161; and a light chain variable region comprising an amino acid sequence selected from any of SEQ ID NOs: 171 and 195, preferably SEQ ID NO: 161.

In a further embodiment, the HSA-BD of the invention comprises: (a) a VH sequence of SEQ ID NO: 161 and a VL sequence of SEQ ID NO: 171; or (b) a VH sequence of SEQ ID NO: 185 and a VL sequence of SEQ ID NO: 195. In a preferred embodiment, the HSA-BD of the invention comprises a VH sequence of SEQ ID NO: 161 and a VL sequence of SEQ ID NO: 171

In one embodiment, the HSA-BD of the invention comprises:

(a) HCDR1, HCDR2, and HCDR3 sequences of SEQ ID NOs: 152, 153, and 154, respectively, and LCDR1, LCDR2, and LCDR3 sequences of SEQ ID NOs: 165, 166, and 167, respectively, a VH sequence having at least 60, 70, 80, 90, 91, 92, 93, 94, 95, 96, 97, 98 or 99 percent identity to SEQ ID NO: 161, and a VL sequence having at least 60, 70, 80, 90, 91, 92, 93, 94, 95, 96, 97, 98 or 99 percent identity to SEQ ID NO: 171; or (b) HCDR1, HCDR2, and HCDR3 sequences of SEQ ID NOs: 176, 177, and 178, respectively, and LCDR1, LCDR2, and LCDR3 sequences of SEQ ID NOs: 189, 190, and 191, respectively, a VH sequence having at least 60, 70, 80, 90, 91, 92, 93, 94, 95, 96, 97, 98 or 99 percent identity to SEQ ID NO: 185, and a VL sequence having at least 60, 70, 80, 90, 91, 92, 93, 94, 95, 96, 97, 98 or 99 percent identity to SEQ ID NO: 195.

In one embodiment, the HSA-BD of the invention comprises:

(a) HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively, a VH sequence having at least 60, 70, 80, 90, 91, 92, 93, 94, 95, 96, 97, 98 or 99 percent identity to SEQ ID NO: 161, and a VL sequence having at least 60, 70, 80, 90, 91, 92, 93, 94, 95, 96, 97, 98 or 99 percent identity to SEQ ID NO: 171; or (b) HCDR1, HCDR2, and HCDR3 sequences of SEQ ID NOs: 173, 174, and 175, respectively, and LCDR1, LCDR2, and LCDR3 sequences of SEQ ID NOs: 186, 187, and 188, respectively, a VH sequence having at least 60, 70, 80, 90, 91, 92, 93, 94, 95, 96, 97, 98 or 99 percent identity to SEQ ID NO: 185, and a VL sequence having at least 60, 70, 80, 90, 91, 92, 93, 94, 95, 96, 97, 98 or 99 percent identity to SEQ ID NO: 195.

Suitably, the HSA-BD of the invention is selected from the group consisting of: a Fab, an Fv, an scFv, dsFv, a scAb, STAB, and binding domains based on alternative scaffolds including but limited to ankyrin-based domains, fynomers, avimers, anticalins, fibronectins, and binding sites being built into constant regions of antibodies (e.g. f-star technology (F-star's Modular Antibody Technology™)).

Suitably, the HSA-BD of the invention is scFv antibody fragment. In one embodiment, the HSA-BD of the present invention is as set forth in SEQ ID NO: 172 or SEQ ID NO: 196, preferably SEQ ID NO: 172.

Other suitable HSA-BD for use in the multispecific antibody of the invention comprises or is derived from an antibody selected from the group consisting of: (i) polypeptides that bind serum albumin (see, for example, Smith et al., 2001, Bioconjugate Chem. 12:750-756; EP0486525; U.S. Pat. No. 6,267,964; WO 2004/001064; WO 2002/076489; and WO 2001/45746); (ii) anti-serum albumin binding single variable domains described in Holt et al., Protein Engineering, Design & Selection, vol 21, 5, pp 283-288, WO 2004/003019, WO 2008/096158, WO 2005/118642, WO 2006/0591056 and WO 2011/006915; (iii) anti-serum albumin antibodies described in WO 2009/040562, WO 2010/035012 and WO 2011/086091.

The multispecific antibody of the invention may be in any suitable format.

Suitably, the binding domains of the multispecific antibody are operably linked. The binding domains of the multispecific antibody of the invention are capable of binding to their respective antigens or receptors simultaneously.

In one embodiment, the multispecific antibody of the invention comprises at least one CD137-BD, at least one PDL1-BD, wherein: (i) said CD137-BD and said PDL1-BD are both operably linked to each other. In one embodiment, the multispecific antibody of the invention comprises at least one CD137-BD, at least one PDL1-BD, at least one HSA-BD, wherein: (i) said CD137-BD and said PDL1-BD are both operably linked to said HSA-BD; or (ii) said CD137-BD and said HSA-BD are both operably linked to said PDL1-BD; or (iii) said PDL1-BD and said HSA-BD are both operably linked to said CD137-BD. In a preferred embodiment, the multispecific antibody of the invention comprises at least one CD137-BD, at least one PDL1-BD, at least one HSA-BD, wherein said CD137-BD and said HSA-BD are both operably linked to said PDL1-BD.

The term "operably linked", as used herein, indicates that two molecules (e.g., polypeptides, domains, binding domains) are attached so as to each retain functional activity. Two molecules can be "operably linked" whether they are attached directly or indirectly (e.g., via a linker, via a moiety, via a linker to a moiety). The term "linker" refers to a peptide or other moiety that is optionally located between binding domains or antibody fragments of the invention. A number of strategies may be used to covalently link molecules together. These include, but are not limited to polypeptide linkages between N- and C-termini of proteins or protein domains, linkage via disulfide bonds, and linkage via chemical cross-linking reagents.

In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility.

In the context of the present invention, the term "polypeptide linker" refers to a linker consisting of a chain of amino acid residues linked by peptide bonds that is connecting two domains, each being attached to one end of the linker. The polypeptide linker should have a length that is adequate to link two molecules in such a way that they assume the correct conformation relative to one another so that they retain the desired activity. In particular embodiments, the polypeptide linker has a continuous chain of between 2 and 30 amino acid residues (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues). In addition, the amino acid residues selected for inclusion in the polypeptide linker should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. In particular embodiments, the polypeptide linker is non-structured polypeptide. Useful linkers include glycine-serine, or GS linkers. By "Gly-Ser" or "GS" linkers is meant a polymer of glycines and serines in series (including, for example, (Gly-Ser)n, (GSGGS)n (SEQ ID NO: 246), (GGGGS)n (SEQ ID NO: 247), and (GGGS)n (SEQ ID NO: 248), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

Suitably, the multispecific antibody is in a format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH3-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs) (bispecific IgGs prepared by the KiH technology); an Fv, scFv, scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH (described in WO 2016/0202457; Egan T., et al., mAbs 9 (2017) 68-84) and DuoBodies (bispecific IgGs prepared by the Duobody technology) (MAbs. 2017 February/March; 9(2):182-212. doi: 10.1080/19420862.2016.1268307). Particularly suitable for use herein is a single-chain diabody (scDb) or scDb-scFv.

In one embodiment, the multispecific antibody of the invention is in a format selected from the list consisting of scDb (diabody), scDb-scFv, triabody, and tribody. Particularly suitable for use herein is a single-chain diabody (scDb), in particular a bispecific monomeric scDb. Also, particularly suitable for use herein is a scDb-scFv, in particular wherein said CD137-BD and said PDL1-BD are in the form of a scDb and said HSA-BD is an scFv operably linked to said scDb.

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. Diabodies may be bivalent or bispecific. Diabodies are described more fully in, for example, EP404097, WO 93/01161, Hudson et al., Nat. Med. 9:129-134 (2003), and Hollinger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. In particular embodiments, the linker L1 and/or L3 comprises one or two units of four (4) glycine amino acid residues and one (1) serine amino acid residue (GGGGS)n (SEQ ID NO: 249), wherein n=1 or 2, preferably n=1. In more particular embodiments, the linker L1 and/or L3 is as set forth in SEQ ID NO: 207 or SEQ ID NO: 204-8, preferably SEQ ID NO: 207.

The middle linker L2 particularly is a peptide of 10-40 amino acids, more particularly 15-30 amino acids, and most particularly 20-25 amino acids. In particular embodiments, said linker L2 comprises one or more units of four (4) glycine amino acid residues and one (1) serine amino acid residue $(GGGGS)_n$ (SEQ ID NO: 250), wherein n=1, 2, 3, 4, 5, 6, 7 or 8, preferably n=4 (SEQ ID NO: 206). In more particular embodiments, the linker L2 is as set forth in SEQ ID NO: 206.

In one embodiment, the multispecific antibody of the invention is a scDb. In a specific embodiment, the multispecific antibody of the invention is a scDb comprising an amino acid sequence having at least 60, 70, 80, 90, 91, 92, 93, 94, 95, 96, 97, 98 or 99 percent identity to any of SEQ ID NOs: 209, 210, 211, 212, 213, 214, and 215. In one embodiment, the multispecific antibody of the invention is a scDb comprising an amino acid sequence selected from any of SEQ ID NOs: 209, 210, 211, 212, 213, 214, and 215. In a further embodiment, the multispecific antibody of the present invention is a scDb consisting of an amino acid sequence selected from any of SEQ ID NOs: 209, 210, 211, 212, 213, 214, and 215.

In one embodiment, the multispecific antibody of the invention is a scDb-scFv. The term "scDb-scFv" refers to an antibody format, wherein a single-chain Fv (scFv) fragment is fused by a flexible Gly-Ser linker to a single-chain diabody (scDb). In one embodiment, said flexible Gly-Ser linker is a peptide of 2-40 amino acids, e.g., 2-35, 2-30, 2-25, 2-20, 2-15, 2-10 amino acids, particularly 10 amino acids. In particular embodiments, said linker comprises one or more units of four (4) glycine amino acid residues and one (1) serine amino acid residue $(GGGGS)_n$ (SEQ ID NO: 250), wherein n=1, 2, 3, 4, 5, 6, 7 or 8, preferably n=2. In more particular embodiments, said linker is as set forth in SEQ ID NO: 208.

In a specific embodiment, the multispecific antibody of the invention is a scDb-scFv comprising an amino acid sequence having at least 60, 70, 80, 90, 91, 92, 93, 94, 95, 96, 97, 98 or 99 percent identity to any of SEQ ID NOs: 216, 217, 218, 219, 220, 221, 222, 223, 224, 225, 226, 227, 228, 229, 230 and 231. Suitably, the multispecific antibody of the invention is a scDb-scFv comprising an amino acid sequence having at least 60, 70, 80, 90, 91, 92, 93, 94, 95, 96, 97, 98 or 99 percent identity to any of SEQ ID NOs: 222. More suitably, the multispecific antibody of the invention is a scDb-scFv comprising an amino acid sequence having at least 60, 70, 80, 90, 91, 92, 93, 94, 95, 96, 97, 98 or 99 percent identity to SEQ ID NOs: 223 or 224.

Suitably, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 216, wherein (a) the CD137-BD of said multispecific antibody comprises HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, and (b) the PDL1-BD of said multispecific antibody comprises HCDR1, HCDR2, and HCDR3 sequences of SEQ ID NOs: 122, 124, and 125, respectively, and LCDR1, LCDR2, and LCDR3 sequences of SEQ ID NOs: 138, 139, and 140, respectively; and (c) the HSA-BD of said multispecific antibody comprises HCDR1, HCDR2, and HCDR3 sequences of SEQ ID NOs: 152, 153, and 154, respectively, and LCDR1, LCDR2, and LCDR3 sequences of SEQ ID NOs: 165, 166, and 167, respectively.

Suitably, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 217, wherein (a) the CD137-BD of said multispecific antibody comprises HCDR1, HCDR2, and HCDR3 sequences of SEQ ID NOs: 38, 39, and 40, respectively, and LCDR1, LCDR2, and LCDR3 sequences of SEQ ID NOs: 51, 52, and 53, respectively, and (b) the PDL1-BD of said multispecific antibody comprises HCDR1, HCDR2, and HCDR3 sequences of SEQ ID NOs: 122, 124, and 125, respectively, and LCDR1, LCDR2, and LCDR3 sequences of SEQ ID NOs: 138, 139, and 140, respectively; and (c) the HSA-BD of said multispecific antibody comprises HCDR1, HCDR2, and HCDR3 sequences of SEQ ID NOs: 152, 153, and 154, respectively, and LCDR1, LCDR2, and LCDR3 sequences of SEQ ID NOs: 165, 166, and 167, respectively.

Suitably, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 218, wherein (a) the CD137-BD of said multispecific antibody comprises HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, and (b) the PDL1-BD of said multispecific antibody comprises HCDR1, HCDR2, and HCDR3 sequences of SEQ ID NOs: 122, 124, and 125, respectively, and LCDR1, LCDR2, and LCDR3 sequences of SEQ ID NOs: 138, 139, and 140, respectively; and (c) the HSA-BD of said multispecific antibody comprises HCDR1, HCDR2, and HCDR3 sequences of SEQ ID NOs: 176, 177, and 178, respectively, and LCDR1, LCDR2, and LCDR3 sequences of SEQ ID NOs: 189, 190, and 191, respectively.

Suitably, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 219, wherein (a) the CD137-BD of said multispecific antibody comprises HCDR1, HCDR2, and HCDR3 sequences of SEQ ID NOs: 38, 39, and 40, respectively, and LCDR1, LCDR2, and LCDR3 sequences of SEQ ID NOs: 51, 52, and 53, respectively, and (b) the PDL1-BD of said multispecific antibody comprises HCDR1, HCDR2, and HCDR3 sequences of SEQ ID NOs: 122, 124, and 125, respectively, and LCDR1, LCDR2, and LCDR3 sequences of SEQ ID NOs: 138, 139, and 140, respectively; and (c) the HSA-BD of said multispecific antibody comprises HCDR1, HCDR2, and HCDR3 sequences of SEQ ID NOs: 176, 177, and 178, respectively, and LCDR1, LCDR2, and LCDR3 sequences of SEQ ID NOs: 189, 190, and 191, respectively.

Suitably, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 220, wherein (a) the CD137-BD of said multispecific antibody comprises HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, and (b) the PDL1-BD of said multispecific antibody comprises the HCDR1, HCDR2, and HCDR3 sequences of SEQ ID NOs: 92, 94, and 95, respectively, and the LCDR1, LCDR2, and LCDR3 sequences of SEQ ID NOs: 108, 109, and 110, respectively; and (c) the HSA-BD of said multispecific antibody comprises the HCDR1, HCDR2, and HCDR3 sequences of SEQ ID NOs: 152, 153, and 154, respectively, and LCDR1, LCDR2, and LCDR3 sequences of SEQ ID NOs: 165, 166, and 167, respectively.

Suitably, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 221, wherein (a) the CD137-BD of said multispecific antibody comprises HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, and (b) the PDL1-BD of said multispecific antibody comprises HCDR1, HCDR2, and HCDR3 sequences of SEQ ID NOs: 92, 94, and 95, respectively, and LCDR1, LCDR2, and LCDR3 sequences of SEQ ID NOs: 108, 109, and 110, respectively; and (c) the HSA-BD of said multispecific antibody comprises HCDR1, HCDR2, and HCDR3 sequences of SEQ ID NOs: 176, 177, and 178, respectively, and LCDR1, LCDR2, and LCDR3 sequences of SEQ ID NOs: 189, 190, and 191, respectively.

In a preferred embodiment, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 222 or SEQ ID NO: 223 or SEQ ID NO: 224, preferably SEQ ID NO: 222, more preferably SEQ ID NO: 223, wherein (a) the CD137-BD of said multispecific antibody comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, and (b) the PDL1-BD of said multispecific antibody comprises HCDR1, HCDR2, and HCDR3 sequences of SEQ ID NOs: 89, 90, and 91, respectively, and LCDR1, LCDR2, and LCDR3 sequences of SEQ ID NOs: 105, 106, and 107, respectively; and (c) the HSA-BD of said multispecific antibody comprises HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively.

In one embodiment, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NO: 225 or SEQ ID NO: 226 or SEQ ID NO: 227 or SEQ ID NO: 228, preferably SEQ ID NO: 225 or SEQ ID NO: 228, more preferably SEQ ID NO: 225, wherein (a) the CD137-BD of said multispecific antibody comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, and (b) the PDL1-BD of said multispecific antibody comprises HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively; and (c) the HSA-BD of said multispecific antibody comprises HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively.

In one embodiment, the multispecific antibody of the invention is a scDb-scFv comprising an amino acid sequence selected from any of SEQ ID NOs: 216, 217, 218, 219, 220, 221, 222, 223, 224, 225, 226, 227, and 228, preferably SEQ ID NO: 222 or 223, more preferably SEQ ID NO: 223. In a further embodiment, the multispecific antibody of the invention is a scDb-scFv consisting of an amino acid sequence selected from any of SEQ ID NOs: 216, 217, 218, 219, 220, 221, 222, 223, 224, 225, 226, 227, and 228, preferably SEQ ID NO: 222 or 223, more preferably SEQ ID NO: 223.

In a further embodiment, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NOs: 229 or SEQ ID NO: 230 or SEQ ID NO: 231, preferably to SEQ ID NO: 229 or SEQ ID NO: 231, more preferably SEQ ID NO: 229, wherein (a) the CD137-BD of said multispecific antibody comprises HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, and (b) the PDL1-BD of said multispecific antibody comprises HCDR1, HCDR2, and HCDR3 sequences of SEQ ID NOs: 119, 120, and 121, respectively, and LCDR1, LCDR2, and LCDR3 sequences of SEQ ID NOs: 135, 136, and 137, respectively; and (c) the HSA-BD of said multispecific antibody comprises HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively.

In a preferred embodiment, the multispecific antibody of the invention is a scDb-scFv comprising an amino acid sequence having at least 60, 70, 80, 90, 91, 92, 93, 94, 95, 96, 97, 98 or 99 percent identity to SEQ ID NOs: 229 or SEQ ID NO: 230 or SEQ ID NO: 231, preferably to SEQ ID NO: 229 or SEQ ID NO: 231, more preferably SEQ ID NO: 229. In particular embodiment, the multispecific antibody of the invention is a scDb-scFv comprising an amino acid sequence having at least 60, 70, 80, preferably at least 90, e.g., 91, 92, 93, 94, 95, 96, 97, 98 or 99, percent identity to SEQ ID NOs: 229 or SEQ ID NO: 230 or SEQ ID NO: 231, preferably to SEQ ID NO: 229 or SEQ ID NO: 231, more preferably SEQ ID NO: 229, wherein (a) the CD137-BD of said multispecific antibody comprises HCDR1, HCDR2, and HCDR3 sequences of SEQ ID NOs: 59, 60 and 61, respectively, and LCDR1, LCDR2, and LCDR3 sequences of SEQ ID NOs: 74, 75 and 76, respectively, and (b) the PDL1-BD of said multispecific antibody comprises HCDR1, HCDR2, and HCDR3 sequences of SEQ ID NOs: 89, 90 and 91, respectively, and LCDR1, LCDR2, and LCDR3 sequences of SEQ ID NOs: 105, 106 and 107, respectively; and (c) the HSA-BD of said multispecific antibody comprises HCDR1, HCDR2, and HCDR3 sequences of SEQ ID NOs: 149, 150, and 151, respectively, and LCDR1, LCDR2, and LCDR3 sequences of SEQ ID NOs: 162, 163, and 164, respectively.

In one embodiment, the multispecific antibody of the invention is a scDb-scFv comprising an amino acid sequence selected from any of SEQ ID NOs: 216, 217, 218, 219, 220, 221, 222, 223, 224, 225, 226, 227, 228, 229, 230 and 231, preferably SEQ ID NO: 222 or 223, more preferably SEQ ID NO: 223. In a further embodiment, the multispecific antibody of the invention is a scDb-scFv consisting of an amino acid sequence selected from any of SEQ ID NOs: 216, 217, 218, 219, 220, 221, 222, 223, 224, 225, 226, 227, 228, 229, 230 and 231, preferably SEQ ID NO: 222 or 223, more preferably SEQ ID NO: 223. In a preferred embodiment, the multispecific antibody of the invention is a scDb-scFv comprising an amino acid sequence selected from any of SEQ ID NOs: 229, 230 and 231, preferably SEQ ID NO: 229 or 231, more preferably SEQ ID NO: 229. In a more particular embodiment, the multispecific antibody of the invention is a scDb-scFv consisting of an amino acid sequence selected from any of SEQ ID NOs: 229, 230 and 231, preferably SEQ ID NO: 229 or 231, more preferably SEQ ID NO: 229.

In one embodiment of the present invention, the multispecific antibody of the invention is in Morrison-L format.

In a specific embodiment, the multispecific antibody of the invention comprises (i) a Morrison-L Light chain comprising an amino acid sequence having at least 60, 70, 80, 90, 91, 92, 93, 94, 95, 96, 97, 98 or 99 percent identity to any of SEQ ID NO: 232, and (ii) a Morrison-L Heavy chain comprising an amino acid sequence having at least 60, 70, 80, 90, 91, 92, 93, 94, 95, 96, 97, 98 or 99 percent identity to any of SEQ ID NO: 233. In one embodiment, the multispecific antibody of the invention comprises (i) a Morrison-L Light chain comprising an amino acid of SEQ ID NO: 232, and (ii) a Morrison-L Heavy chain comprising an amino acid sequence of SEQ ID NO: 233. In a further embodiment, the multispecific antibody of the invention consists of (i) a Morrison-L Light chain comprising an amino acid of SEQ ID NO: 232, and (ii) a Morrison-L Heavy chain comprising an amino acid sequence of SEQ ID NO: 233.

In another embodiment, the multispecific antibody of the invention comprises (i) a Morrison-L Light chain comprising an amino acid sequence having at least 60, 70, 80, 90, 91, 92, 93, 94, 95, 96, 97, 98 or 99 percent identity to any of SEQ ID NO: 236, and (ii) a Morrison-L Heavy chain comprising an amino acid sequence having at least 60, 70, 80, 90, 91, 92, 93, 94, 95, 96, 97, 98 or 99 percent identity to any of SEQ ID NO: 237. In one embodiment, the multispecific antibody of the invention comprises (i) a Morrison-L Light chain comprising an amino acid of SEQ ID NO: 236, and (ii) a Morrison-L Heavy chain comprising an amino acid sequence of SEQ ID NO: 237. In a further embodiment, the multispecific antibody of the invention consists of (i) a Morrison-L Light chain comprising an amino acid of SEQ ID NO: 236, and (ii) a Morrison-L Heavy chain comprising an amino acid sequence of SEQ ID NO: 237.

In one embodiment of the present invention, the multispecific antibody of the invention is in Morrison-H format.

In a specific embodiment, the multispecific antibody of the invention comprises (i) a Morrison-H Light chain comprising an amino acid sequence having at least 60, 70, 80, 90, 91, 92, 93, 94, 95, 96, 97, 98 or 99 percent identity to any of SEQ ID NO: 234, and (ii) a Morrison-H Heavy chain comprising an amino acid sequence having at least 60, 70, 80, 90, 91, 92, 93, 94, 95, 96, 97, 98 or 99 percent identity to any of SEQ ID NO: 235. In one embodiment, the multispecific antibody of the invention comprises (i) a Morrison-H Light chain comprising an amino acid of SEQ ID NO: 234, and (ii) a Morrison-H Heavy chain comprising an amino acid sequence of SEQ ID NO: 235. In a further embodiment, the multispecific antibody of the invention consists of (i) a Morrison-L Light chain comprising an amino acid of SEQ ID NO: 234, and (ii) a Morrison-L Heavy chain comprising an amino acid sequence of SEQ ID NO: 235.

In another embodiment, the multispecific antibody of the invention comprises (i) a Morrison-H Light chain comprising an amino acid sequence having at least 60, 70, 80, 90, 91, 92, 93, 94, 95, 96, 97, 98 or 99 percent identity to any of SEQ ID NO: 238, and (ii) a Morrison-H Heavy chain comprising an amino acid sequence having at least 60, 70, 80, 90, 91, 92, 93, 94, 95, 96, 97, 98 or 99 percent identity to any of SEQ ID NO: 239. In one embodiment, the multispecific antibody of the invention comprises (i) a Morrison-H Light chain comprising an amino acid of SEQ ID NO: 238, and (ii) a Morrison-H Heavy chain comprising an amino acid sequence of SEQ ID NO: 239. In a further embodiment, the multispecific antibody of the invention consists of (i) a Morrison-L Light chain comprising an amino acid of SEQ ID NO: 238, and (ii) a Morrison-L Heavy chain comprising an amino acid sequence of SEQ ID NO: 239.

In one embodiment of the present invention, the multispecific antibody of the invention is in a MATCH format described in WO 2016/0202457; Egan T., et al., mAbs 9 (2017) 68-84.

The multispecific antibody of the invention can be produced using any convenient antibody manufacturing method known in the art (see, e.g., Fischer, N. & Leger, O., Pathobiology 74 (2007) 3-14 with regard to the production of bispecific constructs; Hornig, N. & Farber-Schwarz, A., Methods Mol. Biol. 907 (2012)713-727, and WO 99/57150 with regard to bispecific diabodies and tandem scFvs). Specific examples of suitable methods for the preparation of the bispecific construct of the invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189 (2000) 1-8), and the combination of the antigen-binding domains or fragments or parts thereof of two or more different monoclonal antibodies to give a bispecific or multispecific construct using known molecular cloning techniques.

The multispecific molecules of the invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, two or more binding specificities can be encoded in the same vector and expressed and assembled in the same host cell. This method is particularly useful where the bispecific molecule is a mAb X mAb, mAb X Fab, Fab X F (ab')2 or ligand X Fab fusion protein. A multispecific antibody of the invention can be a single chain molecule comprising one single chain antibody and a binding determinant, or a single chain multispecific antibody comprising two binding determinants. Multispecific antibody may comprise at least two single chain molecules. Methods for preparing multispecific antibodies and molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the multispecific antibodies to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In a further aspect, the invention provides a nucleic acid encoding the multispecific antibody of the invention or fragments thereof or binding domains thereof. Such nucleic acid sequences can be optimized for expression in mammalian cells.

The term "nucleic acid" is used herein interchangeably with the term "polynucleotide(s)" and refers to one or more deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260: 2605-2608, 1985; and Rossolini et al., Mol. Cell. Probes 8:91-98, 1994).

The invention provides substantially purified nucleic acid molecules which encode polypeptides comprising segments or domains of the multispecific antibody described above. When expressed from appropriate expression vectors, polypeptides encoded by these nucleic acid molecules are capable of exhibiting antigen binding capacity or capacities of the multispecific antibody of the present invention.

Also provided in the invention are polynucleotides which encode at least one CDR region and usually all three CDR regions of the binding domains of the multispecific antibody of the present invention set forth in Tables 1 to 3. Because of the degeneracy of the code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding the multispecific antibody of the invention or fragments thereof or binding domains thereof. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68: 109, 1979; the diethylphosphoramidite method of Beaucage et al., Tetra. Lett., 22: 1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif, 1990; Mattila et al., Nucleic Acids Res. 19:967, 1991; and Eckert et al., PCR Methods and Applications 1:17, 1991.

Also provided in the invention are expression vectors and host cells for producing the multispecific antibody of the invention or fragments thereof or binding domains thereof.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In this particular context, the term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system.

Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Various expression vectors can be employed to express the polynucleotides encoding the multispecific antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the CD137-binding polynucleotides and polypeptides in mammalian (e.g., human) cells include pThioHis A, B and C, pcDNA3.1/His, pEBVHis A, B and C, (Invitrogen, San Diego, Calif), MPS V vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68: 143, 1992.

The choice of expression vector depends on the intended host cells in which the vector is to be expressed. Typically, the expression vectors contain a promoter and other regulatory sequences (e.g., enhancers) that are operably linked to the polynucleotides encoding a multispecific antibody chain or a fragment. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a multispecific antibody chain or a fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20: 125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted the multispecific antibody of the invention or fragments thereof or binding domains thereof sequences. More often, the inserted the multispecific antibody of the invention or fragments thereof or binding domains thereof sequences are linked to signal sequences before inclusion in the vector. Vectors to be used to receive sequences encoding binding domains of the multispecific antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The host cells for harboring and expressing the multispecific antibody of the invention or fragments thereof or binding domains thereof can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express CD137-binding polypeptides of the invention. Insect cells in combination with baculovirus vectors can also be used.

In one embodiment, mammalian host cells are used to express and produce the multispecific antibody of the invention or fragments thereof or binding domains thereof. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPS V promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycatiomnucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the multispecific antibody of the invention or fragments thereof or binding domains thereof can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present invention thus provides a method of producing the antibody of the invention or antigen-binding fragment thereof, wherein said method comprises the step of culturing a host cell comprising a nucleic acid or a vector encoding the antibody of the invention or antigen-binding fragment thereof, whereby said antibody of the disclosure or a fragment thereof is expressed.

In one aspect, the present invention relates to a method of producing the multispecific antibody of the invention or a binding domain thereof or a fragment thereof, the method comprising the step of culturing a host cell expressing a nucleic acid encoding the multispecific antibody of the invention or a binding domain thereof or a fragment thereof.

In a further aspect, the present invention relates to a pharmaceutical composition comprising the multispecific antibody of the invention, and a pharmaceutically acceptable carrier. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., the multispecific antibody of the invention, may be coated in a material to protect the compound from the action of acids and other natural conditions that may inactivate the compound.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the multispecific antibody of the invention is employed in the pharmaceutical compositions of the invention. The multispecific antibodies of the invention are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

The multispecific antibody of the invention is usually administered on multiple occasions. Intervals between single dosages can be weekly, monthly or yearly. Intervals can also be irregular as indicated by measuring blood levels of the multispecific antibody of the invention in the patient. Alternatively, the multispecific antibody of the invention can be administered as a sustained release formulation, in which case less frequent administration is required. Dosage and frequency vary depending on the half-life of the antibody in the patient.

In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In one aspect, the present invention relates to the multispecific antibody of the invention or the pharmaceutical composition of the invention for use as a medicament. In a suitable embodiment, the present invention provides the multispecific antibody or the pharmaceutical composition for use in treatment of a proliferative disease, in particular a cancer in a subject in need thereof.

In another aspect, the present invention provides the multispecific antibody or the pharmaceutical composition for use in a manufacture of a medicament for treatment of a proliferative disease, in particular a cancer.

In another aspect, the present invention relates to use of the multispecific antibody or the pharmaceutical composition for treating a proliferative disease, in particular a cancer in a subject in need thereof.

In a further aspect, the present invention relates to use of the multispecific antibody or the pharmaceutical composition in the manufacture of a medicament for treatment of a proliferative disease, in particular a cancer, in a subject in need thereof.

In another aspect, the present invention relates to a method of treating a subject comprising administering to the subject a therapeutically effective amount of the multispecific antibody of the present invention. In a suitable embodiment, the present invention relates to a method of treating a proliferative disease, in particular a cancer in a subject comprising administering to the subject a therapeutically effective amount of the multispecific antibody of the present invention.

The term “subject” includes human and non-human animals. Non-human animals include all vertebrates, e.g., mammals and non-mammals, such as non-human primates, sheep, dog, cow, chickens, amphibians, and reptiles. Except when noted, the terms “patient” or “subject” are used herein interchangeably.

The terms “treatment”, “treating”, “treat”, “treated”, and the like, as used herein, refer to obtaining a desired pharmacologic and/or physiologic effect. The effect may be therapeutic in terms of a partial or complete cure for a disease and/or adverse effect attributable to the disease or delaying the disease progression. “Treatment”, as used herein, covers any treatment of a disease in a mammal, e.g., in a human, and includes: (a) inhibiting the disease, i.e., arresting its development; and (b) relieving the disease, i.e., causing regression of the disease.

The term “therapeutically effective amount” or “efficacious amount” refers to the amount of an agent that, when administered to a mammal or other subject for treating a disease, is sufficient to effect such treatment for the disease. The “therapeutically effective amount” will vary depending on the agent, the disease and its severity and the age, weight, etc., of the subject to be treated.

In one embodiment, the proliferative disease is a cancer. The term “cancer” refers to a disease characterized by the rapid and uncontrolled growth of aberrant cells. Cancer cells can spread locally or through the bloodstream and lymphatic system to other parts of the body.

The terms “tumor” and “cancer” are used interchangeably herein, e.g., both terms encompass solid and liquid, e.g., diffuse or circulating, tumors. As used herein, the term “cancer” or “tumor” includes premalignant, as well as malignant cancers and tumors. The term “cancer” is used herein to mean a broad spectrum of tumors, including all solid and haematological malignancies. Examples of such tumors include, but are not limited to: a benign or especially malignant tumor, solid tumors, brain cancer, kidney cancer, liver cancer, adrenal gland cancer, bladder cancer, breast cancer, stomach cancer (e.g., gastric tumors), oesophageal cancer, ovarian cancer, cervical cancer, colon cancer, rectum cancer, prostate cancer, pancreatic cancer, lung cancer (e.g. non-small cell lung cancer and small cell lung cancer), vaginal cancer, thyroid cancer, melanoma (e.g., unresectable or metastatic melanoma), renal cell carcinoma, sarcoma, glioblastoma, multiple myeloma or gastrointestinal cancer, especially colon carcinoma or colorectal adenoma, a tumor of the neck and head, endometrial cancer, Cowden syndrome, Lhermitte-Duclos disease, Bannayan-Zonana syndrome, prostate hyperplasia, a neoplasia, especially of epithelial character, preferably mammary carcinoma or squamous cell carcinoma, chronic lymphocytic leukemia, chronic myelogenous leukemia (e.g., Philadelphia chromosome-positive chronic myelogenous leukemia), acute lymphoblastic leukemia (e.g., Philadelphia chromosome-positive acute lymphoblastic leukemia), non-Hodgkin’s lymphoma, plasma cell myeloma, Hodgkin’s lymphoma, a leukemia, and any combination thereof. In a preferred embodiment, the cancer is a lung cancer, preferably non-small cell lung cancer (NSCLC). In another embodiment, said cancer is a colorectal cancer.

The multispecific antibody of the present invention, or the composition of the present invention, inhibits the growth of solid tumors, but also liquid tumors. In a further embodiment, the proliferative disease is a solid tumor. The term “solid tumor” especially means a breast cancer, ovarian cancer, colon cancer, rectum cancer, prostate cancer, stomach cancer (especially gastric cancer), cervical cancer, lung cancer (e.g., non-small cell lung cancer and small cell lung cancer), and a tumor of the head and neck. Further, depending on the tumor type and the particular combination used, a decrease of the tumor volume can be obtained. The multispecific antibody of the present invention, or the composition of the present invention, is also suited to prevent the metastatic spread of tumors and the growth or development of micrometastases in a subject having a cancer.

In one embodiment, said cancer is PDL1-positive, preferably wherein said cancer expresses high levels of PDL1 in comparison to a healthy tissue, in particular wherein said cancer expresses PDL1 (mRNA or protein) at least 2 times, at least 3 times, at least 4 times, at least 5 times, at least 6 times, at least 7 times, at least 8 times, at least 9 times, at least 10 times, at least 15 times, at least 20 times, at least 30 times, at least 40 times, at least 50 times, at least 60 times, at least 70 times, at least 80 times, at least 90 times, at least 100 times higher level in comparison to PDL1 expression (mRNA or protein respectively) in a healthy tissue. In some embodiments, said cancer is malignant. In some embodiments, said cancer is benign. In some embodiments, said cancer is primary. In some embodiments, said cancer is secondary. In one embodiment, said cancer is lung cancer, preferably non-small cell lung cancer (NSCLC). In another embodiment, said cancer is colorectal cancer.

In one aspect, the present invention relates to a kit comprising the multispecific antibody of the invention or the pharmaceutical composition of the invention. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject. In a specific embodiment, the kit comprises the multispecific antibody of the invention in a pharmaceutically effective amount. In a further embodiment, the kit comprises a pharmaceutically effective amount of the multispecific antibody of the invention in lyophilized form and a diluent and, optionally, instructions for use. Said kit may further comprise a filter needle for reconstitution and a needle for injecting

TABLE 1

Examples of CD137 binding domains of the present invention (CDR residues shown in bold and italic letters).

| SEQ ID NUMBER | Ab region | Sequence |
|---|---|---|
| | | 38-02-A04 |
| SEQ ID NO: 1 | HCDR1 (H27-H42; AHo numbering) | GFSFSNSYWIC |
| SEQ ID NO: 2 | HCDR2 (H57-H76; AHo numbering) | CTFVGSSDSTYYANWAKG |
| SEQ ID NO: 3 | HCDR3 (H108-H138; AHo numbering) | RHPSDAVYGYANNL |
| SEQ ID NO: 4 | HCDR1 (AHo definition) (38-02-A04 sc01) (38-02-A04 sc05 IF) | VSGFSFSNSYW |
| SEQ ID NO: 5 | HCDR1 (AHo definition) (38-02-A04 sc06 Full) (38-02-A04 sc13) | ASGFSFSNSYW |
| SEQ ID NO: 6 | HCDR2 (AHo definition) | TFVGSSDSTYYANWAKGR |
| SEQ ID NO: 7 | HCDR3 (AHo definition) | HPSDAVYGYANN |
| SEQ ID NO: 8 | HCDR1 (Kabat definition) | NSYWIC |
| SEQ ID NO: 9 | HCDR2 (Kabat definition) | CTFVGSSDSTYYANWAKG |
| SEQ ID NO: 10 | HCDR3 (Kabat definition) | HPSDAVYGYANNL |
| SEQ ID NO: 11 | HCDR1 (Chothia definition) | GFSFSNSY |
| SEQ ID NO: 12 | HCDR2 (Chothia definition) | VGSSD |
| SEQ ID NO: 13 | HCDR3 (Chothia definition) | PSDAVYGYANN |
| SEQ ID NO: 14 | VH (VH4) (38-02-A04 sc01) | QVQLQESGPGLVKPSETLSLTCKVS***GFSFSNSYWIC***WIRQPPGKGLEWIG***CTFVGSSDSTYYANWAKG***RVTISVDSSKNQFSLKLSSVTAADTAVYYCA***RHPSDAVYGYANNL***WGQGTLVTVSS |
| SEQ ID NO: 15 | VH (VH4) (38-02-A04 sc05 IF) Mutations VH: I44V; F89V; Y105F. | QVQLQESGPGLVKPSETLSLTCKVS***GFSFSNSYWIC***WVRQPPGKGLEWIG***CTFVGSSDSTYYANWAKG***RVTISVDSSKNQVSLKLSSVTAADTAVYFCA***RHPSDAVYGYANNL***WGQGTLVTVSS |
| SEQ ID NO: 16 | VH (VH4) (38-02-A04 sc06 Full) Mutations VH: V25A; I44V; V82K; F89V; Y105F | QVQLQESGPGLVKPSETLSLTCKAS***GFSFSNSYWIC***WVRQPPGKGLEWIG***CTFVGSSDSTYYANWAKG***RVTISKDSSKNQVSLKLSSVTAADTAVYFCA***RHPSDAVYGYANNL***WGQGTLVTVSS |
| SEQ ID NO: 17 | VH (VH3) (38-02-A04 sc13) Mutations VH: G51C (AHo numbering) | EVQLVESGGGLVQPGGSLRLSCAAS***GFSFSNSYWIC***WVRQAPGKCLEWIG***CTFVGSSDSTYYANWAKG***RFTISRDNSKNTVYLQMNSLRAEDTAVYYCA***RHPSDAVYGYANNL***WGQGTLVTVSS |
| SEQ ID NO: 18 | LCDR1 (L24-L42; AHo numbering) (Kabat definition) | QASQSINNVLA |
| SEQ ID NO: 19 | LCDR2 (L58-L72; AHo numbering) (Kabat definition) | RASTLAS |

TABLE 1-continued

Examples of CD137 binding domains of the present invention (CDR residues shown in bold and italic letters).

| SEQ ID NUMBER | Ab region | Sequence |
|---|---|---|
| SEQ ID NO: 20 | LCDR3 (L107-L138; AHo numbering) (Kabat definition) | QSSYGNYGD |
| SEQ ID NO: 21 | LCDR1 (AHo definition) | ASQSINNV |
| SEQ ID NO: 22 | LCDR2 (AHo definition) | RASTLASGVPSR |
| SEQ ID NO: 23 | LCDR3 (AHo definition) | SYGNYG |
| SEQ ID NO: 24 | LCDR1 (Chothia definition) | SQSINNV |
| SEQ ID NO: 25 | LCDR2 (Chothia definition) | RAS |
| SEQ ID NO: 26 | LCDR3 (Chothia definition) | SYGNYG |
| SEQ ID NO: 27 | VL (Vk1-sk17) (38-02-A04 sc01) | DIQMTQSPSSLSASVGDRVTITC***QASQSINNVLA***WYQQKPGKAPKLLIY***RASTLAS***GVPSRFSGSGSGTDFTLTISSLQPEDFATYYC***QSSYGNYGD***FGTGTKVTVLG |
| SEQ ID NO: 28 | VL (Vk1-sk17) (38-02-A04 sc05 IF) Mutations VL: A51P | DIQMTQSPSSLSASVGDRVTITC***QASQSINNVLA***WYQQKPGKPPKLLIY***RASTLAS***GVPSRFSGSGSGTDFTLTISSLQPEDFATYYC***QSSYGNYGD***FGTGTKVTVLG |
| SEQ ID NO: 29 | VL (Vk1-sk17) (38-02-A04 sc06 Full) Mutations VL: I2L; A51P | DLQMTQSPSSLSASVGDRVTITC***QASQSINNVLA***WYQQKPGKPPKLLIY***RASTLAS***GVPSRFSGSGSGTDFTLTISSLQPEDFATYYC***QSSYGNYGD***FGTGTKVTVLG |
| SEQ ID NO: 30 | VL (Vk1-sk17) (38-02-A04 sc13) Mutations VL: T141C (AHo numbering) | DIQMTQSPSSLSASVGDRVTITC***QASQSINNVLA***WYQQKPGKAPKLLIY***RASTLAS***GVPSRFSGSGSGTDFTLTISSLQPEDFATYYC***QSSYGNYGD***FGCGTKVTVLG |
| SEQ ID NO: 31 | scFv (VL-linker-VH) (38-02-A04 sc01) | DIQMTQSPSSLSASVGDRVTITC***QASQSINNVLA***WYQQKPGKAPKLLIY***RASTLAS***GVPSRFSGSGSGTDFTLTISSLQPEDFATYYC***QSSYGNYGD***FGTGTKVTVLGGGGGSGGGGSGGGGSGGGGSQVQLQESGPGLVKPSETLSLTCKVS***GFSFSNSYWIC***WIRQPPGKGLEWIG***CTFVGSSDSTYYANWAKG***RVTISVDSSKNQFSLKLSSVTAADTAVYYCA***RHPSDAVYGYANNL***WGQGTLVTVSS |
| SEQ ID NO: 32 | scFv (VL-linker-VH) (38-02-A04 sc05 IF) | DIQMTQSPSSLSASVGDRVTITC***QASQSINNVLA***WYQQKPGKPPKLLIY***RASTLAS***GVPSRFSGSGSGTDFTLTISSLQPEDFATYYC***QSSYGNYGD***FGTGTKVTVLGGGGGSGGGGSGGGGSGGGGSQVQLQESGPGLVKPSETLSLTCKVS***GFSFSNSYWIC***WVRQPPGKGLEWIG***CTFVGSSDSTYYANWAKG***RVTISVDSSKNQVSLKLSSVTAADTAVYFCA***RHPSDAVYGYANNL***WGQGTLVTVSS |
| SEQ ID NO: 33 | scFv (VL-linker-VH) (38-02-A04 sc06 Full) | DLQMTQSPSSLSASVGDRVTITC***QASQSINNVLA***WYQQKPGKPPKLLIY***RASTLAS***GVPSRFSGSGSGTDFTLTISSLQPEDFATYYC***QSSYGNYGD***FGTGTKVTVLGGGGGSGGGGSGGGGSGGGGSQVQLQESGPGLVKPSETLSLTCKAS***GFSFSNSYWIC***WVRQPPGKGLEWIG***CTFVGSSDSTYYANWAKG***RVTISKDSSKNQVSLKLSSVTAADTAVYFCA***RHPSDAVYGYANNL***WGQGTLVTVSS |
| SEQ ID NO: 34 | scFv (VL-linker-VH) (38-02-A04 sc13) | DIQMTQSPSSLSASVGDRVTITC***QASQSINNVLA***WYQQKPGKAPKLLIY***RASTLAS***GVPSRFSGSGSGTDFTLTISSLQPEDFATYYC***QSSYGNYGD***FGCGTKVTVLGGGGGSGGGGSGGGGSGGGGSEVQLVESGGGLVQPGGSLRLSCAAS***GFSFSNSYWIC***WVRQAPGKCLEWIG***CTFVGSSDSTYYANWAKG***RFTISRDNSKNTVYLQMNSLRAEDTAVYYCA***RHPSDAVYGYANNL***WGQGTLVTVSS |
| | 38-27-C05 sc01 | |
| SEQ ID NO: 35 | HCDR1 (H27-H42; AHo numbering) | GFSFNNDYDMC |
| SEQ ID NO: 36 | HCDR2 (H57-H76; AHo numbering) | CIDTGDGSTYYASWAKG |

TABLE 1-continued

Examples of CD137 binding domains of the present invention (CDR residues shown in bold and italic letters).

| SEQ ID NUMBER | Ab region | Sequence |
|---|---|---|
| SEQ ID NO: 37 | HCDR3 (H108-H138; AHo numbering) | REAASSSGYGMGYFDL |
| SEQ ID NO: 38 | HCDR1 (AHo definition) | VSGFSFNNDYD |
| SEQ ID NO: 39 | HCDR2 (AHo definition) | IDTGDGSTYYASWAKGR |
| SEQ ID NO: 40 | HCDR3 (AHo definition) | EAASSSGYGMGYFD |
| SEQ ID NO: 41 | HCDR1 (Kabat definition) | NDYDMC |
| SEQ ID NO: 42 | HCDR2 (Kabat definition) | CIDTGDGSTYYASWAKG |
| SEQ ID NO: 43 | HCDR3 (Kabat definition) | EAASSSGYGMGYFDL |
| SEQ ID NO: 44 | HCDR1 (Chothia definition) | GFSFNNDY |
| SEQ ID NO: 45 | HCDR2 (Chothia definition) | TGDG |
| SEQ ID NO: 46 | HCDR3 (Chothia definition) | AASSSGYGMGYFD |
| SEQ ID NO: 47 | VH (VH4) | QVQLQESGPGLVKPSETLSLTCKVS***GFSFNNDYDMC***WIRQPPGKGLEWIG***CIDTGDGSTYYASWAKG***RVTISVDSSKNQFSLKLSSVTAADTAVYYCA***REAASSSGYGMGYFDL***WGQGTLVTVSS |
| SEQ ID NO: 48 | LCDR1 (L24-L42; AHo numbering) (Kabat definition) | QSSQSVYDNNWLA |
| SEQ ID NO: 49 | LCDR2 (L58-L72; AHo numbering) (Kabat definition) | RASNLAS |
| SEQ ID NO: 50 | LCDR3 (L107-L138; AHo numbering) (Kabat definition) | QGTYLSSNWYWA |
| SEQ ID NO: 51 | LCDR1 (AHo definition) | SSQSVYDNNW |
| SEQ ID NO: 52 | LCDR2 (AHo definition) | RASNLASGVPSR |
| SEQ ID NO: 53 | LCDR3 (AHo definition) | TYLSSNWYW |
| SEQ ID NO: 54 | LCDR1 (Chothia definition) | SQSVYDNNW |
| SEQ ID NO: 55 | LCDR2 (Chothia definition) | RAS |
| SEQ ID NO: 56 | LCDR3 (Chothia definition) | TYLSSNWYW |
| SEQ ID NO: 57 | VL (Vk1-sk17) | DIQMTQSPSSLSASVGDRVTITC***QSSQSVYDNNWLA***WYQQKPGKAPKLLIY***RASNLAS***GVPSRFSGSGSGTDFTLTISSLQPEDFATYYC***QGTYLSSNWYWA***FGTGTKVTVLG |
| SEQ ID NO: 58 | scFv (VL-linker-VH) | DIQMTQSPSSLSASVGDRVTITC***QSSQSVYDNNWLA***WYQQKPGKAPKLLIY***RASNLAS***GVPSRFSGSGSGTDFTLTISSLQPEDFATYYC***QGTYLSSNWYWA***FGTGTKVTVLGGGGGSGGGGSGGGGSGGGGSQVQLQESGPGLVKPSETLSLTCKVS***GFSFNNDYDMC***WIRQPPGKGLEWIG***CIDTGDGSTYYASWAKG***RVTISVDSSKNQFSLKLSSVTAADTAVYYCA***REAASSSGYGMGYFDL***WGQGTLVTVSS |

TABLE 1-continued

Examples of CD137 binding domains of the present invention (CDR residues shown in bold and italic letters).

| SEQ ID NUMBER | Ab region | Sequence |
|---|---|---|
| | | 38-27-A11 |
| SEQ ID NO: 59 | HCDR1 (H27-H42; AHo numbering) | GFSFSANYYPC |
| SEQ ID NO: 60 | HCDR2 (H57-H76; AHo numbering) | CIYGGSSDITYDANWTK |
| SEQ ID NO: 61 | HCDR3 (H108-H138; AHo numbering) | RSAWYSGWGGDL |
| SEQ ID NO: 62 | HCDR1 (AHo definition) | ASGFSFSANYY |
| SEQ ID NO: 63 | HCDR2 (AHo definition) | IYGGSSDITYDANWTKG |
| SEQ ID NO: 64 | HCDR3 (AHo definition) | SAWYSGWGGD |
| SEQ ID NO: 65 | HCDR1 (Kabat definition) | ANYYPC |
| SEQ ID NO: 66 | HCDR2 (Kabat definition) | CIYGGSSDITYDANWTK |
| SEQ ID NO: 67 | HCDR3 (Kabat definition) | SAWYSGWGGDL |
| SEQ ID NO: 68 | HCDR1 (Chothia definition) | GFSFSANY |
| SEQ ID NO: 69 | HCDR2 (Chothia definition) | GGSS |
| SEQ ID NO: 70 | HCDR3 (Chothia definition) | AWYSGWGGD |
| SEQ ID NO: 71 | VH (VH3) (38-27-A11 sc02) | EVQLVESGGGLVQPGGSLRLSCAAS***GFSFSANYYPC***WVRQAPGKGLEWIG***CIYGGSSDITYDANWTK***GRFTISRDNSKNTVYLQMNSLRAEDTAVYYCA***RSAWYSGWGGDL***WGQGTLVTVSS |
| SEQ ID NO: 72 | VH (VH3) (38-27-A11 sc03) | ESQLVESGGGLVQPGGSLRLSCAAS***GFSFSANYYPC***WVRQAPGKGLEWIG***CIYGGSSDITYDANWTK***GRFTISRDNSKNTVYLQMNSLRAEDTAVYFCA***RSAWYSGWGGDL***WGPGTLVTVSS |
| SEQ ID NO: 73 | VH (VH3) (38-27-A11 sc07) (G51C) | EVQLVESGGGLVQPGGSLRLSCAAS***GFSFSANYYPC***WVRQAPGKCLEWIG***CIYGGSSDITYDANWTK***GRFTISRDNSKNTVYLQMNSLRAEDTAVYYCA***RSAWYSGWGGDL***WGQGTLVTVSS |
| SEQ ID NO: 74 | LCDR1 (L24-L42; AHo numbering) (Kabat definition) | QASQSISNRLA |
| SEQ ID NO: 75 | LCDR2 (L58-L72; AHo numbering) (Kabat definition) | SASTLAS |
| SEQ ID NO: 76 | LCDR3 (L107-L138; AHo numbering) (Kabat definition) | QSTYYGNDGNA |
| SEQ ID NO: 77 | LCDR1 (AHo definition) | ASQSISNR |
| SEQ ID NO: 78 | LCDR2 (AHo definition) | SASTLASGVPSR |
| SEQ ID NO: 79 | LCDR3 (AHo definition) | TYYGNDGN |

TABLE 1-continued

Examples of CD137 binding domains of the present invention (CDR residues shown in bold and italic letters).

| SEQ ID NUMBER | Ab region | Sequence |
|---|---|---|
| SEQ ID NO: 80 | LCDR1 (Chothia definition) | SQSISNR |
| SEQ ID NO: 81 | LCDR2 (Chothia definition) | SAS |
| SEQ ID NO: 82 | LCDR3 (Chothia definition) | TYYGNDGN |
| SEQ ID NO: 83 | VL (Vk1-sk17) (38-27-A11 sc02) | DIQMTQSPSSLSASVGDRVTITC***QASQSISNRLA***WYQQKPGKAPKLLIY***SASTLAS***GVPSRFSGSGSGTDFTLTISSLQPEDFATYYC***QSTYYGNDGNA***FGTGTKVTVLG |
| SEQ ID NO: 84 | VL (Vk1-sk17) (38-27-A11 sc03) | DFQLTQSPSSLSASVGDRVTITC***QASQSISNRLA***WYQQKPGKPPKLLIY***SASTLAS***GVPSRFSGSGSGTDFTLTISSLQPEDFATYYC***QSTYYGNDGNA***FGTGTKVTVLG |
| SEQ ID NO: 85 | VL (Vk1-sk17) (38-27-A11 sc07) (T141C) | DIQMTQSPSSLSASVGDRVTITC***QASQSISNRLA***WYQQKPGKAPKLLIY***SASTLAS***GVPSRFSGSGSGTDFTLTISSLQPEDFATYYCQSTYYGNDGNAFGCGTKVTVLG |
| SEQ ID NO: 86 | scFv (VL-linker-VH) (38-27-A11 sc02) (PRO1359) | DIQMTQSPSSLSASVGDRVTITC***QASQSISNRLA***WYQQKPGKAPKLLIY***SASTLAS***GVPSRFSGSGSGTDFTLTISSLQPEDFATYYC***QSTYYGNDGNA***FGTGTKVTVLGGGGGSGGGGSGGGGSGGGGSEVQLVESGGGLVQPGGSLRLSCAAS***GFSFSANYYPC***WVRQAPGKGLEWIG***CIYGGSSDITYDANWTK***GRFTISRDNSKNTVYLQMNSLRAEDTAVYYCA***RSAWYSGWGGDL***WGQGTLVTVSS |
| SEQ ID NO: 87 | scFv (VL-linker-VH) (38-27-A11 sc03) (PRO1360) | DFQLTQSPSSLSASVGDRVTITC***QASQSISNRLA***WYQQKPGKPPKLLIY***SASTLAS***GVPSRFSGSGSGTDFTLTISSLQPEDFATYYC***QSTYYGNDGNA***FGTGTKVTVLGGGGGSGGGGSGGGGSGGGGSESQLVESGGGLVQPGGSLRLSCAAS***GFSFSANYYPC***WVRQAPGKGLEWIG***CIYGGSSDITYDANWTK***GRFTISRDNSKNTVYLQMNSLRAEDTAVYFCA***RSAWYSGWGGDL***WGPGTLVTVSS |
| SEQ ID NO: 88 | scFv (VL-linker-VH) (38-27-A11 sc07) (VL-T141C; VH-G51C) (PRO 1704) | DIQMTQSPSSLSASVGDRVTITC***QASQSISNRLA***WYQQKPGKAPKLLIY***SASTLAS***GVPSRFSGSGSGTDFTLTISSLQPEDFATYYC***QSTYYGNDGNA***FGCGTKVTVLGGGGGSGGGGSGGGGSGGGGSEVQLVESGGGLVQPGGSLRLSCAAS***GFSFSANYYPC***WVRQAPGKCLEWIG***CIYGGSSDITYDANWTK***GRFTISRDNSKNTVYLQMNSLRAEDTAVYYCA***RSAWYSGWGGDL***WGQGTLVTVSS |

TABLE 2

Examples of PDL1 binding domains of the present invention (CDR residues shown in bold and italic letters).

| SEQ ID NUMBER | Ab region | Sequence |
|---|---|---|
| | | 37-20-B03 |
| SEQ ID NO: 89 | HCDR1 (H27-H42; AHo numbering) | GFSFNSDYWIY |
| SEQ ID NO: 90 | HCDR2 (H57-H76; AHo numbering) | SIYGGSSGNTQYASWAQG |
| SEQ ID NO: 91 | HCDR3 (H108-H138; AHo numbering) | RGYVDYGGATDL |
| SEQ ID NO: 92 | HCDR1 (AHo definition) (37-20-B03 sc01) | VSGFSFNSDYW |
| SEQ ID NO: 93 | HCDR1 (AHo definition) (37-20-B03 sc02) (37-20-B03 sc09.1) | ASGFSFNSDYW |

TABLE 2-continued

Examples of PDL1 binding domains of the present invention (CDR residues shown in bold and italic letters).

| SEQ ID NUMBER | Ab region | Sequence |
|---|---|---|
| SEQ ID NO: 94 | HCDR2 (AHo definition) | IYGGSSGNTQYASWAQGR |
| SEQ ID NO: 95 | HCDR3 (AHo definition) | GYVDYGGATD |
| SEQ ID NO: 96 | HCDR1 (Kabat definition) | SDYWIY |
| SEQ ID NO: 97 | HCDR2 (Kabat definition) | SIYGGSSGNTQYASWAQG |
| SEQ ID NO: 98 | HCDR3 (Kabat definition) | GYVDYGGATDL |
| SEQ ID NO: 99 | HCDR1 (Chothia definition) | GFSFNSDY |
| SEQ ID NO: 100 | HCDR2 (Chothia definition) | GGSSG |
| SEQ ID NO: 101 | HCDR3 (Chothia definition) | YVDYGGATD |
| SEQ ID NO: 102 | VH (VH4) (37-20-B03 sc01) | QVQLQESGPGLVKPSETLSLTCKVS***GFSFNSDYWIY***WIRQPPGKGLEWIG***SIYGGSSGNTQYASWAQG***RVTISVDSSKNQFSLKLSSVTAADTAVYYCA***RGYVDYGGATDL***WGQGTLVTVSS |
| SEQ ID NO: 103 | VH (VH1) (37-20-B03 sc02) | QVQLVQSGAEVKKPGASVKVSCKAS***GFSFNSDYWIY***WVRQAPGQGLEWMG***SIYGGSSGNTQYASWAQG***RVTMTRDTSISTAYMELSSLRSEDTAVYYCA***RGYVDYGGATDL***WGQGTLVTVSS |
| SEQ ID NO: 104 | VH (VH3) (37-20-B03 sc09.1) Mutations: G56A; Y105F | EVQLVESGGGLVQPGGSLRLSCAAS***GFSFNSDYWIY***WVRQAPGKGLEWIA***SIYGGSSGNTQYASWAQG***RFTISRDNSKNTVYLQMNSLRAEDTAVYFCA***RGYVDYGGATDL***WGQGTLVTVSS |
| SEQ ID NO: 105 | LCDR1 (L24-L42; AHo numbering) (Kabat definition) | QASQSIGTYLA |
| SEQ ID NO: 106 | LCDR2 (L58-L72; AHo numbering) (Kabat definition) | RAFILAS |
| SEQ ID NO: 107 | LCDR3 (L107-L138; AHo numbering) (Kabat definition) | QSNFYSDSTTIGPNA |
| SEQ ID NO: 108 | LCDR1 (AHo definition) | ASQSIGTY |
| SEQ ID NO: 109 | LCDR2 (AHo definition) | RAFILASGVPSR |
| SEQ ID NO: 110 | LCDR3 (AHo definition) | NFYSDSTTIGPN |
| SEQ ID NO: 111 | LCDR1 (Chothia definition) | SQSIGTY |
| SEQ ID NO: 112 | LCDR2 (Chothia definition) | RAF |
| SEQ ID NO: 113 | LCDR3 (Chothia definition) | NFYSDSTTIGPN |

TABLE 2-continued

Examples of PDL1 binding domains of the present invention (CDR residues shown in bold and italic letters).

| SEQ ID NUMBER | Ab region | Sequence |
|---|---|---|
| SEQ ID NO: 114 | VL (Vk1-sk17) (37-20-B03 sc01) (37-20-B03 sc02) | DIQMTQSPSSLSASVGDRVTITC***QASQSIGTYLA***WYQQKPGKAPKLLIY***RAFILAS***GVPSRFSGSGSGTDFTLTISSLQPEDFATYYC***QSNFYSDSTTIGPNA***FGTGTKVTVLG |
| SEQ ID NO: 115 | VL (Vk1-sk17) (37-20-B03 sc09.1) Mutations: S9A; A51P | DIQMTQSPASLSASVGDRVTITC***QASQSIGTYLA***WYQQKPGKPPKLLIY***RAFILAS***GVPSRFSGSGSGTDFTLTISSLQPEDFATYYC***QSNFYSDSTTIGPNA***FGTGTKVTVLG |
| SEQ ID NO: 116 | scFv (VL-linker-VH) (37-20-B03 sc01) (PRO997) | DIQMTQSPSSLSASVGDRVTITC***QASQSIGTYLA***WYQQKPGKAPKLLIY***RAFILAS***GVPSRFSGSGSGTDFTLTISSLQPEDFATYYC***QSNFYSDSTTIGPNA***FGTGTKVTVLGGGGGSGGGGSGGGGSGGGGSQVQLQESGPGLVKPSETLSLTCKVS***GFSFNSDYWIY***WIRQPPGKGLEWIG***SIYGGSSGNTQYASWAQG***RVTISVDSSKNQFSLKLSSVTAADTAVYYCA***RGYVDYGGATDL***WGQGTLVTVSS |
| SEQ ID NO: 117 | scFv (VL-linker-VH) (37-20-B03 sc02) (PRO1013) | DIQMTQSPSSLSASVGDRVTITC***QASQSIGTYLA***WYQQKPGKAPKLLIY***RAFILAS***GVPSRFSGSGSGTDFTLTISSLQPEDFATYYC***QSNFYSDSTTIGPNA***FGTGTKVTVLGGGGGSGGGGSGGGGSGGGGSQVQLVQSGAEVKKPGASVKVSCKAS***GFSFNSDYWIY***WVRQAPGQGLEWMG***SIYGGSSGNTQYASWAQG***RVTMTRDTSISTAYMELSSLRSEDTAVYYCA***RGYVDYGGATDL***WGQGTLVTVSS |
| SEQ ID NO: 118 | scFv (VL-linker-VH) (37-20-B03 sc09.1) | DIQMTQSPASLSASVGDRVTITC**QASQSIGTYLA**WYQQKPGKPPKLLIY**RAFILAS**GVPSRFSGSGSGTDFTLTISSLQPEDFATYYC**QSNFYSDSTTIGPNA**FGTGTKVTVLGGGGGSGGGGSGGGGSGGGGSEVQLVESGGGLVQPGGSLRLSCAAS**GFSFNSDYWIY**WVRQAPGKGLEWIAS**IYGGSSGNTQYASWAQG**RFTISRDNSKNTVYLQMNSLRAEDTAVYFCARGYVDYGGATDLWGQGTLVTVSS |
| | | 33-03-G02 |
| SEQ ID NO: 119 | HCDR1 (H27-H42; AHo numbering) | GFSFSSGYDMC |
| SEQ ID NO: 120 | HCDR2 (H57-H76; AHo numbering) | CVVAGSVDITYYASWAKG |
| SEQ ID NO: 121 | HCDR3 (H108-H138; AHo numbering) | RKDAYSDAFNL |
| SEQ ID NO: 122 | HCDR1 (AHo definition) (33-03-G02 sc01) | VSGFSFSSGYD |
| SEQ ID NO: 123 | HCDR1 (AHo definition) (33-03-G02 sc03 Full) (33-03-G02 sc18) | ASGFSFSSGYD |
| SEQ ID NO: 124 | HCDR2 (AHo definition) | VVAGSVDITYYASWAKGR |
| SEQ ID NO: 125 | HCDR3 (AHo definition) | KDAYSDAFN |
| SEQ ID NO: 126 | HCDR1 (Kabat definition) | SGYDMC |
| SEQ ID NO: 127 | HCDR2 (Kabat definition) | CVVAGSVDITYYASWAKG |
| SEQ ID NO: 128 | HCDR3 (Kabat definition) | KDAYSDAFNL |
| SEQ ID NO: 129 | HCDR1 (Chothia definition) | GFSFSSGY |
| SEQ ID NO: 130 | HCDR2 (Chothia definition) | AGSVD |
| SEQ ID NO: 131 | HCDR3 (Chothia definition) | DAYSDAFN |

TABLE 2-continued

Examples of PDL1 binding domains of the present invention (CDR residues shown in bold and italic letters).

| SEQ ID NUMBER | Ab region | Sequence |
|---|---|---|
| SEQ ID NO: 132 | VH (VH4) (33-03-G02 sc01) | QVQLQESGPGLVKPSETLSLTCKVS***GFSFSSGYDMC***WIRQPPGKGLEWIG***CVVAGSVDITYYASWAKG***RVTISVDSSKNQFSLKLSSVTAADTAVYYCA***RKDAYSDAFNL***WGQGTLVTVSS |
| SEQ ID NO: 133 | VH (VH4) (33-03-G02 sc03 Full) (Mutations: V2S; V25A; 144V; G56A; V82K; F89V; Y105F) | QSQLQESGPGLVKPSETLSLTCKAS***GFSFSSGYDMC***WVRQPPGKGLEWIA***CVVAGSVDITYYASWAKG***RVTISKDSSKNQVSLKLSSVTAADTAVYFCA***RKDAYSDAFNL***WGQGTLVTVSS |
| SEQ ID NO: 134 | VH (VH4) (33-03-G02 sc18) Mutations VH: V25A; I44; G56A; V82K; F89V (AHo numbering) | QVQLQESGPGLVKPSETLSLTCKAS***GFSFSSGYDMC***WVRQPPGKGLEWIA***CVVAGSVDITYYASWAKG***RVTISKDSSKNQVSLKLSSVTAADTAVYYCA***RKDAYSDAFNL***WGQGTLVTVSS |
| SEQ ID NO: 135 | LCDR1 (L24-L42; AHo numbering) (Kabat definition) | QASQSINDYLA |
| SEQ ID NO: 136 | LCDR2 (L58-L72; AHo numbering) (Kabat definition) | KASTLAS |
| SEQ ID NO: 137 | LCDR3 (L107-L138; AHo numbering) (Kabat definition) | QQGYIITDIDNV |
| SEQ ID NO: 138 | LCDR1 (AHo definition) | AHo: ASQSINDY |
| SEQ ID NO: 139 | LCDR2 (AHo definition) | AHo: KASTLASGVPSR |
| SEQ ID NO: 140 | LCDR3 (AHo definition) | AHo: GYIITDIDN |
| SEQ ID NO: 141 | LCDR1 (Chothia definition) | SQSINDY |
| SEQ ID NO: 142 | LCDR2 (Chothia definition) | KAS |
| SEQ ID NO: 143 | LCDR3 (Chothia definition) | GYIITDIDN |
| SEQ ID NO: 144 | VL (Vk1-sk17) (33-03-G02 sc01) (33-03-G02 sc18) | DIQMTQSPSSLSASVGDRVTITC***QASQSINDYLA***WYQQKPGKAPKLLIY***KASTLAS***GVPSRFSGSGSGTDFTLTISSLQPEDFATYYC***QQGYIITDIDNV***FGTGTKVTVLG |
| SEQ ID NO: 145 | VL (Vk1-sk17) (33-03-G02 sc03 Full) (Mutations VL: I2F; M4L; A51P) | DFQLTQSPSSLSASVGDRVTITC***QASQSINDYLA***WYQQKPGKSPKLLIY***KASTLAS***GVPSRFSGSGSGTDFTLTISSLQPEDFATYYC***QQGYIITDIDNV***FGTGTKVTVLG |
| SEQ ID NO: 146 | scFv (VL-linker-VH) (33-03-G02 sc01) (PRO830) | DIQMTQSPSSLSASVGDRVTITC***QASQSINDYLA***WYQQKPGKAPKLLIY***KASTLAS***GVPSRFSGSGSGTDFTLTISSLQPEDFATYYC***QQGYIITDIDNV***FGTGTKVTVLGGGGGSGGGGSGGGGSGGGGSQVQLQESGPGLVKPSETLSLTCKVS***GFSFSSGYDMC***WIRQPPGKGLEWIG***CVVAGSVDITYYASWAKG***RVTISVDSSKNQFSLKLSSVTAADTAVYYCA***RKDAYSDAFNL***WGQGTLVTVSS |
| SEQ ID NO: 147 | scFv (VL-linker-VH) (33-03-G02 sc03 Full) | DFQLTQSPSSLSASVGDRVTITC***QASQSINDYLA***WYQQKPGKSPKLLIY***KASTLAS***GVPSRFSGSGSGTDFTLTISSLQPEDFATYYC***QQGYIITDIDNV***FGTGTKVTVLGGGGGSGGGGSGGGGSGGGGSQSQLQESGPGLVKPSETLSLTCKAS***GFSFSSGYDMC***WVRQPPGKGLEWIA***CVVAGSVDITYYASWAKG***RVTISKDSSKNQVSLKLSSVTAADTAVYFCA***RKDAYSDAFNL***WGQGTLVTVSS |

TABLE 2-continued

| Examples of PDL1 binding domains of the present invention (CDR residues shown in bold and italic letters). | | |
|---|---|---|
| SEQ ID NUMBER | Ab region | Sequence |
| SEQ ID NO: 148 | scFv (VL-linker-VH) (33-03-G02 sc18) | DIQMTQSPSSLSASVGDRVTITC***QASQSINDYLA***WYQQKPGKAPKLLIY***KASTLAS***GVPSRFSGSGSGTDFTLTISSLQPEDFATYYC***QQGYIITDIDNV***FGTGTKVTVLGGGGGSGGGGSGGGGSGGGGSQVQLQESGPGLVKPSETLSLTCKAS***GFSFSSGYDMC***WVRQPPGKGLEWIA***CVVAGSVDITYYASWAKG***RVTISKDSSKNQVSLKLSSVTAADTAVYYCA***RKDAYSDAFNL***WGQGTLVTVSS |

TABLE 3

| Examples of human serum albumin binding domains of the present invention (CDR residues shown in bold and italic letters). | | |
|---|---|---|
| SEQ ID NUMBER | Ab region | Sequence |
| | | 19-01-H04 sc03 |
| SEQ ID NO: 149 | HCDR1 (H27-H42; AHo numbering) | GFSLSSNAMG |
| SEQ ID NO: 150 | HCDR2 (H57-H76; AHo numbering) | IISVGGFTYYASWAKG |
| SEQ ID NO: 151 | HCDR3 (H108-H138; AHo numbering) | RDRHGGDSSGAFYL |
| SEQ ID NO: 152 | HCDR1 (AHo definition) | ASGFSLSSNA |
| SEQ ID NO: 153 | HCDR2 (AHo definition) | ISVGGFTYYASWAKGR |
| SEQ ID NO: 154 | HCDR3 (AHo definition) | DRHGGDSSGAFY |
| SEQ ID NO: 155 | HCDR1 (Kabat definition) | SNAMG |
| SEQ ID NO: 156 | HCDR2 (Kabat definition) | IISVGGFTYYASWAKG |
| SEQ ID NO: 157 | HCDR3 (Kabat definition) | DRHGGDSSGAFYL |
| SEQ ID NO: 158 | HCDR1 (Chothia definition) | GFSLSSN |
| SEQ ID NO: 159 | HCDR2 (Chothia definition) | VGG |
| SEQ ID NO: 160 | HCDR3 (Chothia definition) | RDRHGGDSSGAFY |
| SEQ ID NO: 161 | VH | EVQLVESGGGLVQPGGSLRLSCAAS***GFSLSSNAMG***WVRQAPGKGLEYIG***IISVGGFTYYASWAKG***RFTISRDNSKNTVYLQMNSLRAEDTATYFCA***RDRHGGDSSGAFYL***WGQGTLVTVSS |
| SEQ ID NO: 162 | LCDR1 (L24-L42; AHo numbering) (Kabat definition) | QSSESVYSNNQLS |
| SEQ ID NO: 163 | LCDR2 (L58-L72; AHo numbering) (Kabat definition) | DASDLAS |
| SEQ ID NO: 164 | LCDR3 (L107-L138; AHo numbering) (Kabat definition) | AGGFSSSSDTA |

TABLE 3-continued

Examples of human serum albumin binding domains of the present invention (CDR residues shown in bold and italic letters).

| SEQ ID NUMBER | Ab region | Sequence |
|---|---|---|
| SEQ ID NO: 165 | LCDR1 (AHo definition) | SSESVYSNNQ |
| SEQ ID NO: 166 | LCDR2 (AHo definition) | DASDLASGVPSR |
| SEQ ID NO: 167 | LCDR3 (AHo definition) | GFSSSSDT |
| SEQ ID NO: 168 | LCDR1 Chothia definition) | SESVYSNNQ |
| SEQ ID NO: 169 | LCDR2 (Chothia definition) | DAS |
| SEQ ID NO: 170 | LCDR3 (Chothia definition) | GFSSSSDT |
| SEQ ID NO: 171 | VL | DIQMTQSPSSLSASVGDRVTITC***QSSESVYSNNQLS***WYQQKPGQPPKLLIY***DASDLAS***GVPSRFSGSGSGTDFTLTISSLQPEDFATYYC***AGGFSSSSDTA***FGGGTKLTVLG |
| SEQ ID NO: 172 | scFv (VL-linker-VH) | DIQMTQSPSSLSASVGDRVTITC***QSSESVYSNNQLS***WYQQKPGQPPKLLIY***DASDLAS***GVPSRFSGSGSGTDFTLTISSLQPEDFATYYC***AGGFSSSSDTA***FGGGTKLTVLGGGGGSGGGGSGGGGSGGGGSEVQLVESGGGLVQPGGSLRLSCAAS***GFSLSSNAMG***WVRQAPGKGLEYIG***IISVGGFTYYASWAKG***RFTISRDNSKNTVYLQMNSLRAEDTATYFCA***RDRHGGDSSGAFYL***WGQGTLVTVSS |
| | | 23-13-A01 sc03 |
| SEQ ID NO: 173 | HCDR1 (H27-H42; AHo numbering) | GFSFSSSYWIC |
| SEQ ID NO: 174 | HCDR2 (H57-H76; AHo numbering) | CVFTGDGTTYYASWAKG |
| SEQ ID NO: 175 | HCDR3 (H108-H138; AHo numbering) | RPVSVYYYGMDL |
| SEQ ID NO: 176 | HCDR1 (AHo definition) | ASGFSFSSSYW |
| SEQ ID NO: 177 | HCDR2 (AHo definition) | VFTGDGTTYYASWAKGR |
| SEQ ID NO: 178 | HCDR3 (AHo definition) | PVSVYYYGMD |
| SEQ ID NO: 179 | HCDR1 (Kabat definition) | SSYWIC |
| SEQ ID NO: 180 | HCDR2 (Kabat definition) | CVFTGDGTTYYASWAKG |
| SEQ ID NO: 181 | HCDR3 (Kabat definition) | PVSVYYYGMDL |
| SEQ ID NO: 182 | HCDR1 (Chothia definition) | GFSFSSSYW |
| SEQ ID NO: 183 | HCDR2 (Chothia definition) | TGDG |
| SEQ ID NO: 184 | HCDR3 (Chothia definition) | VSVYYYGMD |
| SEQ ID NO: 185 | VH | EVQLVESGGGLVQPGGSLRLSCAAS***GFSFSSSYWIC***WVRQAPGKGLEWVG***CVFTGDGTTYYASWAKG***RFTISRDNSKNTVYLQMNSLRAEDTATYFCA***RPVSVYYYGMDL***WGQGTLVTVSS |
| SEQ ID NO: 186 | LCDR1 (L24-L42; AHo numbering) (Kabat definition) | QASQIISSRSA |

TABLE 3-continued

Examples of human serum albumin binding domains of the present invention (CDR residues shown in bold and italic letters).

| SEQ ID NUMBER | Ab region | Sequence |
|---|---|---|
| SEQ ID NO: 187 | LCDR2 (L58-L72; AHo numbering) (Kabat definition) | QASKLAS |
| SEQ ID NO: 188 | LCDR3 (L107-L138; AHo numbering) (Kabat definition) | QCTYIDSNFGA |
| SEQ ID NO: 189 | LCDR1 (AHo definition) | ASQIISSR |
| SEQ ID NO: 190 | LCDR2 (AHo definition) | QASKLASGVPSR |
| SEQ ID NO: 191 | LCDR3 (AHo definition) | TYIDSNFG |
| SEQ ID NO: 192 | LCDR1 (Chothia definition) | SQIISSR |
| SEQ ID NO: 193 | LCDR2 (Chothia definition) | QAS |
| SEQ ID NO: 194 | LCDR3 (Chothia definition) | TYIDSNFG |
| SEQ ID NO: 195 | VL | DVVMTQSPSSLSASVGDRVTITC***QASQIISSRSA***WYQQKPGQPPKLLIY***QASKLAS***GVPSRFSGSGSGTDFTLTISSLQPEDFATYYC***QCTYIDSNFGA***FGGGTKLTVLG |
| SEQ ID NO: 196 | scFv (VL-linker-VH) | DVVMTQSPSSLSASVGDRVTITC***QASQIISSRSA***WYQQKPGQPPKLLIY***QASKLAS***GVPSRFSGSGSGTDFTLTISSLQPEDFATYYC***QCTYIDSNFGA***FGGGTKLTVLGGGGGSGGGGSGGGGSGGGGSEVQLVESGGGLVQPGGSLRLSCAAS***GFSFSSSYWIC***WVRQAPGKGLEWVG***CVFTGDGTTYYASWAKG***RFTISRDNSKNTVYLQMNSLRAEDTATYFCA***RPVSVYYYGMDL***WGQGTLVTVSS |

TABLE 4

Other sequences related to the present invention.

| SEQ ID NUMBER | Ab region | Sequence |
|---|---|---|
| SEQ ID NO: 197 | Human CD 137 | MGNSCYNIVATLLLVLNFERTRSLQDPCSNCPAGTFCDNNRNQICSPCPPNSFSSAGGQRTCDICRQCKGVFRTRKECSSTSNAECDCTPGFHCLGAGCSMCEQDCKQGQELTKKGCKDCCFGTFNDQKRGICRPWTNCSLDGKSVLVNGTKERDVVCGPSPADLSPGASSVTPPAPAREPGHSPQIISFFLALTSTALLFLLFFLTLRFSVVKRGRKKLLYIFKQPFMRPVQTTQEEDGCSCRFPEEEEGGCEL |

TABLE 4-continued

Other sequences related to the present invention.

| SEQ ID NUMBER | Ab region | Sequence |
|---|---|---|
| SEQ ID NO: 198 | Human PDL1 | MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNERTHLVILGAILLCLGVALTFIFRLRKGRMMDVKKCGIQDTNSKKQSDTHLEET |

TABLE 4-continued

Other sequences related to the present invention.

| SEQ ID NUMBER | Ab region | Sequence |
|---|---|---|
| SEQ ID NO: 199 | Vλ germline-based FR4 (Sk17) | FGTGTKVTVLG |
| SEQ ID NO: 200 | Vλ germline-based FR4 (Sk12) | FGGGTKLTVLG |
| SEQ ID NO: 201 | Vλ germline-based FR4 | FGGGTQLIILG |
| SEQ ID NO: 202 | Vλ germline-based FR4 | FGEGTELTVLG |
| SEQ ID NO: 203 | Vλ germline-based FR4 | FGSGTKVTVLG |
| SEQ ID NO: 204 | Vλ germline-based FR4 | FGGGTQLTVLG |
| SEQ ID NO: 205 | Vλ germline-based FR4 | FGGGTQLTALG |
| SEQ ID NO: 206 | Linker | GGGGSGGGGSGGGGSGGGGS |
| SEQ ID NO: 207 | Linker | GGGGS |
| SEQ ID NO: 208 | Linker | GGGGSGGGGS |

TABLE 5

Examples of multispecific molecules and IgGs of the present invention.

| SEQ ID NUMBER | Ab Format | Sequence |
|---|---|---|
| PRO885 (38-02-A04 sc01 scDb-i/33-03-G02 sc01 scDb-o) | | |
| SEQ ID NO: 209 | scDb | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG**GGGGS**QVQLQESGPGLVKPSETLSLTCKVSGFSFSNSYWICWIRQPPGKGLEWIGCTFVGSSDSTYYANWAKGRVTISVDSSKNQFSLKLSSVTAADTAVYYCARHPSDAVYGYANNLWGQGTLVTVSS**GGGGSGGGGSGGGGSGGGGS**IQMTQSPSSLSASVGDRVTITCQASQSINNVLAWYQQKPGKAPKLLIYRASTLASGVPSRFSGSGSGTDFTLTISSLQPEDFATYYCQSSYGNYGDFGTGTKVTVLG**GGGGS**QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |
| PRO951 (38-27-C05 sc02 scDb-i/33-03-G02 sc01 scDb-o) | | |
| SEQ ID NO: 210 | scDb | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG**GGGGS**EVQLVESGGGLVQPGGSLRLSCAASGFSFNNDYDMCWVRQAPGKGLEWIGCIDTGDGSTYYASWAKGRFTISRDNSKNTVYLQMNSLRAEDTAVYYCAREAASSGYGMGYFDLWGQGTLVTVSS**GGGGSGGGGSGGGGSGGGGS**IQMTQSPSSLSASVGDRVTITCQSSQSVYDNNWLAWYQQKPGKAPKLLIYRASNLASGVPSRFSGSGSGTDFTLTISSLQPEDFATYYCQGTYLSSNWYWAFGTGTKVTVLG**GGGGS**QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |
| PRO1123 (38-02-A04 sc05 IF scDb-i/33-03-G02 sc01 scDb-o) | | |
| SEQ ID NO: 211 | scDb | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG**GGGGS**QVQLQESGPGLVKPSETLSLTCKVSGFSFSNSYWICWVRQPPGKGLEWIGCTFVGSSDSTYYANWAKGRVTISVDSSKNQVSLKLSSVTAADTAVYFCARHPSDAVYGYANNLWGQGTLVTVSS**GGGGSGGGGSGGGGSGGGGS**IQMTQSPSSLSASVGDRVTITCQASQSINNVLAWYQQKPGKPPKLLIYRASTLASGVPSRFSGSGSGTDFTLTISSLQPEDFATYYCQSSYGNYGDFGTGTKVTVLG**GGGGS**QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |
| PRO1124 (38-02-A04 sc06 Full scDb-i/33-03-G02 sc01 scDb-o) | | |
| SEQ ID NO: 212 | scDb | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG**GGGGS**QVQLQESGPGLVKPSETLSLTCKASGFSFSNSYWICWVRQPPGKGLEWIGCTFVGSSDSTYYANWAKGRVTISKDSSKNQVSLKLSSVTAADTAVYFCARHPSDAVYGYANNLWGQGTLVTVSS**GGGGSGGGGSGGGGSGGGGS**LQMTQSPSSLSASVGDRVTITCQASQSINNVLAWYQQKPGKPPKLLIYRASTLASGVPSRFSGSGSGTDFTLTISSLQPEDFATYYCQSSYGNYGDFGTGTKVTVLG**GGGGS**QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |

TABLE 5-continued

Examples of multispecific molecules and IgGs of the present invention.

| SEQ ID NUMBER | Ab Format | Sequence |
|---|---|---|
| PRO1125 (38-02-A04 sc01 scDb-i/33-03-G02 sc02 IF scDb-o) | | |
| SEQ ID NO: 213 | scDb | DIQMTQSPSSLSASVGDRVTITCQASQSINDYLAWYQQKPGKSPKLLIYKASTLAS<br>GVPSRFSGSGSGTDFTLTISSLQPEDFATYYCQQGYIITDIDNVFGTGTKVTVLG**GG**<br>**GGS**QVQLQESGPGLVKPSETLSLTCKVSGFSFSNSYWICWIRQPPGKGLEWIGCTF<br>VGSSDSTYYANWAKGRVTISVDSSKNQFSLKLSSVTAADTAVYYCARHPSDAVY<br>GYANNLWGQGTLVTVSS**GGGGSGGGGSGGGGSGGGGS**IQMTQSPSSLSASVG<br>DRVTITCQASQSINNVLAWYQQKPGKAPKLLIYRASTLASGVPSRFSGSGSGTDFT<br>LTISSLQPEDFATYYCQSSYGNYGDFGTGTKVTVLG**GGGGS**QVQLQESGPGLVK<br>PSETLSLTCKVSGFSFSSGYDMCWVRQPPGKGLEWIACVVAGSVDITYYASWAK<br>GRVTISVDSSKNQFSLKLSSVTAADTAVYFCARKDAYSDAFNLWGQGTLVTVSS |
| PRO1126 (38-02-A04 sc01 scDb-i/33-03-G02 sc03 Full scDb-o) | | |
| SEQ ID NO: 214 | scDb | DFQLTQSPSSLSASVGDRVTITCQASQSINDYLAWYQQKPGKSPKLLIYKASTLAS<br>GVPSRFSGSGSGTDFTLTISSLQPEDFATYYCQQGYIITDIDNVFGTGTKVTVLG**GG**<br>**GGS**QVQLQESGPGLVKPSETLSLTCKVSGFSFSNSYWICWIRQPPGKGLEWIGCTF<br>VGSSDSTYYANWAKGRVTISVDSSKNQFSLKLSSVTAADTAVYYCARHPSDAVY<br>GYANNLWGQGTLVTVSS**GGGGSGGGGSGGGGSGGGGS**IQMTQSPSSLSASVG<br>DRVTITCQASQSINNVLAWYQQKPGKAPKLLIYRASTLASGVPSRFSGSGSGTDFT<br>LTISSLQPEDFATYYCQSSYGNYGDFGTGTKVTVLG**GGGGS**QSQLQESGPGLVKP<br>SETLSLTCKASGFSFSSGYDMCWVRQPPGKGLEWIACVVAGSVDITYYASWAKG<br>RVTISKDSSKNQVSLKLSSVTAADTAVYFCARKDAYSDAFNLWGQGTLVTVSS |
| PRO1134 (38-02-A04 sc01 scDb-i/33-03-G02 sc07 GL VH3 scDb-o) | | |
| SEQ ID NO: 215 | scDb | DIQMTQSPSSLSASVGDAVTITCQASQSINDYLAWYQQKPGKSPKLLIYKASTLAS<br>GVPSRFSGSGSGTDFTLTISSLQPEDFATYYCQQGYIITDIDNVFGTGTKVTVLG**GG**<br>**GGS**QVQLQESGPGLVKPSETLSLTCKVSGFSFSNSYWICWIRQPPGKGLEWIGCTF<br>VGSSDSTYYANWAKGRVTISVDSSKNQFSLKLSSVTAADTAVYYCARHPSDAVY<br>GYANNLWGQGTLVTVSS**GGGGSGGGGSGGGGSGGGGS**IQMTQSPSSLSASVG<br>DRVTITCQASQSINNVLAWYQQKPGKAPKLLIYRASTLASGVPSRFSGSGSGTDFT<br>LTISSLQPEDFATYYCQSSYGNYGDFGTGTKVTVLG**GGGGS**EVQLVESGGGLVQ<br>PGGSLRLSCAASGFSFSSGYDMCWVRQAPGKGLEWVGCVVAGSVDITYYASWA<br>KGRFTISRDNSKNTVYLQMNSLRAEDTATYYCARKDAYSDAFNLWGPGTLVTVS<br>S |
| PRO963 (= PRO1051) (38-02-A04 sc01 scDb-i/33-03-G02 sc01 scDb-o/19-01-H04-sc03 scFv) | | |
| SEQ ID NO: 216 | scDb-scFv | DIQMTQSPSSLSASVGDRVTITCQASQSINDYLAWYQQKPGKAPKLLIYKASTLAS<br>GVPSRFSGSGSGTDFTLTISSLQPEDFATYYCQQGYIITDIDNVFGTGTKVTVLG**GG**<br>**GGS**QVQLQESGPGLVKPSETLSLTCKVSGFSFSNSYWICWIRQPPGKGLEWIGCTF<br>VGSSDSTYYANWAKGRVTISVDSSKNQFSLKLSSVTAADTAVYYCARHPSDAVY<br>GYANNLWGQGTLVTVSS**GGGGSGGGGSGGGGSGGGGS**IQMTQSPSSLSASVG<br>DRVTITCQASQSINNVLAWYQQKPGKAPKLLIYRASTLASGVPSRFSGSGSGTDFT<br>LTISSLQPEDFATYYCQSSYGNYGDFGTGTKVTVLG**GGGGS**QVQLQESGPGLVK<br>PSETLSLTCKVSGFSFSSGYDMCWIRQPPGKGLEWIGCVVAGSVDITYYASWAKG<br>RVTISVDSSKNQFSLKLSSVTAADTAVYYCARKDAYSDAFNLWGQGTLVTVSS**G**<br>**GGGSGGGGS**IQMTQSPSSLSASVGDRVTITCQSSESVYSNNQLSWYQQKPGQPPK<br>LLIYDASDLASGVPSRFSGSGSGTDFTLTISSLQPEDFATYYCAGGFSSSSDTAFGG<br>GTKLTVLG**GGGGSGGGGSGGGGSGGGGS**EVQLVESGGGLVQPGGSLRLSCAA<br>SGFSLSSNAMGWVRQAPGKGLEYIGIISVGGFTYYASWAKGRFTISRDNSKNTVY<br>LQMNSLRAEDTATYFCARDRHGGDSSGAFYLWGQGTLVTVSS |
| PRO966 (= PRO1052) (38-27-C05 sc01 scDb-i/33-03-G02 sc01 scDb-o/19-01-H04-sc03 scFv) | | |
| SEQ ID NO: 217 | scDb-scFv | DIQMTQSPSSLSASVGDRVTITCQASQSINDYLAWYQQKPGKAPKLLIYKASTLAS<br>GVPSRFSGSGSGTDFTLTISSLQPEDFATYYCQQGYIITDIDNVFGTGTKVTVLG**GG**<br>**GGS**QVQLQESGPGLVKPSETLSLTCKVSGFSFNNDYDMCWIRQPPGKGLEWIGCI<br>DTGDGSTYYASWAKGRVTISVDSSKNQFSLKLSSVTAADTAVYYCAREAASSSG<br>YGMGYFDLWGQGTLVTVSS**GGGGSGGGGSGGGGSGGGGS**IQMTQSPSSLSAS<br>VGDRVTITCQSSQSVYDNNWLAWYQQKPGKAPKLLIYRASNLASGVPSRFSGSG<br>SGTDFTLTISSLQPEDFATYYCQGTYLSSNWYWAFGTGTKVTVLG**GGGGS**QVQL<br>QESGPGLVKPSETLSLTCKVSGFSFSSGYDMCWIRQPPGKGLEWIGCVVAGSVDIT<br>YYASWAKGRVTISVDSSKNQFSLKLSSVTAADTAVYYCARKDAYSDAFNLWGQ<br>GTLVTVSS**GGGGSGGGGS**IQMTQSPSSLSASVGDRVTITCQSSESVYSNNQLSWY<br>QQKPGQPPKLLIYDASDLASGVPSRFSGSGSGTDFTLTISSLQPEDFATYYCAGGFS<br>SSSDTAFGGGTKLTVLG**GGGGSGGGGSGGGGSGGGGS**EVQLVESGGGLVQPG<br>GSLRLSCAASGFSLSSNAMGWVRQAPGKGLEYIGIISVGGFTYYASWAKGRFTISR<br>DNSKNTVYLQMNSLRAEDTATYFCARDRHGGDSSGAFYLWGQGTLVTVSS |

TABLE 5-continued

Examples of multispecific molecules and IgGs of the present invention.

| SEQ ID NUMBER | Ab Format | Sequence |
|---|---|---|
| PRO1057 (38-02-A04 sc01 scDb-i/33-03-G02 sc01 scDb-o/23-12-A01-sc03, sk17sh4) | | |
| SEQ ID NO: 218 | scDb-scFv | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG**GGGGS**QVQLQESGPGLVKPSETLSLTCKVSGFSFSNSYWICWIRQPPGKGLEWIGCTFVGSSDSTYYANWAKGRVTISVDSSKNQFSLKLSSVTAADTAVYYCARHPSDAVYGYANNLWGQGTLVTVSS**GGGGSGGGGSGGGGSGGGGS**IQMTQSPSSLSASVGDRVTITCQASQSINNVLAWYQQKPGKAPKLLIYRASTLASGVPSRFSGSGSGTDFTLTISSLQPEDFATYYCQSSYGNYGDFGTGTKVTVLG**GGGGS**QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS**GGGGSGGGGS**VVMTQSPSSLSASVGDRVTITCQASQIISSRSAWYQQKPGQPPKLLIYQASKLASGVPSRFSGSGSGTDFTLTISSLQPEDFATYYCQCTYIDSNFGAFGGGTKLTVLG**GGGGSGGGGSGGGGSGGGGS**EVQLVESGGGLVQPGGSLRLSCAASGFSFSSSYWICWVRQAPGKGLEWVGCVFTGDGTTYYASWAKGRFTISRDNSKNTVYLQMNSLRAEDTATYFCARPVSVYYYGMDLWGQGTLVTVSS |
| PRO1058 (38-27-C05 sc01 scDb-i/33-03-G02 sc01 scDb-o/23-13-A01-sc03, sk17sh4) | | |
| SEQ ID NO: 219 | scDb-scFv | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG**GGGGS**QVQLQESGPGLVKPSETLSLTCKVSGFSFNNDYDMCWIRQPPGKGLEWIGCIDTGDGSTYYASWAKGRVTISVDSSKNQFSLKLSSVTAADTAVYYCAREAASSSGYGMGYFDLWGQGTLVTVSS**GGGGSGGGGSGGGGSGGGGS**IQMTQSPSSLSASVGDRVTITCQSSQSVYDNNWLAWYQQKPGKAPKLLIYRASNLASGVPSRFSGSGSGTDFTLTISSLQPEDFATYYCQGTYLSSNWYWAFGTGTKVTVLG**GGGGS**QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS**GGGGSGGGGS**VVMTQSPSSLSASVGDRVTITCQASQIISSRSAWYQQKPGQPPKLLIYQASKLASGVPSRFSGSGSGTDFTLTISSLQPEDFATYYCQCTYIDSNFGAFGGGTKLTVLG**GGGGSGGGGSGGGGSGGGGS**EVQLVESGGGLVQPGGSLRLSCAASGFSFSSSYWICWVRQAPGKGLEWVGCVFTGDGTTYYASWAKGRFTISRDNSKNTVYLQMNSLRAEDTATYFCARPVSVYYYGMDLWGQGTLVTVSS |
| PRO1175 (37-20-B03-sc01-o/38-02-A04 sc01-i/19-01-H04sc03 scFv) | | |
| SEQ ID NO: 220 | scDb-scFv | DIQMTQSPSSLSASVGDRVTITCQASQSIGTYLAWYQQKPGKAPKLLIYRAFILASGVPSRFSGSGSGTDFTLTISSLQPEDFATYYCQSNFYSDSTTIGPNAFGTGTKVTVLG**GGGGS**QVQLQESGPGLVKPSETLSLTCKVSGFSFSNSYWICWIRQPPGKGLEWIGCTFVGSSDSTYYANWAKGRVTISVDSSKNQFSLKLSSVTAADTAVYYCARHPSDAVYGYANNLWGQGTLVTVSS**GGGGSGGGGSGGGGSGGGGS**IQMTQSPSSLSASVGDRVTITCQASQSINNVLAWYQQKPGKAPKLLIYRASTLASGVPSRFSGSGSGTDFTLTISSLQPEDFATYYCQSSYGNYGDFGTGTKVTVLG**GGGGS**QVQLQESGPGLVKPSETLSLTCKVSGFSFNSDYWIYWIRQPPGKGLEWIGSIYGGSSGNTQYASWAQGRVTISVDSSKNQFSLKLSSVTAADTAVYYCARGYVDYGGATDLWGQGTLVTVSS**GGGGSGGGGS**IQMTQSPSSLSASVGDRVTITCQSSESVYSNNQLSWYQQKPGQPPKLLIYDASDLASGVPSRFSGSGSGTDFTLTISSLQPEDFATYYCAGGFSSSSDTAFGGGTKLTVLG**GGGGSGGGGSGGGGSGGGGS**EVQLVESGGGLVQPGGSLRLSCAASGFSLSSNAMGWVRQAPGKGLEYIGIISVGGFTYYASWAKGRFTISRDNSKNTVYLQMNSLRAEDTATYFCARDRHGGDSSGAFYLWGQGTLVTVSS |
| PRO1186 (38-02-A04 sc01 scDb-i/37-20-B03sc01 scDb-o/23-13-A01-sc03 scFv) | | |
| SEQ ID NO: 221 | scDb-scFv | DIQMTQSPSSLSASVGDRVTITCQASQSIGTYLAWYQQKPGKAPKLLIYRAFILASGVPSRFSGSGSGTDFTLTISSLQPEDFATYYCQSNFYSDSTTIGPNAFGTGTKVTVLG**GGGGS**QVQLQESGPGLVKPSETLSLTCKVSGFSFSNSYWICWIRQPPGKGLEWIGCTFVGSSDSTYYANWAKGRVTISVDSSKNQFSLKLSSVTAADTAVYYCARHPSDAVYGYANNLWGQGTLVTVSS**GGGGSGGGGSGGGGSGGGGS**DIQMTQSPSSLSASVGDRVTITCQASQSINNVLAWYQQKPGKAPKLLIYRASTLASGVPSRFSGSGSGTDFTLTISSLQPEDFATYYCQSSYGNYGDFGTGTKVTVLG**GGGGS**QVQLQESGPGLVKPSETLSLTCKVSGFSFNSDYWIYWIRQPPGKGLEWIGSIYGGSSGNTQYASWAQGRVTISVDSSKNQFSLKLSSVTAADTAVYYCARGYVDYGGATDLWGQGTLVTVSS**GGGGSGGGGS**VVMTQSPSSLSASVGDRVTITCQASQIISSRSAWYQQKPGQPPKLLIYQASKLASGVPSRFSGSGSGTDFTLTISSLQPEDFATYYCQCTYIDSNFGAFGGGTKLTVLG**GGGGSGGGGSGGGGSGGGGS**EVQLVESGGGLVQPGGSLRLSCAASGFSFSSSYWICWVRQAPGKGLEWVGCVFTGDGTTYYASWAKGRFTISRDNSKNTVYLQMNSLRAEDTATYFCARPVSVYYYGMDLWGQGTLVTVSS |
| PRO1430 (38-02-A04 sc 13 scDb-i/37-20-B03 sc01 scDb-o/19-01-H04 sc03 scFv) | | |
| SEQ ID NO: 222 | scDb-scFv | DIQMTQSPSSLSASVGDRVTITCQASQSIGTYLAWYQQKPGKAPKLLIYRAFILASGVPSRFSGSGSGTDFTLTISSLQPEDFATYYCQSNFYSDSTTIGPNAFGTGTKVTVLG**GGGGS**EVQLVESGGGLVQPGGSLRLSCAASGFSFSNSYWICWVRQAPGKCLEWIGCTFVGSSDSTYYANWAKGRFTISRDNSKNTVYLQMNSLRAEDTAVYYCARHPSDAVYGYANNLWGQGTLVTVSS**GGGGSGGGGSGGGGSGGGGS**IQMTQSPSS |

TABLE 5-continued

| Examples of multispecific molecules and IgGs of the present invention. | | |
|---|---|---|
| SEQ ID NUMBER | Ab Format | Sequence |
| | | LSASVGDRVTITCQASQSINNVLAWYQQKPGKAPKLLIYRASTLASGVPSRFSGSG<br>SGTDFTLTISSLQPEDFATYYCQSSYGNYGDFGCGTKVTVLG**GGGGS**QVQLQESG<br>PGLVKPSETLSLTCKVSGFSFNSDYWIYWIRQPPGKGLEWIGSIYGGSSGNTQYAS<br>WAQGRVTISVDSSKNQFSLKLSSVTAADTAVYYCARGYVDYGGATDLWGQGTL<br>VTVSS**GGGGSGGGGS**IQMTQSPSSLSASVGDRVTITCQSSESVYSNNQLSWYQQ<br>KPGQPPKLLIYDASDLASGVPSRFSGSGSGTDFTLTISSLQPEDFATYYCAGGFSSS<br>SDTAFGGGTKLTVLG**GGGGSGGGGSGGGGSGGGGS**EVQLVESGGGLVQPGGS<br>LRLSCAASGFSLSSNAMGWVRQAPGKGLEYIGIISVGGFTYYASWAKGRFTISRD<br>NSKNTVYLQMNSLRAEDTATYFCARDRHGGDSSGAFYLWGQGTLVTVSS |
| PRO1479 (38-02-A04 sc 13 scDb-i/37-20-B03 sc09.1 scDb-o/19-01-H04 sc03 scFv) | | |
| SEQ ID NO: 223 | scDb-scFv | DIQMTQSPASLSASVGDRVTITCQASQSIGTYLAWYQQKPGKPPKLLIYRAFILAS<br>GVPSRFSGSGSGTDFTLTISSLQPEDFATYYCQSNFYSDSTTIGPNAFGTGTKVTVL<br>G**GGGGS**EVQLVESGGGLVQPGGSLRLSCAASGFSFSNSYWICWVRQAPGKCLE<br>WIGCTFVGSSDSTYYANWAKGRFTISRDNSKNTVYLQMNSLRAEDTAVYYCARH<br>PSDAVYGYANNLWGQGTLVTVSS**GGGGSGGGGSGGGGSGGGGS**IQMTQSPSS<br>LSASVGDRVTITCQASQSINNVLAWYQQKPGKAPKLLIYRASTLASGVPSRFSGSG<br>SGTDFTLTISSLQPEDFATYYCQSSYGNYGDFGCGTKVTVLG**GGGGS**EVQLVESG<br>GGLVQPGGSLRLSCAASGFSFNSDYWIYWVRQAPGKGLEWIASIYGGSSGNTQY<br>ASWAQGRFTISRDNSKNTVYLQMNSLRAEDTAVYFCARGYVDYGGATDLWGQ<br>GTLVTVSS**GGGGSGGGGS**IQMTQSPSSLSASVGDRVTITCQSSESVYSNNQLSWY<br>QQKPGQPPKLLIYDASDLASGVPSRFSGSGSGTDFTLTISSLQPEDFATYYCAGGFS<br>SSSDTAFGGGTKLTVLG**GGGGSGGGGSGGGGSGGGGS**EVQLVESGGGLVQPG<br>GSLRLSCAASGFSLSSNAMGWVRQAPGKGLEYIGIISVGGFTYYASWAKGRFTISR<br>DNSKNTVYLQMNSLRAEDTATYFCARDRHGGDSSGAFYLWGQGTLVTVSS |
| PRO1482 (37-20-B03 sc09.1 scDb-i/38-02-A04 sc13 scDb-o//19-01-H04 sc03 scFv) | | |
| SEQ ID NO: 224 | scDb-scFv | DIQMTQSPSSLSASVGDRVTITCQASQSINNVLAWYQQKPGKAPKLLIYRASTLAS<br>GVPSRFSGSGSGTDFTLTISSLQPEDFATYYCQSSYGNYGDFGCGTKVTVLG**GGG**<br>**GS**EVQLVESGGGLVQPGGSLRLSCAASGFSFNSDYWIYWVRQAPGKGLEWIASIY<br>GGSSGNTQYASWAQGRFTISRDNSKNTVYLQMNSLRAEDTAVYFCARGYVDYG<br>GATDLWGQGTLVTVSS**GGGGSGGGGSGGGGSGGGGS**IQMTQSPASLSASVGD<br>RVTITCQASQSIGTYLAWYQQKPGKPPKLLIYRAFILASGVPSRFSGSGSGTDFTLT<br>ISSLQPEDFATYYCQSNFYSDSTTIGPNAFGTGTKVTVLG**GGGGS**EVQLVESGGG<br>LVQPGGSLRLSCAASGFSFSNSYWICWVRQAPGKCLEWIGCTFVGSSDSTYYAN<br>WAKGRFTISRDNSKNTVYLQMNSLRAEDTAVYYCARHPSDAVYGYANNLWGQ<br>GTLVTVSS**GGGGSGGGGS**IQMTQSPSSLSASVGDRVTITCQSSESVYSNNQLSWY<br>QQKPGQPPKLLIYDASDLASGVPSRFSGSGSGTDFTLTISSLQPEDFATYYCAGGFS<br>SSSDTAFGGGTKLTVLG**GGGGSGGGGSGGGGSGGGGS**EVQLVESGGGLVQPG<br>GSLRLSCAASGFSLSSNAMGWVRQAPGKGLEYIGIISVGGFTYYASWAKGRFTISR<br>DNSKNTVYLQMNSLRAEDTATYFCARDRHGGDSSGAFYLWGQGTLVTVSS |
| PRO1431 (38-02-A04 sc13 scDb-i/33-03-G02 sc18 scDb-o/19-01-H04 sc03 scFv) | | |
| SEQ ID NO: 225 | scDb-scFv | DIQMTQSPSSLSASVGDRVTITCQASQSINDYLAWYQQKPGKAPKLLIYKASTLAS<br>GVPSRFSGSGSGTDFTLTISSLQPEDFATYYCQQGYIITDIDNVFGTGTKVTVLG**GG**<br>**GGS**EVQLVESGGGLVQPGGSLRLSCAASGFSFSNSYWICWVRQAPGKCLEWIGC<br>TFVGSSDSTYYANWAKGRFTISRDNSKNTVYLQMNSLRAEDTAVYYCARHPSDA<br>VYGYANNLWGQGTLVTVSS**GGGGSGGGGSGGGGSGGGGS**IQMTQSPSSLSAS<br>VGDRVTITCQASQSINNVLAWYQQKPGKAPKLLIYRASTLASGVPSRFSGSGSGT<br>DFTLTISSLQPEDFATYYCQSSYGNYGDFGCGTKVTVLG**GGGGS**QVQLQESGPGL<br>VKPSETLSLTCKASGFSFSSGYDMCWVRQPPGKGLEWIACVVAGSVDITYYASW<br>AKGRVTISKDSSKNQVSLKLSSVTAADTAVYYCARKDAYSDAFNLWGQGTLVT<br>VSS**GGGGSGGGGS**IQMTQSPSSLSASVGDRVTITCQSSESVYSNNQLSWYQQKP<br>GQPPKLLIYDASDLASGVPSRFSGSGSGTDFTLTISSLQPEDFATYYCAGGFSSSSD<br>TAFGGGTKLTVLG**GGGGSGGGGSGGGGSGGGGS**EVQLVESGGGLVQPGGSLR<br>LSCAASGFSLSSNAMGWVRQAPGKGLEYIGIISVGGFTYYASWAKGRFTISRDNS<br>KNTVYLQMNSLRAEDTATYFCARDRHGGDSSGAFYLWGQGTLVTVSS |
| PRO1473 (38-02-A04 sc 13 scDb-i/33-03-G02 sc03 scDb-o/19-01-H04 sc03 scFv) | | |
| SEQ ID NO: 226 | scDb-scFv | DFQLTQSPSSLSASVGDRVTITCQASQSINDYLAWYQQKPGKSPKLLIYKASTLAS<br>GVPSRFSGSGSGTDFTLTISSLQPEDFATYYCQQGYIITDIDNVFGTGTKVTVLG**GG**<br>**GGS**EVQLVESGGGLVQPGGSLRLSCAASGFSFSNSYWICWVRQAPGKCLEWIGC<br>TFVGSSDSTYYANWAKGRFTISRDNSKNTVYLQMNSLRAEDTAVYYCARHPSDA<br>VYGYANNLWGQGTLVTVSS**GGGGSGGGGSGGGGSGGGGS**IQMTQSPSSLSAS<br>VGDRVTITCQASQSINNVLAWYQQKPGKAPKLLIYRASTLASGVPSRFSGSGSGT<br>DFTLTISSLQPEDFATYYCQSSYGNYGDFGCGTKVTVLG**GGGGS**QSQLQESGPGL<br>VKPSETLSLTCKASGFSFSSGYDMCWVRQPPGKGLEWIACVVAGSVDITYYASW<br>AKGRVTISKDSSKNQVSLKLSSVTAADTAVYFCARKDAYSDAFNLWGQGTLVTV<br>SS**GGGGSGGGGS**IQMTQSPSSLSASVGDRVTITCQSSESVYSNNQLSWYQQKPG<br>QPPKLLIYDASDLASGVPSRFSGSGSGTDFTLTISSLQPEDFATYYCAGGFSSSSDT |

TABLE 5-continued

| SEQ ID NUMBER | Ab Format | Sequence |
|---|---|---|
| | | AFGGGTKLTVLG**GGGGSGGGGSGGGGSGGGGS**EVQLVESGGGLVQPGGSLRL SCAASGFSLSSNAMGWVRQAPGKGLEYIGIISVGGFTYYASWAKGRFTISRDNSK NTVYLQMNSLRAEDTATYFCARDRHGGDSSGAFYLWGQGTLVTVSS |
| PRO1476 (33-03-G02 sc03 scDb-i/38-02-A04 sc13 scDb-o/19-01-H04 sc03 scFv) | | |
| SEQ ID NO: 227 | scDb-scFv | DIQMTQSPSSLSASVGDRVTITCQASQSINNVLAWYQQKPGKAPKLLIYRASTLAS GVPSRFSGSGSGTDFTLTISSLQPEDFATYYCQSSYGNYGDFGCGTKVTVLG**GGG GS**QSQLQESGPGLVKPSETLSLTCKASGFSFSSGYDMCWVRQPPGKGLEWIACVV AGSVDITYYASWAKGRVTISKDSSKNQVSLKLSSVTAADTAVYFCARKDAYSDA FNLWGQGTLVTVSS**GGGGSGGGGSGGGGSGGGGS**FQLTQSPSSLSASVGDRVT ITCQASQSINDYLAWYQQKPGKSPKLLIYKASTLASGVPSRFSGSGSGTDFTLTISS LQPEDFATYYCQQGYIITDIDNVFGTGTKVTVLG**GGGGS**EVQLVESGGGLVQPG GSLRLSCAASGFSFSNSYWICWVRQAPGKCLEWIGCTFVGSSDSTYYANWAKGR FTISRDNSKNTVYLQMNSLRAEDTAVYYCARHPSDAVYGYANNLWGQGTLVTV SS**GGGGSGGGGS**IQMTQSPSSLSASVGDRVTITCQSSESVYSNNQLSWYQQKPG QPPKLLIYDASDLASGVPSRFSGSGSGTDFTLTISSLQPEDFATYYCAGGFSSSDT AFGGGTKLTVLG**GGGGSGGGGSGGGGSGGGGS**EVQLVESGGGLVQPGGSLRL SCAASGFSLSSNAMGWVRQAPGKGLEYIGIISVGGFTYYASWAKGRFTISRDNSK NTVYLQMNSLRAEDTATYFCARDRHGGDSSGAFYLWGQGTLVTVSS |
| PRO1432 (33-03-G02 sc18 scDb-i/38-02-A04 sc13 scDb-o/19-01-H04 sc03 scFv) | | |
| SEQ ID NO: 228 | scDb-scFv | DIQMTQSPSSLSASVGDRVTITCQASQSINNVLAWYQQKPGKAPKLLIYRASTLAS GVPSRFSGSGSGTDFTLTISSLQPEDFATYYCQSSYGNYGDFGCGTKVTVLG**GGG GS**QVQLQESGPGLVKPSETLSLTCKASGFSFSSGYDMCWVRQPPGKGLEWIACV VAGSVDITYYASWAKGRVTISKDSSKNQVSLKLSSVTAADTAVYYCARKDAYSD AFNLWGQGTLVTVSS**GGGGSGGGGSGGGGSGGGGS**IQMTQSPSSLSASVGDRV TITCQASQSINDYLAWYQQKPGKAPKLLIYKASTLASGVPSRFSGSGSGTDFTLTIS SLQPEDFATYYCQQGYIITDIDNVFGTGTKVTVLG**GGGGS**EVQLVESGGGLVQPG GSLRLSCAASGFSFSNSYWICWVRQAPGKCLEWIGCTFVGSSDSTYYANWAKGR FTISRDNSKNTVYLQMNSLRAEDTAVYYCARHPSDAVYGYANNLWGQGTLVTV SS**GGGGSGGGGS**IQMTQSPSSLSASVGDRVTITCQSSESVYSNNQLSWYQQKPG QPPKLLIYDASDLASGVPSRFSGSGSGTDFTLTISSLQPEDFATYYCAGGFSSSDT AFGGGTKLTVLG**GGGGSGGGGSGGGGSGGGGS**EVQLVESGGGLVQPGGSLRL SCAASGFSLSSNAMGWVRQAPGKGLEYIGIISVGGFTYYASWAKGRFTISRDNSK NTVYLQMNSLRAEDTATYFCARDRHGGDSSGAFYLWGQGTLVTVSS |
| PRO1480 (38-27-A11 sc02 scDb-i/37-20-B03 sc09.1 scDb-o/19-01-H04 sc03 scFv) | | |
| SEQ ID NO: 229 | scDb-scFv | DIQMTQSPASLSASVGDRVTITCQASQSIGTYLAWYQQKPGKPPKLLIYRAFILAS GVPSRFSGSGSGTDFTLTISSLQPEDFATYYCQSNFYSDSTTIGPNAFGTGTKVTVL **GGGGGS**EVQLVESGGGLVQPGGSLRLSCAASGFSFSANYYPCWVRQAPGKGLE WIGCIYGGSSDITYDANWTKGRFTISRDNSKNTVYLQMNSLRAEDTAVYYCARS AWYSGWGGDLWGQGTLVTVSS**GGGGSGGGGSGGGGSGGGGS**IQMTQSPSSLS ASVGDRVTITCQASQSISNRLAWYQQKPGKAPKLLIYSASTLASGVPSRFSGSGSG TDFTLTISSLQPEDFATYYCQSTYYGNDGNAFGTGTKVTVLG**GGGGS**EVQLVES GGGLVQPGGSLRLSCAASGFSFNSDYWIYWVRQAPGKGLEWIASIYGGSSGNTQ YASWAQGRFTISRDNSKNTVYLQMNSLRAEDTAVYFCARGYVDYGGATDLWG QGTLVTVSS**GGGGSGGGGS**IQMTQSPSSLSASVGDRVTITCQSSESVYSNNQLSW YQQKPGQPPKLLIYDASDLASGVPSRFSGSGSGTDFTLTISSLQPEDFATYYCAGG FSSSDTAFGGGTKLTVLG**GGGGSGGGGSGGGGSGGGGS**EVQLVESGGGLVQP **GGS**LRLSCAASGFSLSSNAMGWVRQAPGKGLEYIGIISVGGFTYYASWAKGRFTI SRDNSKNTVYLQMNSLRAEDTATYFCARDRHGGDSSGAFYLWGQGTLVTVSS |
| PRO1481 (38-27-A11 sc03 scDb-i/37-20-B03 sc09.1 scDb-o/19-01-H04 sc03 scFv) | | |
| SEQ ID NO: 230 | scDb-scFv | DIQMTQSPASLSASVGDRVTITCQASQSIGTYLAWYQQKPGKPPKLLIYRAFILAS GVPSRFSGSGSGTDFTLTISSLQPEDFATYYCQSNFYSDSTTIGPNAFGTGTKVTVL G**GGGGS**ESQLVESGGGLVQPGGSLRLSCAASGFSFSANYYPCWVRQAPGKGLE WIGCIYGGSSDITYDANWTKGRFTISRDNSKNTVYLQMNSLRAEDTAVYFCARSA WYSGWGGDLWGPGTLVTVSS**GGGGSGGGGSGGGGSGGGGS**FQLTQSPSSLSA SVGDRVTITCQASQSISNRLAWYQQKPGKPPKLLIYSASTLASGVPSRFSGSGSGT DFTLTISSLQPEDFATYYCQSTYYGNDGNAFGTGTKVTVLG**GGGGS**EVQLVESG GGLVQPGGSLRLSCAASGFSFNSDYWIYWVRQAPGKGLEWIASIYGGSSGNTQY ASWAQGRFTISRDNSKNTVYLQMNSLRAEDTAVYFCARGYVDYGGATDLWGQ GTLVTVSS**GGGGSGGGGS**IQMTQSPSSLSASVGDRVTITCQSSESVYSNNQLSWY QQKPGQPPKLLIYDASDLASGVPSRFSGSGSGTDFTLTISSLQPEDFATYYCAGGFS SSSDTAFGGGTKLTVLG**GGGGSGGGGSGGGGSGGGGS**EVQLVESGGGLVQPG GSLRLSCAASGFSLSSNAMGWVRQAPGKGLEYIGIISVGGFTYYASWAKGRFTISR DNSKNTVYLQMNSLRAEDTATYFCARDRHGGDSSGAFYLWGQGTLVTVSS |

Examples of multispecific molecules and IgGs of the present invention.

TABLE 5-continued

| SEQ ID NUMBER | Ab Format | Sequence |
|---|---|---|
| Examples of multispecific molecules and IgGs of the present invention. | | |
| PRO1480diS (38-27-A11 sc07 scDb-i/37-20-B03 sc09.1 scDb-o/19-01-H04 sc03 scFv) | | |
| SEQ ID NO: 231 | scDb-scFv | DIQMTQSPASLSASVGDRVTITCQASQSIGTYLAWYQQKPGKPPKLLIYRAFILAS GVPSRFSGSGSGTDFTLTISSLQPEDFATYYCQSNFYSDSTTIGPNAFGTGTKVTVL **GGGGGS**EVQLVESGGGLVQPGGSLRLSCAASGFSFSANYYPCWVRQAPGKCLE WIGCIYGGSSDITYDANWTKGRFTISRDNSKNTVYLQMNSLRAEDTAVYYCARS AWYSGWGGDLWGQGTLVTVSS**GGGGSGGGGSGGGGSGGGGS**IQMTQSPSSLS ASVGDRVTITCQASQSISNRLAWYQQKPGKAPKLLIYSASTLASGVPSRFSGSGSG TDFTLTISSLQPEDFATYYCQSTYYGNDGNAFGCGTKVTVLG**GGGGS**EVQLVES GGGLVQPGGSLRLSCAASGFSFNSDYWIYWVRQAPGKGLEWIASIYGGSSGNTQ YASWAQGRFTISRDNSKNTVYLQMNSLRAEDTAVYFCARGYVDYGGATDLWG QGTLVTVSS**GGGGSGGGGS**IQMTQSPSSLSASVGDRVTITCQSSESVYSNNQLSW YQQKPGQPPKLLIYDASDLASGVPSRFSGSGSGTDFTLTISSLQPEDFATYYCAGG FSSSSDTAFGGGTKLTVLG**GGGGSGGGGSGGGGSGGGGS**EVQLVESGGGLVQP GGSLRLSCAASGFSLSSNAMGWVRQAPGKGLEYIGIISVGGFTYYASWAKGRFTI SRDNSKNTVYLQMNSLRAEDTATYFCARDRHGGDSSGAFYLWGQGTLVTVSS |
| PRO1059 (33-03-G02 IgG1 LC with 38-02-A04 sc01 scFV, PDL1/CD137(scFv) silent Morrison) | | |
| SEQ ID NO: 232 | Morrison-L Light chain | DIQMTQSPSSLSASVGDRVTITCQASQSINDYLAWYQQKPGKAPKLLIYKASTLAS GVPSRFSGSGSGTDFTLTISSLQPEDFATYYCQQGYIITDIDNVFGTGTKVTVLGTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC**GGGGS GGGGS**IQMTQSPSSLSASVGDRVTITCQASQSINNVLAWYQQKPGKAPKLLIYRA STLASGVPSRFSGSGSGTDFTLTISSLQPEDFATYYCQSSYGNYGDFGTGTKVTVL **GGGGGSGGGGSGGGGSGGGGS**QVQLQESGPGLVKPSETLSLTCKVSGFSFSNS YWICWIRQPPGKGLEWIGCTFVGSSDSTYYANWAKGRVTISVDSSKNQFSLKLSS VTAADTAVYYCARHPSDAVYGYANNLWGQGTLVTVSS |
| SEQ ID NO: 233 | Morrison-L Heavy chain | QVQLQESGPGLVKPSETLSLTCKVSGFSFSSGYDMCWIRQPPGKGLEWIGCVVAG SVDITYYASWAKGRVTISVDSSKNQFSLKLSSVTAADTAVYYCARKDAYSDAFN LWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRVE PKSCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALGAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPGK |
| PRO1060 (33-03-G02 IgG1 HC with 38-02-A04 sc01 scFV, PDL1/CD137(scFv) silent Morrison) | | |
| SEQ ID NO: 234 | Morrison-H Light chain | DIQMTQSPSSLSASVGDRVTITCQASQSINDYLAWYQQKPGKAPKLLIYKASTLAS GVPSRFSGSGSGTDFTLTISSLQPEDFATYYCQQGYIITDIDNVFGTGTKVTVLGTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 235 | Morrison-H Heavy chain | QVQLQESGPGLVKPSETLSLTCKVSGFSFSSGYDMCWIRQPPGKGLEWIGCVVAG SVDITYYASWAKGRVTISVDSSKNQFSLKLSSVTAADTAVYYCARKDAYSDAFN LWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRVE PKSCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALGAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPGK**GGGGSGGGGS**IQMTQSPSSLSASVGDRVTITCQASQSINNVL AWYQQKPGKAPKLLIYRASTLASGVPSRFSGSGSGTDFTLTISSLQPEDFATYYCQ SSYGNYGDFGTGTKVTVLG**GGGGSGGGGSGGGGSGGGGS**QVQLQESGPGLVK PSETLSLTCKVSGFSFSNSYWICWIRQPPGKGLEWIGCTFVGSSDSTYYANWAKG RVTISVDSSKNQFSLKLSSVTAADTAVYYCARHPSDAVYGYANNLWGQGTLVTV SS |
| PRO1061 (33-03-G02 sc01 IgG1 LC with 38-27-C05 sc01 scFv, PDL1/CD137(scFv) silent Morrison) | | |
| SEQ ID NO: 236 | Morrison-L Light chain | DIQMTQSPSSLSASVGDRVTITCQASQSINDYLAWYQQKPGKAPKLLIYKASTLAS GVPSRFSGSGSGTDFTLTISSLQPEDFATYYCQQGYIITDIDNVFGTGTKVTVLGTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC**GGGGS GGGGS**IQMTQSPSSLSASVGDRVTITCQASQSINNVLAWYQQKPGKAPKLLIYRA STLASGVPSRFSGSGSGTDFTLTISSLQPEDFATYYCQSSYGNYGDFGTGTKVTVL **GGGGGSGGGGSGGGGSGGGGS**QVQLQESGPGLVKPSETLSLTCKVSGFSFSNS YWICWIRQPPGKGLEWIGCTFVGSSDSTYYANWAKGRVTISVDSSKNQFSLKLSS VTAADTAVYYCARHPSDAVYGYANNLWGQGTLVTVSS |

TABLE 5-continued

Examples of multispecific molecules and IgGs of the present invention.

| SEQ ID NUMBER | Ab Format | Sequence |
|---|---|---|
| SEQ ID NO: 237 | Morrison-L Heavy chain | QVQLQESGPGLVKPSETLSLTCKVSGFSFSSGYDMCWIRQPPGKGLEWIGCVVAG SVDITYYASWAKGRVTISVDSSKNQFSLKLSSVTAADTAVYYCARKDAYSDAFN LWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRVE PKSCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALGAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPGK |
| PRO1062 (33-03-G02 sc01 IgG1 HC with 38-27-C05 sc01 scFv, PDL1/CD137(scFv) silent Morrison) | | |
| SEQ ID NO: 238 | Morrison-H Light chain | DIQMTQSPSSLSASVGDRVTITCQASQSINDYLAWYQQKPGKAPKLLIYKASTLAS GVPSRFSGSGSGTDFTLTISSLQPEDFATYYCQQGYIITDIDNVFGTGTKVTVLGTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 239 | Morrison-H Heavy chain | QVQLQESGPGLVKPSETLSLTCKVSGFSFSSGYDMCWIRQPPGKGLEWIGCVVAG SVDITYYASWAKGRVTISVDSSKNQFSLKLSSVTAADTAVYYCARKDAYSDAFN LWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRVE PKSCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALGAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPGK**GGGGSGGGGS**IQMTQSPSSLSASVGDRVTITCQASQSINNVL AWYQQKPGKAPKLLIYRASTLASGVPSRFSGSGSGTDFTLTISSLQPEDFATYYCQ SSYGNYGDFGTGTKVTVLG**GGGGSGGGGSGGGGSGGGGS**QVQLQESGPGLVK PSETLSLTCKVSGFSFSNSYWICWIRQPPGKGLEWIGCTFVGSSDSTYYANWAKG RVTISVDSSKNQFSLKLSSVTAADTAVYYCARHPSDAVYGYANNLWGQGTLVTV SS |
| PRO1137 (33-03-G02-sc01 IgG1) | | |
| SEQ ID NO: 240 | Light chain IgG | DIQMTQSPSSLSASVGDRVTITCQASQSINDYLAWYQQKPGKAPKLLIYKASTLAS GVPSRFSGSGSGTDFTLTISSLQPEDFATYYCQQGYIITDIDNVFGTGTKVTVLGTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 241 | Heavy chain IgG | QVQLQESGPGLVKPSETLSLTCKVSGFSFSSGYDMCWIRQPPGKGLEWIGCVVAG SVDITYYASWAKGRVTISVDSSKNQFSLKLSSVTAADTAVYYCARKDAYSDAFN LWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVE WESNGQPENNYKTTPPVLDSDGSFFLYSKLTVDKSRWQQGNVFSCSVMHEALHN HYTQKSLSLSPGK |
| PRO1196 (37-20-B03 sc01 IgG1) | | |
| SEQ ID NO: 242 | Light chain IgG | DIQMTQSPSSLSASVGDRVTITCQASQSIGTYLAWYQQKPGKAPKLLIYRAFILAS GVPSRFSGSGSGTDFTLTISSLQPEDFATYYCQSNFYSDSTTIGPNAFGTGTKVTVL GTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 243 | Heavy chain IgG | QVQLQESGPGLVKPSETLSLTCKVSGFSFNSDYWIYWIRQPPGKGLEWIGSIYGGS SGNTQYASWAQGRVTISVDSSKNQFSLKLSSVTAADTAVYYCARGYVDYGGAT DLWGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVE WESNGQPENNYKTTPPVLDSDGSFFLYSKLTVDKSRWQQGNVFSCSVMHEALHN HYTQKSLSLSPGK |
| PRO1138 (38-02-A04 sc01 IgG4) | | |
| SEQ ID NO: 244 | Light chain IgG | DIQMTQSPSSLSASVGDRVTITCQASQSINNVLAWYQQKPGKAPKLLIYRASTLAS GVPSRFSGSGSGTDFTLTISSLQPEDFATYYCQSSYGNYGDFGTGTKVTVLGTVAA PSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC |

TABLE 5-continued

Examples of multispecific molecules and IgGs of the present invention.

| SEQ ID NUMBER | Ab Format | Sequence |
|---|---|---|
| SEQ ID NO: 245 | Heavy chain IgG | QVQLQESGPGLVKPSETLSLTCKVSGFSFSNSYWICWIRQPPGKGLEWIGCTFVGS SDSTYYANWAKGRVTISVDSSKNQFSLKLSSVTAADTAVYYCARHPSDAVYGYA NNLWGQGTLVTVSSASTKGPSVFPLAPCSRSTSESTAALGCLVKDYFPEPVTVSW NSGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVSN KGLPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHNH YTQKSLSLSLGK |

Throughout the text of this application, should there be a discrepancy between the text of the specification (e.g., Tables 1 to 5) and the sequence listing, the text of the specification shall prevail.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The following Examples illustrates the invention described above, but is not, however, intended to limit the scope of the invention in any way. Other test models known as such to the person skilled in the pertinent art can also determine the beneficial effects of the claimed invention.

EXAMPLES

Example 1: Affinities to PDL1, CD137, HSA and MSA

Methods:

Affinity to PDL1 of the different species was determined by SPR measurements using a Biacore T200 device (GE Healthcare). An antibody specific for the Fc region of human IgGs was immobilized on a sensor chip (CM5 sensor chip, GE Healthcare) by amine-coupling. For all formats, with the exception of the Fc containing Morrison formats, PDL1-Fc chimeric protein from different species were captured by the immobilized antibody. In this experiment, Fc tagged human CD137 (R&D Systems, cat. 838-4B-100) and Fc tagged human PDL1 (Sino Biological, cat. 10084-H02H) were captured using the Human Antibody Capture kit from GE Healthcare (cat. BR-1008-39).

Three-fold serial dilutions of the molecules specific for PDL1 (0.12-90 nM) were injected into the flow cells for three minutes and dissociation was monitored for 10 minutes. After each injection cycle, surfaces were regenerated with one injection of a 3 M $MgCl_2$ solution. The apparent dissociation ($k_d$) and association ($k_a$) rate constants and the apparent dissociation equilibrium constant (KD) were calculated using one-to-one Langmuir binding model. Affinity to CD137 of the different species was determined using the identical setup as for PDL1 with the exception that CD137-Fc chimeric protein from different species were captured by the immobilized antibody.

The Fc containing formats were directly captured by the antibody specific for the Fc region of human IgGs. Two-fold serial dilutions of PDL1 extracellular domain or CD137 extracellular domain ranging from 90 to 0.35 nM were tested for binding to the IgG captured on the biosensor chip. After each injection cycle, surfaces were regenerated with one injection of a 3 M $MgCl_2$ solution.

Affinity of molecules to serum albumin (SA) of the different species was determined by SPR measurements using a Biacore T200 device (GE Healthcare). SA was directly coupled to a CM5 sensor chip (GE Healthcare) using amine coupling chemistry. After performing a regeneration scouting and surface performance test to find best assay conditions, a dose response was measured and obtained binding curves were double-referenced (empty reference channel and zero analyte injection) and fitted using the 1:1 Langmuir model to retrieve kinetic parameters. The assay was run in a 1×PBS-Tween buffer at pH 5.5.

Results:

The affinities to human PDL1 of the scDb-scFvs are provided in Table 6. The binding to human PDL1 was confirmed for all scDb-scFvs. The measurements of the binding kinetics for the humanized constructs show a difference in binding affinity for PDL1 when comparing the CDR and structural (STR) grafts of clone 33-03-G02 the STR graft shows a 20-fold improvement in affinity compared to the CDR graft of the same clone (PRO885 versus PRO 1126 in Table 6). The CDR graft derived from clone 37-20-B03 (PR0997) shows approximately two-fold higher affinity when compared to the STR graft of clone 33-03-G02. The binding affinities for the CDR graft of 33-03-G02 are similar to the binding affinity of the parental scFv when they are combined into different multispecific formats (compare PRO830 to PRO885, PRO951, PRO1123, PRO1124, PRO963, PRO966, PRO1057, PRO1058, PRO1059 and PRO1060 in Table 6). The scFv derived from both clones show nearly identical affinity to human and cynomolgus monkey PDL1 (see PRO977 and PRO830 in Table 6). When compared to the corresponding scFvs, the affinities of the multi-specifics containing the anti-PDL1 moieties 33-03-G02 sc18, 37-20-B03 sc01, and 37-20-B03 sc09.1 were found to be similar (PRO1392, scFv of 33-03-G02 sc18: KD=9.94E-12 M; PR0908, scFv of 37-20-B03 sc01: KD=5.94E-12 M; and PRO1347, scFv of 37-20-sc09.1: KD=9.00E-12 M, respectively). In contrast, a decrease in affinity to human PDL1 was observed for all scDb-scFvs carrying the anti-PDL1 moiety 33 03-G02 sc03 when compared to the corresponding scFv PRO1183 (scFv of 33 03-G02 sc03: KD<2.09E-12 M). The loss in affinity of these constructs is mainly due to an accelerated off-rate resulting in an in-creased dissociation constant. The highest affinity for PDL1 was found for PRO1430 with the anti-PDL1 binding moiety 37-20-B03 sc09.1.

As shown in Table 6, binding to human CD137 was confirmed for all scDb-scFvs. The measurement of binding kinetics for the CDR grafts of the two CD137 specific humanized constructs derived from clone 38-02-A04 and 38-27-C05 show nearly identical affinities (compare PRO885 and PRO951 in Table 6). For clone 38-02-04 the described structural residues engrafted in the framework regions led to an improvement of affinity of more than 200-fold (compare PRO885 and PRO1124 in Table 6). In addition, for constructs derived from clone 38-02-04 binding to mouse CD137 was observed, however with very much reduced affinity. Interestingly, whereas the affinity to human CD137 was similar for the multispecific molecules that contain the anti-CD137 binding moiety 38-02-A04 sc13 and 38-27-A11 sc03 when compared to the affinities of their corresponding scFvs (PRO1352, scFv of 38-02-A04 sc13, KD=1.47E-09 M and PRO1360, scFv of 38-27-A11 sc03, KD=2.34E-10 M, respectively), the affinity of the scDb-scFv molecules carrying the anti-CD137 moiety 38-27-A11 sc02 in the inner part of the scDb hairpin (scDb-i domain, namely PRO1480) was substantially better than the affinity of the corresponding scFv (PRO1359, KD=3.24E-09 M; PRO1359, KD=3.07E-09 M). In contrast, when the anti-CD137 moiety 38-27-A11 sc02 was placed in the outer part of the scDb hairpin, the affinity is comparable to the one of the scFv PRO1359. One could speculate that this gain in affinity might be caused by an increased stabilization of the domain when located in the inner part of the scDb hairpin. As a consequence, the affinity to human CD137 of the multi-specifics containing the anti-CD137 moiety 38-27-A11 sc02 in the inner part of scDb hairpin is almost identical to the affinity of the scDb-scFvs with the anti-CD137 moiety 38-27-A11 sc03 (compare PRO1480 and PRO1481), which represents an unexpected finding.

Binding of scDb-scFvs to serum albumin (SA) was confirmed by SPR. The scDb-scFvs containing the SA binding domain derived from clone 19-01-H04 show high affinity binding to human serum albumin, while no binding was observed to rodent SA. For the scDb-scFvs containing clone 23-13-A01 binding was observed for human SA, in addition the molecules bind with reduced affinity to rodent SA (see Table 6). The binding to HSA at pH5.5 for PRO1430, PRO14379 and PRO1480 was found to be of high affinity (KD value of low nanomolar concentrations) and comparable among tested molecules, which represents an expected finding as tested molecules share the identical anti-SA domain (IgG clone 19-01-H04). Increasing the pH value to 7.4, moreover, did not affect the affinity of molecules to HSA substantially (data not shown).

Example 2: Blockade of the PDL1/PD-1 Interaction in a Cell-Based Reporter Gene Assay Using CHO Cells Expressing PDL1 and a TCR Activator Molecule, and Jurkat Cells Expressing PD-1 and Containing a Luciferase Gene Under the NFAT Response Element Method: In the bioluminescent reporter gene assay, engineered Jurkat T cells stably expressing NFAT (nuclear factor of activated T-cells)-luciferase reporter and human PD-1 act as effector T cells. Cells stably expressing human PDL1 and a T cell receptor (TCR) activator act as antigen presenting cells. Co-cultivating the two cell lines induces activation of the Jurkat NFAT pathway via crosslinking of TCR activator/TCR complex. Upon engagement of PDL1 expressing cells, PD-1 signaling in PD-1 effector T cells inhibits T-cell function, and results in NFAT pathway inhibition. Blockade of PD-1 and PDL1 receptor interaction leads to re-activation of the NFAT pathway. 35,000 CHO/PDL1/TCR activator (BPS Bioscience) cells in 100 μl of cell culture medium (DMEM/F12, 10% FCS) were added to the inner wells of a white cell culture plate and incubated for 16-20 h at 37° C. and 5% $CO_2$. Next day, 95 μl of cell culture medium was removed from each well and 50 μl of 2-fold concentrated serial dilutions of the respective molecules to be tested (from 3,000 to 0.46 ng/ml), including the reference avelumab, were added. Then, 50 μl of effector Jurkat cells expressing PD-1 (BPS Bioscience) diluted at 400,000 cell/ml in assay buffer (RPMI1640 with 10% FCS) were added to each well and plates were incubated 6 h at 37° C. and 5% $CO_2$. Finally, 50 μL luciferase substrate (BPS Bioscience) prepared according to manufacturer's protocol, was added per well and plates were incubated 30 min in the dark, luminescence was measured using Top-count.

Results:

Individual IC50 values on each plate were calibrated against the $IC_{50}$ of the reference molecule avelumab that was taken along on each plate (relative $IC_{50}$: $IC_{50,\ avelumab}/IC_{50,\ test\ scFv}$). Potencies are summarized in Table 7 which shows that $IC_{50}$ of all molecules tested are between 0.1-fold and 3.73-fold the $IC_{50}$ of avelumab.

Figure 3:
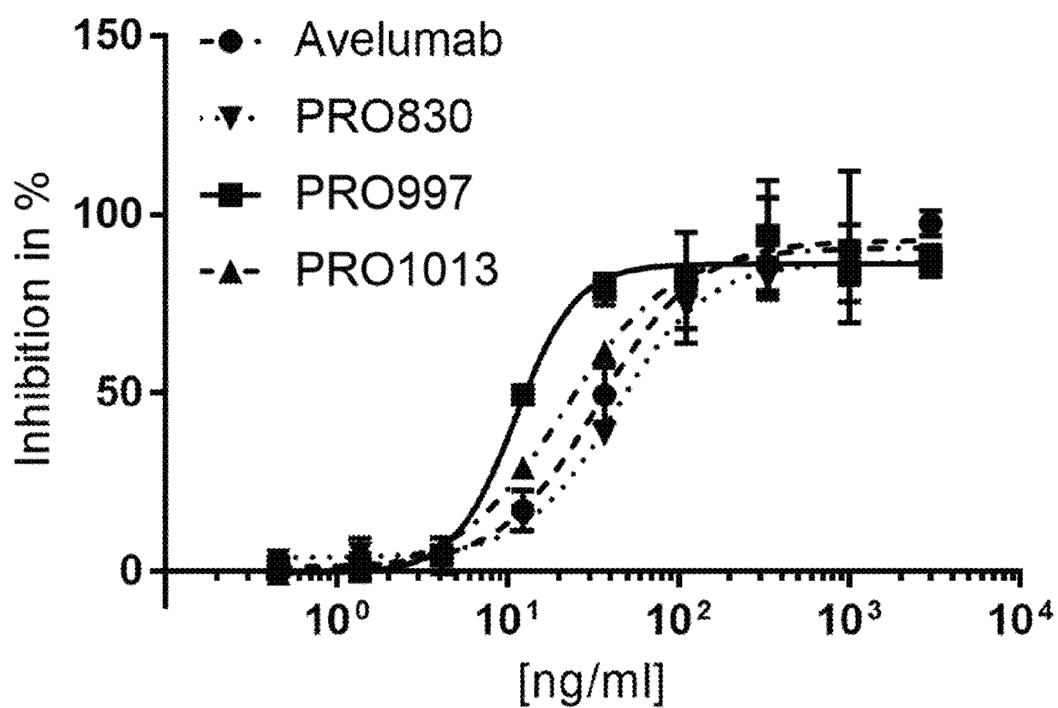
FIG. 3 Effect of CDR set and framework selection on neutralization of the PDL1/PD-1 interaction in the NFAT-Luciferase reporter gene assay. % inhibition proportional to the luminescence signal obtained in the assay is represented in function of the molecules concentrations in ng/ml. Avelumab was used as reference.

In order to assess the influence of the CDR set and framework selection on potency to neutralize the PDL1 binding to PD-1, three anti-PDL1 scFvs were tested in the NFAT reporter gene cell-based assay. PRO830 comprises the CDR set of clone 33-03-G02 grafted on a VH4 framework and PRO997 and PRO1013 comprise the CDR set of clone 37-20-B03 grafted on either a VH4 or a VH1 framework, respectively. PRO830 has the lowest potency of the three scFvs tested with an $IC_{50}$ value of 42.88 ng/ml, and has similar potency as avelumab with an $IC_{50}$ value of 34.09 ng/ml. PR0997 is the most potent molecule. Potency of the same CDR set was about 2-fold higher when grafted on a VH4 framework than on VH1 framework. $IC_{50}$ values were 11.12 ng/ml versus 21.29 ng/ml, respectively. (FIG. 3 and Table 7)

Figure 4:
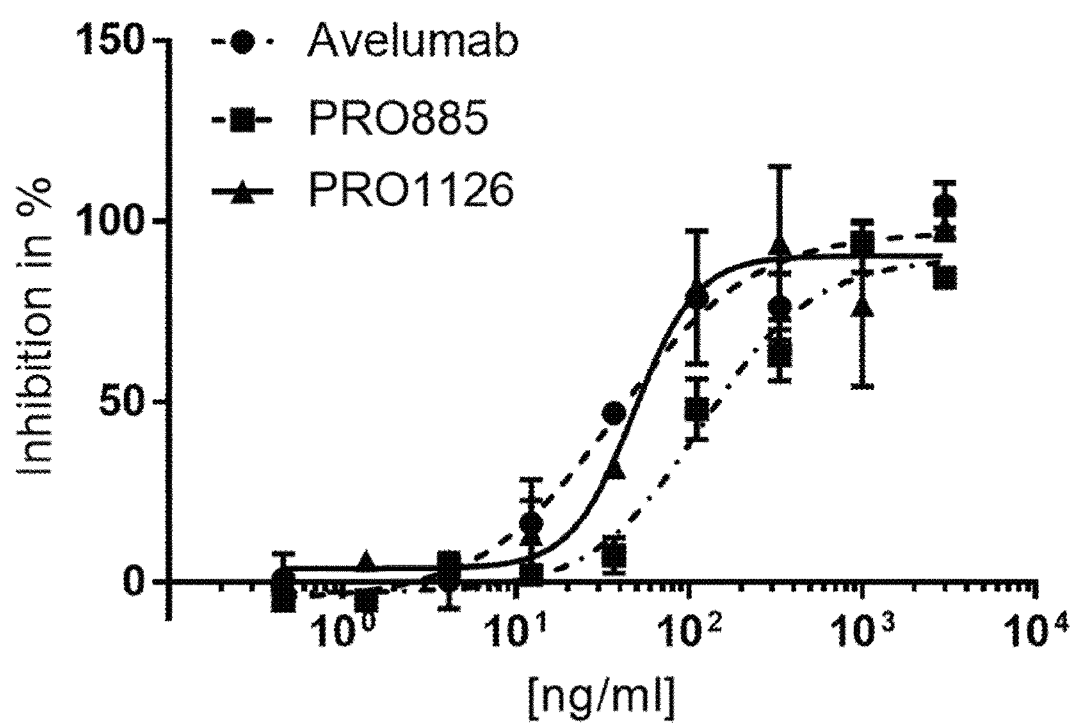
FIG. 4 Effect of domain optimization on neutralization potency of the PDL1/PD-1 interaction in the NFAT-Luciferase reporter gene assay. % inhibition proportional to the luminescence signal obtained in the assay is represented in function of the scFvs concentrations in ng/ml. Avelumab was used as reference.

Neutralization potency of the PDL1 binding to PD-1 was determined for bi-specific molecules possessing the 33-03-G02 PDL1 domain before (CDR graft) and after (structural graft) domain optimization. The CDR graft (PRO885) was compared to a structural graft (PRO1126). The domain optimization improved the neutralization potency by a factor of three with $IC_{50}$ values being 137.2 ng/ml for PRO885 and 48.15 ng/ml for PRO1126. (FIG. 4 and Table 7).

Potency to neutralize the PDL1/PD-1 interaction was also assessed for several tri-specific molecules possessing the anti-CD137 domain derived from clone 38-02-A04 or 38-27-A11, the anti-PDL1 domain derived from clone 33-03-G02 or clone 37-20-B03 and two different human serum albumin binding domain, for half-life extension (FIG. 5 and Table 7). The HSA domain derived from clone 23-12-A01-sc03 is also binding mouse serum albumin. Experiments were performed in presence of 25 mg/ml HSA. Neutralization potency of PRO1057 ($IC_{50}$=665.1 ng/ml) was lower than for avelumab (FIG. 5 and Table 7).

Figure 6:
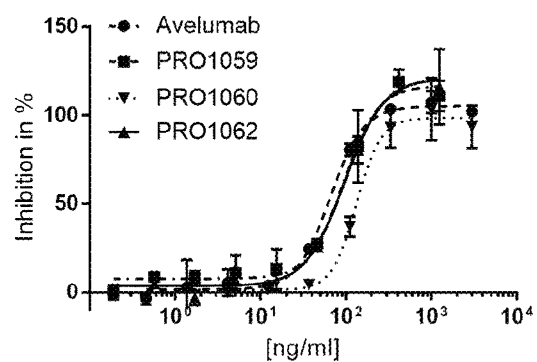
FIG. 6 Potency of bivalent molecule and influence of LC or HC scFv fusion in Morrison formats on neutralization potency of the PDL1/PD-1 interaction in the NFAT-Luciferase reporter gene assay. % inhibition proportional to the luminescence signal obtained in the assay is represented in function of the molecules concentrations in ng/ml. Avelumab was used as reference.

Another format which would extend the half-life in serum, the so-called Morrison format, was tested in the cell based potency reporter gene assay. In this format, one specificity is carried by the IgG moiety (bi-valency) and two scFvs with specificities to the second target are linked by flexible peptide linkers either to the heavy chain (HC) or light chain (LC) of the IgG. All Morrison molecules tested carried the anti-PDL1 domain of the CDR graft of clone 33-03-G02 on both IgG arms. The two constructs PRO1059 and PRO1060 differ by the fusion of two anti-CD137 scFvs either to the heavy chain (HC) or to the light chain (LC). PRO1062 has the same architecture as PRO1060 with a different CD137 domain. Neutralization potencies of all molecules were similar (FIG. 6 and Table 7).

Example 3: Blockade of the Interaction of PDL1 with PD-1 and B7.1 Using Competition ELISA These assays were performed to assess the ability of PDL1 inhibitors to block the interaction between PDL1 and PD-1 or PDL1 and B.71. Different formats including scFvs, scDbs, scDb-scFv and Morrison were analyzed in the competition ELISA and compared to the reference IgG avelumab.

PDL1/PD-1 Competition ELISA

Method

ELISA microplates coated overnight at 4° C. with 4 μg/ml human PD-1 were washed three times with 450 μl wash buffer per well. Plates were blocked for 1 hour at room temperature by adding 300 μl of PBS with 1% BSA and 0.2% tween (dilution buffer) to each well. Inhibitors were serially diluted in 3-fold steps to final concentrations ranging from 300 to 0.005 ng/ml in dilution buffer containing 1 ng/ml biotinylated human PDL1. The mixtures were pre-incubated for 1 hour at room temperature under gentle agitation on a rotating mixer (21 rpm) and added to the microplates after 3 wash cycles with 450 μl wash buffer per well. Plates were incubated for 1.5 hours at room temperature under gentle agitation, then 10 ng/ml streptavidin-polyHRP40 was added to each microplate well after three washes with 450 μl of wash buffer per well. After 1 h incubation at RT, plates were washed three times with 450 μl wash buffer and TMB substrate solution was added. The enzymatic reaction was stopped after 6 minutes by addition of 1 M HCl and absorbance was measured at 450 nm using 690 nm as a reference wavelength. For calculation of $IC_{50}$ values, a four-parameter logistic (4PL) curve fit was performed in Graph Pad Prism using reference subtracted values.

Results

Figure 7:
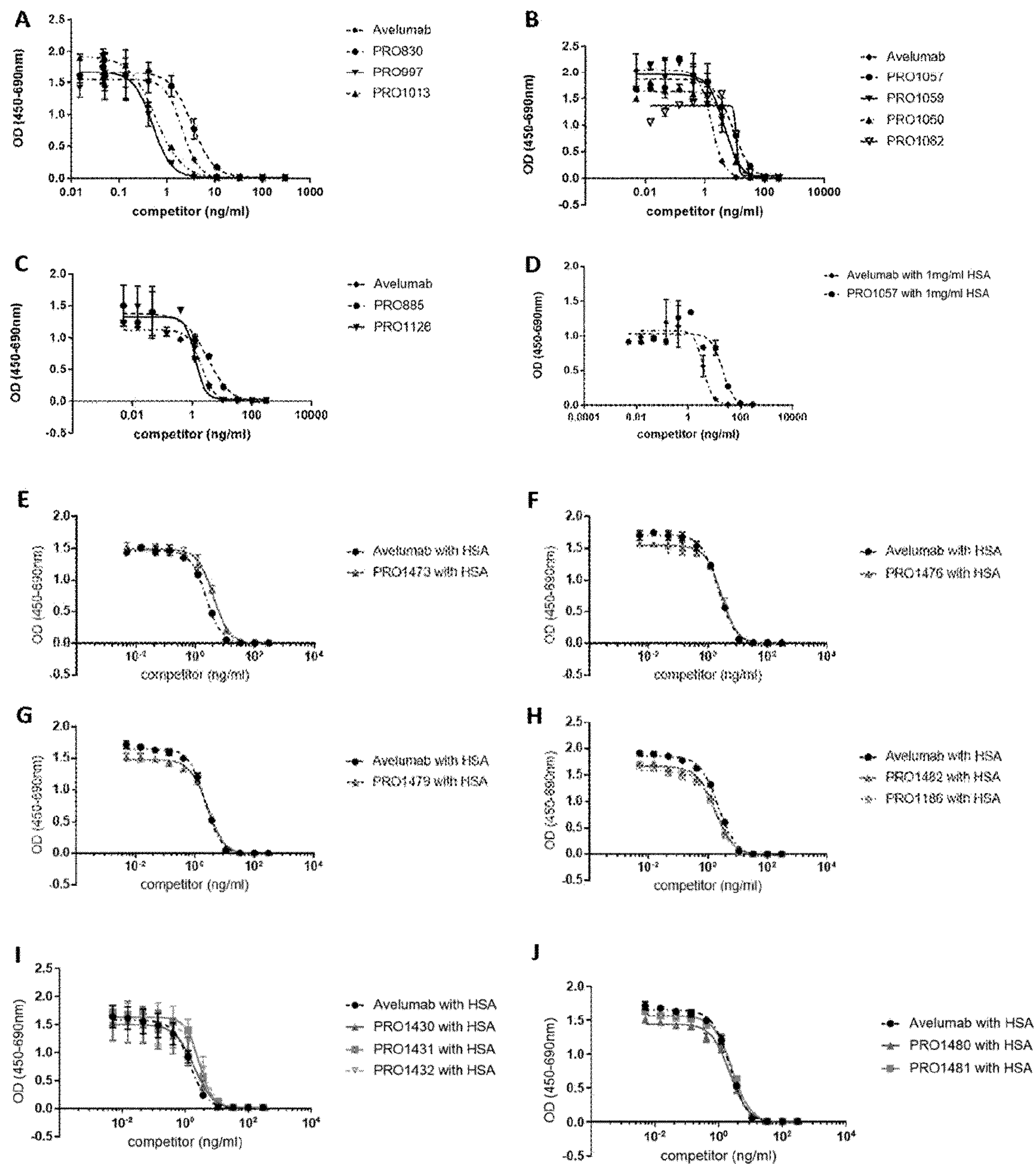
FIG. 7 PD-1/PDL1 competition ELISA. All molecules potently blocked the interaction between PD-1 and PDL1, with similar or smaller IC50 values than the reference IgG avelumab.

Individual IC50 values on each plate were calibrated against the $IC_{50}$ of the reference molecule avelumab that was taken along on each plate (relative $IC_{50}$: $IC_{50,\ avelumab}/IC_{50,\ test\ scFv}$). Potencies are summarized in Table 8. As illustrated in FIG. 7 and Table 8, all PDL1 inhibitors blocked the interaction of PD-1 with PDL1 when tested in the competition ELISA. The scFv PRO830 blocked the interaction with similar potency while PR0997 and PRO1013 exhibited significantly lower $IC_{50}$ values than avelumab and are thus more potent inhibitors. When combined into multispecific formats, i.e. scDbs or Morrisons, all molecules conserved their inhibiting properties. PRO885 was less potent than avelumab whereas a lower $IC_{50}$ value was determined for PRO1126 comprising an improved anti-PDL1 domain. The Morrison formats were slightly less potent when compared to avelumab. The neutralizing effect of PRO1057 was also shown in presence of human serum albumin, where $IC_{50}$ values were approximately two-fold higher.

PDL1/B7.1 Competition ELISA

Method

ELISA microplates coated overnight at 4° C. with 4 μg/ml human B7.1 were washed three times with 450 μl wash buffer per well. Plates were blocked for 1 hour at room temperature by adding 300 μl of PBS with 1% BSA and 0.2% tween (dilution buffer) to each well. Inhibitors were serially diluted in 3-fold steps to final concentrations ranging from 900 to 0.015 ng/ml in dilution buffer containing 40 ng/ml biotinylated PDL1. The mixtures were pre-incubated for 1 hour at room temperature under gentle agitation on a rotating mixer (21 rpm) and added to the microplates after 3 wash cycles with 450 μl wash buffer per well. Plates were incubated for 1.5 hours at room temperature under gentle agitation, then 10 ng/ml streptavidin-polyHRP40 was added to each microplate well after three washes with 450 μl of wash buffer per well. After 1 h incubation at RT, plates were washed three times with 450 μl wash buffer and TMB substrate solution was added. The enzymatic reaction was stopped after 6 minutes by addition of 1 M HCl and absorbance was measured at 450 nm using 690 nm as a reference wavelength. For calculation of $IC_{50}$ values, a four-parameter logistic (4PL) curve fit was performed in Graph Pad Prism using reference subtracted values.

Results

Figure 8:
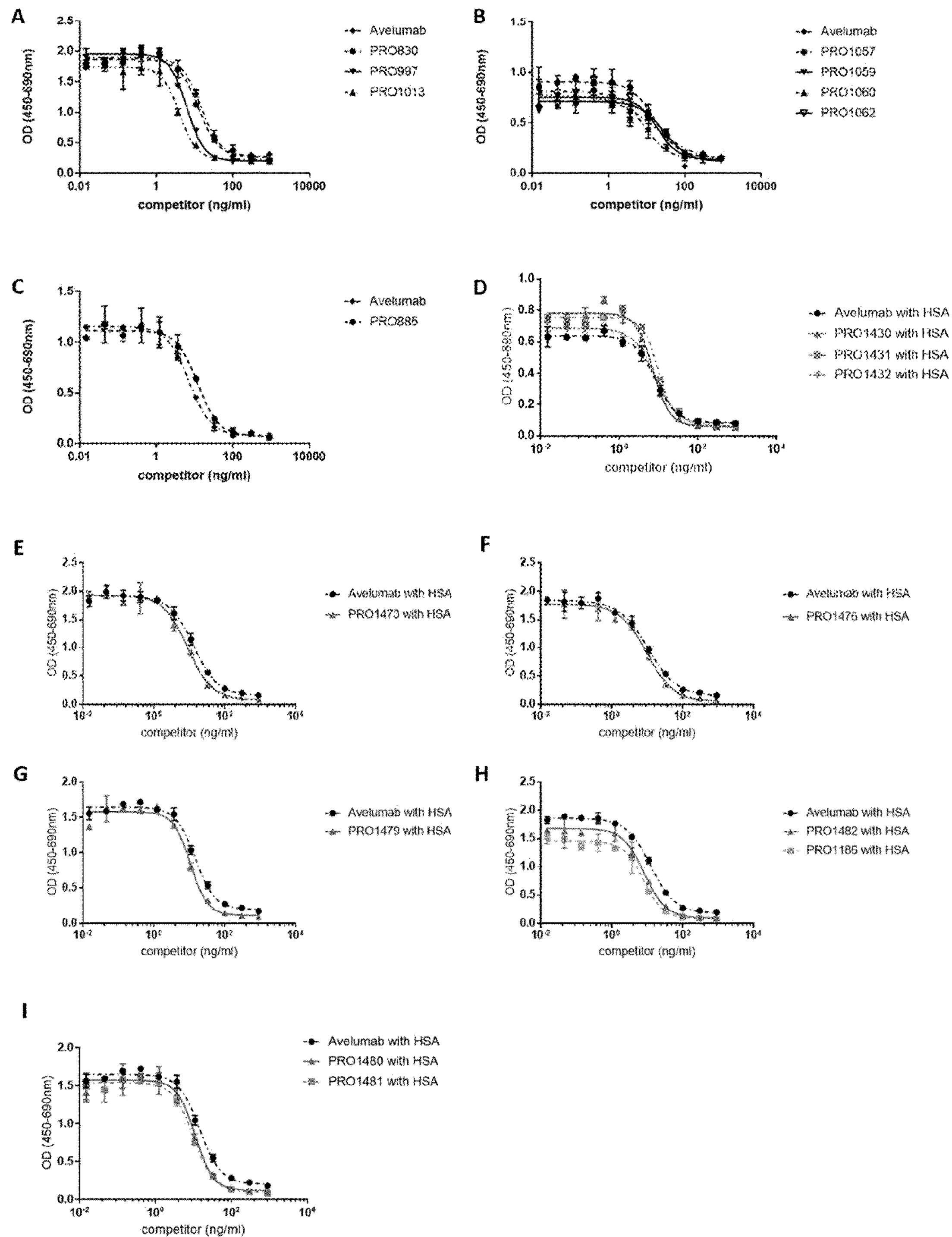
FIG. 8 B7.1/PDL1 competition ELISA. Similarly to avelumab, all molecules potently blocked the interaction between B7.1 and PDL1.

Individual IC50 values on each plate were calibrated against the IC50 of the reference molecule avelumab that was taken along on each plate (relative $IC_{50}$: $IC_{50,\ avelumab}/IC_{50,\ test\ scFv}$). Potencies are summarized in Table 8. Except for PRO 1126, all PDL1 inhibitors were also tested for their ability to block the interaction of PD-1 with B7.1. PRO830 showed similar potency than avelumab whereas lower $IC_{50}$ values were determined for PR0997 and PRO1013. All scDbs and Morrisons also inhibited the interaction between PDL1 and B.7-1. The scDb PRO885 exhibited similar potency than avelumab whereas the $IC_{50}$ values for the Morrisons were about 2-3.4 fold lower. Data shown in FIG. 8 and Table 8.

Example 4: No Inhibition of CD137 and CD137 Neutralization by Humanized Anti-CD137 Domains Methods:

To show that PRO885 does not interfere with the binding of CD137 ligand (CD137L) to CD137, a competitive ELISA was employed. The commercial inhibitory polyclonal anti-CD137 goat antibody (Antibodies online, Cat #ABIN636609) served as a reference. In brief, CD137 was coated on the ELISA plate overnight and serial dilutions of PRO885 were added to the ELISA plate. Afterwards, biotinylated CD137L was added and bound ligand was detected by addition of Streptavidin-HRP. Finally, the HRP substrate TMB was added. After development for 5 min, the reaction was stopped with 1 M HCl solution. The absorbance was measured at 450 nm and 690 nm as reference.

Figure 9:
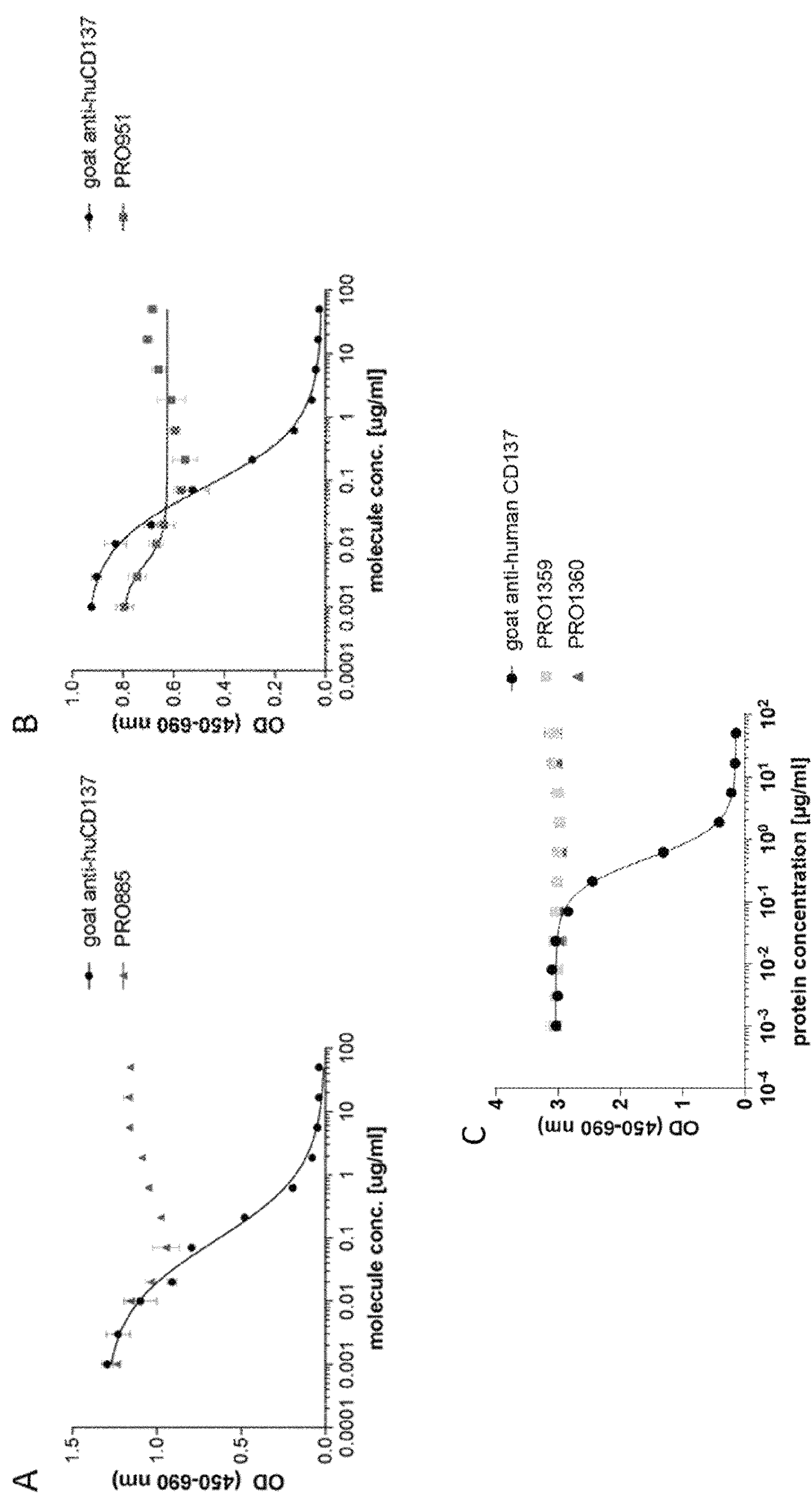
FIG. 9 No inhibition of CD137 binding to CD137L in competition ELISA. The absorbance measured in the competitive ELISA assessing the binding of CD137L to CD137 are represented in function of increasing concentrations of PRO885 (A), PR0951 (B), PRO1359 and PRO1360 (C). The inhibitory antibody goat anti-human CD137 served as a reference.

Results:

The titration curves obtained for PRO885 containing the CD137 domain derived from clone 38-02-A04 are represented in FIG. 9A and the binding curves obtained for PR0951 containing the CD137 domain derived from clone 38-27-C05 are represented in FIG. 9B. The titration curves obtained for PRO1359 and PRO1360 containing the CD137 domain derived from clone 38-27-A11 are represented in FIG. 9C. While the reference antibody completely prevented binding of CD137L to CD137, PRO885, PR0951, PRO1359 and PRO1360 did not significantly inhibit the CD137L binding to CD137 and therefore were defined as non-neutralizing.

Example 5: Epitope Binning of 38-02-A04 and 38-27-C05 Against Urelumab and Utomilumab Methods:

The binding epitopes on CD137 of the proteins PRO885 (scDb containing 38-02-A04 CDR graft), PR0951 (scDb containing 38-27-C05 CDR graft), rabbit IgG derived from clone 38-27-A11 and the competitor molecules urelumab (BMS) and utomilumab (Pfizer) were compared in a SPR epitope binning assay using a MASS-1 device (Sierra Sensors). A sandwich setup was chosen to examine if the molecules block one another's binding to CD137. Therefore, PRO885, PR0951, rabbit IgG derived from clone 38-27-A11, urelumab and utomilumab were immobilized on high capacity amine sensor chips (HCA, Sierra Sensors). Then, 90 nM of the antigen CD137 (PeproTech, cat. 310-15) was injected and captured on the scDbs, the rabbit IgG 38-27-A11, urelumab or utomilumab, followed immediately by an injection of 22.5 nM of the second antibody (PRO885, PR0951, the rabbit IgG 38-27-A11, urelumab or utomilumab). The capture levels of CD137 on each protein and the second binder response levels were determined (response units, RU). By calculating the theoretical maximum response (Rmax), which depends on the molecular weights of the involved proteins and the capture levels, the relative binding level (%) of the proteins on the captured antigen were determined. If the molecules bind the same, overlapping (e.g., a structurally similar or spatially proximal) or similar epitopes on CD137, no binding of the antibody injected over the captured CD137 should be observed. Consequently, when binding of the antibody is observed the two antibody pairs bind non-overlapping epitopes. The relative binding levels (in %) were determined for each antibody pair. By definition, a binding level below 10% indicates the same or an overlapping (e.g., a structurally similar or spatially proximal) on CD137 and above 30% refers to non-overlapping epitopes.

Figure 10:
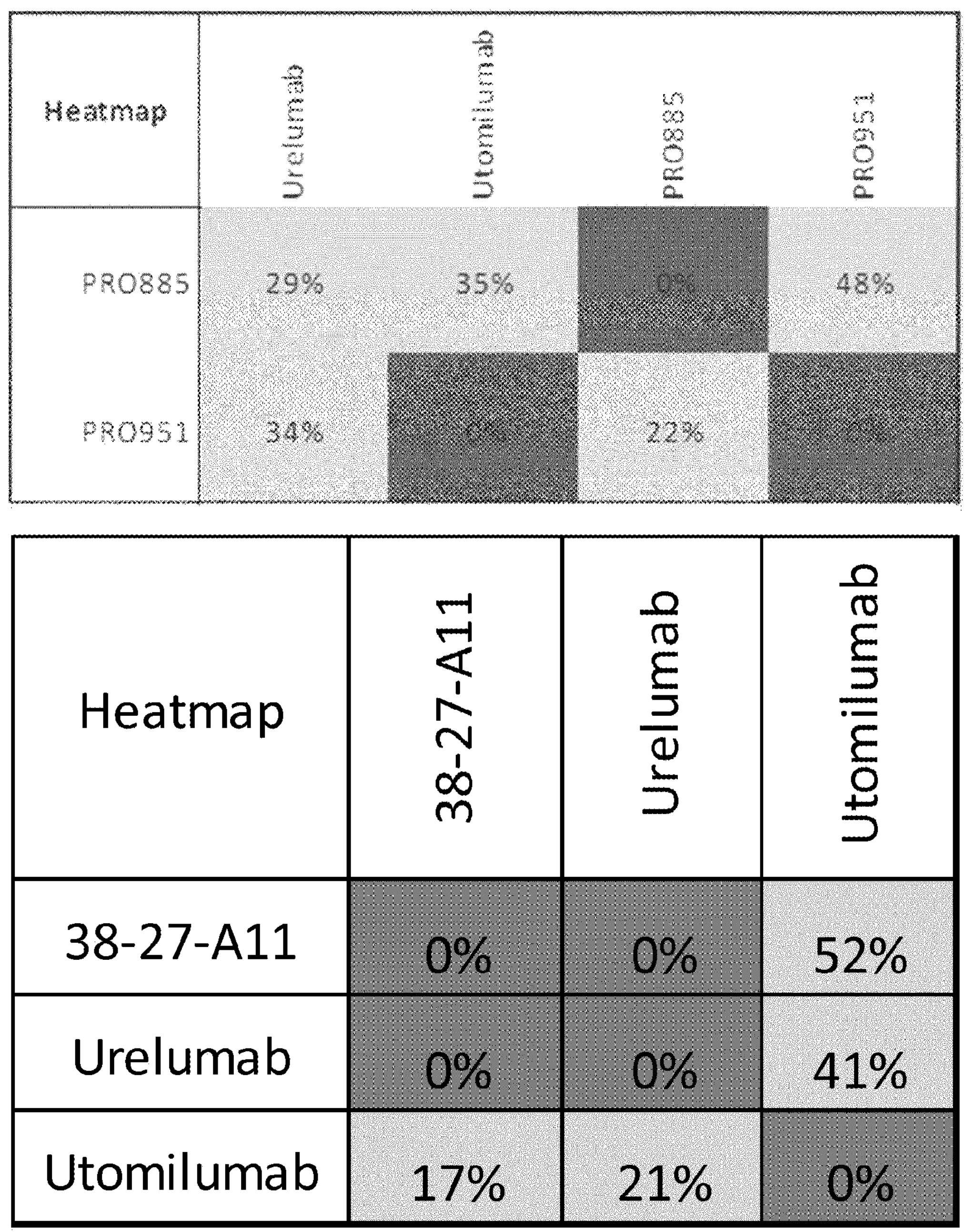
FIG. 10 Heatmap of epitope binning results of PRO885, PR0951, rabbit IgG derived from clone 38-27-A11 and urelumab and utomilumab. Binding level normalized to theoretical Rmax in percent (%) of analyte molecules (column) to immobilized molecules (row). No binding (dark grey) means same epitope, bright grey means the secondary molecule (analyte) can bind and has another epitope than the immobilized molecule.
Figure 11:
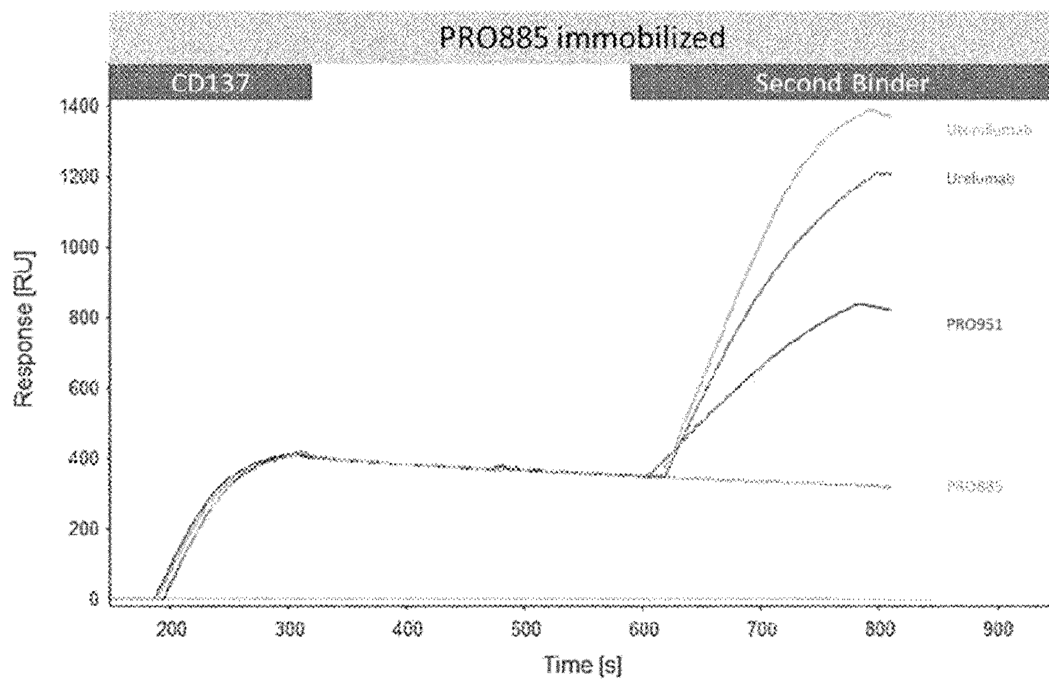
FIG. 11 Epitope binning sensorgram of PRO885. PRO885 was immobilized on sensor chip and CD137 was captured by PRO885 in a first step (left hand side) followed by injections of the 4 different antibodies (right hand side). PR0951 as well as competitors were able to bind to captured CD137 whereas an injection of PRO885 did not show any binding.
Figure 12:
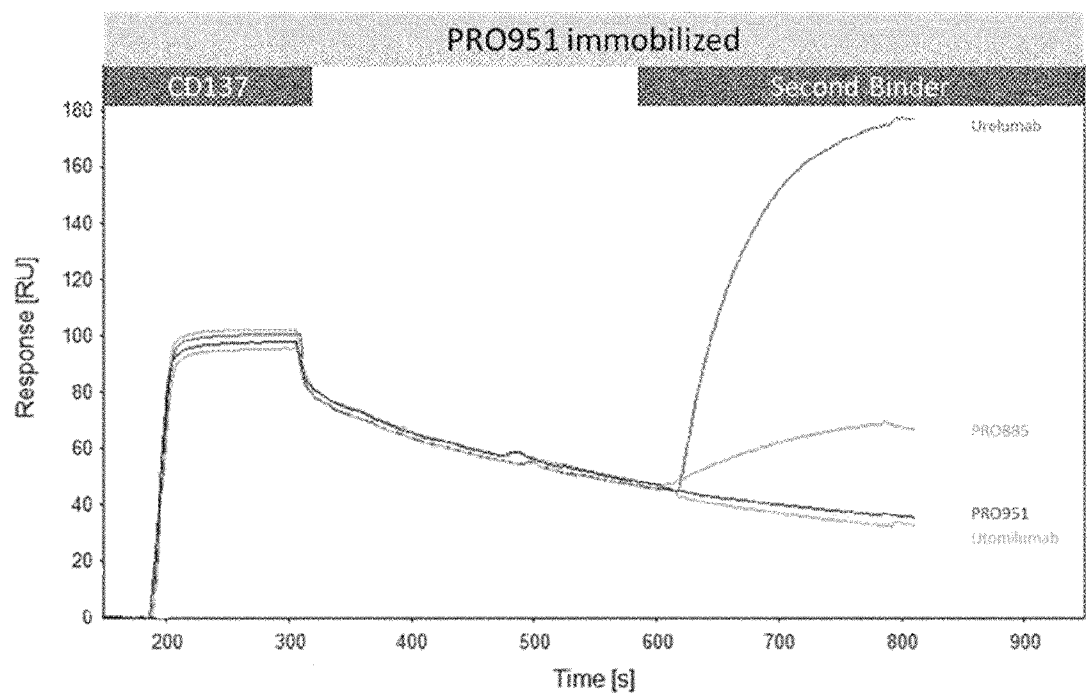
FIG. 12 Epitope binning sensorgram of PR0951. PR0951 was immobilized on sensor chip and CD137 was captured by PR0951 in a first step (left hand side) followed by injections of the 4 different antibodies (right hand side). PRO885 as well as urelumab was able to bind to captured CD137 whereas an injection of utomilumab and PR0951 did not show further binding.

Results:

When PRO885 was immobilized on a sensor chip, all 3 antibodies PR0951, urelumab and utomilumab showed binding to CD137 captured by PRO885. As expected, no binding was observed for PRO885 that was used a control (FIG. 10 and FIG. 11). When PR0951 was immobilized on the sensor chip, urelumab and PRO885 showed binding while utomilumab and PR0951 that was used as control did not show any significant binding (FIG. 10 and FIG. 12). These results show that PRO885 derived from clone 38-02-A04 binds to different epitopes on CD137 than urelumab, utomilumab and PR0951 derived from 38-27-C05. In contrast, R0951 binds to an epitope that is overlapping with utomilumab but not with urelumab and PRO885.

The IgG 38-27-A11 did not compete with utomilumab for binding to CD137 suggesting non-overlapping epitopes, while competed with urelumab for binding to CD137 suggesting either the same or overlapping epitopes (FIG. 10).

Example 6: Assessment of the CD137 Agonistic Effect of Anti-PDL1×CD137 Molecules by Using a Cell-Based Assay of Transgenic NFkB Jurkat Reporter Cell Line Expressing CD137

Introduction

In this assay, the activation of CD137 signaling in Jurkat cells was assessed. The activity of CD137 signaling is reported by measurement of Luciferase expression which is driven by CD137 induced NF-kB activation in a Jurkat reporter cell line. The expression of Luciferase directly correlates with the activity of CD137. Moreover, clustering of CD137 which is required for activation of the signal pathway is facilitated via then formation of an immunological synapse between the Jurkat cells and a PDL1 expressing cell line. Therefore, PDL1 expression is needed for clustering and activation of CD137 on the reporter cell line.

Methods

PDL1 expressing CHO (clone A2) and HCC827 cells unstimulated or stimulated for 24 h with 10 ng/ml IFNy to increase PDL1 expression were seeded at 25,000 cells per well on 96-well culture plates. As a negative control, CHO WT cells without PDL1 expression were seeded at the same cell density. Then, serial dilutions of the anti-PDL1×CD137 molecules as well as the competitor urelumab were prepared and added to the cells. Next, Jurkat reporter cells were prepared in assay medium containing HSA at 25 mg/ml or without and added at a cell density of 40,000 cells per well. Luciferase expression was detected by addition of Luciferase reagent and was read by a luminescence reader 6 or 24 h after addition of Jurkat cells. Data were analyzed by normalization the relative luminescence units (RLU) of the test samples to the RLU measured for urelumab (FIGS. 13 to 18, FIG. 19A) or PRO885 (FIG. 19B) yielding values of the relative activation of CD137 signaling.

PDL1 expressing HCC827 cells stimulated for 24 h with 10 ng/ml IFNy to increase PDL1 expression were seeded at 25,000 cells in 50 μl of cell culture medium (RPMI, 10% FCS) per well on 96-well culture plates. As a negative control, CHO-K1 WT cells without PDL1 expression were seeded at the same cell density. Then, 25 μl of 4-fold concentrated 5-fold serial dilutions of the respective molecules to be tested and the references PRO 1186 and PRO885 from 40,000 to 0.02 ng/ml were added. Then, 25 μl of CD137 expressing effector Jurkat cells (Promega) diluted at 1.6E+06 cell/ml in assay buffer (RPM11640 with 10% FCS and 100 mg/ml HSA) were added to each well resulting in a final concentration of HSA of 25 mg/ml. Plates were then incubated for 6 h and 24 at 37° C. and 5% CO2. Finally, 50 μL luciferase substrate (BPS Bioscience) prepared according to manufacturer's protocol was added per well and plates were incubated 15 min in the dark, luminescence was measured using Flexstation 111. Individual EC50, IC10/EC90, and AUC values on each plate were calibrated against the respective values of the reference molecule PRO1186 that was taken along on each plate (Table 16C). The EC50 and EC90 values of the dose response curve were obtained by using a four parameter logistic fit of the points with increasing relative luminescence units (RLU) and, on the other hand, the points with decreasing RLUs were fitted by using a four parameter logistic fit with constrained bottom to calculate the IC10 value. The area under the curve (AUC)

was calculated for all samples using PRO885 normalized data. All parameters were retrieved by using GraphPad prism software.

Results

Figure 13:
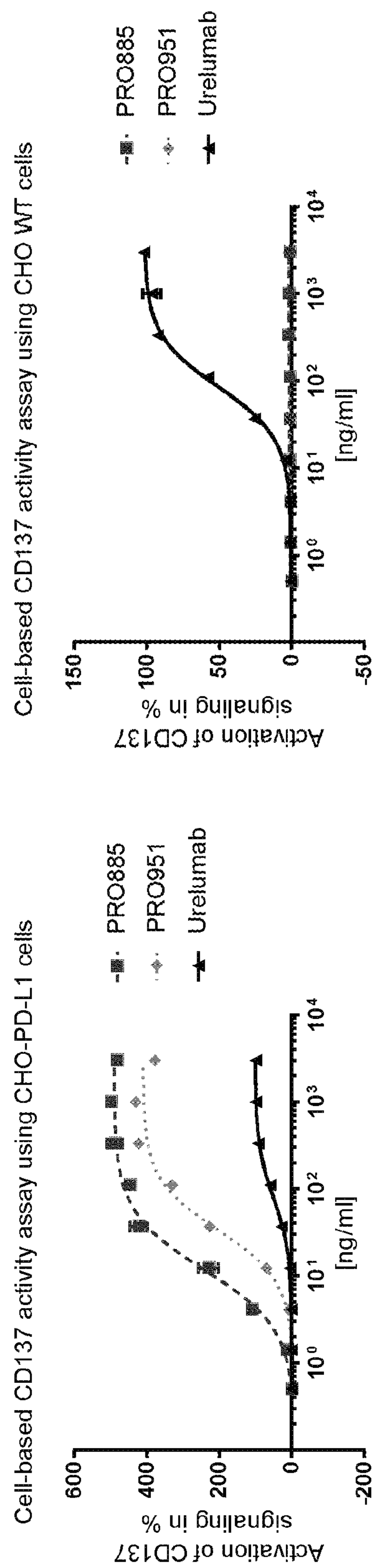
FIG. 13 CD137 activation by PRO885 and PR0951 as assessed in the NFkB-Luciferase reporter gene assay. In the presence of PDL1 expressing cells, PRO885 and PR0951 activated CD137 signaling in Jurkat cells whereas no activation was observed when CHO WT cells were tested. Urelumab activated CD137 signaling independently of PDL1 expression. Luminescence was read 6 h after addition of Jurkat reporter cells and data were fitted using sigmoidal 4PL fit (GraphPad Prism).

I. Test of PRO885 and PR0951 using CHO-PDL1 Cells:

As shown in FIG. 13, PRO885 and PR0951 activated CD137 signaling more efficient in the presence of PDL1 expressing CHO cells than urelumab. PRO885 showed the best potency and highest signal of activation (PRO885, $EC_{50}$=11.72 ng/ml, PR0951: $EC_{50}$=33.68 ng/ml; urelumab: $EC_{50}$=79.11 ng/ml, Table 9). In the absence of PDL1, neither PRO885 nor PR0951 could activate CD137 in reporter cells while urelumab showed activation of CD137 signaling independently of PDL1.

TABLE 9

EC50 values for anti-PDL1 × CD137 molecules using CHO-PDL1 cells.

| | urelumab | PRO885 | PRO951 |
|---|---|---|---|
| Bottom | −0.4628 | −8.1 | −4.066 |
| Top | 101.5 | 491.2 | 411.4 |
| EC50 in ng/ml | 79.11 | 11.72 | 33.68 |
| R square | 0.995 | 0.9922 | 0.9899 |

Figure 14:
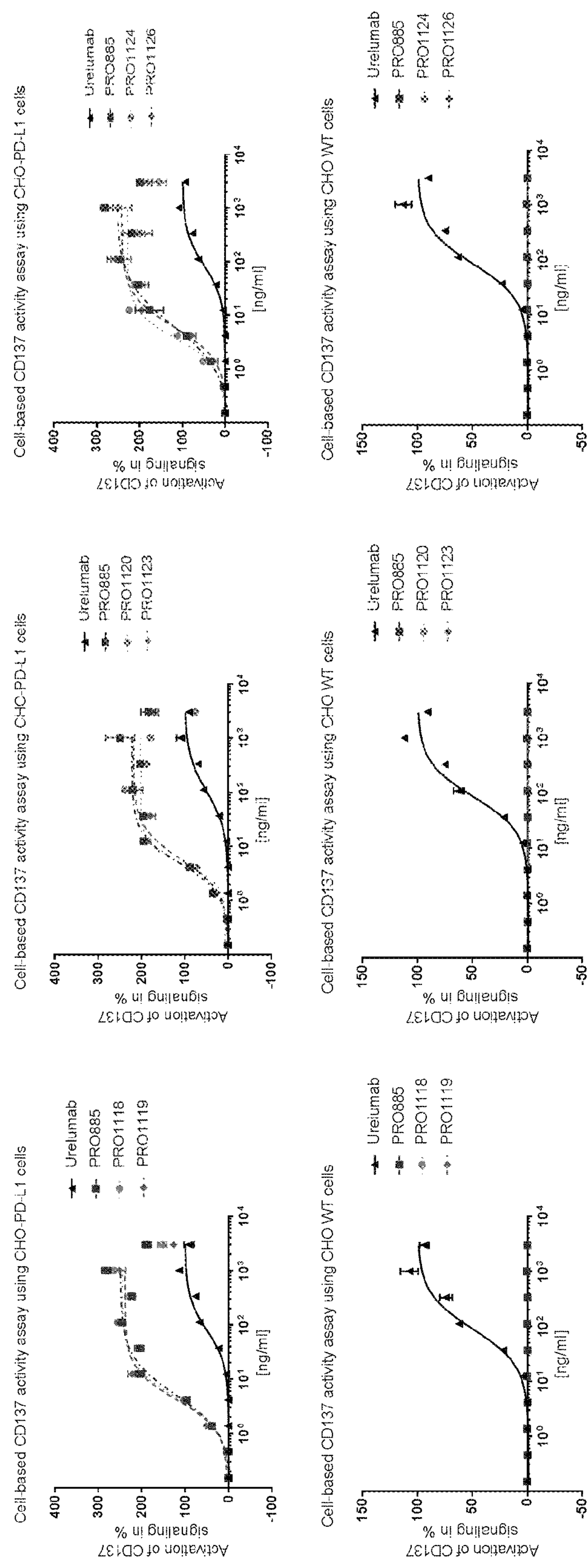
FIG. 14 CD137 activation in the NFkB-Luciferase reporter gene assay by scDb with different affinities to PDL1 and CD137. In the presence of PDL1 expressing CHO cells, all scDb activated CD137 signaling in Jurkat cells whereas no activation was observed when CHO WT cells were tested. Urelumab activated CD137 signaling independently of PDL1 expression. Luminescence was read 6 h after addition of Jurkat reporter cells and data were fitted using sigmoidal 4PL fit (GraphPad Prism).

II. Test of STR-Grafted scDbs Using CHO-PDL1 Cells:

As shown in FIG. 14 and Table 10, the anti-PDL1×CD137 scDb molecules stimulated CD137 signaling more efficiently than urelumab. In contrast to urelumab, the stimulatory effect was only seen for the scDb when PDL1 expressing target cells were present. All scDbs showed identical potency to stimulate Nf-kB reporter gene activation in presence of CHO cells expressing PDL1 at high levels. Next, the same molecules were tested in the presence of cells expressing a lower amount of PDL1.

Figure 15:
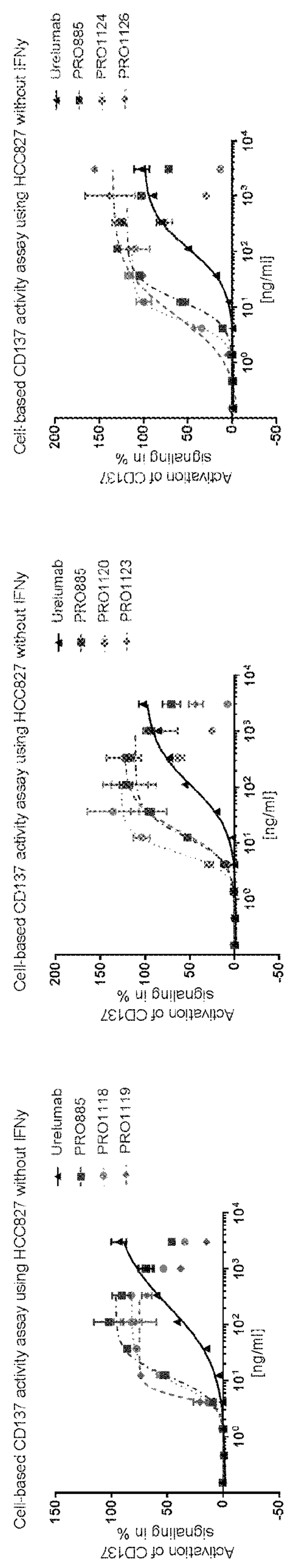
FIG. 15 CD137 activation in the NFkB-Luciferase reporter gene assay by scDb with different affinities to PDL1 and CD137. In the presence of PDL1 expressing HCC827 cells, all scDb activated CD137 signaling in Jurkat cells. Urelumab served as reference molecule to assess the relative activation of CD137 signaling. Potency increased slightly with increasing affinity to CD137 and PDL1. A signal decrease at high concentrations (bell-shaped curve) was more pronounced with increasing affinity to CD137, while increased affinity to PDL1 did not contribute to this effect. Luminescence was read 6 h after addition of Jurkat reporter cells and data were fitted using sigmoidal 4PL fit (GraphPad Prism).

III. Test of STR-Grafted scDb Using HCC827 Cells without IFNγ:

As shown in FIG. 15 and Table 11, the anti-PDL1×CD137 scDb molecules stimulated CD137 signaling more efficiently than urelumab. The scDbs with affinity improved CD137 domain (STR grafts of 38-02-A04, PRO 1120 and PRO 1124) showed an improved potency in CD137 activation when compared to the CDR grafted CD137 domain (for instance, PRO885, $EC_{50}$=13.02 ng/ml, PRO 1124: $EC_{50}$=5.62 ng/ml, Table 11). Of note, increased affinity to PDL1 as it was found for the STR graft of the PDL1 domain (Prol 126) also resulted in increased potency when compared to the parental molecule PRO885 (PRO885, $EC_{50}$=13.02 ng/ml, PRO 1126: $EC_{50}$=6.97 ng/ml, Table 11). At high concentrations, the STR grafted scDb showed a tendency of decreasing signal of activation. This was more pronounced for molecules having a STR grafted CD137 domain (PRO1120 and PRO 1126). Interestingly, when the STR graft of the PDL1 domain was combined with the CDR graft of CD137 the signal decrease at high concentrations was not observed (compare PRO885 and PRO1124 in FIG. 15). Thus, potency increased slightly with increasing affinity to CD137 and PDL1. A signal decrease at high concentrations (bell-shaped curve) was more pronounced with increasing affinity to CD137, while increased affinity to PDL1 did not contribute to this effect. Thus, rather the ratio between affinity to CD137 and PDL1, than the absolute affinities of each domain seem critical to extend the concentration window of maximal activity.

Figure 16:
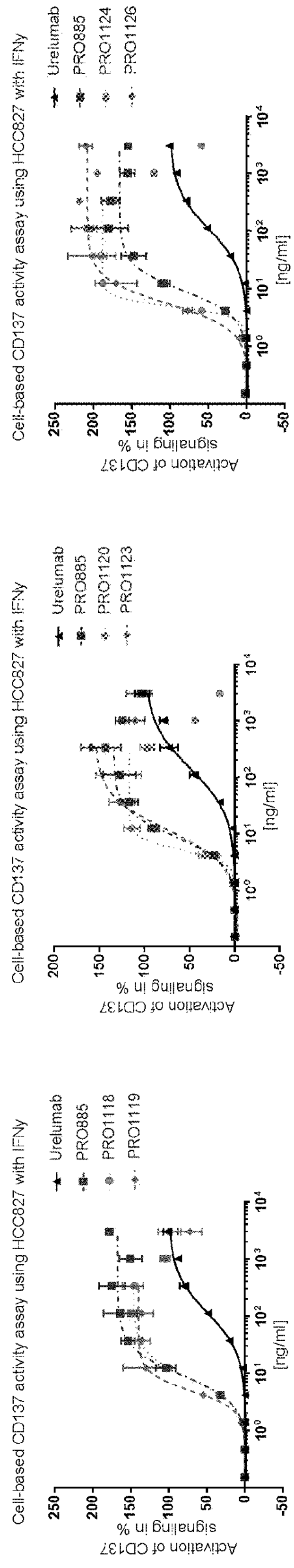
FIG. 16 CD137 activation in the NFkB-Luciferase reporter gene assay by scDb with different affinities to PDL1 and CD137. In the presence of PDL1 expressing HCC827 cells stimulated with IFNy for 24 h at 10 ng/ml, STR grafted scDb activated CD137 signaling in Jurkat cells. Urelumab served as reference molecule to assess the relative activation of CD137 signaling. Potency increased slightly with increasing affinity to CD137 and PDL1. A signal decrease at high concentrations (bell-shaped curve) was more pronounced with increasing affinity to CD137, while increased affinity to PDL1 did not contribute to this effect. Luminescence was read 6 h after addition of Jurkat reporter cells and data were fitted using sigmoidal 4PL fit (GraphPad Prism).

IV. Test of STR-Grafted scDb Using HCC827 Cells with IFNγ:

Stimulation of HCC827 with IFNγ led to increased signal of activation without changing the potency of the scDb molecules. Of note, the drop of signal at high concentration of the tested scDb was less obvious in this setting suggesting a correlation with PDL1 expression (FIG. 16 and Table 12).

Figure 17:
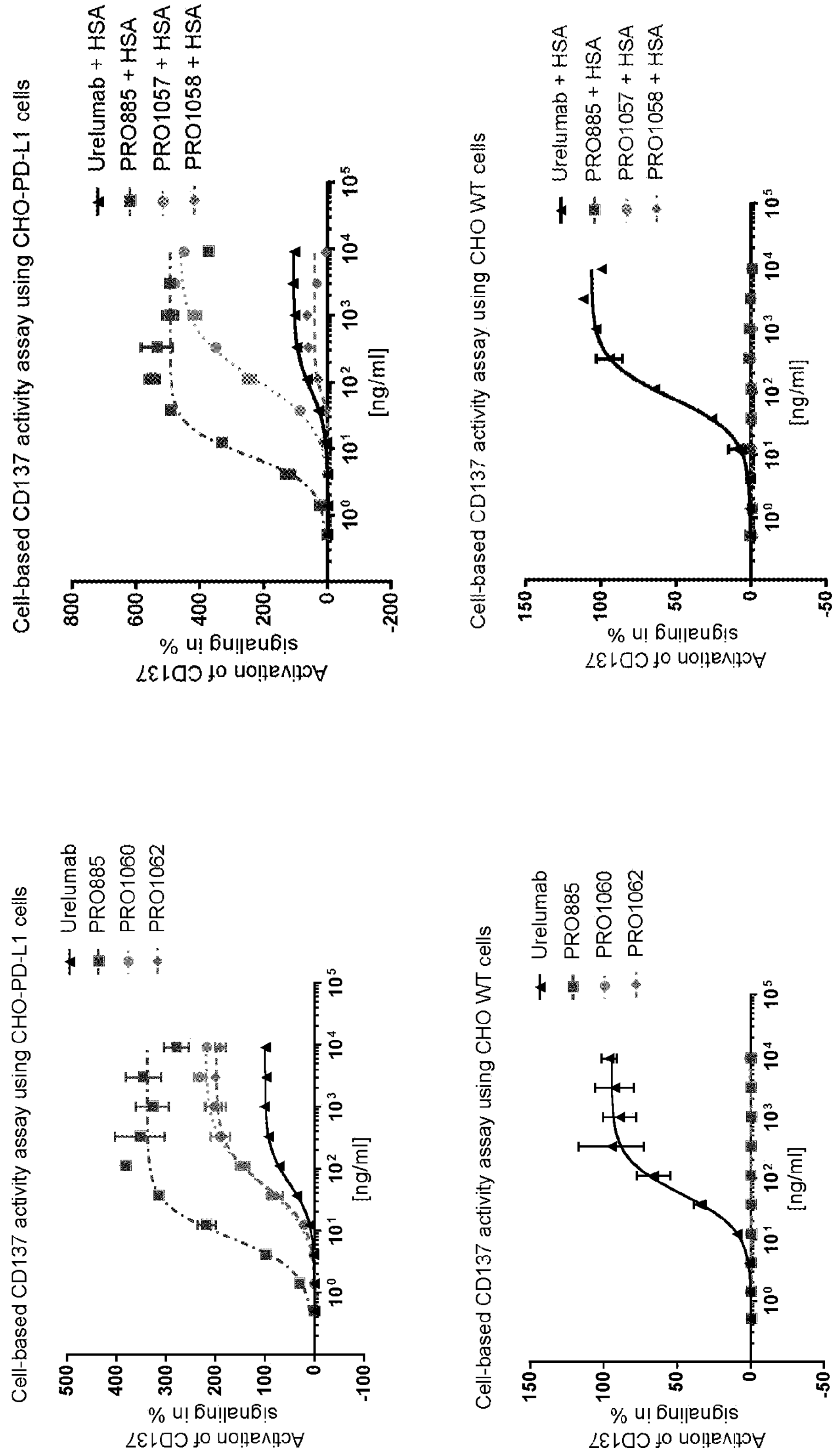
FIG. 17 CD137 activation by molecules with prolonged serum half-life in the NFkB-Luciferase reporter gene assay after 6 h. In the presence of PDL1 expressing CHO cells, long half-life molecules activated CD137 signaling in Jurkat cells whereas no activation was observed when CHO WT cells were tested. Urelumab activated CD137 signaling independently of PDL1 expression. Interestingly, despite similar affinities to both targets, PRO1057 showed a much higher maximal signal than PRO1058. And further, the monovalent scDb-scFv PRO1057 showed stronger activation than the respective bivalent Morrison format PRO1060.

V. Test of Long Half-Life Molecules Using CHO-PDL1 Cells:

As shown in FIGS. 17 and 18, Tables 13 and 14, tested long half-life anti-PDL1×CD137 molecules stimulated CD137 signaling to the same extend as urelumab did. There was a difference when the Morrision formats (PRO1060, PRO1062) were compared to the scDb-scFv formats (PRO1057, PRO1058). While the Morrison formats showed a higher potency, the maximum signal of activation was substantially increased when the scDb-scFv were tested. Of note, after 24 h of incubation PRO1057 showed a remarkable high signal of activation. All tested long half-life molecules activated CD137 signaling only in the presence of PDL1 expressing cells. Interestingly, despite similar affinities to both targets, PRO1057 showed a much higher maximal signal than PRO1058. And further, the monovalent scDb-scFv PRO1057 showed stronger activation than the respective bivalent Morrison format PRO1060.

Figure 19A:
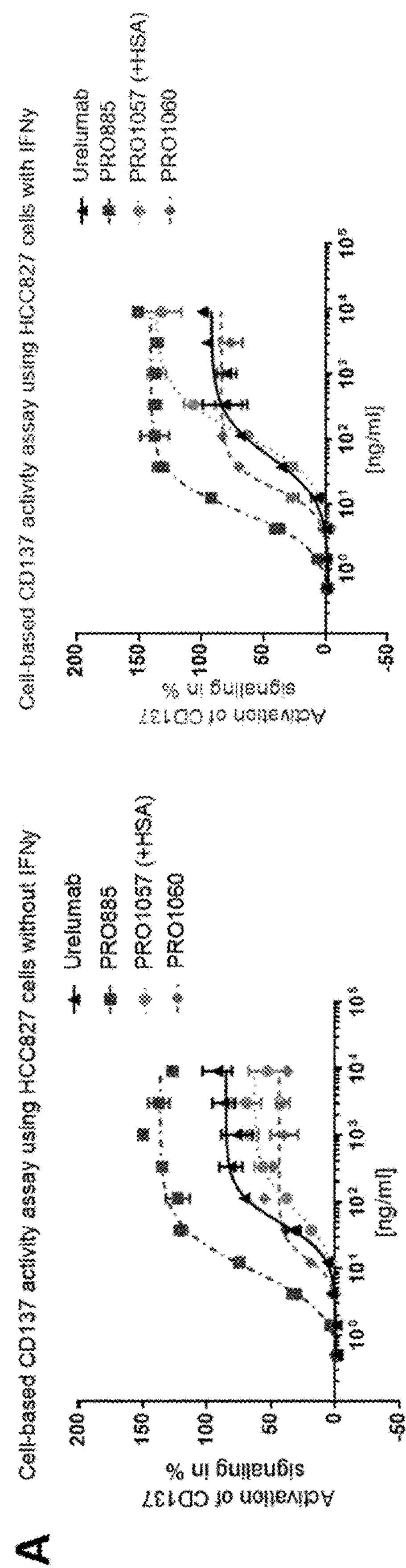

VI. Test of Long Half-Life Molecules Using HCC827 Cells without and with IFNγ:

As shown in FIG. 19A and Table 15, tested long half-life anti-PDL1×CD137 molecules stimulated CD137 signaling to the same extend as urelumab in the presence of cells expressing lower amounts of PDL1. The maximum activation of tested molecules was further increased when the target cells were stimulated by IFNγ suggesting a direct correlation of CD137 activation with the levels of PDL1 expression on the target cells. As already stated above, PRO1057 showed a higher level of reporter gene activation when compared to the Morrison formats (PRO1060).

Figure 19B:
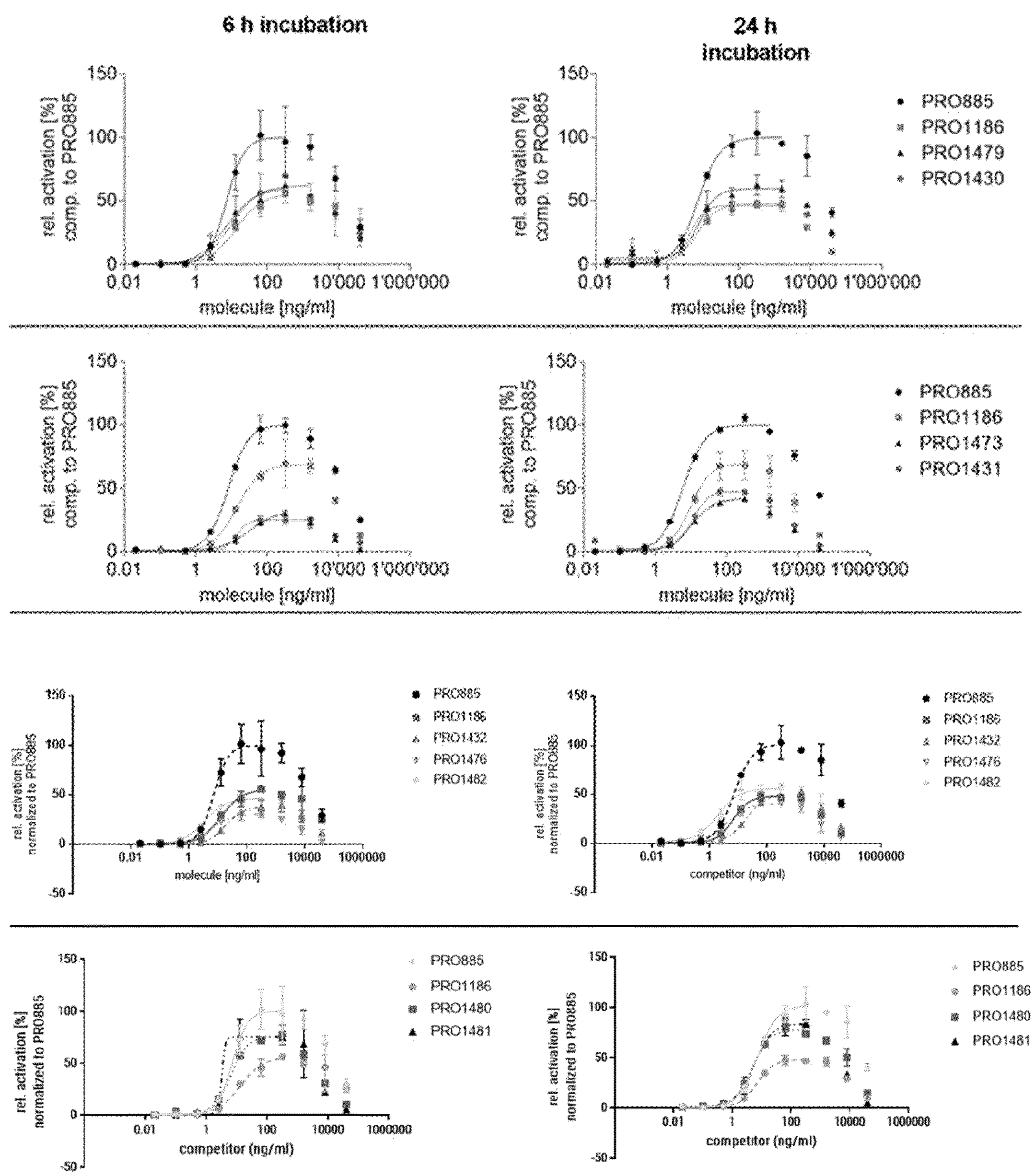

FIG. 19B represents results of the tests of tri-specific scDb-scFv molecules PRO1430, PRO1431, PRO1432, PRO1473, PRO1476, PRO1479, PRO1480, PRO1481 and PRO1482 in CD137 activity assay in the presence of IFNγ (10 ng/ml) stimulated HCC827 for 6 h and 24 h.

Data for NF-kB reporter gene activation by PDL1× CD137 multispecific constructs are summarized in Tables 16A, 16B and 16C.

In order to compare the shape of the activity curves for the candidate molecules, the area under the curve (AUC, representing a combined measure for signal amplitude and width of the bell-shaped curve, the effect size) and the width of the plateau (EC90/IC10 ratio, providing an indication of the therapeutic window) were calculated (see Table 16C). The best rel. AUC values (at least above 1 at one time point when normalized to PRO1186) were found for PRO1430, PRO1479, PRO1480 and PRO1481. Of note, a high EC90/IC10 ratio of the test sample indicates a broad bell-shaped dose-response curve and, as a consequence, proposes a larger concentration range of full activity. Thus, the top candidates show full activity in a concentration range of several hundred-fold.

Based on these parameters, the best performing scDb-scFvs in NF-kB reporter gene assay were PRO1430, PRO1479 and PRO1480.

TABLE 10

$EC_{50}$ values for anti-PDL1 × CD137 molecules using CHO-PDL1 cells.

| | Urelumab | PRO885 | PRO1118 | PRO1119 | | Urelumab | PRO885 |
|---|---|---|---|---|---|---|---|
| Bottom | −0.5169 | −6.408 | −2.387 | 2.039 | Bottom | −0.6273 | 0.5392 |
| Top | 99.99 | 249.1 | 245.3 | 238.9 | Top | 100 | 222.1 |
| EC50 in ng/ml | 79.47 | 5.135 | 4.596 | 4.22 | EC50 in ng/ml | 104.2 | 4.856 |
| R square | 0.9637 | 0.9708 | 0.9761 | 0.9726 | R square | 0.9677 | 0.9769 |

| | PRO1120 | PRO1123 | | Urelumab | PRO885 | PRO1124 | PRO1126 |
|---|---|---|---|---|---|---|---|
| Bottom | 6.497 | −1.816 | Bottom | −0.499 | −11.51 | 2.552 | −2.922 |
| Top | 201.1 | 219.2 | Top | 100 | 253.8 | 228.6 | 242.1 |
| EC50 in ng/ml | 4.689 | 5.753 | EC50 in ng/ml | 86.51 | 6.299 | 3.681 | 5.997 |
| R square | 0.963 | 0.9568 | R square | 0.979 | 0.9714 | 0.9561 | 0.9467 |

TABLE 11

$EC_{50}$ values for anti-PDL1 × CD137 molecules using HCC827 cells without IFNγ.

| | Urelumab | PRO885 | PRO1118 | PRO1119 | | Urelumab | PRO885 |
|---|---|---|---|---|---|---|---|
| Bottom | −2.035 | −0.5477 | −0.3666 | 0.1789 | Bottom | −1.986 | −0.2298 |
| Top | 100 | 96.45 | 81.98 | 74.91 | Top | 99.96 | 111.1 |
| EC50 in ng/ml | 212.5 | 11.5 | 8.559 | 5.045 | EC50 in ng/ml | 109.9 | 13.06 |
| R square | 0.9815 | 0.9852 | 0.995 | 0.9725 | R square | 0.9895 | 0.9759 |

| | PRO1120 | PRO1123 | | Urelumab | PRO885 | PRO1124 | PRO1126 |
|---|---|---|---|---|---|---|---|
| Bottom | 0.0807 | −0.8367 | Bottom | −1.384 | −0.3237 | −1.084 | −8.28 |
| Top | 126.5 | 123.2 | Top | 99.98 | 118.7 | 113.2 | 135.1 |
| EC50 in ng/ml | 6.685 | 16.12 | EC50 in ng/ml | 111.7 | 13.02 | 5.616 | 6.966 |
| R square | 0.9609 | 0.96 | R square | 0.9941 | 0.9816 | 0.9875 | 0.9577 |

TABLE 12

$EC_{50}$ values for STR grafted scDb using HCC827 cells stimulated with IFNγ.

| | Urelumab | PRO885 | PRO1118 | PRO1119 | | Urelumab | PRO885 |
|---|---|---|---|---|---|---|---|
| Bottom | −1.208 | −1.446 | −1.564 | 0.1399 | Bottom | −1.009 | −2.023 |
| Top | 100 | 167.4 | 146.5 | 139.9 | Top | 99.98 | 134.2 |
| EC50 in ng/ml | 114.2 | 9.266 | 7.965 | 4.855 | EC50 in ng/ml | 144.8 | 8.883 |
| R square | 0.9939 | 0.9803 | 0.996 | 0.9767 | R square | 0.9811 | 0.9795 |

| | PRO1120 | PRO1123 | | Urelumab | PRO885 | PRO1124 | PRO1126 |
|---|---|---|---|---|---|---|---|
| Bottom | 0.1813 | −3.584 | Bottom | −1.28 | −0.7258 | 1.572 | −1.561 |
| Top | 117.3 | 154.4 | Top | 100 | 165.8 | 188.5 | 207.7 |
| EC50 in ng/ml | 5.15 | 11.87 | EC50 in ng/ml | 108.2 | 9.229 | 4.833 | 5.48 |
| R square | 0.9554 | 0.9883 | R square | 0.9976 | 0.9764 | 0.9906 | 0.9825 |

TABLE 13

$EC_{50}$ values for long half-life molecules using PDL1 expressing CHO cells (6 h).

| | Urelumab | PRO885 | PRO1060 | PRO1062 | | Urelumab + HSA | PRO885 + HSA | PRO1057 + HSA | PRO1058 + HSA |
|---|---|---|---|---|---|---|---|---|---|
| Bottom | −0.09762 | 6.019 | −5.304 | −1.947 | Bottom | −0.8837 | 6.69 | −7.721 | −0.5282 |
| Top | 99.96 | 337.5 | 220.4 | 199.1 | Top | 106.3 | 492.8 | 462.9 | 40.06 |

TABLE 13-continued

EC$_{50}$ values for long half-life molecules using PDL1 expressing CHO cells (6 h).

| | Urelumab | PRO885 | PRO1060 | PRO1062 | | Urelumab + HSA | PRO885 + HSA | PRO1057 + HSA | PRO1058 + HSA |
|---|---|---|---|---|---|---|---|---|---|
| EC50 in ng/ml | 56.45 | 7.843 | 56.42 | 52.16 | EC50 in ng/ml | 77.72 | 7.916 | 111.5 | 70.93 |
| R square | 0.9948 | 0.9474 | 0.9874 | 0.993 | R square | 0.9957 | 0.9457 | 0.9943 | 0.6132 |

TABLE 14

EC$_{50}$ values for long half-life molecules using PDL1 expressing CHO cells (24 h).

| | Urelumab | PRO885 | PRO1060 | PRO1062 | | Urelumab + HSA | PRO885 + HSA | PRO1057 + HSA | PRO1058 + HSA |
|---|---|---|---|---|---|---|---|---|---|
| Bottom | 0.2207 | −11.83 | −5.151 | −3.914 | Bottom | −0.3454 | −5.805 | −7.71 | −0.4289 |
| Top | 88.59 | 196.1 | 141.1 | 130.5 | Top | 90.45 | 258.5 | 744.9 | 20.53 |
| EC50 in ng/ml | 46.63 | 13.75 | 80.85 | 86.87 | EC50 in ng/ml | 78.17 | 14.85 | 792.4 | 121.4 |
| R square | 0.9739 | 0.9869 | 0.991 | 0.9737 | R square | 0.9893 | 0.9812 | 0.9955 | 0.6294 |

TABLE 15

EC$_{50}$ values for long half-life molecules using HCC827 cells stimulated with IFNγ.

| | HCC827 without IFNy stimulation | | | | | HCC827 with IFNy stimulation | | | |
|---|---|---|---|---|---|---|---|---|---|
| | Urelumab | PRO885 | PRO1057 (+HSA) | PRO1060 | | Urelumab | PRO885 | PRO1057 (+HSA) | PRO1060 |
| Bottom | −0.7119 | −5.806 | 0.08644 | −0.6993 | Bottom | −2.649 | −3.386 | −3.323 | −1.177 |
| Top | 85.16 | 136.6 | 63.18 | 43.56 | Top | 91.62 | 140.2 | 136.6 | 83.61 |
| EC50 in ng/ml | 47.49 | 9.518 | 76.61 | 13.57 | EC50 in ng/ml | 52.77 | 7.515 | 115 | 17.51 |
| R square | 0.975 | 0.9838 | 0.9478 | 0.9255 | R square | 0.9743 | 0.9901 | 0.9911 | 0.972 |

TABLE 16C

Potencies of scDb-scFv to activate CD137 activity in NF-kB reporter gene assay Anti-CD137 domains are derived from IgG clones 38-02-A04and 38-27-A11; anti-PDL1 domains are derived from IgG clones 37-20-B03 and 33-03-G02; anti-SA domain is derived from IgG clone 19-01-H04.

| PRO ID | scDb-i domain | scDb-o domain | scFv domain | Time point [h] | EC$_{50}$ [ng/ml] | rel. EC$_{50}$ (EC$_{50}$, PRO1186/ EC$_{50}$, sample) |
|---|---|---|---|---|---|---|
| PRO1430 | 38-02-A04-sc13 | 37-20-B03-sc01 | 19-01-H04-sc03 | 6 | 9.80 | 1.31 |
| | | | | 24 | 4.42 | 1.51 |
| PRO1431 | 38-02-A04 sc13 | 33-03-G02 sc18 | 19-01-H04 sc03 | 6 | 21.02 | 0.68 |
| | | | | 24 | 18.39 | 1.02 |
| PRO1432 | 33-03-G02 sc18 | 38-02-A04 sc13 | 19-01-H04 sc03 | 6 | 19.36 | 0.67 |
| | | | | 24 | 21.89 | 0.75 |
| PRO1473 | 38-02-A04 sc13 | 33-03-G02 sc03 | 19-01-H04 sc03 | 6 | 2.40 | 2.30 |
| | | | | 24 | 0.91 | 3.55 |
| PRO1476 | 33-03-G02 sc03 | 38-02-A04 sc13 | 19-01-H04 sc03 | 6 | 5.97 | 2.02 |
| | | | | 24 | 3.90 | 1.83 |
| PRO1479 | 38-02-A04 sc13 | 37-20-B03 sc09.1 | 19-01-H04 sc03 | 6 | 7.38 | 1.74 |
| | | | | 24 | 7.61 | 0.87 |
| PRO1480 | 38-27-A11 sc02 | 37-20-B03 sc09.1 | 19-01-H04 sc03 | 6 | 6.44 | 1.93 |
| | | | | 24 | 4.67 | 1.00 |
| PRO1481 | 38-27-A11 sc03 | 37-20-B03 sc09.1 | 19-01-H04 sc03 | 6 | 7.22 | 1.04 |
| | | | | 24 | 5.51 | 0.58 |

TABLE 16C-continued

Potencies of scDb-scFv to activate CD137 activity in NF-kB reporter gene assay Anti-CD137 domains are derived from IgG clones 38-02-A04and 38-27-A11; anti-PDL1 domains are derived from IgG clones 37-20-B03 and 33-03-G02; anti-SA domain is derived from IgG clone 19-01-H04.

| PRO ID | Maximum NF-kB activation (rel. to PRO1186) [%] | $IC_{10}$/ $EC_{90}$ ratio | rel. $IC_{10}$/ $EC_{90}$ (ratio of sample/ratio of PRO1186) | Area under the curve (calculated using PRO885 normalized data) | rel. Area under the curve ($AUC_{sample}$/ $AUC_{PRO1186}$) |
|---|---|---|---|---|---|
| PRO1430 | 110.08 | 72.42 | 0.22 | 196.40 | 1.03 |
| | 98.57 | 1240.89 | 3.94 | 179.90 | 0.87 |
| PRO1431 | 55.29 | 5.03 | 0.30 | 83.15 | 0.40 |
| | 68.62 | 16.07 | 1.74 | 118.70 | 0.54 |
| PRO1432 | 63.36 | 26.84 | 0.36 | 111.40 | 0.59 |
| | 83.76 | 3.57 | 0.16 | 149.60 | 0.81 |
| PRO1473 | 36.19 | 53.87 | 1.01 | 52.34 | 0.31 |
| | 67.40 | 15.73 | 0.12 | 187.90 | 0.73 |
| PRO1476 | 36.35 | 34.24 | 2.66 | 93.49 | 0.39 |
| | 76.14 | 35.73 | 1.63 | 134.60 | 0.59 |
| PRO1479 | 108.25 | 81.94 | 0.25 | 191.10 | 1.11 |
| | 118.64 | 522.81 | 1.66 | 206.60 | 1.37 |
| PRO1480 | 114.29 | 42.99 | 0.54 | 232.10 | 1.20 |
| | 120.91 | 359.55 | 1.86 | 261.20 | 1.29 |
| PRO1481 | 147.28 | 23.74 | 1.71 | 291.90 | 1.37 |
| | 116.81 | 40.98 | 5.72 | 253.80 | 1.00 |

TABLE 17

Induction of IL-2 secretion by T cells upon treatment with PRO885.

| | ug/ml of anti-CD3 antibody | | | | | |
|---|---|---|---|---|---|---|
| | 2 | | | 1 | | |
| CHO-A1 cells/well | 50,000 | 100,000 | 200,000 | 50,000 | 100,000 | 200,000 |
| EC50 (ng/ml) | 52.01 | 41.85 | 30.05 | 12.85 | 86.22 | 80.62 |

Example 7: Assessment of T Cell Stimulatory Effect of Concomitant PDL1 Blockade and CD137 Stimulation in a Cell-Based Assay Using Human PBMC and Transgenic CHO Cells Expressing PDL1

Method

CHO-A2 cells expressing PDL1 were seeded at three different densities, ranging from 50,000 to 200,000 cells per well on 96-well culture plates pre-coated with an anti-human CD3 antibody. The plates were incubated overnight at 37° C., 5% $CO_2$. On the next day, peripheral blood mononuclear cells (PBMC) were isolated from fresh human whole blood by means of density gradient centrifugation. 100,000 PBMCs per well were added to the 96-well plate, followed by the addition of the anti-PDL1×CD137 scDb PRO885 at concentrations of 500, 50 and 5 ng/ml. After 76 hours of incubation, cell supernatants were harvested. Human interleukin-2 (IL-2) levels in the culture supernatants were quantified using the IL-2 human ELISA MAX assay from Biolegend, according to kit instructions. IL-2 concentrations were interpolated from a IL-2 standard curve, back-calculated and plotted against PRO885 concentrations for calculation of EC50 values.

Results

As shown in FIG. 20, IL-2 was secreted by T cells following concomitant blockade of PD-1/PDL1 interaction and stimulation of CD137 by the addition of the bispecific molecule PRO885. Secreted IL-2 levels increased with augmenting anti-CD3 antibody and CHO-A2 cell-densities, and increasing PRO885 concentrations. In the absence of anti-CD3 antibodies, IL-2 levels were comparable to basal IL-2 secretion. PRO885 only activated T-cells co-stimulated by an anti-CD3 antibody. No dose-dependent production of IL-2 in absence of stimulation with anti-CD3 confirms selective activation of antigen-specific T cells. This finding demonstrates that PRO885 only stimulates activated T-cells and suggests that in vivo PRO885 would specifically stimulate tumor specific T-cells.

Example 8: Assessment of the Stimulatory Effect of Concomitant PDL1 Blockade and CD137 Stimulation in a Cell-Based Assay Using Human PBMC Stimulated with Superantigen SEA In this experiment, the synergistic effect of PD-1/PDL1 inhibition and CD137 agonism was assessed. The assay used peripheral blood mononuclear cells (PBMC) that were stimulated with the superantigen Staphylococcal Enterotoxin A (SEA) in order to induce expression of PDL1 on antigen-presenting cells (APC) and T cells respectively and CD137 on T-cells. By applying anti-PDL1×CD137 molecules two T-cell regulatory signaling pathways were targeted concomitantly: inhibition of the inhibitory PD-1/PDL1 pathway as well as activation of the CD137 pathway via formation of an immunological synapse mediated by the 15 bispecific anti-PDL1×CD137 molecule PRO885 or by the trispecific anti-PDL1×CD137×HSA molecule PRO1175, PRO1430, PRO1479 or PRO1480. The activation of T-cells by the bispecific anti-PDL1×CD137 molecule PRO885 (SEQ ID NO: 209) or by the trispecific anti-PDL1×CD137×HSA molecule PRO1175 (SEQ ID NO: 220), PRO1430 (SEQ ID NO: 222), PRO1479 (SEQ ID NO: 223) or PRO1480 (SEQ ID NO: 229) was assessed. The activation of T-cells was assessed by the secretion of Interleukin-2 (IL-2) and compared to the effect mediated by PDL1 inhibition mediated by the benchmarking reference antibody avelumab. In addition, the anti-PDL1 scFv, PR0997, was tested and compared to avelumab in the same experimental setup. Furthermore, the activation of T-cells by the bispecific anti-PDL1×CD137 molecule PRO885 (SEQ ID NO: 209) or by the trispecific anti-PDL1×CD137×HSA molecule PRO1175 (SEQ ID NO: 220), PRO1430 (SEQ ID NO: 222), PRO1479 (SEQ ID NO: 223) or PRO1480 (SEQ ID NO: 229) was compared to the effect of reference antibody avelumab or urelumab, or a combination thereof.

Method

Peripheral blood mononuclear cells (PBMC) were isolated from fresh human whole blood by means of density gradient centrifugation. Then, PBMC were depleted for NK cells using anti-CD56 antibody and the MACS cell separation kit (Miltenyi Biotec). Next, 100,000 PBMCs per well were added to the 96-well plate, followed by the addition of serial dilutions of PRO885, PR0997, PRO1175, PRO1430, PRO1479 or PRO1480, avelumab, urelumab and the combination of avelumab and urelumab in assay buffer containing SEA at a concentration of 10 ng/ml. After 96 hours of incubation at 37° C. and 5% $CO_2$, cell supernatants were harvested and human Interleukin-2 (IL-2) levels in the culture supernatants were quantified using the IL-2 human ELISA MAX assay from BioLegend according to kit instructions. IL-2 concentrations were interpolated from a IL-2 standard curve, back-calculated and plotted against avelumab, the combination of avelumab and urelumab and PRO885 concentrations for calculation of EC50 values (FIG. 21 and Table 18), or plotted against avelumab, urelumab, the combination of avelumab and urelumab, PRO885 and PR01175, or PR01186 concentrations for calculation of EC50 values (FIG. 23 and Table 19).

Results

TABLE 18

EC50 values for PRO885 and PRO997 in PBMC assay using SEA stimulation.

| | Avelumab | PRO885 |
|---|---|---|
| Bottom | 2479 | 7463 |
| Top | 8687 | 20663 |
| EC50 in ng/ml | 69.89 | 39.92 |
| R square | 0.8589 | 0.9052 |
| | **Avelumab** | **PRO997** |
| Bottom | 2117 | 3226 |
| Top | 8588 | 9480 |
| EC50 in ng/ml | 90.18 | 40.86 |
| R square | 0.8783 | 0.867 |

As shown in FIG. 21, IL-2 was secreted by T-cells following concomitant blockade of PD-1/PDL1 interaction and stimulation of CD137 by the addition of the bispecific molecule PRO885. When compared to avelumab, PRO885 showed higher T cell activation and better potency (PRO885, $EC_{50}$=39.92 ng/ml; avelumab, $EC_{50}$=69.89 ng/ml, Table 18). This finding demonstrates that the bispecific anti-PDL1×CD137 scDb PRO885 is able to induce stronger T cell stimulation than mere PDL1 blockade by avelumab. Moreover, the high-affinity anti-PDL1 scFv PR0997 was found to be more potent in stimulation of T-cells than avelumab (PR0997, $EC_{50}$=40.86 ng/ml; avelumab, $EC_{50}$=90.18 ng/ml, Table 18). In addition, it was demonstrated that the bispecific anti-PDL1×CD137 scDb PRO885: (i) was able to induce stronger T cell stimulation than urelumab (FIG. 23), and (ii) was more potent in stimulation of T-cells than urelumab (PRO885, $EC_{50}$=55.21 ng/ml, urelumab, $EC_{50}$=278.3 ng/ml, Table 19).

Furthermore, while the combination of avelumab and urelumab was able to induce stronger T cell stimulation than avelumab alone (FIG. 23), the scDb-scFvs PRO1175, PRO1186, PRO1430, PRO1479 and PRO1480 triggered an even stronger production of IL-2 (FIGS. 21 and 23), probably due to its ability to hypercluster CD137. The scDb-scFv PRO1175 (i) was able to induce significantly stronger T cell stimulation than the combination of avelumab and urelumab (FIG. 23), and (ii) was more potent in stimulation of T-cells than the combination of avelumab and urelumab (PRO1175, $EC_{50}$=31.11 ng/ml, avelumab+urelumab, $EC_{50}$=318.6 ng/ml, Table 19). In addition, PRO1430, PRO1479, PRO1482 and PRO1480 demonstrated superior potency to stimulate IL-2 production in PMBCs when compared to the other scDb-scFv molecules (FIGS. 21 and 23). The scDb-scFv PRO1480 demonstrated the highest potency to stimulate IL-2 production in PMBCs when compared to the other scDb-scFv molecules tested (FIG. 21).

Example 9: Costim Signaling Only Occurs in Combination with TCR Stimulus and is More Pronounced with PDL1×CD137 scDb-scFv than with the Combination of PDL1 IgG1 and CD137 IgG4

In this experiment, the synergistic effect of PD-1/PDL1 inhibition and CD137 agonism was assessed. The assay used peripheral blood mononuclear cells (PBMC) in presence of PDL1 expressing CHO cells an anti-CD3 antibody in order to induce expression of CD137 on T-cells. By applying anti-PDL1×CD137 molecules two T-cell regulatory signaling pathways were targeted concomitantly: inhibition of the inhibitory PD-1/PDL1 pathway as well as activation of the CD137 pathway via formation of an immunological synapse mediated by the trispecific anti-PDL1×CD137×HSA molecule (PRO1186). The activation of T-cells by the trispecific anti-PDL1×CD137×HSA molecule PRO1186 was assessed by the secretion of Interleukin-2 (IL-2) or IFNy and compared to the effect mediated by PDL1 inhibition mediated by the benchmarking reference antibody avelumab, CD137 cross-linking mediated by urelumab or a combination thereof.

Method

Peripheral blood mononuclear cells (PBMC) were isolated from fresh human whole blood by means of density gradient centrifugation. Next, 100,000 PBMCs per well were added to the 96-well plate containing anti-CD3 antibody (BD Pharmingen, Cat. No. 551916) at a concentration of 2 mcg/ml and 10,000 CHO cells expressing human PDL1 per well, followed by the addition of serial dilutions of PRO1186, avelumab, urelumab and the combination of avelumab and urelumab in assay buffer. After 72 hours of incubation at 37° C. and 5% $CO_2$, cell supernatants were harvested and human Interleukin-2 (IL-2) and IFNy levels in the culture supernatants were quantified. Human Interleukin-2 (IL-2) levels were quantified using the IL-2 human ELISA MAX assay from BioLegend according to kit instructions. IL-2 concentrations were interpolated from a IL-2 standard curve (FIG. 23E). Human IFNγ levels were quantified using the Human IFN-γ DuoSet ELISA assay from R&D Systems according to kit instructions by ELISA (FIG. 23F).

Results

As shown in FIGS. 23 (E) and (F), IL-2 and IFNγ were secreted by T-cells following concomitant blockade of PD-1/PDL1 interaction and stimulation of CD137 by the addition of the trispecific molecule PRO1186. This finding demonstrates that the trispecific anti-PDL1×CD137×HSA scDb-scFv PRO1186 is able to induce stronger T cell stimulation than mere PDL1 blockade by avelumab, or CD137 blockade by urelumab, or the combination thereof. PRO1186 was more potent to induce IL-2 (FIG. 23E) and IFNγ (FIG. 23F) production than avelumab or urelumab, or the combination of the two. In absence of anti-CD3 antibodies, IL-2 and IFNγ levels were comparable to basal cytokine secretion at all concentrations tested, showing the requirement of TCR signaling or CD3 engagement for productive CD137 signaling.

Example 10: Assessment of the Anti-Tumor Efficacy of PDL1 Blockade and Concomitant Localized Stimulation of CD137 in the Human Cell Line-Derived Lung Cancer Xenograft Model HCC827

Anti-tumor activity of the multispecific antibody of the present invention was compared to anti-PDL1 and anti-CD137 therapy in human HCC827 NSCLC xenografts using the immunodeficient NOG mice strain from Taconic and allogenic human peripheral blood mononuclear cells. Engrafted human T lymphocytes show xeno-reactivity against foreign major histocompatibility (MHC) class I and II and other antigens from mice cells. As a result, T lymphocytes cause an inflammatory infiltrate in different organs that leads to death of the animals after several weeks, a process known as xenograft-versus-host disease (xGVHD). Treatment with immunomodulatory antibodies such as anti-PDL1 and anti-CD137 was shown to exacerbate xGVHD (Sanmamed M F et al. Nivolumab and urelumab enhance antitumor activity of human T lymphocytes engrafted in Rag2−/−IL2Rgnull immunodeficient mice. Cancer Res 2015; 75(17):3466-3478). Effects of PRO1057 (scDb-scFv; SEQ ID NO: 218) and PRO1060 (IgG-scFv with CD137 scFv fused to the C-terminus of the heavy chain of the IgG; SEQ ID Nos: 234 and 235) on tumor volume were compared to treatment with the IgG1 containing the same PDL1 specific variable domain as the multispecific antibody of the present invention (e.g., PRO1137) and with the IgG4 with the same CD137 specific variable domain (PRO 1138). To provide further evidence of localized anti-tumor immune response, frequency of tumor infiltrating lymphocytes such as CD8+, CD4+ and regulatory T cells was analyzed by flow cytometry. To explore modulation of the immune system systemically following anti-CD137/anti-PDL1 treatment the frequency of CD4+ and CD8+ T cells in liver and spleen was analyzed by flow cytometry. Moreover, systemic IFNg levels were analyzed using a quantitative ELISA method.

Study Set-Up and Treatment Schedule

Female NOG mice received unilateral injections of $5\times10^6$ HCC827 cells. Cells were injected in a mixture of 50% cell suspension in PBS and 50% matrigel in a total injection volume of 100 μl. After injection of tumor cells into NOG mice and successful tumor engraftment (median group tumor volume of 80-100 $mm^3$), mice were substituted with $5\times10^6$ human PBMCs by intravenous injection. On the day of randomization, four mice of each group were reconstituted with PBMCs of donor A and another four mice with PBMCs of donor B. Treatment started 1-2 hours after the injection of PBMCs and was applied as follows:

| group ID | compound | total daily dose [mg] | Relative units (r.U) | dosing days | route | no. of mice |
|---|---|---|---|---|---|---|
| 1 | Vehicle | na | na | 0, 3, 7, 10 | ip | 8 |
| 2 | PRO1057 low dose | 0.08 mg | 0.04 r.U | 0, 3, 7, 10 | ip | 8 |
| 3 | PRO1057 medium dose | 0.4 mg | 0.2 r.U | 0, 3, 7, 10 | ip | 8 |
| 4 | PRO1057 high dose | 2 mg | 1 r.U | 0, 3, 7, 10 | ip | 8 |
| 5 | PRO1137 | 0.2 mg | 1 r.U | 0, 3, 7, 10 | ip | 8 |
| 6 | PRO1138 | 0.2 mg | | 0, 3, 7, 10 | ip | 8 |
| 7 | PRO1060 | 0.2 mg | 1 r.U | 0, 3, 7, 10 | ip | 8 |

The high dose (HD) of PRO1057 as well as the 0.2 mg doses for PRO1060 and PRO 1137 were set to achieve the same relative activity modeled for a 0.1 mg dose of Aavelumab (per mouse) based on in vitro activity of the antibodies to block the PD-1/PDL1 interaction in the NF-AT reporter gene assay. Thus, a dose of 2 mg of PRO1057, or 0.2 mg of PRO1060, or 0.2 mg of PRO1137 could be represented as one relative unit (1 r.U) in relation to the 0.1 mg dose of avelumab.

Body weight measurements and tumor volume measurements by caliper were performed twice weekly. Animals were sacrificed at defined time-points depending on the study results. All but 3 animals were sacrificed at the 'same' time-point (on day 17 and day 18). Three animals were euthanized already on day 14 due to the onset of xenograft-versus-host disease (xGVHD). Sample collection and processing of the first half of each group were performed on the first day, and sample collection and processing of the second half of each group were performed on the following day for capacity reasons. Animals reconstituted with PBMCs from the two different donors were equally represented in the two sampling cohorts. Tumors, spleens and livers from all animals were collected at the end of the study and were processed for flow cytometry where the following human markers were analyzed: Live/Dead, CD4, CD8, CD25, FOXP3, TIM3, PD-1 and Granzyme B. Serum samples were analyzed for IFNg levels by ELISA using the DuoSet® ELISA Development System from R&D Systems according to the manufacturer's instructions.

Results

Anti-tumor activity of the multispecific antibodies PRO1057 (scDb-scFv anti-PDL1×CD137×HSA) and PRO1060 (Morrison format anti-PDL1×CD137), anti-PDL1 (PRO1137) and anti-CD137 (PRO1138 or urelumab) in human HCC827 NSCLC xenografts using the immunodeficient NOG mice strain and allogeneic human peripheral blood mononuclear cells (hPBMC) was assessed by measuring tumor volumes (FIG. 24). Tumor volumes were measured twice per week until mice were sacrificed on day 17 or day 18. Tumor volumes were normalized to the tumor volume at the start of the treatment (relative tumor volume). As shown in FIG. 24, HCC827 tumor bearing mice treated with anti-CD137 (PRO1138 or urelumab) or anti-PDL1 (PRO1137) monoclonal antibodies showed similar tumor growth as the vehicle control group. In contrast, treatment with anti-PDL1×CD137 bispecific antibodies such as a scDb-scFv (PRO1057) and an IgG-scFv (PRO1060) resulted in a clear stabilization of the tumor growth. Moreover, treatment with the bispecific anti-PDL1×CD137 molecules in mice reconstituted with PBMCs from donor B resulted in tumor regression (FIGS. 24B and 24D). Notably, treatment with the bispecific molecules did not lead to loss in median body weight implicating that the molecules are well tolerated at the dose levels tested, while treatment with urelumab leads to a decrease in median body weight 17 days after the start of the treatment (FIG. 25).

In addition, frequencies of T lymphocytes, namely human regulatory T cells (CD4+, FoxP3+; FIG. 26A) and human CD8+T cells, were analyzed in tumors at day 17 or day 18 of the treatment (FIG. 26). Tumor infiltrating lymphocytes were studied by flow cytometry, and ratio of frequency of human CD8+ T cells and frequency of human regulatory T cells (Treg) in the tumor microenvironment (TME) was determined (FIG. 26B).

Urelumab treatment alone resulted in a decreased frequency of regulatory T cells in the tumor microenvironment, while anti-PDL1 (PRO1137) treatment resulted in an increase of regulatory T cells (FIG. 26A). Interestingly, blockade of PD1/PDL1 and simultaneous triggering of CD137 (presumably on the same cell) in PRO1057 and PRO1060 treatment groups prevented an increase in regulatory T cells observed in the anti-PDL1 treatment group (FIG. 26A).

Moreover, treatment with bispecific anti-PDL1×CD137 antibodies (PRO1057 and PRO1060) showed more than two-fold improvement in the intratumoral human CD8+ T cells/human Treg (CD4+FoxP3+) ratio when compared to the treatment groups with monotherapies or to the vehicle control group (FIG. 26B). The increased CD8+/Treg ratio observed in the groups treated with PRO1057 and PRO1060 indicates that an effective antitumor response was elicited by the bispecific anti-PDL1×CD137 antibodies in the tumor microenviroment. Decrease in frequencies of regulatory T cells and increased the intratumoral human CD8+ T cells/human Treg (CD4+FoxP3+) ratios after treatment with the bispecific anti-PDL1×CD137 antibodies indicate that an antitumor effector/memory T-cell response was successfully elicited.

Further, the frequency of CD4+ and CD8+ cells that were positive for PD1 was determined to assess the percentage of activated T cells in the tumor microenvironment (FIG. 27). A dose-dependent increase in PD1-positive CD8+ and CD4+ T cells was observed for PRO1057, which at the high-dose reached similar levels of PD1-positive T cell as the treatment with PRO1060 and PRO1037, confirming equal dosing of the three compounds in terms of PDL1 blocking activity (FIGS. 27A and B). The two anti-CD137 antibodies PRO1038 and urelumab seemingly had no effect on the percentage of PD1-positive CD4+ or CD8+ T cells.

Example 11: Assessment of the Anti-Tumor Efficacy of PDL1 Blockade and Concomitant Localized Stimulation of CD137 in NOG Mice Engrafted with Human Umbilical Cord Blood-Derived CD34+ Hematopoietic Stem Cells (UCB HSCs)

Anti-tumor activity of the multispecific antibody of the present invention was compared to anti-PDL1 and anti-CD137 mono and combination therapy in human HCC827 NSCLC xenografts using NOG mice strain engrafted with human umbilical cord blood-derived CD34+ hematopoietic stem cells (UCB HSCs). Effect of PRO1186 (scDb-scFv; SEQ ID NO: 221) on tumor volume was compared to treatment with the IgG1 containing the same PDL1 specific variable domain as the multispecific antibody of the present invention (e.g., PRO1196, SEQ ID NOs: 242 and 243), Aavelumab, urelumab. Further, the effect of PRO1186 (scDb-scFv; SEQ ID NO: 221) on tumor volume was compared to the combination treatment of the IgG1 containing the same PDL1 specific variable domain as the multispecific antibody of the present invention (PRO1196, SEQ ID NOs: 242 and 243) with the IgG4 with the same CD137 specific variable domain (PRO1138, SEQ ID Nos: 244 and 245). To provide further evidence of localized antitumor immune response, frequency of tumor infiltrating lymphocytes such as CD8+, CD4+ and regulatory T cells was analyzed by flow cytometry. To explore modulation of the immune system systemically following anti-CD137/anti-PDL1 treatment the frequency of CD4+ and CD8+ T cells in liver and spleen was analyzed by flow cytometry. Moreover, systemic IFNy levels were analyzed using a quantitative ELISA method.

Study Set-Up and Treatment Schedule

Female NOG mice engrafted with human umbilical cord blood-derived CD34+ hematopoietic stem cells (UCB HSCs) were subcutaneously injected with HCC827 NSCLC cells. The mice received unilateral injections of $5\times10^6$ HCC827 cells. Cells were injected in a mixture of 50% cell suspension in PBS and 50% matrigel in a total injection volume of 100 μl. After injection of tumor cells into NOG mice and successful tumor engraftment (median group tumor volume of 80-100 $mm^3$), the mice (n=10) were randomized into treatment groups:

| group ID | compound | total daily dose [mg] | dosing days | route | no. of mice |
|---|---|---|---|---|---|
| 1 | Vehicle (Palivizumab) | 0.1 mg | 0, 5, 10, 15, 20 | ip | 10 |
| 2 | anti-PDL1 IgG1 (PRO1196) | 0.1 mg | 0, 5, 10, 15, 20 | ip | 10 |
| 3 | avelumab | 0.1 mg | 0, 5, 10, 15, 20 | ip | 10 |
| 4 | urelumab | 0.1 mg | 0, 5, 10, 15, 20 | ip | 10 |
| 5 | PRO1186 low dose | 0.02 mg | 0, 5, 10, 15, 20 | ip | 10 |
| 6 | PRO1186 medium dose | 0.1 mg | 0, 5, 10, 15, 20 | ip | 10 |
| 7 | PRO1186 high dose | 0.5 mg | 0, 5, 10, 15, 20 | ip | 10 |
| 8 | Combination anti-PDL1 IgG1 (PRO1196) and anti-CD137 IgG4 (PRO1138) | 0.1 mg each | 0, 5, 10, 15, 20 | ip | 10 |

Body weight measurements and tumor volume measurements by caliper were performed twice weekly. Tumors were harvested at the end of the study and assessed for infiltration of human T cells by flow cytometry. Tumors, spleens and livers from all animals were collected at the end of the study and were processed for flow cytometry where the following human markers were analyzed: Live/Dead, CD4, CD8, CD25, FOXP3, TIM3, PD-1, and Granzyme B. Serum samples were analyzed for IFNγ levels by ELISA using the DuoSet® ELISA Development System from R&D Systems according to the manufacturer's instructions.

Results

Anti-tumor activity of the multispecific antibodies PRO1186 (scDb-scFv anti-PDL1×CD137×HSA), anti-PDL1 (PRO1196 or avelumab) and anti-CD137 (urelumab) in human HCC827 NSCLC xenografts using the immuno-deficient NOG mice strain engrafted with human umbilical cord blood-derived CD34+ hematopoietic stem cells (UCB HSCs) was assessed by measuring tumor volumes (FIGS. 28 and 29). Tumor volumes were measured twice per week until mice were sacrificed on day 25, 29 or 30. Tumor volumes were normalized to the tumor volume at the start of the treatment (relative tumor volume). As shown in FIGS. 28 and 29, treatment with anti-PDL1×CD137×HSA trispecific antibodies such as a scDb-scFv (PRO1186) and the combination of anti-PDL1 (PRO1196) and anti-CD137 (PRO1138) resulted in a clear stabilization of the tumor growth. Notably, treatment with the trispecific molecules (PRO1186) did not lead to loss in median body weight implicating that the molecules are well tolerated at the dose levels tested, while treatment with the combination of anti-PDL1 (PRO1196) and anti-CD137 (PRO1138) leads to an increased number of animals with a body weight loss more than 10% or 15%, respectively, 24 days after the start of the treatment (FIG. 30). Anti-PDL1×CD137×HSA (PRO1186) therapy resulted in stronger reduction of tumor growth than therapy with anti-PDL1 IgG (PRO1196) or anti-CD137 IgG (urelumab). Anti-PDL1×CD137×HSA (PRO1186) therapy led to higher response rates (30% vs 20%) and was generally better tolerated than combination therapy with anti-PDL1 and anti-CD137. This correlates with higher frequency of cytotoxic T cells (CD8+ and CD8+, GrB+) and increased CD8+/CD4+ and CD8+, GrB+/Treg ratio in the tumor (FIGS. 31 and 32). Frequencies of T lymphocytes, namely cytotoxic T cells (CD8+, GrB+) CD4+ T cells and Tregs cells (FIGS. 31 and 32), were analyzed in tumors at day 24, day 29 and day 30 of the treatment.

In addition, pharmacokinetic analysis to quantify anti-PDL1×CD137×HSA (PRO1186) in serum samples from animals in HCC827 xenograft study using human CD34+ stem cell substituted NOG mice was performed (FIG. 33, Table 20). ELISA plates were coated overnight with CD137 and serial dilutions of anti-PDL1×CD137×HSA (PRO1186) were added to yield a calibration curve. Bound anti-PDL1×CD137×HSA (PRO1186) was detected with biotinylated human PDL1 followed by streptavidin poly-HRP. PRO1186 concentrations in diluted serum samples were interpolated from the calibration curve. Pharmacokinetic parameters were estimated by means of PK solver software add-in using a non-compartmental approach. Half-lives of 41.7 hours, 36.8 hours and 38.4 hours were determined by analyzing the first elimination phase after dosing for groups PRO1186-HD (0.5 mg), PRO1186-MD (0.1 mg) and PRO1186-LD (0.02 mg), respectively.

TABLE 20

Pharmacokinetic analysis of anti-PDL1 × CD137 × HSA (PRO1186) in serum samples from animals in HCC827 xenograft study using human CD34+ stem cell substituted NOG mice.

| Molecule | Dose/mouse/ occasion [mg] | Route | $T_{1/2}$ [h] | $AUC_{0-d5}$ [mg/ml*h] | Ratio AUC higher/ lower dose |
|---|---|---|---|---|---|
| PRO1186 | 0.5 | i.p. | 41.6 | 16'978'964 | |
| | 0.1 | i.p. | 36.8 | 2'475'621 | 6.9 |
| | 0.02 | i.p. | 38.4 | 331'269 | 7.5 |

Example 12: Assessment of the Anti-Tumor Efficacy of PDL1 Blockade and Concomitant Localized Stimulation of CD137 in a Syngeneic MC38 Colon Cancer Model In addition, anti-tumor activity of the multispecific antibody of the present invention will be tested in a MC38 colon carcinoma model in syngeneic C57BL/6 mice with an intact immune system. This model has been used by others to show enhanced antitumor activity by combination treatment with CD137 agonists and PD-1/PDL1 antagonists (Chen S et al. Combination of 4-1BB agonist and PD-1 antagonist promotes antitumor effector/memory CD8 T cells in a poorly immunogenic tumor model. Cancer Immunol Res 2014; 3(2):149-160 and Rodriguez-Ruiz M E et al. Abscopal effects of radiotherapy are enhanced by combined immunostimulatory mAbs and are dependent on CD8 T cells and crosspriming. Cancer Res 2016; 76(20):5994-6005).

Since both, the anti-CD137 domain and the anti-PDL1 domain of the multispecific antibody of the present invention are not cross-reactive to mouse PDL1 an engineered human CD137 knock-in model established by CrownBio will be used. In this model, the extracellular and transmembrane domain of mouse CD137 was replaced by the respective sequence of human CD137 in the C57BL/6 mice background using the CRISPR/Cas9 system. In addition, a modified MC38 tumor cell line expressing human PDL1 under control of a CMV promoter instead of mouse PDL1 will be used. Effects of the multispecific antibody of the present invention on tumor volume will be compared to combination treatment with the humanized IgG1 containing the same PDL1 specific variable domain as ND021 and with the humanized IgG4 with the same CD137 specific variable domain. To provide further evidence of localized antitumor immune response, frequency of tumor infiltrating lymphocytes such as CD8+, CD4+ and regulatory T cells will be analyzed by flow cytometry. To explore modulation of the immune system systemically following anti-CD137/anti-PDL1 treatment, the frequency of CD4+ and CD8+ T cells in liver and spleen will be analyzed by flow cytometry and possibly immunohistochemistry. Moreover, systemic IFNg levels could be analyzed using a quantitative ELISA method. To further characterize the safety profile of the anti-CD137/anti-PDL1 combination therapy, clinical chemistry pathology parameters associated primarily with liver toxicity (observed for anti-CD137 therapy in the clinic), such as increased levels of alanine aminotransferase, glutamate dehydrogenase and aspartate aminotransferase could be assessed.

Example 13: Exemplary Multispecific Antibodies of the Present Invention

General Description scDb

Single chain Diabodies (scDb) are small bivalent antibody fragments composed of one chain, comprising two VH and two VL domains from two different antibodies (Holliger et al. PNAS, 1993 Jul. 15; 90(14):6444-8). In the Numab scDb format, variable domains are connected in VLA-VHB-VLB-VHA domain orientation by GS linkers. The linkers in these single-chain diabodies (scDbs) force correct assembly of the domains and improve stability without altering the antigen-binding activity. Short $G_4S$ (SEQ ID NO: 207) linkers connecting VLA with VHB and VLB with VHA are substantially shorter than that required to allow assembly of adjacent domains and keep the domains in an open conformation allowing correct pairing of corresponding domains. VLA-VHB and VLB-VHA diabody arms are connected by a long $(G_4S)_4$ (SEQ ID NO: 206) linker between VHB and VLB domains allowing dimerization in a head-to-tail orientation resulting in a compact bispecific molecule with a molecular mass of –50 kDa. The scDb can be expressed recombinantly in either *E. coli* or CHO-S host cells. See FIG. 22A.

PRO885

PRO885 is a scDb molecule comprising an outer (VLA/VHA) PDL1-binding domain (33-03-G02 sc01) and an inner (VHB/VLB) CD137-specific domain (38-02-A04 sc01) connected by two short flanking $G_4S$ (SEQ ID NO: 207) linkers and a long central $(G_4S)_4$ (SEQ ID NO: 206) linker. Both domains consist of rabbit CDRs that were engrafted on a VH4-like human acceptor framework.

PRO951

PRO951 is a scDb molecule comprising an outer (VLA/VHA) PDL1-binding domain (33-03-G02 sc01) and an inner (VHB/VLB) CD137-specific domain (38-27-C05 sc02) connected by two short flanking $G_4S$ (SEQ ID NO: 207) linkers and a long central $(G_4S)_4$ (SEQ ID NO: 206) linker. Both domains consist of rabbit CDRs that were engrafted on human acceptor frameworks. PDL1-specific CDR's were engrafted on a VH4 consensus-like human acceptor framework while CD137-specific CDR's were engrafted on a VH3 consensus-like human acceptor framework.

PRO1123

PRO1123 is a scDb molecule comprising an outer (VLA/VHA) PDL1-binding domain (33-03-G02 sc01) and an inner (VHB/VLB) CD137-specific domain (38-02-A04 sc05) connected by two short flanking $G_4S$ (SEQ ID NO: 207) linkers and a long central $(G_4S)_4$ (SEQ ID NO: 206) linker. Both domains consist of rabbit CDRs that were engrafted on a VH4 consensus-like human acceptor framework. In addition, CD137 domain contains few rabbit residues participating in formation of VL-VH interface.

PRO1124

PRO1124 is a scDb molecule comprising an outer (VLA/VHA) PDL1-binding domain (33-03-G02 sc01) and an inner (VHB/VLB) CD137-specific domain (38-02-A04 sc06) connected by two short flanking $G_4S$ (SEQ ID NO: 207) linkers and a long central $(G_4S)_4$ (SEQ ID NO: 206) linker. Both domains consist of rabbit CDRs that were engrafted on a VH4 consensus-like human acceptor framework. In addition, CD137 domain contains few rabbit residues participating in formation of VL-VH interface and potentially interacting with the antigen.

PRO1125

PRO1125 is a scDb molecule comprising an outer (VLA/VHA) PDL1-binding domain (33-03-G02 sc02) and an inner (VHB/VLB) CD137-specific domain (38-02-A04 sc01) connected by two short flanking $G_4S$ (SEQ ID NO: 207) linkers and a long central $(G_4S)_4$ (SEQ ID NO: 206) linker. Both domains consist of rabbit CDRs that were engrafted on a VH4 consensus-like human acceptor framework. In addition, PDL1 domain contains few rabbit residues participating in formation of VL-VH interface.

PRO1126

PRO1126 is a scDb molecule comprising an outer (VLA/VHA) PDL1-binding domain (33-03-G02 sc03) and an inner (VHB/VLB) CD137-specific domain (38-02-A04 sc01) connected by two short flanking $G_4S$ (SEQ ID NO: 207) linkers and a long central $(G_4S)_4$ (SEQ ID NO: 206) linker. Both domains consist of rabbit CDRs that were engrafted on a VH4 consensus-like human acceptor framework. In addition, PDL1 domain contains back mutated rabbit residues participating in formation of VL-VH interface and potentially interacting with the antigen.

PRO1134

PRO1134 is a scDb molecule comprising an outer (VLA/VHA) PDL1-binding domain (33-03-G02 sc07) and an inner (VHB/VLB) CD137-specific domain (38-02-A04 sc01) connected by two short flanking $G_4S$ (SEQ ID NO: 207) linkers and a long central $(G_4S)_4$ (SEQ ID NO: 206) linker. Both domains consist of rabbit CDRs that were engrafted on a VH4 consensus-like human acceptor framework. In addition, PDL1 domain contains rabbit germline residues participating in formation of VL-VH interface and potentially interacting with the antigen.

General Description scDb-scFv

A scDb-scFv) is a format developed at Numab that adds a third single chain variable domain pair (VLC/VHC) connected via $(G_4S)2$ (SEQ ID NO: 208) linker to the highly stable single chain diabody (scDb) format as described above (VLA-VHB-VLB-VHA domain orientation with short $G_4S$ (SEQ ID NO: 207) core linkers and long $(G_4S)_4$ (SEQ ID NO: 206) central linker). Thus, scDb-scFv format consists of a tandem arrangement of a scDb with an scFv entity on a single protein chain and a molecular weight of ~80 kDa. The scDb-scFv antibody fragment can be expressed recombinantly in mammalian cells. See FIG. 22B.

PRO963

PRO963 is a scDb-scFv molecule consisting of an anti-PDL1 (33-03-G02 sc01, VLA/VHA) and anti-CD137 (38-02-A04 sc01, VHB/VLB) scDb core fused at the C-terminus with an anti-HSA scFv entity (19-01-H04-sc03, VLC/VHC). PDL1 and CD137 specific domains are human VH4 consensus-like acceptor frameworks with engrafted rabbit CDR's, while the HSA domain consists of rabbit CDR's engrafted on a human VH3-based acceptor framework containing additional rabbit residues supporting preservation of parental rabbit IgG binding characteristics.

PRO966 (PRO1052)

PRO966 is a scDb-scFv molecule consisting of an anti-PDL1 (33-03-G02 sc01, VLA/VHA) and anti-CD137 (38-27-C05 sc01, VHB/VLB) scDb core fused at the C-terminus with an anti-HSA scFv entity (19-01-H04-sc03, VLC/VHC). PDL1 and CD137 specific domains are human VH4 consensus-like acceptor frameworks with engrafted rabbit CDR's, while the HSA domain consists of rabbit CDR's engrafted on a human VH3-based acceptor framework containing additional rabbit residues supporting preservation of parental rabbit IgG binding characteristics.

PRO1057

PRO1057 is a scDb-scFv molecule consisting of an anti-PDL1 (33-03-G02 sc01, VLA/VHA) and anti-CD137 (38-02-A04 sc01, VHB/VLB) scDb core fused at the C-terminus with an anti-HSA scFv entity (23-13-A01-sc03, VLC/VHC). PDL1 and CD137 specific domains are human VH4 consensus-like acceptor frameworks with engrafted rabbit CDR's, while the HSA domain consists of rabbit CDR's engrafted on a human VH3-based acceptor framework containing additional rabbit residues supporting preservation of parental rabbit IgG binding characteristics including cross-reactivity to murine serum albumin.

PRO1058

PRO1058 is a scDb-scFv molecule consisting of an anti-PDL1 (33-03-G02 sc01, VLA/VHA) and anti-CD137 (38-27-C05 sc01, VHB/VLB) scDb core fused at the C-terminus with an anti-HSA scFv entity (23-13-A01-sc03, VLC/VHC). PDL1 and CD137 specific domains are human VH4 consensus-like acceptor frameworks with engrafted rabbit CDR's, while the HSA domain consists of rabbit CDR's engrafted on a human VH3-based acceptor framework containing additional rabbit residues supporting preservation of parental rabbit IgG binding characteristics including cross-reactivity to murine serum albumin.

PRO1186

PRO1086 is a scDb-scFv molecule consisting of an anti-PDL1 (37-20-B03 sc01, VLA/VHA) and anti-CD137 (38-02-A04 sc01, VHB/VLB) scDb core fused at the C-terminus with an anti-HSA scFv entity (23-13-A01-sc03, VLC/VHC). PDL1 and CD137 specific domains are human VH4 consensus-like acceptor frameworks with engrafted rabbit CDR's, while the HSA domain consists of rabbit CDR's engrafted on a human VH3-based acceptor framework containing additional rabbit residues supporting preservation of parental rabbit IgG binding characteristics including cross-reactivity to murine serum albumin.

PRO1430

PRO1430 is a scDb-scFv molecule consisting of an anti-PDL1 (37-20-B03 sc01, VLA/VHA) and anti-CD137 (38-02-A04 sc13, VHB/VLB) scDb core fused at the C-terminus with an 5 anti-HSA scFv entity (19-01-H04 sc03, VLC/VHC). PDL1 specific domain is a human VH4 consensus-like acceptor framework with engrafted rabbit CDR's, while the CD137 and HSA domains consist of rabbit CDR's engrafted on human VH3-based acceptor frameworks. The HSA domain contains additional rabbit framework residues supporting preservation of parental rabbit IgG binding characteristics and the CD137 specific domain contains a stabilizing VL/VH inter-domain disulfide bond.

PRO1479

PRO1479 is a scDb-scFv molecule consisting of an anti-PDL1 (37-20-B03 sc09.1, VLA/VHA) and anti-CD137 (38-02-A04 sc13, VHB/VLB) scDb core fused at the C-terminus 15 with an anti-HSA scFv entity (19-01-H04 sc03, VLC/VHC). All domains are human VH3 consensus-like acceptor frameworks with engrafted rabbit CDR's. The PDL1 and HSA specific domains contain additional rabbit framework residues supporting preservation of parental rabbit IgG binding characteristics and the CD137 specific domain contains a stabilizing VL/VH inter-domain disulfide bond.

PRO1482

PRO1482 is a scDb-scFv molecule consisting of an anti-CD137 (38-02-A04-sc13, VLA/VHA) and anti-PDL1 (37-20-B03 sc03, VHB/VLB) scDb core fused at the C-terminus with an anti-HSA scFv entity (19-01-H04 sc03, VLC/VHC). PDL1 specific domain is a human VH4 consensus-like acceptor framework with engrafted rabbit CDR's, while the CD137 and HSA specific domains consist of rabbit CDR's engrafted on human VH3-based acceptor frameworks. All domains contain additional rabbit framework residues supporting preservation of parental rabbit IgG binding characteristics.

PRO1431

PRO1431 is a scDb-scFv molecule consisting of an anti-PDL1 (33-03-G02 sc18, VLA/VHA) and anti-CD137 (38-02-A04 sc13, VHB/VLB) scDb core fused at the C-terminus with an anti-HSA scFv entity (19-01-H04 sc03, VLC/VHC). PDL1 specific domain is a human VH4 consensus-like acceptor framework with engrafted rabbit CDR's, while the CD137 and HSA specific domains consist of rabbit CDR's engrafted on human VH3-based acceptor frameworks. The HSA domain contains additional rabbit framework residues supporting preservation of parental rabbit IgG binding characteristics and the CD137 specific domain contains a stabilizing VL/VH inter-domain disulfide bond.

PRO1473

PRO1473 is a scDb-scFv molecule consisting of an anti-PDL1 (33-03-G02 sc03, VLA/VHA) and anti-CD137 (38-02-A04 sc13, VHB/VLB) scDb core fused at the C-terminus with an anti-HSA scFv entity (19-01-H04 sc03, VLC/VHC). PDL1 specific domain is a human VH4 consensus-like acceptor framework with engrafted rabbit CDR's, while the CD137 and HSA specific domains consist of rabbit CDR's engrafted on human VH3-based acceptor frameworks. HSA and PDL1 specific domains contain additional rabbit framework residues supporting preservation of parental rabbit IgG binding characteristics and the CD137 domain contains a stabilizing VL/VH inter-domain disulfide bond.

PRO1476

PRO1476 is a scDb-scFv molecule consisting of an anti-CD137 (38-02-A04 sc13, VLA/VHA) and anti-PDL1 (33-03-G02 sc03, VHB/VLB) scDb core fused at the C-terminus with an anti-HSA scFv entity (19-01-H04 sc03, VLC/VHC). PDL1 specific domain is a human VH4 consensus-like acceptor framework with engrafted rabbit CDR's, while the CD137 and HSA specific domains consist of rabbit CDR's engrafted on human VH3-based acceptor frameworks. HSA and PDL1 specific domains contain additional rabbit framework residues supporting preservation of parental rabbit IgG binding characteristics and CD137 specific domain contains a stabilizing VL/VH inter-domain disulfide bond.

PRO1432

PRO1432 is a scDb-scFv molecule consisting of an anti-CD137 (38-02-A04 sc13, VLA/VHA) and anti-PDL1 (33-03-G02 sc18, VHB/VLB) scDb core fused at the C-terminus with an anti-HSA scFv entity (19-01-H04 sc03, VLC/VHC). PDL1 specific domain is a human VH4 consensus-like acceptor framework with engrafted rabbit CDR's, while the CD137 and HSA specific domains consist of rabbit CDR's engrafted on human VH3-based acceptor frameworks. HSA and PDL1 specific domains contain additional rabbit framework residues supporting preservation of parental rabbit IgG binding characteristics and CD137 specific domain contains a stabilizing VL/VH inter-domain disulfide bond.

PRO1480

PRO1480 is a scDb-scFv molecule consisting of an anti-PDL1 (37-20-B03 sc09.1, VLA/VHA) and anti-CD137 (38-27-A11sc02, VHB/VLB) scDb core fused at the C-terminus with an anti-HSA scFv entity (19-01-H04 sc03, VLC/VHC). All domains are human VH3 consensus-like acceptor frameworks with engrafted rabbit CDR's. The PDL1 and HSA specific domains contain additional rabbit framework residues supporting preservation of parental rabbit IgG binding characteristics.

PRO1481

PRO1481 is a scDb-scFv molecule consisting of an anti-PDL1 (37-20-B03 sc09.1, VLA/VHA) and anti-CD137 (38-27-A11sc03, VHB/VLB) scDb core fused at the C-terminus with an anti-HSA scFv entity (19-01-H04 sc03, VLC/VHC). All domains are human VH3 consensus-like acceptor frameworks with engrafted rabbit CDR's. The PDL1, CD137 and HSA specific domains contain additional rabbit framework residues supporting preservation of parental rabbit IgG binding characteristics.

PRO1480 with DiS

PRO1480 with DiS is a scDb-scFv molecule consisting of an anti-PDL1 (37-20-B03 sc09.1, VLA/VHA) and anti-CD137 (38-27-A11sc07, VHB/VLB) scDb core fused at the C-terminus with an anti-HSA scFv entity (19-01-H04 sc03, VLC/VHC). All domains are human VH3 consensus-like acceptor frameworks with engrafted rabbit CDR's. The PDL1 and HSA specific domains contain additional rabbit framework residues supporting preservation of parental rabbit IgG binding characteristics and the CD137 specific domain contains a stabilizing VL/VH inter-domain disulfide bond.

General Description IgG-scFv

IgG-scFv molecules are bispecific antibodies consisting of scFv moieties fused to a monospecific IgG (Coloma M. J., Morrison S. L. Nat. Biotechnol. 1997; 15:159-163.). Either the amino or the carboxy terminus of each light or heavy chain can be appended with scFv domains of even different specificities, which leads to a diverse repertoire of IgG-scFv bispecific antibody types. The molecules produced at Numab are of the IgG(H)-scFv or IgG(L)-scFv type, two scFvs with same specificity linked to the C terminus of the full-length IgG heavy chain (HC) or light chain (LC), containing a silenced Fc-portion and $(G_4S)_2$ (SEQ ID NO: 208) linker connecting IgG portion with scFv portion. The total molecular weight of both types is ~200 kDa and the molecules can be expressed recombinantly in mammalian cells. See FIGS. 22C and 22D.

PRO1059 (IgG(L)-scFv)

Silent anti-PDL1 (33-03-G02-sc01) hIgG1 with an anti-CD137 scFv domain (38-02-A04 sc01) fused to the C-terminus of the LC. A $(G_4S)_2$ (SEQ ID NO: 208) linker is connecting IgG portion with scFv portion, which itself consists of a VL domain connected via $(G_4S)_4$ (SEQ ID NO: 206) linker to the corresponding VH domain.

PRO1060 (IgG(H)-scFv)

Silent anti-PDL1 (33-03-G02-sc01) hIgG1 with an anti-CD137 (38-02-A04 sc01) scFv domain fused to the C-terminus of the HC. A $(G_4S)_2$ (SEQ ID NO: 208) linker is connecting IgG portion with scFv portion, which itself consists of a VL domain connected via $(G_4S)_4$ (SEQ ID NO: 206) linker to the corresponding VH domain.

PRO1061 (IgG(L)-scFv)

Silenced anti-PDL1 (33-03-G02-sc01) hIgG1 with an anti-CD137 scFv domain (38-27-C05 sc01) fused to the C-terminus of the LC. A $(G_4S)_2$ (SEQ ID NO: 208) linker is connecting IgG portion with scFv portion, which itself consists of a VL domain connected via $(G_4S)_4$ (SEQ ID NO: 206) linker to the corresponding VH domain.

PRO1062 (IgG(H)-scFv)

Silent anti-PDL1 (33-03-G02-sc01) hIgG1 with an anti-CD137 (38-27-C05 sc01) scFv domain fused to the C-terminus of the HC. A $(G_4S)_2$ (SEQ ID NO: 208) linker is connecting IgG portion with scFv portion, which itself consists of a VL domain connected via $(G_4S)_4$ (SEQ ID NO: 206) linker to the corresponding VH domain.

Example 14: Biophysical Characterization

Biophysical Characterization of the Selected Domains

Selected domains were produced at larger scale (0.2 L-1.2 L expression volume), and were concentrated to >10 mg/mL using centrifugal concentration tubes after purification (Table 21).

ScFvs were subjected to stability studies such as a four-week stability study, in which the scFvs were formulated in an aqueous buffer (50 mM phosphate citrate buffer with 150 mM NaCL at pH6.4) at 10 mg/ml and stored at <−80° C., 4° C. and 40° C. for four weeks. At the minimum, the fraction of monomers and oligomers in the formulation were evaluated by integration of SE-HPLC peak areas after one week, two weeks and at the end of each study. Additional time points were recorded for some of the molecules. Table 22 compares d7 and endpoint measurements obtained at d28 of the study.

In addition, the compatibility of the scFv molecules was assessed with respect to freeze-thawing (F/T) cycles (colloidal stability). For the F/T stability assessment the same analytical methods and parameters (% monomer content and % monomer loss) as for the storage stability study (SE-HPLC, SDS-PAGE) were applied to monitor the quality of the molecules over five F/T cycles. Table 23 shows the course of monomer content in % over five repeated F/T cycles. None of the molecules lost >4% monomeric content after repeated F/T cycles.

Thermal unfolding of the molecules was assessed by using the fluorescence dye SYPRO orange. Samples in relevant excipient conditions were prepared and the assay was performed in a qPCR machine. Fluorescence emission was detected using the software's custom dye calibration routine. The PCR plate containing the test samples was subjected to a 30 temperature ramp from 25° C. to 96° C. in increments of 1° C. The midpoint of the unfolding transition (Tm) was calculated by the software GraphPad Prism using a mathematical second derivative method to calculate the inflection point of the curve. The reported Tm is an average of three measurements. Table 24 shows melting temperatures of the molecules formulated in generic buffer (phosphate-citrate buffer at pH 6.4, 150 mM NaCl).

Top selected molecules were subjected to a short-term pH stress stability study, in which the scFv molecules were formulated at 1 mg/ml in a set of aqueous (phosphate-citrate) buffer systems with pH values between 3.5 and 7.5. Monomeric content in % and % monomer loss was analyzed after storage for 2 weeks at 40° C. in the respective buffer systems (data not shown). A tabulated summary of monomeric content, monomeric loss, concentration and concentration loss over the course of the study is shown in Table 25.

Biophysical Characterization of the Multispecific Antibodies

The selected multispecific molecules were subjected to stability studies such as a four-week stability study, in which the multispecific molecules were formulated in the following buffer: 25 mM phosphate citrate buffer with 150 mM NaCl, 1 M sucrose at pH5.5 at 10 mg/ml and stored at <−20° C., 4° C., 20° C. and 40° C. for four weeks. At the minimum, the fraction of monomers and oligomers in the formulation were evaluated after one day, 4 days, one week, and every weeks until 12 weeks utilizing SE-HPLC. Table summarizes the findings Table 26.

TABLE 21

Manufacture of domains for stability study

| Clone ID | Protein ID | Grafting Strategy | Expression volume [mL] | Expression system | Protein amount post protein L [mg] | Yield post protein L [mg/L] |
|---|---|---|---|---|---|---|
| 38-02-A04-sc05 | PRO1181 | IF | 1200 | BL21 | 9.3 | 7.8 |
| 38-02-A04-sc06 | PRO1182 | FULL | 1200 | BL21 | 19.8 | 16.5 |
| 38-02-A04-sc09 | PRO1348 | CDR | 200 | CKO | 16.6 | 83.1 |
| 38-02-A04-sc13 | PRO1352 | CDR with ID diS | 200 | CHO | 12.2 | 61 |
| 38-27-A11 sc02 | PRO1359 | CDR | 200 | CHO | 13.7 | 68.5 |
| 38-27-A11 sc03 | PRO1360 | FULL | 200 | CHO | 12.9 | 64.7 |

| Clone ID | SEC Y/N? | Final yield [mg] | Yield per L expression [mg/L] | Purity SE-HPLC [% monomer] | Monomeric content at 10 mg/mL [%] | Monomeric loss upon concentration to 10 mg/mL |
|---|---|---|---|---|---|---|
| 38-02-A04-sc05 | Y | 4.7 | 3.9 | 88 | 77.8 | 10.2 |
| 38-02-A04-sc06 | Y | 5.6 | 4.7 | 95 | 72.9 | 22.1 |
| 38-02-A04-sc09 | N | 8 | 39.8 | 97 | 94.3 | 2.7 |
| 38-02-A04-sc13 | Y | 3.9 | 19.3 | 99.1 | 99.0 | 0.1 |
| 38-27-A11 sc02 | Y | 6.8 | 34.2 | 99 | 99.0 | 0.0 |
| 38-27-A11 sc03 | Y | 6.2 | 30.8 | 99.1 | 98.7 | 0.4 |

| Clone ID | Protein ID | Frame work | Expression volume [mL] | Yield post Capto L [mg] | Yield post capture [mg/L] | SEC purifi-cation? | Final yield [mg] | Final yield per L expression [mg/L] | Purity SE-HPLC [% monomer] | Tm [° C.] | Monomer content at 10 mg/mL [% monomer] | Monomer content loss upon con-centration [%] |
|---|---|---|---|---|---|---|---|---|---|---|---|---|
| 33-03-G02-sc01 | PRO830* | VH4 | 300 | 2.0 | 6.7 | NO | 2.0 | 6.7 | 99.0 | 80.0 | 98.3 | −0.7 |
| 33-03-G02-sc03 | PRO1183* | VH4 | 1200 | 16.9 | 14.1 | YES | 4.0 | 3.3 | 100.0 | NA | 99.7 | −0.3 |
| 33-03-G02-sc18 | PRO1392 | VH4 | 200 | 9.3 | 46.7 | NO | 7.4 | 37.2 | 97.0 | 72.4 | 97.4 | 0.4 |
| 37-20-B03-sc01 | PRO908* | VH4 | 1200 | 18.6 | 15.5 | YES | 5.3 | 4.4 | 89.0 | NA | 75.4 | −15.3 |
| 37-20-B03-sc09 | PRO1347 | VH3 | 200 | 8.0 | 38.9 | YES | 2.3 | 11.5 | 98.1 | 74.8 | 98.5 | 0.4 |

*bacterial expression

TABLE 22A

Four week stability study of the anti-CD137 scFv domains.

| | | | | monomeric content [%] | | | monomeric content loss [%] | | Protein concentration [mg/mL] | | | protein content loss [%] | |
|---|---|---|---|---|---|---|---|---|---|---|---|---|---|
| Clone ID | Protein ID | Temp. [° C.] | Initial monomeric content [%] | d 0 | d 7 | d 28 | d 7 | d 28 | d 0 | d 7 | d 28 | d 7 | d 28 |
| 38-02-A04-sc05 | PRO1181 | −80 | 77.8 | NA | NA | NA | NA | NA | NA | NA | NA | NA | NA |
| | | 4 | | NA | NA | NA | NA | NA | NA | NA | NA | NA | NA |
| | | 40 | | 77.8 | 78.2 | 77.8 | −0.5 | 0.1 | 10.4 | 10.4 | 9.6 | 0.2 | 7.7 |
| 38-02-A04-sc06 | PRO1182 | −80 | 72.9 | 72.9 | 72.8 | 72.9 | 0.1 | 0.0 | 20.6 | 21.0 | 24.8 | −2.0 | −20.5 |
| | | 4 | | 72.9 | 72.8 | 73.5 | 0.1 | −0.8 | 20.6 | 20.7 | 19.9 | −0.7 | 3.3 |
| | | 40 | | 72.9 | 72.8 | 72.1 | 0.1 | 1.1 | 20.6 | 20.5 | 20.7 | 0.3 | −0.6 |
| 38-02-A04-sc09 | PRO1348 | −80 | 94.3 | 94.3 | 93.2 | 91.2 | 1.1 | 3.3 | 10.0 | 11.0 | 11.2 | −10.3 | −11.8 |
| | | 4 | | 94.3 | 84.6 | 83.4 | 10.3 | 11.5 | 10.0 | 11.2 | 11.3 | −12.1 | −13.2 |
| | | 40 | | 94.3 | 85.7 | 84.5 | 9.1 | 10.4 | 10.0 | 11.5 | 12.0 | −15.2 | −20.5 |
| 38-02-A04-sc13 | PRO1352 | −80 | 99.0 | 99.0 | 99.1 | 99.1 | 0.0 | −0.1 | 11.4 | 11.8 | 11.7 | −3.6 | −2.7 |
| | | 4 | | 99.0 | 99.1 | 99.1 | −0.1 | −0.1 | 11.4 | 11.9 | 11.8 | −4.3 | −3.7 |
| | | 40 | | 99.0 | 99.1 | 99.0 | −0.1 | 0.0 | 11.4 | 12.5 | 12.9 | −9.3 | −13.2 |
| 38-27-A11 sc02 | PRO1359 | −80 | 99.0 | 99.0 | 98.8 | 98.8 | 0.2 | 0.2 | 10.5 | 11.2 | 11.6 | −7.0 | −11.0 |
| | | 4 | | 99.0 | 98.8 | 97.9 | 0.2 | 1.2 | 10.5 | 11.2 | 11.1 | −6.6 | −5.5 |
| | | 40 | | 99.0 | 80.1 | 79.1 | 19.1 | 20.1 | 10.5 | 10.8 | 11.1 | −3.2 | −6.3 |
| 38-27-A11 sc03 | PRO1360 | −80 | 98.7 | 98.7 | 98.6 | 97.4 | 0.1 | 1.3 | 10.9 | 9.7 | 10.3 | 11.1 | 5.6 |
| | | 4 | | 98.7 | 97.7 | 93.1 | 1.0 | 5.7 | 10.9 | 10.6 | 9.3 | 2.8 | 14.6 |
| | | 40 | | 98.7 | 79.0 | 77.4 | 20.0 | 21.6 | 10.9 | 12.0 | 11.2 | −9.9 | −2.7 |

TABLE 22B

Four week stability study of the anti-PDL1 scFv domains.

| Clone ID | Protein ID | Temp. [° C.] | Monomeric content [%] d 0 | d 7 | d 28 | Monomeric content loss [%] d 7 | d 28 | Protein concentration [mg/mL] d 0 | d 7 | d 28 | Protein content loss [%] d 7 | d 28 |
|---|---|---|---|---|---|---|---|---|---|---|---|---|
| 33-03-G02-sc01 | PRO830 | −80 | 98.3 | 98.5 | 98.4 | −0.2 | −0.1 | 10.5 | 12.0 | 11.4 | −14.2 | −9.2 |
| | | 4 | 98.3 | 97.9 | 96.8 | 0.4 | 1.6 | 10.5 | 12.4 | 12.0 | −18.6 | −14.5 |
| | | 40 | 98.3 | 93.3 | 84.9 | 5.0 | 13.6 | 10.5 | 10.4 | 11.6 | 0.6 | −10.6 |
| 33-03-G02-sc03 | PRO1183 | −80 | 99.7 | NA | 99.4 | NA | 0.3 | 20.6 | 20.8 | 21.1 | NA | −2.6 |
| | | 4 | 99.7 | NA | 87.9 | NA | 11.8 | 20.6 | 20.8 | 21.0 | NA | −1.9 |
| | | 40 | 99.7 | NA | 71.0 | NA | 28.8 | 20.6 | 21.0 | 22.0 | NA | −7.1 |
| 33-03-G02-sc18 | PRO1392 | −80 | 97.4 | 97.4 | 97.2 | 0.0 | 0.2 | 10.6 | 9.4 | 11.0 | 11.7 | −3.9 |
| | | 4 | 97.4 | 97.1 | 96.9 | 0.2 | 0.5 | 10.6 | 10.7 | 10.7 | −0.9 | −1.3 |
| | | 40 | 97.4 | 94.2 | 84.7 | 3.2 | 13.0 | 10.6 | 10.7 | 11.2 | −0.8 | −5.9 |
| 37-20-B03-sc09 | PRO1347 | −80 | NA | NA | NA | NA | NA | NA | NA | NA | NA | NA |
| | | 4 | 98.5 | 97.1 | 94.6 | 1.4 | 4.0 | 10.6 | 11.4 | 11.5 | −7.6 | −8.0 |
| | | 40 | 98.5 | 83.1 | 75.6 | 15.6 | 23.3 | 10.6 | 11.9 | 11.7 | −12.1 | −10.0 |
| 37-20-B03-sc01 | PRO908 | −80 | 75.4 | 74.4 | 73.5 | 1.4 | 2.5 | 10.4 | 10.3 | 9.9 | 1.1 | 4.8 |
| | | 4 | 75.4 | 74.1 | 73.8 | 1.7 | 2.1 | 10.4 | 9.9 | 9.9 | 4.9 | 4.7 |
| | | 40 | 75.4 | 75.4 | 73.2 | 0.0 | 3.0 | 10.4 | 11.5 | 11.4 | −11.0 | −9.6 |

TABLE 23

Assessment of F/T stability over time course of 28 d.

| Clone ID | PRO ID | F/T-1* | F/T-2* | F/T-3* | F/T-4* | F/T-5* |
|---|---|---|---|---|---|---|
| 38-02-A04-sc13 | PRO1352 | 0.0 | 0.1 | NA | NA | NA |
| 38-27-A11 sc02 | PRO1359 | 0.0 | −0.2 | −0.1 | −0.1 | −0.2 |
| 38-27-A11 sc03 | PRO1360 | −0.1 | −0.1 | −0.3 | −0.2 | −1.3 |

*monomeric loss % upon F/T

| Clone ID | Grafting Strategy | Framework | PRO ID | F/T-1* | F/T-2* | F/T-3* | F/T-4* | F/T-5* |
|---|---|---|---|---|---|---|---|---|
| 37-20-B03-sc01 | CDR | VH4 | PRO908 | −0.8 | −1.0 | −1.1 | −0.4 | −1.9 |
| 33-03-G02-sc03 | FULL | VH4 | PRO1183 | −0.1 | −0.4 | −0.3 | −0.4 | −0.3 |
| 33-03-G02-sc18 | PRO1183 opt. | VH4 | PRO1392 | −0.1 | 0.0 | 0.0 | −0.2 | −0.2 |
| 33-03-G02-sc01 | CDR | VH4 | PRO830 | 0.2 | 0.1 | 0.1 | NA | NA |
| 33-02-G02-s09 | FULL | VH3 | PRO1400 | 0.0 | 0.0 | −0.1 | NA | NA |

*monomeric loss % upon F/T cycle X
NA: not assessed

TABLE 24

Differential Scanning Fluorimetry of the scFv domains.

| Clone ID | Protein ID | Grafting Strategy | Tm [° C.] | Tonset [° C.] |
|---|---|---|---|---|
| 38-02-A04-sc09 | PRO1348 | CDR (*) | 61.1 | 56.7 |
| 38-02-A04-sc13 | PRO1352 | CDR with ID diS (*) | 55.2 | 50.0 |
| 38-02-A04-sc13 | PRO1352 | CDR with ID diS (**) | 62.6 | 58.0 |
| 38-27-A11 sc02 | PRO1359 | CDR (*) | 64.4 | 61.0 |
| 38-27-A11 sc02 | PRO1359 | CDR (**) | 68.3 | 64.3 |

TABLE 24-continued

Differential Scanning Fluorimetry of the scFv domains.

| Clone ID | Protein ID | Tm [° C.] | Tonset [° C.] |
|---|---|---|---|
| 33-03-G02-sc18 | PRO1392 | 72.40 | 67.00 |
| 37-20-B03-sc01 | PRO997 | 64.39 | 59.00 |
| 37-20-B03-sc09 | PRO1347 | 74.85 | 67.33 |

(*) Results of experiments using a standard protein concentration of 100 μg/ml.

(**) Results of experiments using a protein concentration of 50 μg/ml (experiment repeated due to non-ideal shape of melting curve at standard concentration).

TABLE 25

Tabulated summary of pH stability assessment

| Clone ID | Protein ID | Temperature | Final buffer | monomeric content [%] | | | monomeric loss [%] | | protein concentration [mg/mL] | | | content loss [%] | |
|---|---|---|---|---|---|---|---|---|---|---|---|---|---|
| | | | | d 0 | d 7 | d 14 | d 7 | d 14 | d 0 | d 7 | d 14 | d 7 | d 14 |
| 38-02-A04 sc13 | PRO1352 | 4° C. | pH 3.5 | 98.2 | 98.4 | 98.2 | 0.2 | −0.2 | 1.1 | 1.0 | 1.1 | −3.3 | 3.0 |
| | | | pH 4.5 | 98.2 | 98.4 | 98.3 | 0.2 | −0.2 | 0.9 | 1.0 | 1.0 | 10.1 | −0.5 |
| | | | pH 5.5 | 98.1 | 98.4 | 98.2 | 0.4 | −0.2 | 1.0 | 1.0 | 1.1 | −0.6 | 9.5 |
| | | | pH 6.5 | NA | 98.0 | 98.1 | NA | 0.1 | 1.0 | 0.8 | 1.0 | −14.1 | 26.5 |
| | | | pH 7.5 | NA | 98.0 | 98.2 | NA | 0.2 | 1.0 | 1.0 | 1.0 | 1.1 | 6.7 |
| | | 40° C. | pH 3.5 | 98.2 | 98.0 | 98.2 | −0.2 | 0.2 | 1.1 | 1.1 | 1.1 | 6.5 | −6.6 |
| | | | pH 4.5 | 98.2 | 98.0 | 98.1 | 1.1 | 0.1 | 0.9 | 1.1 | 1.0 | 18.4 | −4.1 |
| | | | pH 5.5 | 98.1 | 98.0 | 98.1 | 1.3 | 0.1 | 1.0 | 1.0 | 1.1 | 3.6 | 3.3 |
| | | | pH 6.5 | NA | 98.0 | 98.2 | 1.4 | 0.2 | 1.0 | 1.0 | 1.1 | 6.7 | 2.8 |
| | | | pH 7.5 | NA | 98.0 | 98.1 | 1.4 | 0.1 | 1.0 | 1.0 | 1.1 | 4.1 | 6.3 |
| 38-27-A11 sc02 | PRO1359 | 4° C. | pH 3.5 | NA | 96.9 | 96.8 | NA | −0.1 | 1.0 | 1.0 | 1.0 | −8.6 | 0.8 |
| | | | pH 4.5 | 96.9 | 97.0 | 97.0 | 0.1 | 0.0 | 1.0 | 1.0 | 1.0 | −7.3 | 3.8 |
| | | | pH 5.5 | 96.7 | 97.0 | 96.8 | 0.3 | −0.2 | 1.0 | 0.9 | 1.0 | −6.7 | 7.7 |
| | | | pH 6.5 | 96.7 | 97.0 | 96.9 | 0.3 | −0.1 | 1.0 | 1.0 | 1.0 | 4.0 | −3.2 |
| | | | pH 7.5 | 96.6 | 97.0 | 96.7 | 0.4 | −0.3 | 1.0 | 1.0 | 1.0 | 4.0 | −2.4 |
| | | 40° C. | pH 3.5 | NA | 97.2 | 97.3 | NA | 0.1 | 1.0 | 1.0 | 1.0 | −5.8 | 4.1 |
| | | | pH 4.5 | 96.9 | 97.0 | 97.3 | 0.1 | 0.3 | 1.0 | 0.9 | 1.0 | −9.0 | 8.9 |
| | | | pH 5.5 | 96.7 | 97.0 | 97.4 | 0.3 | 0.4 | 1.0 | 0.9 | 1.0 | −7.9 | 10.8 |
| | | | pH 6.5 | 96.7 | 97.5 | 97.5 | 0.9 | 0.0 | 1.0 | 0.9 | 1.0 | −4.6 | 7.0 |
| | | | pH 7.5 | 96.6 | 98.0 | 97.6 | 1.4 | −0.4 | 1.0 | 1.0 | 1.0 | −0.2 | 4.5 |
| 38-27-A11 sc03 | PRO1360 | 4° C. | pH 3.5 | 94.1 | 94.0 | 93.9 | −0.1 | −0.1 | 1.1 | 1.0 | 1.2 | −11.1 | 21.1 |
| | | | pH 4.5 | 93.8 | 94.0 | 93.7 | 0.3 | −0.3 | 1.0 | 1.0 | 1.1 | 2.5 | 7.7 |
| | | | pH 5.5 | 93.7 | 94.0 | 93.7 | 0.4 | −0.3 | 0.9 | 1.0 | 1.1 | 10.5 | 4.8 |
| | | | pH 6.5 | NA | 94.0 | 93.7 | NA | −0.3 | 1.0 | 1.0 | 1.0 | 5.8 | 2.8 |
| | | | pH 7.5 | NA | 94.0 | 93.9 | NA | −0.1 | 1.0 | 1.0 | 1.1 | 3.1 | 4.2 |
| | | 40° C. | pH 3.5 | 94.1 | 97.0 | 97.3 | 3.1 | 0.3 | 1.1 | 1.0 | 1.0 | −8.7 | 1.6 |
| | | | pH 4.5 | 93.8 | 97.0 | 96.9 | 3.5 | −0.1 | 1.0 | 1.0 | 1.1 | −0.5 | 6.6 |
| | | | pH 5.5 | 93.7 | 97.0 | 96.9 | 3.6 | −0.1 | 0.9 | 1.0 | 1.1 | 8.1 | 9.4 |
| | | | pH 6.5 | NA | 97.0 | 96.9 | NA | −0.1 | 1.0 | 1.0 | 1.1 | 2.1 | 8.1 |
| | | | pH 7.5 | NA | NA | 97.0 | NA | NA | 1.0 | NA | 1.1 | NA | NA |

The invention claimed is:

1. A multispecific antibody comprising:

a) one binding domain for human CD137 (huCD137-BD); and b) one binding domain for human PDL1 (huPDL1-BD), wherein said multispecific antibody comprises a sequence selected from the group consisting of SEQ ID NOs: 229, 230 and 231.

2. A pharmaceutical composition comprising the multispecific antibody of claim 1 and a pharmaceutically acceptable carrier.

3. A method of producing the multispecific antibody according to claim 1, the method comprising the step of in vitro culturing a host cell comprising a nucleic acid encoding the multispecific antibody according to claim 1 or a vector comprising said nucleic acid.

* * * * *